(12) United States Patent
Behlke et al.

(10) Patent No.: US 10,266,889 B2
(45) Date of Patent: Apr. 23, 2019

(54) $T_m$-ENHANCED BLOCKING OLIGONUCLEOTIDES AND BAITS FOR IMPROVED TARGET ENRICHMENT AND REDUCED OFF-TARGET SELECTION

(71) Applicants: Integrated DNA Technologies, Inc., Coralville, IA (US); Foundation Medicine, Inc., Cambridge, MA (US)

(72) Inventors: Mark Aaron Behlke, Coralville, IA (US); John Robert Havens, Evergreen, CO (US); Mirna Jarosz, Palo Alto, CA (US); Zachary Zwirko, Brighton, MA (US); Doron Lipson, Chestnut Hill, MA (US); Frank Soo Juhn, Brookline, MA (US)

(73) Assignees: ROCHE FINANCE LTD, Basel (CH); INTEGRATED DNA TECHNOLOGIES, INC., Coralville, IA (US)

(*) Notice: Subject to any disclaimer, the term of this patent is extended or adjusted under 35 U.S.C. 154(b) by 0 days.

(21) Appl. No.: 13/935,451

(22) Filed: Jul. 3, 2013

(65) Prior Publication Data

US 2014/0031240 A1     Jan. 30, 2014

Related U.S. Application Data

(60) Provisional application No. 61/667,919, filed on Jul. 3, 2012, provisional application No. 61/745,435, filed on Dec. 21, 2012.

(51) Int. Cl.
| | |
|---|---|
| *C12Q 1/68* | (2018.01) |
| *C12Q 1/6874* | (2018.01) |
| *C12N 15/10* | (2006.01) |
| *C12Q 1/6876* | (2018.01) |
| *C12Q 1/6869* | (2018.01) |
| *C12Q 1/6886* | (2018.01) |

(52) U.S. Cl.
CPC ....... *C12Q 1/6874* (2013.01); *C12N 15/1003* (2013.01); *C12N 15/1006* (2013.01); *C12Q 1/6869* (2013.01); *C12Q 1/6876* (2013.01); *C12Q 1/6886* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 5,849,497 A | * | 12/1998 | Steinman | 435/6.11 |
| 6,110,676 A | | 8/2000 | Coull et al. | |
| 6,936,443 B2 | * | 8/2005 | Cohenford et al. | 435/91.2 |
| 2004/0023207 A1 | * | 2/2004 | Polansky | A61K 31/00 435/5 |
| 2005/0181394 A1 | | 8/2005 | Steemers et al. | |
| 2005/0244830 A1 | | 11/2005 | Frebourg et al. | |
| 2005/0260608 A1 | * | 11/2005 | Zimmer | C07K 16/18 435/6.1 |
| 2007/0111960 A1 | * | 5/2007 | Stender et al. | 514/44 |
| 2009/0068643 A1 | * | 3/2009 | Behlke et al. | 435/6 |
| 2010/0029498 A1 | | 2/2010 | Gnirke et al. | |
| 2010/0143923 A1 | * | 6/2010 | Stender et al. | 435/6 |
| 2011/0065604 A1 | | 3/2011 | Sampson et al. | |
| 2011/0091939 A1 | * | 4/2011 | Cui | C07H 21/04 435/91.5 |
| 2011/0111462 A1 | * | 5/2011 | Picone | C12Q 1/6853 435/91.2 |
| 2012/0029891 A1 | | 2/2012 | Behlke et al. | |
| 2012/0208706 A1 | | 8/2012 | Downing et al. | |
| 2013/0203628 A1 | | 8/2013 | Bergmann et al. | |
| 2013/0230857 A1 | | 9/2013 | Gnirke et al. | |

FOREIGN PATENT DOCUMENTS

| | | |
|---|---|---|
| WO | 9824933 A1 | 6/1998 |
| WO | 2007117256 A1 | 10/2007 |
| WO | 2009099602 A1 | 8/2009 |
| WO | 2011000836 A1 | 1/2011 |
| WO | 2011139920 A2 | 11/2011 |
| WO | 2012018697 A1 | 2/2012 |
| WO | 2012061600 A1 | 5/2012 |

(Continued)

OTHER PUBLICATIONS

Brandt O, Feldner J, Stephan A, Schröder M, Schnölzer M, Arlinghaus HF, Hoheisel JD, Jacob A. PNA microarrays for hybridisation of unlabelled DNA samples. Nucleic Acids Res. Oct. 1, 2003; 31(19):e119.*

Choi JJ, Kim C, Park H. Peptide nucleic acid-based array for detecting and genotyping human papillomaviruses. J Clin Microbiol. Jun. 2009; 47(6):1785-90. Epub Apr. 15, 2009.*

Jensen KK, Orum H, Nielsen PE, Nordén B. Kinetics for hybridization of peptide nucleic acids (PNA) with DNA and RNA studied with the BIAcore technique. Biochemistry. Apr. 22, 1997; 36(16):5072-7.*

Kerman, Kagan, et al. Peptide nucleic acid modified magnetic beads for intercalator based electrochemical detection of DNA hybridization. 2004.Science and technology of Advanced Materials 5(3): 351-357.*

(Continued)

*Primary Examiner* — Gary Benzion
*Assistant Examiner* — Olayinka A Oyeyemi
(74) *Attorney, Agent, or Firm* — Klintworth & Rozenblat IP LLP

(57) ABSTRACT

The invention is directed to modified oligonucleotide compositions and methods for selectively reducing unwanted nucleic acid contaminants and enriching for desired nucleic acid targets from complex genomic nucleic acid mixtures for sequencing applications. The modified oligonucleotide compositions include one or more modified groups that increase the $T_m$ of the resultant oligonucleotide composition.

3 Claims, 16 Drawing Sheets

Specification includes a Sequence Listing.

(56) References Cited

FOREIGN PATENT DOCUMENTS

| WO | 2012092426 A1 | 7/2012 |
|---|---|---|
| WO | 2014008447 A1 | 1/2014 |

OTHER PUBLICATIONS

Illumina Technical Bulletin, 2005, Whole Genome Expression Analysis using the Sentrix Human-6 and HumanRef-8 Expression BeadChips.*
Mamanova L, Coffey AJ, Scott CE, Kozarewa I, Turner EH, Kumar A, Howard E, Shendure J, Turner DJ. Target-enrichment strategies for next-generation sequencing. Nat Methods. Feb. 2010; 7(2):111-8. Review.*
Okou DT, Steinberg KM, Middle C, Cutler DJ, Albert TJ, Zwick ME. Microarray-based genomic selection for high-throughput resequencing. Nat Methods. Nov. 2007; 4(11):907-9. Epub Oct. 14, 2007.*
Okou DT, Locke AE, Steinberg KM, Hagen K, Athri P, Shetty AC, Patel V, Zwick ME. Combining microarray-based genomic selection (MGS) with the Illumina Genome Analyzer platform to sequence diploid target regions. Ann Hum Genet. Sep. 2009; 73(Pt 5):502-13. Epub Jul. 1, 2009.*
Weiler J, Gausepohl H, Hauser N, Jensen ON, Hoheisel JD. Hybridisation based DNA screening on peptide nucleic acid (PNA) oligomer arrays. Nucleic Acids Res. Jul. 15, 1997; 25(14):2792-9.*
Behlke, M. A., Dames, S. A., McDonald, W. H., Gould, K. L., Devor, E. J., & Walder, J. A. (2000). Use of high specific activity StarFire oligonucleotide probes to visualize low-abundance pre-mRNA splicing intermediates in S. pombe. Biotechniques, 29(4), 892-897.*
Castoldi M, Schmidt S, Benes V, Noerholm M, Kulozik AE, Hentze MW, Muckenthaler MU. A sensitive array for microRNA expression profiling (miChip) based on locked nucleic acids (LNA). RNA. May 2006; 12(5):913-20. Epub Mar. 15, 2006.*
Dames S, Margraf RL, Pattison DC, Wittwer CT, Voelkerding KV. Characterization of aberrant melting peaks in unlabeled probe assays. J Mol Diagn. Jul. 2007; 9(3):290-6.*
Di Giusto DA, King GC. Strong positional preference in the interaction of LNA oligonucleotides with DNA polymerase and proofreading exonuclease activities: implications for genotyping assays. Nucleic Acids Res. Feb. 18, 2004; 32(3):e32: pp. 1-8.*
Gamper HB, Reed MW, Cox T, Virosco JS, Adams AD, Gall AA, Scholler JK, Meyer RB Jr. Facile preparation of nuclease resistant 3' modified oligodeoxynucleotides. Nucleic Acids Res. Jan. 11, 1993; 21(1):145-50.*
Jacobsen N, Fenger M, Bentzen J, Rasmussen SL, Jakobsen MH, Fenstholt J, Skouv J. Genotyping of the apolipoprotein B R3500Q mutation using immobilized locked nucleic acid capture probes. Clin Chem. 2002; 48(4):657-60.*
Koizumi M, Morita K, Takagi M, Yasumo H, Kasuya A. Improvement of single nucleotide polymorphism genotyping by allele-specific PCR using primers modified with an ENA residue. Anal Biochem. May 15, 2005; 340(2):287-94.*
Orum H, Jakobsen MH, Koch T, Vuust J, Borre MB. Detection of the factor V Leiden mutation by direct allele-specific hybridization of PCR amplicons to photoimmobilized locked nucleic acids. Clin Chem. Nov. 1999; 45(11):1898-905.*
Vestheim H, Deagle BE, Jarman SN. Application of blocking oligonucleotides to improve signal-to-noise ratio in a PCR. Methods Mol Biol. 2011; 687:265-74.*
Blumenstiel B, Cibulskis K, Fisher S, DeFelice M, Barry A, Fennell T, Abreu J, Minie B, Costello M, Young G, Maguire J, Kernytsky A, Melnikov A, Rogov P, Gnirke A, Gabriel S. Targeted exon sequencing by in-solution hybrid selection. Curr Protoc Hum Genet. Jul. 2010; Chapter 18: Unit 18.4. pp. 18.4.1-18.4.24.*
Craig DW, Pearson JV, Szelinger S, Sekar A, Redman M, Corneveaux JJ, Pawlowski TL, Laub T, Nunn G, Stephan DA, Homer N, Huentelman MJ. Identification of genetic variants using bar-coded multiplexed sequencing. Nat Methods. Oct. 2008; 5(10):887-93. Epub Sep. 14, 2008.*
Craig et al. (2008, Nat Methods 5(10):887-893) Supporting Information. pp. 1-10.*
Hodges E, Rooks M, Xuan Z, Bhattacharjee A, Benjamin Gordon D, Brizuela L, Richard McCombie W, Hannon GJ. Hybrid selection of discrete genomic intervals on custom-designed microarrays for massively parallel sequencing. Nat Protoc. 2009; 4(6):960-74.*
McTigue PM, Peterson RJ, Kahn JD. Sequence-dependent thermodynamic parameters for locked nucleic acid (LNA)-DNA duplex formation. Biochemistry. May 11, 2004 ;43(18):5388-405.*
Singh SK, Koshkin AA, Wengel J, Nielsen P. LNA (locked nucleic acids): synthesis and high-affinity nucleic acid recognition. Chem Commun 1998:455-456.*
Vester B, Wengel J. LNA (locked nucleic acid): high-affinity targeting of complementary RNA and DNA. Biochemistry. Oct. 26, 2004; 43(42):13233-41.*
Wagle N, Berger MF, Davis MJ, Blumenstiel B, Defelice M, Pochanard P, Ducar M, Van Hummelen P, Macconaill LE, Hahn WC, Meyerson M, Gabriel SB, Garraway LA. High-throughput detection of actionable genomic alterations in clinical tumor samples by targeted, massively parallel sequencing. Cancer Discov. Jan. 2012; 2(1):82-93. Epub Nov. 7, 2011.*
Albers, et al., "Dindel: accurate indel calls from short-read data," Genome Res. Jun. 2011;21(6):961-73.
Aslanidis, et al.,"Ligation-independent cloning of PCR products (LIC-PCR)," Nucleic Acids Research. 1990; 18(20):6069-6074.
Blumenstiel, et al., "Targeted Exon Sequencing by In-Solution Hybrid Selection," Current Protocols in Human Genetics Jul. 2010, Chapter 18, Unit 18.4 (18.4.1-18.4.24), 24 pages.
Browning, et al., "Simultaneous Genotype Calling and Haplotype Phasing Improves Genotype Accuracy and Reduces False-Positive Associations for Genome-wide Association Studies," The American Journal of Human Genetics. Dec. 11, 2009; 85(6):847-61.
Clark, et al., "Performance comparison of exome DNA sequencing technologies," Nature Biotechnology. Oct. 2011; 29(10):908-916.
Cronin, et al., "Measurement of Gene Expression in Archival Paraffin-Embedded Tissues," American Journal of Pathology. Jan. 2004;164(1): pp. 35-42.
Egholm, et al, "PNA hybridizes to complementary oligonucleotides obeying the Watson-Crick hydrogen-bonding rules," Nature. Oct. 7, 1993; 365:566-568.
Fiandaca, et al., "PNA Blocker Probes Enhance Specificity in Probe Assays," Peptide Nucleic Acids. Jan. 1, 1999; 129-141 (Horizon Scientific Press, Wymondham, UK).
Gnirke, et al., "Solution hybrid selection with ultra-long oligonucleotides for massively parallel targeted sequencing," Nature Biotechnology. Feb. 1, 2009; 27(2):182-189.
Goya, et al., "SNVMix: predicting single nucleotide variants from next-generation sequencing of tumors," Bioinformatics. 2010; 26(6):730-736.
Hodges, et al., "Hybrid selection of discrete genomic intervals on custom-designed microarrays for massively parallel sequencing," Nature Protocols. 2009; 4(6):960-974.
Kaur, et al., "Thermodynamic, Counterion, and Hydration Effects for the Incorporation of Locked Nucleic Acid Nucleotides into DNA Duplexes". Biochemistry. 2006; 45 (23) 7347-55.
Le, et al., "SNP detection and genotyping from low-coverage sequencing data on multiple diploid samples," Genome Res. Jun. 2011;21(6):952-60.
Li, et al. "Fast and accurate long-read alignment with Burrows-Wheeler transform," Bioinformatics, 2010; 26 (5):589-595.
Li, et al., "Genotype imputation," Annu. Rev. Genom. Human Genet. 2009; 10:387-406.
Li, et al., "The Sequence Alignment/Map format and SAMtools," Bioinformatics. 2009; 25(16):2078-2079.
Lunter, et al., "Stampy: a statistical algorithm for sensitive and fast mapping of Illumina sequence reads," Genome Res. Jun. 2011;21(6):936-9.
Mamanova, et al., "Target-enrichment strategies for next-generation sequencing," Nature Methods. Feb. 2010; 7(2):111-118.
Masuda, et al., "Analysis of chemical modification of RNA from formalin-fixed samples and optimization of molecular biology applications for such samples," Nucleic Acids Research. 1999; 27(22): 4436-4443.

(56) References Cited

OTHER PUBLICATIONS

McKenna, et al., "The Genome Analysis Toolkit: a MapReduce framework for analyzing next-generation DNA sequencing data," Genome Res. 2010; 20(9):1297-1303.

McTigue, et al., "Sequence-Dependent Thermodynamic Parameters for Locked Nucleic Acid (LNA)-DNA Duplex Formation," Biochemistry. Apr. 15, 2004; 43:5388-5405.

Mercer, et al., "Targeted RNA sequencing reveals the deep complexity of the human transcriptome," Nature Biotechnology. Jan. 2012; 30(1):99-106.

Metzker, "Sequencing technologies—the next generation," Nature Reviews Genetics, 2010; 11:31-46.

Mokry, et al., "Accurate SNP and mutation detection by targeted custom microarray-based genomic enrichment of short-fragment sequencing libraries," Nucleic Acids Research. 2010; 38(10):e116 (9 pages).

Ng, et al., "Targeted capture and massively parallel sequencing of 12 human exomes," Nature Sep. 10, 2009; 461:272-276; 2 additional pages of supplemental information regarding methods.

Owczarzy, et al., "Stability and mismatch discrimination of locked nucleic acid-DNA duplexes," Biochemistry. 2011 50:9352-9367.

PCT International Search Report and Written Opinion for PCT/US2013/049402, dated Oct. 21, 2013, 18 pages.

Petersen, et al., "LNA: a versatile tool for therapeutics and genomics," Trends in Biotechnology. Feb. 1, 2003; 21(2):74-81.

Specht, et al., "Quantitative Gene Expression Analysis in Microdissected Archival Formalin-Fixed and Paraffin-Embedded Tumor Tissue," Am. J. Pathol. Feb. 2001; 158(2):419-429.

Wong, et al., "Use of tagged random hexamer amplification (TRHA) to clone and sequence minute quantities of DNA—application to a 180 kb plasmid isolated from Sphingomonas F199," Nucleic Acids Res. 1996; 24(19) pp. 3778-3783.

Ye, et al., "Pindel: a pattern growth approach to detect break points of large deletions and medium sized insertions from paired-end short reads," Bioinformatics, 2009; 25(21):2865-2871.

Written Opinion from corresponding Singapore application No. 11201408807Y dated Nov. 5, 2015, 14 pages.

Communication pursuant to Article 94(3) EPC dated Jul. 7, 2016 for corresponding EPO application No. 13 737 778.4-1404, 11 pages.

Communication pursuant to Article 94(3) EPC dated Mar. 21, 2017 for corresponding EPO application No. 13 737 778.4-1404, 5 pages.

JP Notice of Rejection and English Translation for JP App. No. 2015-520698, dated Jun. 6, 2017, 19 pages.

International Preliminary Report on Patentability for PCT/US2013/049402, dated Jan. 6, 2015, 12 pages.

\* cited by examiner

$T_m$-ENHANCED BLOCKING OLIGONUCLEOTIDES AND BAITS FOR IMPROVED TARGET ENRICHMENT AND REDUCED OFF-TARGET SELECTION

CROSS-REFERENCE TO RELATED APPLICATIONS

This application claims benefit of priority under 35 U.S.C. 119 from U.S. Provisional Application No. 61/667,919, filed Jul. 3, 2012 and entitled "METHODS AND COMPOSITIONS FOR REDUCING OFF-TARGET SELECTION" and U.S. Provisional Application No. 61/745,435, filed Dec. 21, 2012 and entitled "$T_M$-ENHANCED BLOCKING OLIGONUCLEOTIDES AND BAITS FOR IMPROVED TARGET ENRICHMENT IN MASSIVELY PARALLEL SEQUENCING EXPERIMENTS," the contents of both which are incorporated by reference herein in their entireties.

FIELD OF THE INVENTION

This invention relates to modified oligonucleotide compositions and their use in methods for nucleic acid selection and sequencing. In particular, the invention pertains to $T_m$-enhanced oligonucleotides as blockers and baits, as well as other reagents for improved target enrichment and reduced off-target selection. The oligonucleotide compositions and reagents find robust applications for preparing nucleic acid templates for next generation sequencing applications.

The SEQ ID NOs. disclosed herein are included in the Sequence Listing found at the end of the specification and are included in a computer readable form entitled "IDT01-001-US_CORRECTED_ST25.txt," filed by electronic means via the EFS-Web e-filing system, the contents of which are incorporated by reference in its entirety.

BACKGROUND OF THE INVENTION

Nucleic acid hybridization has a significant role in biotechnology applications pertaining to identification, selection, and sequencing of nucleic acids. Sequencing applications with genomic nucleic acids as the target materials demand one to select nucleic acid targets of interest from a highly complex mixture. The quality of the sequencing efforts depends on the efficiency of the selection process, which, in turn, relies upon how well nucleic acid targets can be enriched relative to non-target sequences.

A variety of methods have been used to enrich for desired sequences from a complex pool of nucleic acids, such as genomic DNA or cDNA. These methods include the polymerase chain reaction (PCR), molecular inversion probes (MIPs), or sequence capture by hybrid formation ("hybrid capture;" See, for example, Mamanova, L., Coffey, A. J., Scott, C. E., Kozarewa, I., Turner, E. H., Kumar, A., Howard, E., Shendure, J. and Turner, D. J. (2010) "Target-enrichment strategies for next-generation sequencing," *Nat. Methods* 7:111-118.). Hybrid capture offers advantages over other methods in that this method requires fewer enzymatic amplification or manipulation procedures of the target nucleic acid as compared to the other methods. The hybrid capture method introduces fewer errors into the final sequencing library as a result. For this reason, the hybrid capture method is a preferred method for enriching for desired sequences from a complex pool of nucleic acids and is ideal for preparing templates in next generation sequencing (NGS) applications.

The NGS applications usually involve randomly breaking long genomic DNA or cDNA into smaller fragment sizes having a size distribution of 200-500 bp in length, depending upon the NGS platform used. The DNA termini are enzymatically treated to facilitate ligation and universal DNA adaptors are ligated to the ends to provide the resultant NGS templates. The terminal adaptor sequences provide a universal site for primer hybridization so that clonal expansion of the desired DNA targets can be achieved and introduced into the automated sequencing processes used in NGS applications. The hybrid capture method is intended to reduce the complexity of the pool of random DNA fragments from, for example, from $3 \times 10^9$ bases (the human genome) to much smaller subsets of $10^4$ to $10^8$ bases that are enriched for specific sequences of interest. The efficiency of this process directly relates to the quality of capture and enrichment achieved for desired DNA sequences from the starting complex pool.

The NGS applications typically use the hybrid capture method of enrichment in the following manner. A prepared pool of NGS templates is heat denatured and mixed with a pool of capture probe oligonucleotides ("baits"). The baits are designed to hybridize to the regions of interest within the target genome and are usually 60-200 bases in length and further are modified to contain a ligand that permits subsequent capture of these probes. One common capture method incorporates a biotin group (or groups) on the baits. After hybridization is complete to form the DNA template:bait hybrids, capture is performed with a component having affinity for only the bait. For example, streptavidin-magnetic beads can be used to bind the biotin moiety of biotinylated-baits that are hybridized to the desired DNA targets from the pool of NGS templates. Washing removes unbound nucleic acids, reducing the complexity of the retained material. The retained material is then eluted from the magnetic beads and introduced into automated sequencing processes.

Though DNA hybridization with the baits can be exquisitely specific, unwanted sequences remain in the enriched pool following completion of the hybrid capture method. The largest fraction of these unwanted sequences is present due to undesired hybridization events between NGS templates having no complementarity to the baits and NGS templates that do. Two types of undesired hybridizations arising in the hybrid capture method include the following sequences: (1) highly repetitive DNA elements that are found in endogenous genomic DNA; and (2) the terminal adaptor sequences that are engineered into each of the NGS templates of the pool.

The repetitive endogenous DNA elements, such as an Alu sequence or LINE sequence, present in one DNA fragment in the complex pool can hybridize to another similar element present in another unrelated DNA fragment. These fragments, which may originally derive from very different locations within the genome, become linked during the hybridization process of the hybrid capture method. If one of these DNA fragments represents a desired fragment that contains a binding site for a bait, the unwanted fragment will be captured along with the desired fragment. This class of unwanted NGS templates can be reduced by adding an excess of the repeat elements to the hybridization reaction. Most commonly, human $C_o$t-1 DNA is added to the hybridization reaction, which binds Alu, LINE, and other repeat sites in the target and blocks the ability of NGS templates to interact with each other on that basis.

A more problematic class of unwanted NGS templates that are recovered during hybrid capture arises from interactions between terminal adaptor sequences that are engineered on each of the NGS templates of the pool. Because the pool of NGS templates typically will contain the identical terminal adaptor sequences on every DNA fragment, the adaptor sequences are present at a very high effective concentration(s) in the hybridization solution. Consequently, unrelated NGS templates can anneal to each other through their termini, thereby resulting in a "daisy chain" of otherwise unrelated DNA fragments being linked together. So if one of these linked fragments contains a binding site for a bait, the entire daisy chain is captured. In this way, capture of a single desired fragment can bring along a large number of undesired fragments, which reduces the overall efficiency of enrichment for the desired fragment. This class of unwanted capture event can be reduced by adding an excess of single-stranded adaptor sequences to the hybridization reaction. Yet the ability to effectively reduce the so-called daisy chain capture events with an excess of adaptor sequences is limited to an efficiency of about 50%-60% for capturing the desired fragment.

In spite of the use of $C_o t$-1 DNA and adaptor blocking oligonucleotides in the hybridization reaction, a significant amount of contaminating unwanted DNA fragments remain in the sequencing pool after the hybrid capture step, largely because the blocking methods are not completely successful. Thus, there is a need to improve capture efficiency and to reduce contamination from undesired sequences so that one can devote resources to sequencing a greater fraction of targets of interest and fewer targets that are not of interest.

Thus, off-target nucleic acid interactions can limit the efficiency of the selection of target nucleic acids by hybridization (for example, solution hybridization) to a capture probe, for example, an oligonucleotide bait. Off-target selection can result, for example, in one or more of decreased yields of hybridization capture and/or artifactual hybrid capture, which in turn lead to inefficiencies in subsequent steps, for example, sequencing.

Off-target selection is typically increased when the stringency conditions of hybrid selection are reduced, for example, when selecting for a target:capture duplex having a lower nucleic acid melting temperature (for example, DNA:DNA duplexes as compared to RNA:DNA duplexes). Thus, capture of off-target sequence can be more of a problem in DNA:DNA hybridizations.

Typically, library members include a library insert, often a segment of sequence from a gene of interest, for example, a segment for sequencing. If a member is on-target, the library insert forms a duplex with the capture probe. Typically, library members also include and one or more non-target sequences. These are typically not portions of a gene of interest but rather are adaptor sequences, amplification primers or tags, or bar code tags. The non-target sequence of the capture probe-hybridized library member, can, by duplex formation with other sequences in the reaction mixture, lead to the selection of undesired sequences, for example, off-target library members. While not wishing to be bound by theory, concatenation between an on-target library member and off-target sequences can result in selection of off-target sequences.

Methods and compositions for minimizing selection of off-target nucleic acid, for example, minimizing the selection of library members that do not from a duplex with the capture probe are disclosed herein. Methods and compositions are disclosed herein that reduce non-target sequence, for example, adaptor-mediated selection.

BRIEF SUMMARY OF THE INVENTION

In one aspect, the invention relates to an oligonucleotide for use in a selection method of a desired template nucleic acid, comprising an oligonucleotide having at least one $T_m$-enhancing group. In first respect, the oligonucleotide is useful in selection methods such as the hybrid capture method. In second respect, the oligonucleotide includes as desired template nucleic acid at least one member selected from a population of templates. In a third respect, the oligonucleotide is substantially complementary to at least one sequence of the desired template. In a fourth respect, the oligonucleotide includes at least one member selected from a blocker or a bait. In a fifth respect, the oligonucleotide includes as the at least one $T_m$-enhancing group at least one member selected from the group consisting of a locked nucleic acid group, a bicyclic nucleic acid group, a C5-modified pyrimidine, a peptide nucleic acid group and combinations thereof. In the sixth respect, the oligonucleotide includes as the at least one $T_m$-enhancing group one of a locked nucleic acid group, a bicyclic nucleic acid group or a combination thereof. In a seventh respect, the oligonucleotide includes as the at least one $T_m$-enhancing group a locked nucleic acid group or a bicyclic nucleic acid group. As a preferred embodiment of the seventh respect, the oligonucleotide has as the locked nucleic acid group or the bicyclic nucleic acid group a nucleobase selected from the group consisting of cytosine, adenine and thymine, including mixtures of cytosine and adenine and mixtures of cytosine and thymine. In a ninth respect, the oligonucleotide includes as the at least one $T_m$-enhancing group one that provides an optimal enhanced $T_m$ value in the range comprising from about 1.4° C. to about 25° C. In a tenth respect, the oligonucleotide includes at least one member selected from the group consisting of SEQ ID NOS: 2, 3, 4, 5, 6, 7, 8, 10, 11, 12, 13, 14, 15, 16, 18, 19, 21, 22, 24, 25, 27, 28, 30, 32, 34 and 36. In an eleventh respect, oligonucleotide includes a blocker. In a preferred embodiment of these respects, the blocker has substantial sequence complementarity to at least one sequence at a terminus of the desired template nucleic acid. In a further elaboration of this preferred embodiment, the blocker includes a barcode domain having a plurality of nucleotides. In a further embodiment of this respect, the plurality of nucleotides includes from about 5 to about 12 nucleotides arranged substantially contiguous. In another embodiment, the barcode domain comprises nucleotides having as nucleobases at least one member selected from the group selected from adenine, thymine, cytosine, guanine, inosine, 3-nitropyrrole, 5-nitroindole, and combinations thereof. In a twelfth respect, the oligonucleotide provides an improvement in the selection method of a desired template nucleic acid. In a preferred embodiment of this respect, the improvement consists of an improved enrichment of the desire template nucleic acid relative to undesired template nucleic acids. In yet another embodiment, the improved enrichment comprises of an enrichment of at least 65%. In the thirteenth respect, the oligonucleotide further includes a 3'-terminal modification. In this respect, preferred embodiments of the 3'-terminal modification prevents polymerase directed synthesis from the oligonucleotide. In another respect, the 3'-terminal modification includes a 2',3'-dideoxynucleotide, a 3'-spacer C3 group, among others.

In a second aspect, the invention relates to a method of selecting a desired template nucleic acid from a population of template nucleic acids. The method includes two steps. The first step is contacting the population of template nucleic acids with a first oligonucleotide comprising a $T_m$-enhanced oligonucleotide to form a mixture. The second step includes isolating the desired template nucleic acid from the mixture. In a first respect, the method provides as part of the contacting step the sub-step of incubating the mixture at a temperature of about optimal enhanced $T_m$ value of the $T_m$-enhanced oligonucleotide. In a first preferred embodiment of this respect, the $T_m$-enhanced oligonucleotide includes a plurality of $T_m$-enhancing groups. In this regard, the plurality of $T_m$-enhancing groups comprises from about 2 to about 25 $T_m$-enhancing groups. Further embodiments provide that the plurality of $T_m$-enhancing groups comprises locked nucleic acid groups or a bicyclic nucleic acid groups. Preferred aspects of these embodiments include features of the locked nucleic acid groups or the bicyclic nucleic acid groups having nucleobases selected from the group consisting of cytosine, adenine and thymine. In a second respect, the method includes as the $T_m$-enhanced oligonucleotide at least one member selected from the group consisting of SEQ ID NOS: 2, 3, 4, 5, 6, 7, 8, 10, 11, 12, 13, 14, 15, 16, 18, 19, 21, 22, 24, 25, 27, 28, 30, 32, 34 and 36. In a third respect, method provides the $T_m$-enhanced oligonucleotide that includes a blocker. In a first preferred embodiment of this respect, the blocker has substantial sequence complementarity to at least one sequence at a terminus of each member of the population of template nucleic acids. In yet another preferred embodiment, the blocker further includes a barcode domain having a plurality of nucleotides. In some embodiments, the plurality of nucleotides includes from about 5 to about 12 nucleotides arranged substantially contiguous. In other embodiments, the barcode domain includes nucleotides having as nucleobases at least one member selected from the group selected from adenine, thymine, cytosine, guanine, inosine, 3-nitropyrrole, 5-nitroindole, and combinations thereof. In a third respect, the method has as the contacting step the objective of resulting in substantial inhibition of complex formation between the desired template nucleic acid and undesired template nucleic acids. In a fourth respect, the method includes as the step of isolating the desired template nucleic acid two additional steps. The first step is forming a hybrid complex between the desired nucleic acid and a second oligonucleotide. The second step is separating the hybrid complex from the mixture. With regard to this fourth respect, the second oligonucleotide includes a bait. In certain embodiments, the bait comprises a sequence having substantial sequence complementarity to a sequence within the desired template nucleic acid. In other embodiments, the bait comprises a plurality of $T_m$-enhancing groups. In yet other embodiments, the bait includes a covalent modification to enable selection of the hybrid complex. As part of these latter embodiments, the covalent modification is a biotinylated group. Yet other embodiments provide for the hybrid complex being contacted with a solid support immobilized with avidin or streptavidin.

In a third aspect, the invention relates to a method of performing massively parallel sequencing. The method includes four steps. The first step is preparing a library population of template nucleic acids. The second step is contacting the library population of template nucleic acids with at least one $T_m$-enhanced oligonucleotide as a blocker, a plurality of oligonucleotides as baits and $C_o$t-1 DNA to form a mixture. The third step is isolating a plurality of desired template nucleic acids from the mixture. The fourth step is sequencing the plurality of desired template nucleic acids. The at least one member of the plurality of oligonucleotides as baits has substantial complementarity to a sequence within at least one member of the plurality of desired template nucleic acids. In a first respect, the method includes members of the library population of template nucleic acids each includes at least one identical terminal adaptor sequence having a size range from about 15 nucleotides to about 75 nucleotides. In a second respect, the method includes a blocker having substantial sequence complementarity to the at least one identical terminal adaptor sequence of the library population of template nucleic acids. In a third respect, the method includes as the at least one identical terminal adaptor sequence a barcode domain. In a fourth respect, the method provides a blocker having substantial sequence complementarity to the at least one identical terminal adaptor sequence. In a fifth respect, method includes as the contacting step the step of incubating the mixture at a temperature of about optimal enhanced $T_m$ value of the at least one $T_m$-enhanced oligonucleotide. In a sixth respect, the method provides that the at least one $T_m$-enhanced oligonucleotide as a blocker includes at least one member selected from the group consisting of SEQ ID NOS: 2, 3, 4, 5, 6, 7, 8, 10, 11, 12, 13, 14, 15, 16, 18, 19, 21, 22, 24, 25, 27, 28, 30, 32, 34 and 36. In a seventh respect, method provides that the step of isolating a plurality of desired template nucleic acids from the mixture includes two steps. The first step is forming a plurality of hybrid complexes between the plurality of desired template nucleic acids and plurality of oligonucleotides as baits. The second step is separating the plurality of hybrid complexes from the mixture. In an eighth respect, the method provides as the plurality of oligonucleotides as baits includes a plurality of $T_m$-enhancing groups. In an embodiment of this respect, each bait includes a covalent modification to enable selection of the hybrid complex that includes the bait. In a further embodiment of this respect, the covalent modification is a biotinylated group. As another embodiment of this respect, the plurality of hybrid complexes is contacted with a solid support immobilized with avidin or streptavidin.

In another aspect, the invention features, a method of selecting nucleic acids or of reducing off-target nucleic acid selection in hybridization reactions. The hybridization reaction can be a solid phase or solution phase hybridization. The method can be used in the selection of library members for subsequent processing, for example, for sequencing.

The method comprises:

(a) optionally, acquiring a library comprising a plurality of target members, for example, target nucleic acid (for example, DNA or RNA) members, wherein one or more of the target members comprise an insert sequence (for example, a segment of a gene of interest) and a non-target nucleic acid sequence (for example, an adaptor sequence); and (b) contacting the library with a capture probe, for example, a bait set or a plurality of bait sets, and a blocking oligonucleotide, wherein, (i) a blocking oligonucleotide is complementary to, or can form a duplex with, the non-target nucleic acid sequence of the library member (for example, an adaptor sequence), and (ii) the value for a parameter related to the binding interaction between the blocking oligonucleotide and a non-target nucleic acid sequence of the library member is higher than the value for the non-target nucleic acid sequence to a background nucleic acid, for example, other complementary non-target nucleic acid sequences, thereby minimizing off-target selection.

In an embodiment the method further comprising providing selected library members (sometimes referred to herein as "library catch").

In an embodiment, the method further comprises separating the selected library members from the capture probe.

In an embodiment, the method further comprises sequencing the insert of a selected library member, for example, sequencing the inserts from least 2, 5, 10, 15, 20, 30, or 50, genes or nucleic acid alterations, for example, genes or nucleic acid alterations described herein.

In an embodiment, the value for a parameter related to binding interaction can be a value for affinity, association rate, the inverse of dissociation rate, or nucleic acid melting temperature (for example, $T_m$, the temperature at which half of the DNA strands are in the double-helical state and half are in the random coil state).

In an embodiment, the method comprises the use of a first blocking oligonucleotide which forms a duplex with a first non-target nucleic acid sequence, for example, a first adaptor sequence, and, optionally, a second blocking oligonucleotide which forms a duplex with a second non-target nucleic acid sequence, for example, a second adaptor sequence. A set of oligonucleotide blockers comprises a plurality of different oligonucleotide blockers.

In an embodiment the blocking oligonucleotide inhibits the formation of a duplex between a sequence in the reaction and the non-target sequence of a library member that is duplexed to the capture probe (for example, the blocking oligonucleotide inhibits formation of concatenated chains of library members).

In an embodiment, a library member comprises an insert, for example, a subgenomic interval, and a non-target sequence, for example, a sequence common to a plurality of library members. In an embodiment, the inserts are subgenomic sequences, for example, from nucleic acid from a tumor sample, and the non-target sequence is non-genomically occurring sequence or a sequence not present in the subgenomic sequences, for example, an amplification tag or bar coding tag.

In an embodiment, the library members, or selected library members, include subgenomic intervals from at least 2, 5, 10, 15, 20, 30, or 50, genes or nucleic acid alterations, for example, genes or nucleic acid alterations described herein.

In an embodiment, a plurality of library members, or selected library members, for example, at X (wherein X is equal to 2, 5, 10, 20, 50, 100, or 200) library members, or selected library members, have a first non-target sequence at the 5' end of the insert and a second non-target sequence at the 3' end of the insert.

In an embodiment the non-target sequence includes a non-target sequence that is present in a plurality of non-target sequences, for example, a sequence for amplification, and a non-target sequence that is unique, for example, a barcode. Typically some, most substantially all or all of the members of the library will include a common non-target sequence. In embodiments the library, or the selected library members, comprises at least X members, (wherein X is equal to 1, 2, 5, 10, 20, 50, 100, or 200) having a common non-target sequence.

In one embodiment, the blocking oligonucleotide forms a duplex with a non-target nucleic acid sequence of at least X library members (wherein X is equal to 1, 2, 5, 10, 20, 50, 100, or 200), which duplex has a $T_m$ that is higher than the $T_m$ of a duplex formed by a non-target nucleic acid sequence to a background nucleic acid, for example, the complement of the non-target sequence. In one embodiment, the higher nucleic acid melting temperature of the blocking oligonucleotide duplex is from about 5° C. to 25° C., or greater (for example, 5° C., 10° C., 15° C., 20° C., 25° C., or greater). In one embodiment, the $T_m$ for the duplex between the blocking oligonucleotide and the non-target nucleic acid sequence of the library member is higher than is the $T_m$ for a duplex of the non-target nucleic acid sequence and its exact complement.

In other embodiments, the blocking oligonucleotide has an association rate to a non-target nucleic acid sequence of at least X library members (wherein X is equal to 1, 2, 5, 10, 20, 50, 100, or 200), that is higher than the association rate of the non-target nucleic acid sequence to a background nucleic acid, for example, the complement of the non-target sequence. In one embodiment, the higher association rate is about 2- to greater than 10-fold that of the non-target nucleic acid sequence to the background nucleic acid (for example, 2-, 4-, 6-, 8-, 10-fold, or greater).

In yet other embodiments, the blocking oligonucleotide has a dissociation rate to the non-target nucleic acid sequence of at least X library members (wherein X is equal to 1, 2, 5, 10, 20, 50, 100, or 200) that is lower than the dissociation rate of the non-target nucleic acid sequence to a background nucleic acid, for example, the complement of the non-target sequence. In one embodiment, the lower dissociation rate is about 2- to greater than 10-fold that of the non-target nucleic acid sequence to the background nucleic acid (for example, 2-, 4-, 6-, 8-, 10-fold, or greater).

In one embodiment, the length of the blocking oligonucleotide results in an increase in the binding interaction of the blocking oligonucleotide for the non-target nucleic acid sequence of the library member (for example, the adaptor sequence), relative to the background nucleic acid.

In an embodiment, the duplex formed between the blocking oligonucleotide and non-target nucleic acid sequence of at least X library members (wherein X is equal to 1, 2, 5, 10, 20, 50, 100, or 200), is longer than the duplex formed between the non-target sequence and its complement, for example, between the Watson and Crick strands of a double-stranded adaptor. In embodiments, the duplex between a blocking oligonucleotide and non-target nucleic acid sequence is at least 1, 2, 3, 4, 5, 6, 7, 8, 9, 10, 15, or 20 nucleotides longer than the duplex formed between the non-target sequence and its complement, for example, between the Watson and Crick strands of a double-stranded adaptor.

In an embodiment, the blocking oligo comprises one or more non-naturally-occurring nucleotides. In embodiments a duplex formed between the blocking oligonucleotide having non-naturally-occurring nucleotides and the non-target nucleic acid sequence of at least X library members (wherein X is equal to 1, 2, 5, 10, 20, 50, 100, or 200), has the value for a parameter related to the binding interaction (for example, affinity, association rate, inverse of dissociation rate, or $T_m$) that is higher than the value for the non-target nucleic acid sequence to a background nucleic acid, for example, other complementary non-target nucleic acid sequences. Exemplary non-naturally occurring oligonucleotides include modified DNA or RNA nucleotides. Exemplary modified nucleotides (for example, modified RNA or DNA nucleotides) include, but are not limited to, a locked nucleic acid (LNA), wherein the ribose moiety of an LNA nucleotide is modified with an extra bridge connecting the 2' oxygen and 4' carbon; peptide nucleic acid (PNA), for example, a PNA composed of repeating N-(2-aminoethyl)-glycine units linked by peptide bonds; a DNA or RNA oligonucleotide modified to capture low GC regions; a bicyclic nucleic acid (BNA); a crosslinked oligonucleotide; a modified 5-methyl deoxycytidine; and 2,6-diaminopurine. Other modified DNA and RNA nucleotides are known in the art.

In an embodiment, the blocking oligonucleotide is or comprises RNA and the non-target nucleic acid sequence, for example, an adaptor, is or comprises DNA. In an embodiment, the non-target nucleic acid sequence is a sequence common to a plurality of library members, for example, at least X library members (wherein X is equal to 2, 5, 10, 20, 50, 100, or 200), for example, a sequence that can be used for amplification, for example, PCR, bridge PCR, amplification.

In an embodiment the non-target nucleic acid sequence is a sequence that can be used for amplification, for example, PCR, bridge PCR, amplification, and the background nucleic acid is a second non-target sequence In an embodiment, the capture probe is DNA (for example, as opposed to RNA). In embodiments, the capture probe includes one or more DNA oligonucleotides (for example, a naturally or non-naturally occurring DNA oligonucleotide.

In an embodiment, the capture probe is RNA. In embodiments, the capture probe includes one or more RNA oligonucleotides (for example, a naturally or non-naturally occurring RNA oligonucleotide.

In embodiment a blocking oligonucleotide is 20-80, 30-80, 40-80, 50-80, 70-80, 30-75, 30-65, 30-55, 30-45, 40-70, 40-60, 40-50, 50-60, 50-70, 60-70, nucleotides in length. In an embodiment, the library insert is 50-200, 77-150, or 100-150 nucleotides in lengths as described elsewhere herein.

In another aspect, the invention features, a preparation, comprising a plurality of blocking oligonucleotides, for example, as described herein. In an embodiment the preparation further comprises one or both of: a plurality of library members, for example, as described herein; and a capture probe, for example, as described herein.

In another aspect, the invention features, a kit, comprising a plurality of blocking oligonucleotides, for example, as described herein. In an embodiment the kit further comprises one or both of: a plurality of library members, for example, as described herein; and a capture probe, for example, as described herein. In embodiments the components are provided in separate containers, for example, the blocking oligonucleotide is provided in a container and another component, for example, a buffer, or a plurality of library members, for example, as described herein or a capture probe, for example, as described herein, is provided in a different container(s).

In another aspect, the invention features, a method of reducing off-target nucleic acid selection described herein combined with another method described herein, for example, a sequencing method described herein, an alignment method described herein, a mutation calling method described herein, or a method that uses a bait described herein.

Off-target selection can also be minimized by the use of non-target sequences that are sufficiently short that a duplex of non-target sequences is less stable than is a duplex of the insert sequence of a library member and the capture probe. Thus, in another aspect, the invention features a method of reducing off-target nucleic acid selection, for example, in solid phase or solution hybridization. The method can be used in the selection of library members for subsequent sequencing.

The method comprises:

(a) optionally, acquiring a library comprising a plurality of target members, for example, target nucleic acid (for example, DNA or RNA) members, wherein one or more of the target members comprise an insert sequence (for example, a segment of a gene of interest) and a non-target nucleic acid sequence (for example, an adaptor sequence); and (b) contacting the library with a capture probe, for example, a bait set or a plurality of bait sets;

wherein, the non-target sequences are sufficiently short such that the value for a parameter related to the binding interaction between the insert sequence and the capture probe is higher for than that value for the non-target nucleic acid sequence and its complement, thereby minimizing off-target selection.

In an embodiment the method further comprising providing selected library members (sometimes referred to herein as "library catch").

In an embodiment, the method further comprises separating the selected library members from the capture probe.

In an embodiment, the method further comprises sequencing the insert of a selected library member, for example, sequencing the inserts from least 2, 5, 10, 15, 20, 30, or 50, genes or nucleic acid alterations, for example, genes or nucleic acid alterations described herein.

In an embodiment, the value for a parameter related to binding interaction can be a value for affinity, association rate, the inverse of dissociation rate, or nucleic acid melting temperature (for example, $T_m$, the temperature at which half of the DNA strands are in the double-helical state and half are in the random coil state).

In an embodiment, a library member comprises an insert, for example, a subgenomic interval, and a non-target sequence, for example, a sequence common to a plurality of library members. In an embodiment, the inserts are subgenomic sequences, for example, from nucleic acid from a tumor sample, and the non-target sequence is non-naturally occurring sequence or a sequence not present in the subgenomic sequences, for example, a amplification tag or bar coding tag.

In an embodiment, the library members, or selected library members, include subgenomic intervals from at least 2, 5, 10, 15, 20, 30, or 50, genes or nucleic acid alterations, for example, genes or nucleic acid alterations described herein.

In an embodiment, a plurality of library members, or selected library members, for example, at X (wherein X is equal to 2, 5, 10, 20, 50, 100, or 200) library members, or selected library members, have a first non-target sequence at the 5' end of the insert and a second non-target sequence at the 3' end of the insert.

In an embodiment the non-target sequence includes a non-target sequence that is present in a plurality of non-target sequences, for example, a sequence for amplification, and a non-target sequence that is unique, for example, a barcode. Typically some, most substantially all or all of the members of the library will include a common non-target sequence. In embodiments the library, or the selected library members, comprises at least X members, (wherein X is equal to 1, 2, 5, 10, 20, 50, 100, or 200) having a common non-target sequence.

In one embodiment, the insert sequence forms a duplex with the capture probe for at least X library members (wherein X is equal to 1, 2, 5, 10, 20, 50, 100, or 200), which duplex has a $T_m$ that is higher than the $T_m$ of a duplex formed by a non-target nucleic acid sequence to a background nucleic acid, for example, the complement of the non-target sequence. In one embodiment, the higher nucleic acid melting temperature of the insert sequence/capture probe duplex is from about 5° C. to 25° C., or greater (for example, 5° C., 10° C., 15° C., 20° C., 25° C., or greater). In one embodiment, the $T_m$ for the duplex between the insert sequence/capture probe is higher than is the $T_m$ for a duplex of the non-target nucleic acid sequence and its exact complement.

In other embodiments, the insert sequence has an association rate to the probe for at least X library members (wherein X is equal to 1, 2, 5, 10, 20, 50, 100, or 200), that is higher than the association rate of the non-target nucleic acid sequence to a background nucleic acid, for example, the complement of the non-target sequence. In one embodiment, the higher association rate is about 2- to greater than 10-fold that of the non-target nucleic acid sequence to the background nucleic acid (for example, 2-, 4-, 6-, 8-, 10-fold, or greater).

In yet other embodiments, the insert sequence has a dissociation rate to for the capture probe for at least X library members (wherein X is equal to 1, 2, 5, 10, 20, 50, 100, or 200) that is lower than the dissociation rate of the non-target nucleic acid sequence to a background nucleic acid, for example, the complement of the non-target sequence. In one embodiment, the lower dissociation rate is about 2- to greater than 10-fold that of the non-target nucleic acid sequence to the background nucleic acid (for example, 2-, 4-, 6-, 8-, 10-fold, or greater).

In an embodiment the non-target nucleic acid sequence is a sequence that can be used for amplification, for example, PCR, bridge PCR, amplification, and the background nucleic acid is a second non-target sequence In an embodiment, the capture probe is DNA (for example, as opposed to RNA). In an embodiment, the capture probe is RNA.

In an embodiment, the library insert is 50-200, 77-150, or 100-150 nucleotides in lengths as described elsewhere herein.

In an embodiment the method further comprises the use of a blocking oligonucleotide, as described herein.

Additional features and embodiments of the invention are described herein.

In one embodiment, the method further comprises:

(c) acquiring a read for a subgenomic interval from a tumor member from said library or library catch, for example, by sequencing, for example, with a next generation sequencing method;

(d) aligning said read; and (e) assigning a nucleotide value (for example, calling a mutation, for example, with a Bayesian method) from said read for a preselected nucleotide position, for example, for a preselected nucleotide position in each of a plurality of subgenomic intervals, for example, each of a plurality genes, thereby analyzing said sample.

In an embodiment:

(i) each of X nucleotide positions is analyzed under a unique set of conditions for one or a combination of steps (b), (c), (d), or (e) (wherein unique means different from the other X-1 sets of conditions and wherein X is at least 2, 5, 10, 20, 30, 40, 50, 100, 200, 300 or 500). For example, a first set of conditions, for example, a set of conditions described herein, is used for a first nucleotide position, for example, in a first subgenomic interval or gene, and a second set of conditions, for example, a second set of conditions described herein, is used for a second nucleotide position, for example, in a second subgenomic interval or gene;

(ii) for each of X nucleotide positions, responsive to a characteristic, for example, a characteristic described herein, of a preselected alteration, for example, mutation, that can occur at the nucleotide position, the nucleotide position is analyzed under a unique set of conditions (wherein unique means different from the other X-1 sets of conditions and wherein X is at least 2, 5, 10, 20, 30, 40, 50, 100, 200, 300 or 500). For example, responsive to a characteristic, for example, a characteristic described herein, of a preselected alteration, for example, mutation, that can occur at a nucleotide position in a first subgenomic interval, the nucleotide position is analyzed under a first set of conditions, and responsive to a characteristic, for example, a characteristic described herein, of a preselected alteration, for example, mutation, that can occur at a nucleotide position in a second subgenomic interval, the nucleotide position is analyzed under second set of conditions;

(iii) wherein said method is performed on a sample, for example, a preserved tumor sample, under conditions that allow for 95, 98, or 99% sensitivity or specificity for nucleotide positions in at least 2, 5, 10, 20, 50 or 100 subgenomic intervals, for example, genes; or (iv) wherein the method comprises one or more or all of:

a) sequencing a first subgenomic interval to provide for about 500× or higher sequencing depth, for example, to sequence a mutation present in no more than 5% of the cells from the sample;

b) sequencing a second subgenomic interval to provide for about 200× or higher, for example, about 200×-about 500×, sequencing depth, for example, to sequence a mutation present in no more than 10% of the cells from the sample;

c) sequencing a third subgenomic interval to provide for about 10-100× sequencing depth, for example, to sequence one or more subgenomic intervals (for example, exons) that are chosen from: a) a pharmacogenomic (PGx) single nucleotide polymorphism (SNP) that may explain the ability of patient to metabolize different drugs, or b) a genomic SNPs that may be used to uniquely identify (for example, fingerprint) a patient;

d) sequencing a fourth subgenomic interval to provide for about 5-50× sequencing depth, for example, to detect a structural breakpoint, such as a genomic translocation or an indel. For example, detection of an intronic breakpoint requires 5-50× sequence-pair spanning depth to ensure high detection reliability. Such bait sets can be used to detect, for example, translocation/indel-prone cancer genes; or e) sequencing a fifth subgenomic interval to provide for about 0.1-300× sequencing depth, for example, to detect copy number changes. In one embodiment, the sequencing depth ranges from about 0.1-10× sequencing depth to detect copy number changes. In other embodiments, the sequencing depth ranges from about 100-300× to detect a genomic SNPs/loci that is used to assess copy number gains/losses of genomic DNA or loss-of-heterozygosity (LOH).

Exemplary first and second sets of conditions include those wherein:

a first bait set is used for the first subgenomic interval and a second bait set is used for the second subgenomic interval;

a first alignment method is applied to a read for the first subgenomic interval and a second alignment method is applied to a read for second subgenomic interval;

a first mutation calling method is applied to a nucleotide position of the first subgenomic interval and a second mutation calling method is applied to a nucleotide position of the second subgenomic interval.

In an embodiment:

a first nucleotide position is analyzed with a first set of bait conditions, a first alignment method, and a first mutation calling method;

a second nucleotide position is analyzed with said first set of bait conditions, a second alignment method, and said first mutation calling method;

a third nucleotide position is analyzed with said first set of bait conditions, said first alignment method, and a second mutation calling method, to provide three nucleotide positions each analyzed under unique, as compared to the other two, conditions.

In an embodiment, the conditions comprise those wherein:

a first bait set is used for the first subgenomic interval and a second bait set is used for the second subgenomic interval;

a first alignment method is applied to a read for the first subgenomic interval and a second alignment method is applied to a read for second subgenomic interval; or a first mutation calling method is applied to a nucleotide position of the first subgenomic interval and a second mutation calling method is applied to a nucleotide position of the second subgenomic interval.

Exemplary characteristics include:

(i) the gene, or type of gene, in which the alteration is located, for example, an oncogene or tumor suppressor, a gene or type of gene characterized by a preselected or variant or type of variant, for example, a mutation, or by a mutation of a preselected frequency, or other gene or type of gene described herein;

(ii) the type of alteration, for example, a substitution, insertion, deletion, or translocation;

(iii) the type of sample, for example, an FFPE sample, being analyzed for the alteration;

(iv) sequence in or near said the nucleotide position of the alteration being evaluated, for example, sequence which can affect the expected propensity for misalignment for the subgenomic interval, for example, the presence of repeated sequences in or near the nucleotide position;

(v) a prior (for example, literature) expectation of observing a read showing the alteration, for example, mutation, for example, in a tumor of preselected type;

(vi) the probability of observing a read showing the alteration due to base-calling error alone); or (vii) a preselected depth of sequencing desired for detecting the alteration.

In an embodiment, the characteristic is other than the identity of the nucleotide being sequenced, that is, the characteristic is not whether the sequence is a or t.

In an embodiment, subgenomic intervals from at least X genes, for example, at least X genes from Tables 1 and 1A, for example, genes having the priority 1 annotation in Table 1 and 1A, are analyzed under different conditions, and X is equal to 2, 3, 4, 5, 10, 15, 20, or 30.

In an embodiment, the method comprises one or more of the following:

(i) the method, for example, (b) of the method above, comprises the use of a bait set described herein;

(ii) the method, for example, (c) of the method above, comprises acquiring reads for a set or group of subgenomic intervals or from a set or group of genes described herein;

(iii) the method, for example, (d) of the method above, comprises the use of a plurality of alignment methods described herein;

(iv) the method, for example, (e) of the method above, comprises the use of a plurality of methods for assigning a nucleotide value to a preselected nucleotide position, described herein;" or (v) the method comprises assigning a nucleotide value to a set of subgenomic intervals described herein.

In an embodiment, the method includes: (i) and one, two, three, or all of (ii)-(v). In an embodiment, the method includes: (ii) and one, two, three, or all of (i) and (iii)-(v). In an embodiment, the method includes: (iii) and one, two, three, or all of (i), (ii), (iv) and (v). In an embodiment, the method includes: (iv) and one, two, three, or all of (i)-(iii) and (v). In an embodiment, the method includes: (v) and one, two, three, or all of (i)-(iv).

Baits

Methods described herein provide for selection and/or sequencing of a large number of genes and gene products from samples, for example, tumor samples, from one or more subjects by the appropriate selection of baits, for example, baits for use in solution hybridization, for the selection of target nucleic acids to be sequenced. The efficiency of selection for various subgenomic intervals, or classes thereof, are matched according to bait sets having preselected efficiency of selection. As used in this section, "efficiency of selection" refers to the level or depth of sequence coverage as it is adjusted according to a target subgenomic interval(s).

Thus, a method (for example, element (b) of the method recited above) comprises contacting the library with a plurality of baits to provide selected members (for example, a library catch). In certain embodiments, the method comprises contacting the library with a plurality, for example, at least two, three, four, or five, of baits or bait sets, wherein each bait or bait set of said plurality has a unique (as opposed to the other bait sets in the plurality), preselected efficiency for selection. For example, each unique bait or bait set provides for a unique depth of sequencing. The term "bait set", as used herein, collectively refers to one bait or a plurality of bait molecules.

In an embodiment, the efficiency of selection of a first bait set in the plurality differs from the efficiency of a second bait set in the plurality by at least 2 fold. In an embodiment, the first and second bait sets provide for a depth of sequencing that differs by at least 2 fold.

In another embodiment, the method comprises contacting one, or a plurality of the following bait sets with the library:

a) a bait set that selects sufficient members comprising a subgenomic interval to provide for about 500× or higher sequencing depth, for example, to sequence a mutation present in no more than 5% of the cells from the sample;

b) a bait set that selects sufficient members comprising a subgenomic interval to provide for about 200× or higher, for example, about 200×-about 500×, sequencing depth, for example, to sequence a mutation present in no more than 10% of the cells from the sample;

c) a bait set that selects sufficient members comprising a subgenomic interval to provide for about 10-100× sequencing depth, for example, to sequence one or more subgenomic intervals (for example, exons) that are chosen from: a) a pharmacogenomic (PGx) single nucleotide polymorphism (SNP) that may explain the ability of patient to metabolize different drugs, or b) a genomic SNPs that may be used to uniquely identify (for example, fingerprint) a patient;

d) a bait set that selects sufficient members comprising a subgenomic interval to provide for about 5-50× sequencing depth, for example, to detect a structural breakpoint, such as a genomic translocation or an indel. For example, detection of an intronic breakpoint requires 5-50× sequence-pair spanning depth to ensure high detection reliability. Such bait sets can be used to detect, for example, translocation/indel-prone cancer genes; or e) a bait set that selects sufficient members comprising a subgenomic interval to provide for about 0.1-300× sequencing depth, for example, to detect copy number changes.

In one embodiment, the sequencing depth ranges from about 0.1-10× sequencing depth to detect copy number changes. In other embodiments, the sequencing depth ranges from about 100-300× to detect a genomic SNPs/loci that is used to assess copy number gains/losses of genomic DNA or loss-of-heterozygosity (LOH). Such bait sets can be used to detect, for example, amplification/deletion-prone cancer genes. The level of sequencing depth as used herein (for example, X-fold level of sequencing depth) refers to the level of coverage of reads (for example, unique reads), after detection and removal of duplicate reads, for example, PCR duplicate reads.

In one embodiment, the bait set selects a subgenomic interval containing one or more rearrangements, for example, an intron containing a genomic rearrangement. In such embodiments, the bait set is designed such that repetitive sequences are masked to increase the selection efficiency. In those embodiments where the rearrangement has a known juncture sequence, complementary bait sets can be designed to the juncture sequence to increase the selection efficiency.

In embodiments, the method comprises the use of baits designed to capture two or more different target categories, each category having a different bait design strategies. In embodiments, the hybrid capture methods and compositions disclosed herein capture a defined subset of target sequences (for example, target members) and provide homogenous coverage of the target sequence, while minimizing coverage outside of that subset. In one embodiment, the target sequences include the entire exome out of genomic DNA, or a selected subset thereof. The methods and compositions disclosed herein provide different bait sets for achieving different depths and patterns of coverage for complex target nucleic acid sequences (for example, nucleic acid libraries).

In an embodiment, the method comprises providing selected members of a nucleic acid library (for example, a library catch). The method includes:

providing a library (for example, a nucleic acid library) comprising a plurality of members, for example, target nucleic acid members (for example, including a plurality of tumor members, reference members, and/or PGx members);

contacting the library, for example, in a solution-based reaction, with a plurality of baits (for example, oligonucleotide baits) to form a hybridization mixture comprising a plurality of bait/member hybrids;

separating the plurality of bait/member hybrids from said hybridization mixture, for example, by contacting said hybridization mixture with a binding entity that allows for separation of said plurality of bait/member hybrid, thereby providing a library-catch (for example, a selected or enriched subgroup of nucleic acid molecules from the library), wherein the plurality of baits includes two or more of the following:

a) a first bait set that selects a high-level target (for example, one or more tumor members that include a subgenomic interval, such as a gene, an exon, or a base) for which the deepest coverage is required to enable a high level of sensitivity for an alteration (for example, one or more mutations) that appears at a low frequency, for example, about 5% or less (that is, 5% of the cells from the sample harbor the alteration in their genome). In one embodiment; the first bait set selects (for example, is complementary to) a tumor member that includes an alteration (for example, a point mutation) that requires about 500× or higher sequencing depth;

b) a second bait set that selects a mid-level target (for example, one or more tumor members that include a subgenomic interval, such as a gene, an exon, or a base) for which high coverage is required to enable high level of sensitivity for an alteration (for example, one or more mutations) that appears at a higher frequency than the high-level target in a), for example, a frequency of about 10% (that is, 10% of the cells from the sample harbor the alteration in their genome). In one embodiment; the second bait set selects (for example, is complementary to) a tumor member that includes an alteration (for example, a point mutation) that requires about 200× or higher sequencing depth;

c) a third bait set that selects a low-level target (for example, one or more PGx members that includes a subgenomic interval, such as a gene, an exon, or a base) for which low-medium coverage is required to enable high level of sensitivity, for example, to detect heterozygous alleles. For example, detection of heterozygous alleles requires 10-100× sequencing depth to ensure high detection reliability. In one embodiment, third bait set selects one or more subgenomic intervals (for example, exons) that are chosen from: a) a pharmacogenomic (PGx) single nucleotide polymorphism (SNP) that may explain the ability of patient to metabolize different drugs, or b) a genomic SNPs that may be used to uniquely identify (for example, fingerprint) a patient;

d) a fourth bait set that selects a first intron target (for example, a member that includes an intron sequence) for which low-medium coverage is required, for example, to detect a structural breakpoint, such as a genomic translocation or an indel. For example, detection of an intronic breakpoint requires 5-50× sequence-pair spanning depth to ensure high detection reliability. Said fourth bait sets can be used to detect, for example, translocation/indel-prone cancer genes; or e) a fifth bait set that selects a second intron target (for example, an intron member) for which sparse coverage is required to improve the ability to detect copy number changes. For example, detection of a one-copy deletion of several terminal exons requires 0.1-300× coverage to ensure high detection reliability. In one embodiment, the coverage depth ranges from about 0.1-10× to detect copy number changes. In other embodiments, the coverage depth ranges from about 100-300× to detect a genomic SNPs/loci that is used to assess copy number gains/losses of genomic DNA or loss-of-heterozygosity (LOH). Said fifth bait sets can be used to detect, for example, amplification/deletion-prone cancer genes.

Any combination of two, three, four or more of the aforesaid bait sets can be used, for example, a combination of the first and the second bait sets; first and third bait sets; first and fourth bait sets; first and fifth bait sets; second and third bait sets; second and fourth bait sets; second and fifth bait sets; third and fourth bait sets; third and fifth bait sets; fourth and fifth bait sets; first, second and third bait sets; first, second and fourth bait sets; first, second and fifth bait sets; first, second, third, fourth bait sets; first, second, third, fourth and fifth bait sets, and so on.

In one embodiment, each of the first, second, third, fourth, or fifth bait set has a preselected efficiency for selection (for example, capture). In one embodiment, the value for efficiency of selection is the same for at least two, three, four of all five baits according to a)-e). In other embodiments, the value for efficiency of selection is different for at least two, three, four of all five baits according to a)-e). In some embodiments, at least two, three, four, or all five bait sets have a preselected efficiency value that differ.

For example, a value for efficiency of selection chosen from one of more of:

(i) the first preselected efficiency has a value for first efficiency of selection that is at least about 500× or higher sequencing depth (for example, has a value for efficiency of selection that is greater than the second, third, fourth or fifth preselected efficiency of selection (for example, about 2-3 fold greater than the value for the second efficiency of selection; about 5-6 fold greater than the value for the third efficiency of selection; about 10 fold greater than the value for the fourth efficiency of selection; about 50 to 5000-fold greater than the value for the fifth efficiency of selection);

(ii) the second preselected efficiency has a value for second efficiency of selection that is at least about 200× or higher sequencing depth (for example, has a value for efficiency of selection that is greater than the third, fourth or fifth preselected efficiency of selection (for example, about 2 fold greater than the value for the third efficiency of selection; about 4 fold greater than the value for the fourth efficiency of selection; about 20 to 2000-fold greater than the value for the fifth efficiency of selection);

(iii) the third preselected efficiency has a value for third efficiency of selection that is at least about 100× or higher sequencing depth (for example, has a value for efficiency of selection that is greater than the fourth or fifth preselected efficiency of selection (for example, about 2 fold greater than the value for the fourth efficiency of selection; about 10 to 1000-fold greater than the value for the fifth efficiency of selection);

(iv) the fourth preselected efficiency has a value for fourth efficiency of selection that is at least about 50× or higher sequencing depth (for example, has a value for efficiency of selection that is greater than the fifth preselected efficiency of selection (for example, about 50 to 500-fold greater than the value for the fifth efficiency of selection); or (v) the fifth preselected efficiency has a value for fifth efficiency of selection that is at least about 10× to 0.1× sequencing depth.

In certain embodiments, the value for efficiency of selection is modified by one or more of: differential representation of different bait sets, differential overlap of bait subsets, differential bait parameters, mixing of different bait sets, and/or using different types of bait sets.

For example, a variation in efficiency of selection (for example, relative sequence coverage of each bait set/target category) can be adjusted by altering one or more of:

(i) Differential representation of different bait sets—The bait set design to capture a given target (for example, a target member) can be included in more/fewer number of copies to enhance/reduce relative target coverage depths;

(ii) Differential overlap of bait subsets—The bait set design to capture a given target (for example, a target member) can include a longer or shorter overlap between neighboring baits to enhance/reduce relative target coverage depths;

(iii) Differential bait parameters—The bait set design to capture a given target (for example, a target member) can include sequence modifications/shorter length to reduce capture efficiency and lower the relative target coverage depths;

(iv) Mixing of different bait sets—Bait sets that are designed to capture different target sets can be mixed at different molar ratios to enhance/reduce relative target coverage depths;

(v) Using different types of oligonucleotide bait sets—In certain embodiments, the bait set can include:
(a) one or more chemically (for example, non-enzymatically) synthesized (for example, individually synthesized) baits,
(b) one or more baits synthesized in an array,
(c) one or more enzymatically prepared, for example, in vitro transcribed, baits;
(d) any combination of (a), (b) and/or (c),
(e) one or more DNA oligonucleotides (for example, a naturally or non-naturally occurring DNA oligonucleotide),
(f) one or more RNA oligonucleotides (for example, a naturally or non-naturally occurring RNA oligonucleotide),
(g) a combination of (e) and (f), or
(h) a combination of any of the above.

The different oligonucleotide combinations can be mixed at different ratios, for example, a ratio chosen from 1:1, 1:2, 1:3, 1:4, 1:5, 1:10, 1:20, 1:50; 1:100, 1:1000, or the like. In one embodiment, the ratio of chemically-synthesized bait to array-generated bait is chosen from 1:5, 1:10, or 1:20. The DNA or RNA oligonucleotides can be naturally- or non-naturally-occurring. In certain embodiments, the baits include one or more non-naturally-occurring nucleotide to, for example, increase melting temperature. Exemplary non-naturally occurring oligonucleotides include modified DNA or RNA nucleotides. Exemplary modified nucleotides (for example, modified RNA or DNA nucleotides) include, but are not limited to, a locked nucleic acid (LNA), wherein the ribose moiety of an LNA nucleotide is modified with an extra bridge connecting the 2' oxygen and 4' carbon; peptide nucleic acid (PNA), for example, a PNA composed of repeating N-(2-aminoethyl)-glycine units linked by peptide bonds; a DNA or RNA oligonucleotide modified to capture low GC regions; a bicyclic nucleic acid (BNA); a cross-linked oligonucleotide; a modified 5-methyl deoxycytidine; and 2,6-diaminopurine. Other modified DNA and RNA nucleotides are known in the art.

In certain embodiments, a substantially uniform or homogeneous coverage of a target sequence (for example, a target member) is obtained. For example, within each bait set/target category, uniformity of coverage can be optimized by modifying bait parameters, for example, by one or more of:

(i) Increasing/decreasing bait representation or overlap can be used to enhance/reduce coverage of targets (for example, target members), which are under/over-covered relative to other targets in the same category;

(ii) For low coverage, hard to capture target sequences (for example, high GC content sequences), expand the region being targeted with the bait sets to cover, for example, adjacent sequences (for example, less GC-rich adjacent sequences);

(iii) Modifying a bait sequence can be made to reduce secondary structure of the bait and enhance its efficiency of selection;

(iv) Modifying a bait length can be used to equalize melting hybridization kinetics of different baits within the same category. Bait length can be modified directly (by producing baits with varying lengths) or indirectly (by producing baits of consistent length, and replacing the bait ends with arbitrary sequence);

(v) Modifying baits of different orientation for the same target region (that is, forward and reverse strand) may have different binding efficiencies. The bait set with either orientation providing optimal coverage for each target may be selected;

(vi) Modifying the amount of a binding entity, for example, a capture tag (for example, biotin), present on each bait may affect its binding efficiency. Increasing/decreasing the tag level of baits targeting a specific target may be used to enhance/reduce the relative target coverage;

(vii) Modifying the type of nucleotide used for different baits can be altered to affect binding affinity to the target, and enhance/reduce the relative target coverage; or (viii) Using modified oligonucleotide baits, for example, having more stable base pairing, can be used to equalize melting hybridization kinetics between areas of low or normal GC content relative to high GC content.

For example, different types of oligonucleotide bait sets can be used. In one embodiment, the value for efficiency of selection is modified by using different types of bait oligonucleotides to encompass pre-selected target regions. For example, a first bait set (for example, an array-based bait set comprising 10,000-50,000 RNA or DNA baits) can be used to cover a large target area (for example, 1-2 MB total target area). The first bait set can be spiked with a second bait set (for example, individually synthesized RNA or DNA bait set comprising less than 5,000 baits) to cover a pre-selected target region (for example, selected subgenomic intervals of interest spanning, for example, 250 kb or less, of a target area) and/or regions of higher secondary structure, for example, higher GC content. Selected subgenomic intervals of interest may correspond to one or more of the genes or gene products described herein, or a fragment thereof. The second bait set may include about 1-5,000, 2-5,000, 3-5,000, 10-5,000, 100-5,000, 500-5,000, 100-5,000, 1000-5,000, 2,000-5,000 baits depending on the bait overlap desired. In other embodiments, the second bait set can include selected oligo baits (for example, less than 400, 200, 100, 50, 40, 30, 20, 10, 5, 4, 3, 2 or 1 baits) spiked into the first bait set. The second bait set can be mixed at any ratio of individual oligo baits. For example, the second bait set can include individual baits present as a 1:1 equimolar ratio. Alternatively, the second bait set can include individual baits present at different ratio (for example, 1:5, 1:10, 1:20), for example, to optimize capture of certain targets (for example, certain targets can have a 5-10× of the second bait compared to other targets).

In other embodiments, the efficiency of selection is adjusted by leveling the efficiency of individual baits within a group (for example, a first, second or third plurality of baits) by adjusting the relative abundance of the baits, or the density of the binding entity (for example, the hapten or affinity tag density) in reference to differential sequence capture efficiency observed when using an equimolar mix of baits, and then introducing a differential excess of internally-leveled group 1 to the overall bait mix relative to internally-leveled group 2.

In an embodiment, the method comprises the use of a plurality of bait sets that includes a bait set that selects a tumor member, for example, a nucleic acid molecule comprising a subgenomic interval from a tumor cell (also referred to herein as "a tumor bait set"). The tumor member can be any nucleotide sequence present in a tumor cell, for example, a mutated, a wild-type, a PGx, a reference or an intron nucleotide sequence, as described herein, that is present in a tumor or cancer cell. In one embodiment, the tumor member includes an alteration (for example, one or more mutations) that appears at a low frequency, for example, about 5% or less of the cells from the tumor sample harbor the alteration in their genome. In other embodiments, the tumor member includes an alteration (for example, one or more mutations) that appears at a frequency of about 10% of the cells from the tumor sample. In other embodiments, the tumor member includes a subgenomic interval from a PGx gene or gene product, an intron sequence, for example, an intron sequence as described herein, a reference sequence that is present in a tumor cell.

In another aspect, the invention features, a bait set described herein, combinations of individual bait sets described herein, for example, combinations described herein. The bait set(s) can be part of a kit which can optionally comprise instructions, standards, buffers or enzymes or other reagents.

Gene Selection

Preselected subgenomic intervals for analysis, for example, a group or set of subgenomic intervals for sets or groups of genes and other regions, are described herein.

Thus, in embodiments, a method comprises selection and/or sequencing of library members that include a subgenomic interval from at least five, six, seven, eight, nine, ten, fifteen, twenty, twenty-five, thirty or more genes or gene products from the acquired nucleic acid sample, wherein the genes or gene products are chosen from: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53, thereby analyzing the tumor sample.

In other embodiments, the method comprises selection and/or sequencing of library members that include a subgenomic interval from at least five, six, seven, eight, nine, ten, fifteen, twenty, twenty-five, thirty or more genes or gene products from the sample, wherein the genes or gene products are chosen from: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53.

In another embodiment, subgenomic intervals of one of the following sets or groups are analyzed. For example, subgenomic intervals associated with a tumor or cancer gene or gene product, a reference (for example, a wild type) gene or gene product, and a PGx gene or gene product, can provide a group or set of subgenomic intervals from the tumor sample.

In an embodiment, the method comprises selection and/or sequencing of library members of a set of subgenomic intervals from the tumor sample, wherein the subgenomic intervals are chosen from at least 1, 2, 3, 4, 5, 6, 7, 8, 9, 10, 11, 12, 13 or all of the following:

A) at least five, six, seven, eight, nine, ten, fifteen, twenty, twenty-five, thirty or more subgenomic intervals from a mutated or wild-type gene or gene product chosen from at least five or more of: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53;

B) at least five, six, seven, eight, nine, ten, fifteen, twenty, twenty-five, thirty, thirty-five, forty, forty-five, fifty, fifty-five, sixty, sixty-five, seventy, seventy-five, eighty, eighty-five, ninety, ninety-five, one hundred, one hundred and five, one hundred and ten, one hundred and fifteen, one hundred and twenty or more of subgenomic intervals from a mutated or wild type gene or gene product chosen from at least five or more of: ABL2, ARAF, ARFRP1, ARID1A, ATM, ATR, AURKA, AURKB, BAP1, BCL2, BCL2A1, BCL2L1, BCL2L2, BCL6, BRCA1, BRCA2, CBL, CARD11, CBL, CCND2, CCND3, CCNE1, CD79A, CD79B, CDH1, CDH2, CDH20, CDH5, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDM6A, KDR, LRP1B, LRP6, LTK, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK2, PAK3, PAX5, PDGFRB, PKHD1, PLCG1, PRKDC, PTPN11, PTPRD, RAFT, RARA, RICTOR, RPTOR, RUNX1, SMAD2, SMAD3, SMAD4, SMARCA4, SMARCB1, SOX10, SOX2, SRC, TBX22, TET2, TGFBR2, TMPRSS2, TNFAIP3, TNK, TNKS2, TOP1, TSC1, TSC2, USP9X, VHL, or WT1;

C) at least five, six, seven, eight, nine, ten, fifteen, twenty, or more subgenomic intervals from a gene or gene product according to Table 1, 1A, 2, 3 or 4;

D) at least five, six, seven, eight, nine, ten, fifteen, twenty, or more subgenomic intervals from a gene or gene product that is associated with a tumor or cancer (for example, is a positive or negative treatment response predictor, is a positive or negative prognostic factor for, or enables differential diagnosis of a tumor or cancer, for example, a gene or gene product chosen from one or more of: ABL1, AKT1, ALK, AR, BRAF, BRCA1, BRCA2, CEBPA, EGFR, ERBB2, FLT3, JAK2, KIT, KRAS, MET, NPM1, PDGFRA, PIK3CA, RARA, AKT2, AKT3, MAP2K4, NOTCH1, and TP53;

E) at least five, six, seven, eight, nine, ten, or more subgenomic intervals including a mutated or a wild type codon chosen from one or more of: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; codon 175, 245, 248, 273, or 306 of TP53 (for example, at least five, ten, fifteen, twenty or more subgenomic intervals that include one or more of the codons shown in Table 1).

F) at least five, six, seven, eight, nine, ten, fifteen, twenty, twenty-five, thirty, or more of subgenomic intervals from a mutated or wild type gene or gene product (for example, single nucleotide polymorphism (SNP)) of a subgenomic interval that is present in a gene or gene product associated with one or more of drug metabolism, drug responsiveness, or toxicity (also referred to therein as "PGx" genes) chosen from: ABCB1, BCC2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, or UMPS;

G) at least five, six, seven, eight, nine, ten, fifteen, twenty, twenty-five, thirty, or more of subgenomic intervals from a mutated or wild type PGx gene or gene product (for example, single nucleotide polymorphism (SNP)) of a subgenomic interval that is present in a gene or gene product associated with one or more of: (i) better survival of a cancer patient treated with a drug (for example, better survival of a breast cancer patient treated with paclitaxel (for example, an ABCB1 gene)); (ii) paclitaxel metabolism (for example, CYP2C8 genes at different loci and mutations shown in Table 2; CYP3A4 gene); (iii) toxicity to a drug (for example, 6-MP toxicity as seen with ABCC4 gene (Table 2); 5-FU toxicity as seen with DPYD gene, TYMS gene, or UMPS gene (Table 2); purine toxicity as seen with a TMPT gene (Table 2); daunorubicin toxicity as seen with NRP2 gene; C1orf144 gene, CYP1B1 gene (Table 2); or (iv) a side effect to a drug (for example, ABCG2, TYMS, UGT1A1, ESR1 and ESR2 genes (Table 2));

H) a translocation alteration of at least 5, 10, 15, 20, 25, 30, 35, 40, 45, 50, 75, 110 or more genes or gene products according to Table 3;

I) a translocation alteration of at least 5, 10, 15, 20, 25, 30, 35, 40, 45, 50, 75, 110 or more genes or gene products according to Table 3 in a solid tumor sample from the cancer types specified therein;

J) a translocation alteration of at least 5, 10, 15, 20, 25, 30, 35, 40, 45, 50, 75, 100, 150, 200 or more genes or gene products according to Table 4;

K) a translocation alteration of at least 5, 10, 15, 20, 25, 30, 35, 40, 45, 50, 75, 100, 150, 200 or more genes or gene products according to Table 4 in a heme tumor sample from the cancer types specified therein;

L) at least five genes or gene products selected from Table 1-4, wherein an allelic variation, for example, at the preselected position, is associated with a preselected type of tumor and wherein said allelic variation is present in less than 5% of the cells in said tumor type;

M) at least five genes or gene products selected from Table 1, 1A-4, which are embedded in a GC-rich region; or N) at least five genes or gene products indicative of a genetic (for example, a germline risk) factor for developing cancer (for example, the gene or gene product is chosen from one or more of BRCA1, BRCA2, EGFR, HRAS, KIT, MPL, ALK, PTEN, RET, APC, CDKN2A, MLH1, MSH2, MSH6, NF1, NF2, RB1, TP53, VHL or WT1).

In yet another embodiment, the method comprises selection and/or sequencing of library members that include a set of subgenomic intervals from the tumor sample, wherein the subgenomic intervals are chosen from one, two, three, four, five, ten, fifteen or all of the alterations described in Table 1B.

In one embodiment, the subgenomic interval includes an alteration classified in one or more of Category A, B, C, D or E.

In other embodiments, the subgenomic interval includes an alteration in KRAS G13D in a tumor sample, for example, a colon, lung or breast tumor sample.

In other embodiments, the subgenomic interval includes an alteration in NRAS Q61K in a tumor sample, for example, a melanoma or colon tumor sample.

In yet other embodiments, the subgenomic interval includes an alteration in BRAF V600E in a tumor sample, for example, a melanoma, colon, or lung tumor sample.

In other embodiments, the subgenomic interval includes an alteration in BRAF D594G in a tumor sample, for example, a lung tumor sample.

In other embodiments, the subgenomic interval includes an alteration in PIK3CA H1047R in a tumor sample, for example, a breast or colon tumor sample.

In yet other embodiments, the subgenomic interval includes an alteration in EGFR L858R or T790M in a tumor sample, for example, a lung tumor sample.

In other embodiments, the subgenomic interval includes an alteration in ERBB2 in a tumor sample, for example, an ERBB2 amplification in a breast tumor sample.

In other embodiments, the subgenomic interval includes an alteration in BRCA1 in a tumor sample, for example, a BRCA1 biallelic inactivation in a breast tumor sample.

In other embodiments, the subgenomic interval includes an alteration in BRCA2 in a tumor sample, for example, a BRCA2 biallelic inactivation in a pancreatic tumor sample.

In other embodiments, the subgenomic interval includes an alteration in ATM in a tumor sample, for example, an ATM biallelic inactivation in a breast tumor sample.

In other embodiments, the subgenomic interval includes an alteration in TSC in a tumor sample, for example, a TSC biallelic inactivation in a colon tumor sample.

In other embodiments, the subgenomic interval includes an alteration in PTEN in a tumor sample, for example, a PTEN biallelic inactivation in a breast or colon tumor sample.

In yet other embodiments, the subgenomic interval includes an alteration in VHL in a tumor sample, for example, a VHL biallelic inactivation in a kidney tumor sample.

In other embodiments, the subgenomic interval includes an alteration in ATR in a tumor sample, for example, an ATR biallelic inactivation in a breast tumor sample.

In other embodiments, the subgenomic interval includes an alteration in MYC in a tumor sample, for example, a MYC biallelic inactivation in a breast tumor sample.

These and other sets and groups of subgenomic intervals are discussed in more detail elsewhere herein.

BRIEF DESCRIPTION OF THE DRAWINGS

FIG. 3A depicts a flowchart depiction of an embodiment for sample receipt, quality control and DNA isolation.

FIG. 3B depicts a flowchart depiction of an embodiment for DNA quality control and library generation.

FIG. 3C depicts a flowchart depiction of an embodiment for hybrid capture and sequencing.

FIG. 3D depicts a flowchart depiction of an embodiment for sequence data quality control and mutation calling.

FIG. 3E depicts a flowchart depiction of an embodiment for report generation.

FIG. 3F depicts a flowchart depiction of an embodiment for additional details of report generation.

DETAILED DESCRIPTION OF THE INVENTION

Figure 1:
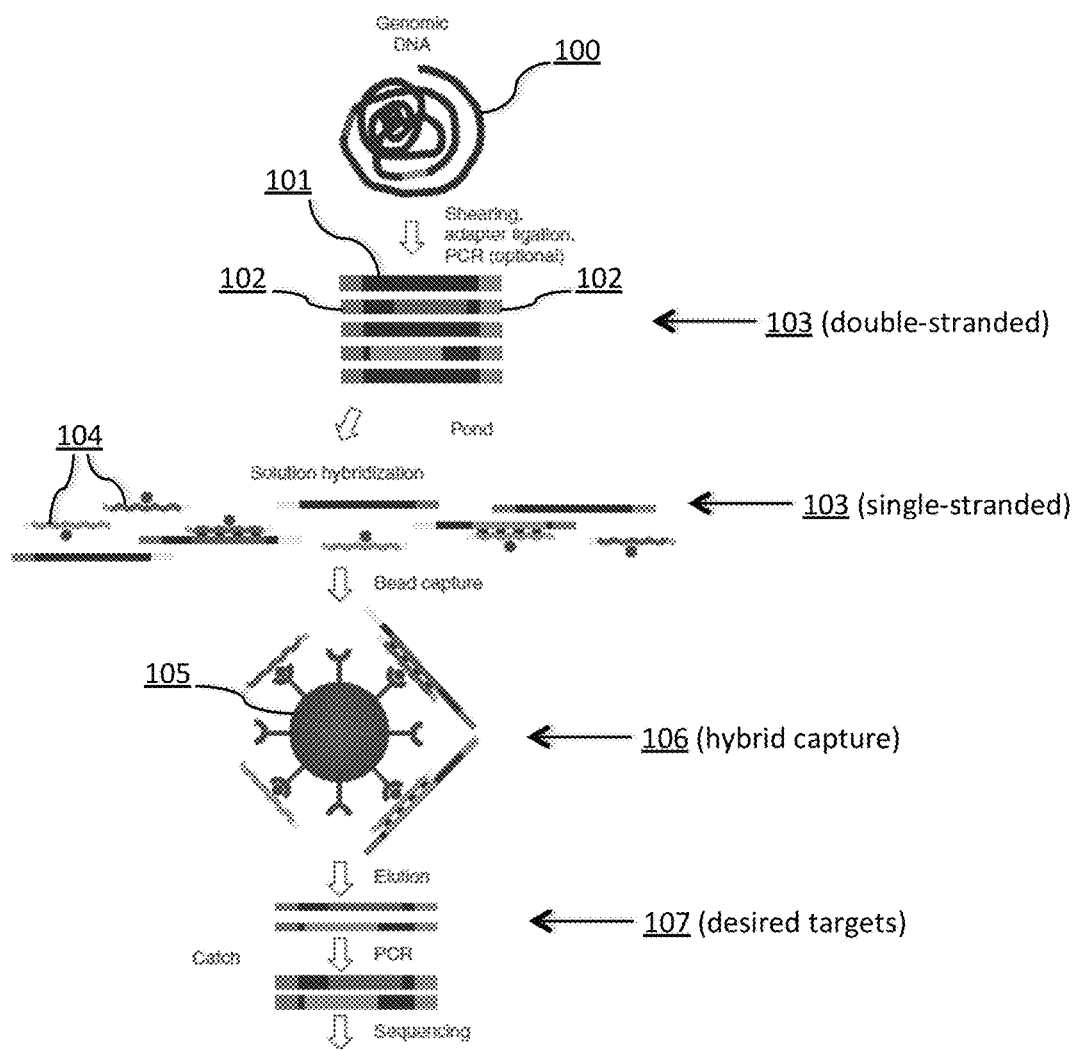
FIG. 1 depicts the typical set-up of a template library leading to selection of desired templates with the hybrid capture method.

Certain terms are first defined. Additional terms are defined throughout the specification.

Terms used herein are intended as "open" terms (for example, the term "including" should be interpreted as "including but not limited to," the term "having" should be interpreted as "having at least," the term "includes" should be interpreted as "includes but is not limited to," etc.).

Furthermore, in those instances where a convention analogous to "at least one of A, B and C, etc." is used, in general such a construction is intended in the sense of one having ordinary skill in the art would understand the convention (for example, "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "from," "to," "up to," "at least," "greater than," "less than," and the like, include the number recited and refer to ranges which can subsequently be broken down into sub-ranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the articles "a" and "an" refer to one or to more than one (for example, to at least one) of the grammatical object of the article.

"About" and "approximately" shall generally mean an acceptable degree of error for the quantity measured given the nature or precision of the measurements. Exemplary degrees of error are within 20-25 percent (%), typically, within 10%, and more typically, within 5% of a given value or range of values.

"Acquire" or "acquiring" as the terms are used herein, refer to obtaining possession of a physical entity, or a value, for example, a numerical value, by "directly acquiring" or "indirectly acquiring" the physical entity or value. "Directly acquiring" means performing a process (for example, performing a synthetic or analytical method) to obtain the physical entity or value. "Indirectly acquiring" refers to receiving the physical entity or value from another party or source (for example, a third party laboratory that directly acquired the physical entity or value). Directly acquiring a physical entity includes performing a process that includes a physical change in a physical substance, for example, a starting material. Exemplary changes include making a physical entity from two or one starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, for example, performing an analytical process which includes a physical change in a substance, for example, a sample, analyte, or reagent (sometimes referred to herein as "physical analysis"), performing an analytical method, for example, a method which includes one or more of the following: separating or purifying a substance, for example, an analyte, or a fragment or other derivative thereof, from another substance; combining an analyte, or fragment or other derivative thereof, with another substance, for example, a buffer, solvent, or reactant; or changing the structure of an analyte, or a fragment or other derivative thereof, for example, by breaking or forming a covalent or non-covalent bond, between a first and a second atom of the analyte; or by changing the structure of a reagent, or a fragment or other derivative thereof, for example, by breaking or forming a covalent or non-covalent bond, between a first and a second atom of the reagent.

"Acquiring a sequence" or "acquiring a read" as the term is used herein, refers to obtaining possession of a nucleotide sequence or amino acid sequence, by "directly acquiring" or "indirectly acquiring" the sequence or read. "Directly acquiring" a sequence or read means performing a process (for example, performing a synthetic or analytical method) to obtain the sequence, such as performing a sequencing method (for example, a Next Generation Sequencing (NGS) method). "Indirectly acquiring" a sequence or read refers to receiving information or knowledge of, or receiving, the sequence from another party or source (for example, a third party laboratory that directly acquired the sequence). The sequence or read acquired need not be a full sequence, for example, sequencing of at least one nucleotide, or obtaining information or knowledge, that identifies one or more of the alterations disclosed herein as being present in a subject constitutes acquiring a sequence.

Directly acquiring a sequence or read includes performing a process that includes a physical change in a physical substance, for example, a starting material, such as a tissue or cellular sample, for example, a biopsy, or an isolated nucleic acid (for example, DNA or RNA) sample. Exemplary changes include making a physical entity from two or more starting materials, shearing or fragmenting a substance, such as a genomic DNA fragment; separating or purifying a substance (for example, isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, for example, a tissue sample or nucleic acid sample, by "directly acquiring" or "indirectly acquiring" the sample. "Directly acquiring a sample" means performing a process (for example, performing a physical method such as a surgery or extraction) to obtain the sample. "Indirectly acquiring a sample" refers to receiving the sample from another party or source (for example, a third party laboratory that directly acquired the sample). Directly acquiring a sample includes performing a process that includes a physical change in a physical substance, for example, a starting material, such as a tissue, for example, a tissue in a human patient or a tissue that has was previously isolated from a patient. Exemplary changes include making a physical entity from a starting material, dissecting or scraping a tissue; separating or purifying a substance (for example, a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, for example, as described above.

"Alteration" or "altered structure" as used herein, of a gene or gene product (for example, a marker gene or gene product) refers to the presence of a mutation or mutations within the gene or gene product, for example, a mutation, which affects amount or activity of the gene or gene product, as compared to the normal or wild-type gene. The alteration can be in amount, structure, and/or activity in a cancer tissue or cancer cell, as compared to its amount, structure, and/or activity, in a normal or healthy tissue or cell (for example, a control), and is associated with a disease state, such as cancer. For example, an alteration which is associated with cancer, or predictive of responsiveness to anti-cancer therapeutics, can have an altered nucleotide sequence (for example, a mutation), amino acid sequence, chromosomal translocation, intra-chromosomal inversion, copy number, expression level, protein level, protein activity, or methylation status, in a cancer tissue or cancer cell, as compared to a normal, healthy tissue or cell. Exemplary mutations include, but are not limited to, point mutations (for example, silent, missense, or nonsense), deletions, insertions, inversions, linking mutations, duplications, translocations, inter- and intra-chromosomal rearrangements. Mutations can be present in the coding or non-coding region of the gene. In certain embodiments, the alteration(s) is detected as a rearrangement, for example, a genomic rearrangement comprising one or more introns or fragments thereof (for example, one or more rearrangements in the 5'- and/or 3'-UTR). In certain embodiments, the alterations are associated (or not associated) with a phenotype, for example, a cancerous phenotype (for example, one or more of cancer risk, cancer progression, cancer treatment or resistance to cancer treatment). In one embodiment, the alteration is associated with one or more of: a genetic risk factor for cancer, a positive treatment response predictor, a negative treatment response predictor, a positive prognostic factor, a negative prognostic factor, or a diagnostic factor.

"Bait", as used herein, is type of hybrid capture reagent. A bait can be a nucleic acid molecule, for example, a DNA or RNA molecule, which can hybridize to (for example, be complementary to), and thereby allow capture of a target nucleic acid. In one embodiment, a bait is an RNA molecule (for example, a naturally-occurring or modified RNA molecule); a DNA molecule (for example, a naturally-occurring or modified DNA molecule), or a combination thereof. In other embodiments, a bait includes a binding entity, for example, an affinity tag, that allows capture and separation, for example, by binding to a binding entity, of a hybrid formed by a bait and a nucleic acid hybridized to the bait. In one embodiment, a bait is suitable for solution phase hybridization.

"Bait set," as used herein, refers to one or a plurality of bait molecules.

"Binding entity" means any molecule to which molecular tags can be directly or indirectly attached that is capable of specifically binding to an analyte. The binding entity can be an affinity tag on each bait sequence. In certain embodiments, the binding entity allows for separation of the bait/member hybrids from the hybridization mixture by binding to a partner, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers.

"Likely to" or "increased likelihood," as used herein, refers to an increased probability that an item, object, thing or person will occur. Thus, in one example, a subject that is likely to respond to treatment has an increased probability of responding to treatment relative to a reference subject or group of subjects.

"Unlikely to" refers to a decreased probability that an event, item, object, thing or person will occur with respect to a reference. Thus, a subject that is unlikely to respond to treatment has a decreased probability of responding to treatment relative to a reference subject or group of subjects.

"Control member" refers to a member having sequence from a non-tumor cell.

"Indel alignment sequence selector," as used herein, refers to a parameter that allows or directs the selection of a sequence to which a read is to be aligned with in the case of a preselected indel. Use of such a sequence can optimize the sequencing of a preselected subgenomic interval comprising an indel. The value for an indel alignment sequence selector is a function of a preselected indel, for example, an identifier for the indel. In an embodiment the value is the identity of the indel.

As used herein, the term "library" refers to a collection of members. In one embodiment, the library includes a collection of nucleic acid members, for example, a collection of whole genomic, subgenomic fragments, cDNA, cDNA fragments, RNA, RNA fragments, or a combination thereof. In one embodiment, a portion or all of the library members comprises a non-target adaptor sequence. The adaptor sequence can be located at one or both ends. The adaptor sequence can be useful, for example, for a sequencing method (for example, an NGS method), for amplification, for reverse transcription, or for cloning into a vector.

The library can comprise a collection of members, for example, a target member (for example, a tumor member, a reference member, a PGx member, or a combination thereof). The members of the library can be from a single individual. In embodiments, a library can comprise members from more than one subject (for example, 2, 3, 4, 5, 6, 7, 8, 9, 10, 20, 30 or more subjects), for example, two or more libraries from different subjects can be combined to from a library having members from more than one subject. In one embodiment, the subject is human having, or at risk of having, a cancer or tumor.

"Library-catch" refers to a subset of a library, for example, a subset enriched for preselected subgenomic intervals, for example, product captured by hybridization with preselected baits.

"Member" or "library member" or other similar term, as used herein, refers to a nucleic acid molecule, for example, a DNA, RNA, or a combination thereof, that is the member of a library. Typically, a member is a DNA molecule, for example, genomic DNA or cDNA. A member can be fragmented, for example, sheared or enzymatically prepared, genomic DNA. Members comprise sequence from a subject and can also comprise sequence not derived from the subject, for example, a non-target sequence such as adaptors sequence, a primer sequence, or other sequences that allow for identification, for example, "barcode" sequences.

"Next-generation sequencing or NGS or NG sequencing" as used herein, refers to any sequencing method that determines the nucleotide sequence of either individual nucleic acid molecules (for example, in single molecule sequencing) or clonally expanded proxies for individual nucleic acid molecules in a high through-put fashion (for example, greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, for example, in Metzker, M. (2010) *Nature Biotechnology Reviews* 11:31-46, incorporated herein by reference. Next generation sequencing can detect a variant present in less than 5% of the nucleic acids in a sample.

"Nucleotide value" as referred herein, represents the identity of the nucleotide(s) occupying or assigned to a preselected nucleotide position. Typical nucleotide values include: missing (for example, deleted); additional (for example, an insertion of one or more nucleotides, the identity of which may or may not be included); or present (occupied); A; T; C; or G. Other values can be, for example, not Y, wherein Y is A, T, G, or C; A or X, wherein X is one or two of T, G, or C; T or X, wherein X is one or two of A, G, or C; G or X, wherein X is one or two of T, A, or C; C or X, wherein X is one or two of T, G, or A; a pyrimidine nucleotide; or a purine nucleotide. A nucleotide value can be a frequency for 1 or more, for example, 2, 3, or 4, bases (or other value described herein, for example, missing or additional) at a nucleotide position. For example, a nucleotide value can comprise a frequency for A, and a frequency for G, at a nucleotide position.

"Or" is used herein to mean, and is used interchangeably with, the term "and/or", unless context clearly indicates otherwise. The use of the term "and/or" in some places herein does not mean that uses of the term "or" are not interchangeable with the term "and/or" unless the context clearly indicates otherwise.

"Primary control" refers to a non-tumor tissue other than NAT tissue in a tumor sample. Blood is a typical primary control.

"Rearrangement alignment sequence selector," as used herein, refers to a parameter that allows or directs the selection of a sequence to which a read is to be aligned with in the case of a preselected rearrangement. Use of such a sequence can optimize the sequencing of a preselected subgenomic interval comprising a rearrangement. The value for a rearrangement alignment sequence selector is a function of a preselected rearrangement, for example, an identifier for the rearrangement. In an embodiment the value is the identity of the rearrangement. An "indel alignment sequence selector" (also defined elsewhere herein) is an example of a rearrangement alignment sequence selector.

"Sample," "tissue sample," "patient sample," "patient cell or tissue sample" or "specimen" each refers to a collection of similar cells obtained from a tissue, or circulating cells, of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, for example, an FFPE block or a frozen sample.

In one embodiment, the sample is a tumor sample, for example, includes one or more premalignant or malignant cells. In certain, embodiments, the sample, for example, the tumor sample, is acquired from a solid tumor, a soft tissue tumor or a metastatic lesion. In other embodiments, the sample, for example, the tumor sample, includes tissue or cells from a surgical margin. In another embodiment, the sample, for example, tumor sample, includes one or more circulating tumor cells (CTC) (for example, a CTC acquired from a blood sample).

"Sensitivity," as used herein, is a measure of the ability of a method to detect a preselected sequence variant in a heterogeneous population of sequences. A method has a sensitivity of S % for variants of F % if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%). Exemplary sensitivities include those of S=90%, 95%, 99% for sequence variants at F=1%, 5%, 10%, 20%, 50%, 100% at confidence levels of C=90%, 95%, 99%, and 99.9%.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. For example, a method has a specificity of 90% if, when applied to a sample set of 1,000 sequences, in which 500 sequences are truly variant and 500 are not truly variant, the method selects 90% of the 500 not truly variant sequences as not variant. Exemplary specificities include 90, 95, 98, and 99%.

A "tumor nucleic acid sample" as used herein, refers to nucleic acid molecules from a tumor or cancer sample. Typically, it is DNA, for example, genomic DNA, or cDNA derived from RNA, from a tumor or cancer sample. In certain embodiments, the tumor nucleic acid sample is purified or isolated (for example, it is removed from its natural state).

A "control" or "reference" "nucleic acid sample" as used herein, refers to nucleic acid molecules from a control or reference sample. Typically, it is DNA, for example, genomic DNA, or cDNA derived from RNA, not containing the alteration or variation in the gene or gene product. In certain embodiments, the reference or control nucleic acid sample is a wild type or a non-mutated sequence. In certain embodiments, the reference nucleic acid sample is purified or isolated (for example, it is removed from its natural state). In other embodiments, the reference nucleic acid sample is from a non-tumor sample, for example, a blood control, a normal adjacent tumor (NAT), or any other non-cancerous sample from the same or a different subject.

"Sequencing" a nucleic acid molecule requires determining the identity of at least 1 nucleotide in the molecule. In embodiments the identity of less than all of the nucleotides in a molecule are determined. In other embodiments, the identity of a majority or all of the nucleotides in the molecule is determined.

"Subgenomic interval" as referred to herein, refers to a portion of genomic sequence. In an embodiment a subgenomic interval can be a single nucleotide position, for example, a nucleotide position variants of which are associated (positively or negatively) with a tumor phenotype. In an embodiment a subgenomic interval comprises more than one nucleotide position. Such embodiments include sequences of at least 2, 5, 10, 50, 100, 150, or 250 nucleotide positions in length. Subgenomic intervals can comprise an entire gene, or a preselected portion thereof, for example, the coding region (or portions thereof), a preselected intron (or portion thereof) or exon (or portion thereof). A subgenomic interval can comprise all or a part of a fragment of a naturally occurring, for example, genomic, nucleic acid. For example, a subgenomic interval can correspond to a fragment of genomic DNA which is subjected to a sequencing reaction. In embodiments a subgenomic interval is continuous sequence from a genomic source. In embodiments a subgenomic interval includes sequences that are not contiguous in the genome, for example, it can include junctions formed found at exon-exon junctions in cDNA.

In an embodiment, a subgenomic interval comprises or consists of: a single nucleotide position; an intragenic region or an intergenic region; an exon or an intron, or a fragment thereof, typically an exon sequence or a fragment thereof; a coding region or a non-coding region, for example, a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; an alteration, for example, a point or a single mutation; a deletion mutation (for example, an in-frame deletion, an intragenic deletion, a full gene deletion); an insertion mutation (for example, intragenic insertion); an inversion mutation (for example, an intrachromosomal inversion); a linking mutation; a linked insertion mutation; an inverted duplication mutation; a tandem duplication (for example, an intrachromosomal tandem duplication); a translocation (for example, a chromosomal translocation, a non-reciprocal translocation); a rearrangement (for example, a genomic rearrangement (for example, a rearrangement of one or more introns, or a fragment thereof; a rearranged intron can include a 5'- and/or 3'-UTR); a change in gene copy number; a change in gene expression; a change in RNA levels, or a combination thereof. The "copy number of a gene" refers to the number of DNA sequences in a cell encoding a particular gene product. Generally, for a given gene, a mammal has two copies of each gene. The copy number can be increased, for example, by gene amplification or duplication, or reduced by deletion.

"Threshold value," as used herein, is a value that is a function of the number of reads required to be present to assign a nucleotide value to a subgenomic interval. For example, it is a function of the number of reads having a specific nucleotide value, for example, A, at a nucleotide position, required to assign that nucleotide value to that nucleotide position in the subgenomic interval. The threshold value can, for example, be expressed as (or as a function of) a number of reads, for example, an integer, or as a proportion of reads having the preselected value. By way of example, if the threshold value is X, and X+1 reads having the nucleotide value of "A" are present, then the value of "A" is assigned to the preselected position in the subgenomic interval. The threshold value can also be expressed as a function of a mutation or variant expectation, mutation frequency, or of Bayesian prior. In an embodiment, a preselected mutation frequency would require a preselected number or proportion of reads having a nucleotide value, for example, A or G, at a preselected position, to call that that nucleotide value. In embodiments the threshold value can be a function of mutation expectation, for example, mutation frequency, and tumor type. For example, a preselected variant at a preselected nucleotide position could have a first threshold value if the patient has a first tumor type and a second threshold value if the patient has a second tumor type.

As used herein, "target member" refers to a nucleic acid molecule that one desires to isolate from the nucleic acid library. In one embodiment, the target members can be a tumor member, a reference member, a control member, or a PGx member as described herein.

"Tumor member," or other similar term (for example, a "tumor or cancer-associated member"), as used herein refers to a member having sequence from a tumor cell. In one embodiment, the tumor member includes a subgenomic interval having a sequence (for example, a nucleotide sequence) that has an alteration (for example, a mutation) associated with a cancerous phenotype. In other embodiments, the tumor member includes a subgenomic interval having a wild type sequence (for example, a wild type nucleotide sequence). For example, a subgenomic interval from a heterozygous or homozygous wild type allele present in a cancer cell. A tumor member can include a reference member or a PGx member.

"Reference member," or other similar term (for example, a "control member"), as used herein, refers to a member that comprises a subgenomic interval having a sequence (for example, a nucleotide sequence) that is not associated with the cancerous phenotype. In one embodiment, the reference member includes a wild-type or a non-mutated nucleotide sequence of a gene or gene product that when mutated is associated with the cancerous phenotype. The reference member can be present in a cancer cell or non-cancer cell.

"PGx member" or other similar term, as used herein, refers to a member that comprises a subgenomic interval that is associated with the pharmacogenetic or pharmacogenomic profile of a gene. In one embodiment, the PGx member includes an SNP (for example, an SNP as described herein). In other embodiments, the PGx member includes a subgenomic interval according to Table 1 or Table 2.

As used herein, a "universal nucleobase" refers to a nucleobase that exhibits the ability to replace any of the four normal nucleobases without significantly destabilizing neighboring base-pair interactions. When such mixed nucleobase compositions, including universal nucleobase compositions, are present in blockers, they occupy a plurality of substantially contiguous nucleotide positions ranging in lengths preferably from about 5 to about 12 nucleotides.

"Variant," as used herein, refers to a structure that can be present at a subgenomic interval that can have more than one structure, for example, an allele at a polymorphic locus.

Headings, for example, (a), (b), (i) etc., are presented merely for ease of reading the specification and claims. The use of headings in the specification or claims does not require the steps or elements be performed in alphabetical or numerical order or the order in which they are presented.

The invention pertains to novel $T_m$-enhanced oligonucleotides as blockers and baits to improve target enrichment and to reduce off-target selection. The oligonucleotide compositions have robust application preparing nucleic acid templates for next generation sequencing applications. The oligonucleotides are modified with $T_m$-enhancing groups to increase the binding affinity of the oligonucleotides to their respective targets that permits hybridization/capture reactions to be run at higher temperatures and under more stringent wash conditions than unmodified oligonucleotides. For oligonucleotide blockers having the identical sequence to the terminal adaptors of NGS templates, inclusion of $T_m$-enhanced oligonucleotides as blockers in the hybrid capture method reduces the level of unwanted contaminating sequences resulting from adaptor-mediated hybrid formation among NGS templates (the "daisy-chain effect"), thereby increasing the overall efficiency of the enrichment process for the desired NGS templates. Compositions of novel $T_m$-enhanced oligonucleotides as blockers and baits as well as their specific use for improved target enrichment and for reduced off-target selection, including their use in applications such as in massively parallel sequencing experiments, are disclosed in further detail below.

Referring to FIG. 1, input DNA 100 is fragmented to provide appropriate size ranges. Preferred size ranges for the resultant DNA fragments 101 will depend upon the particular application and/or NGS platform, but typically range from 200-500 bp in length. The preferred method of fragmenting DNA 100 is by shearing the DNA using sonication procedures. Commercially available sonifiers and other sonication instrumentation can be used to fragment DNA 100 to the appropriate size ranges. While fragmenting DNA 100 by shearing is preferred fragmentation means, other fragmentation procedures can be used, such as partial digestion of DNA 100 using endonucleases (for example, DNAses or restriction endonucleases).

The resultant DNA fragments 101 are enzymatically treated to prepare flush-ended termini to which oligonucleotide adaptors 102 having at least one flush-end are ligated to yield the NGS templates 103. Typically, sheared DNA can include a variety of termini, such a flush termini, 5'-overhang termini, and 3'-overhang termini. Those DNA fragments that include 5'-overhang termini can be made flush-ended by filling in the recessed 3'-termini using a suitable polymerase (for example, T4 DNA polymerase, the Large (Klenow) Fragment of DNA polymerase I, Vent DNA polymerase, Deep Vent DNA polymerase, among others). Those DNA fragments that include a 3'-overhang can be made flush-ended by using the 3'→5' exonuclease activity of a DNA polymerase, preferably in the presence of dNTPs (for example, T4 DNA polymerase, Large (Klenow) Fragment of DNA polymerase I, Pfu polymerase, among others). DNA fragments having 5'-overhang or 3'-overhang termini can also be made flush-ended using single-strand nucleases (for example, Mung Bean Nuclease, P1 nuclease, S1 nuclease, among others). The use of a DNA polymerase is preferable for use to prepared flush-ended termini for fragments 101.

Optionally, the resultant fragments 101 can be enzymatically manipulated to include a single nucleotide overhang (for example, a 3'-dA overhang) that can facilitate ligation with adaptors 102 having at least one terminus with the complementary single-nucleotide overhang (in the above example, a 3'-dT overhang). Such fragments 101 are typically made with flush-ended termini as described above and then subsequently treated with an enzyme having 3'-polymerase ("tailing") activity (for example, Tth DNA polymerase, Bst DNA polymerase, Taq DNA polymerase, Klenow DNA polymerase (exo⁻), among others).

Furthermore, sheared DNA can include internal breaks (for example, nicks) within one of the two complementary strands that do not result in complete breakage of the double-stranded DNA structure. Such internal breaks can be repaired using a DNA polymerase having nick-translation activity in the presence of dNTPs (for example, T4 DNA polymerase or Large (Klenow) Fragment of DNA Polymerase I, among others) or in the presence of a suitable ligase in the presence of ATP (for example, T4 DNA ligase). It is preferable to repair any single-stranded breaks within the sheared DNA of fragments 101 since the final templates 103 preferably include two adaptors 102 ligated onto each end of the two continuous strands.

Adaptors 102 are preferably designed to include different types of termini. This preferred design is chosen to provide a single copy of double-stranded adaptor 102 for each end of the resultant templates 103. For fragments 101 enzymatically treated to include flush-ended termini, adaptors 102 are designed to include a first terminus having a flush end and a second terminus having an overhang end. For such adaptors 102, the second terminus is further designed to include one or more features that preclude ligation to other adaptors 102 (for example, lacking a ligase-competent substrate, such as a 5'-phosphate group, 3'-hydroxyl group, and/or sequence complementarity, among others). For fragments 101 enzymatically treated to include single-nucleotide termini, adaptors 102 are designed to include a first terminus having a complementary single-nucleotide overhang and a second terminus having a different type of end. Like that described above, the second terminus of the latter adaptors 102 preferably designed to include one or more features that precludes ligation to other adaptors 102.

The oligonucleotide composition of adaptors 102 preferably includes conventional nucleobases, wherein the internucleotidyl linkages are conventional phosphodiester moieties. The adaptors 102 preferably exclude chemical groups that display $T_m$-enhanced properties, as further explained below. The preferred lengths of oligonucleotide adaptors 102 range from about 15 nucleotides to about 75 nucleotides.

For certain NGS applications, it is desirable to include "barcode" sequences to enable multiplex sequencing in massively parallel sequencing experiments. For this purpose, adaptors 102 represent the barcode sequence tags. Preferably, the plurality of substantially contiguous nucleotide positions that includes these nucleobases is located within the oligonucleotide at a central position away from the termini.

The primary sequence composition of adaptors 102 can depend upon a number of considerations. One consideration is the NGS platform used for the massively parallel sequencing experiments. For example, the commercially available automated instrumentation used for NGS applications have different libraries of templates 103 containing different adaptors 102, so the selection of primary sequence compositions for any given commercial NGS instrumentation platform will depend upon that criterion. Another consideration is the primary sequence compositional design of the complementary $T_m$-enhanced oligonucleotide as the blocker. As will become evident below, certain primary sequence compositions for the blockers are preferred, which can influence design decisions regarding the primary sequence composition of the complementary adaptors 102.

Figure 2A:
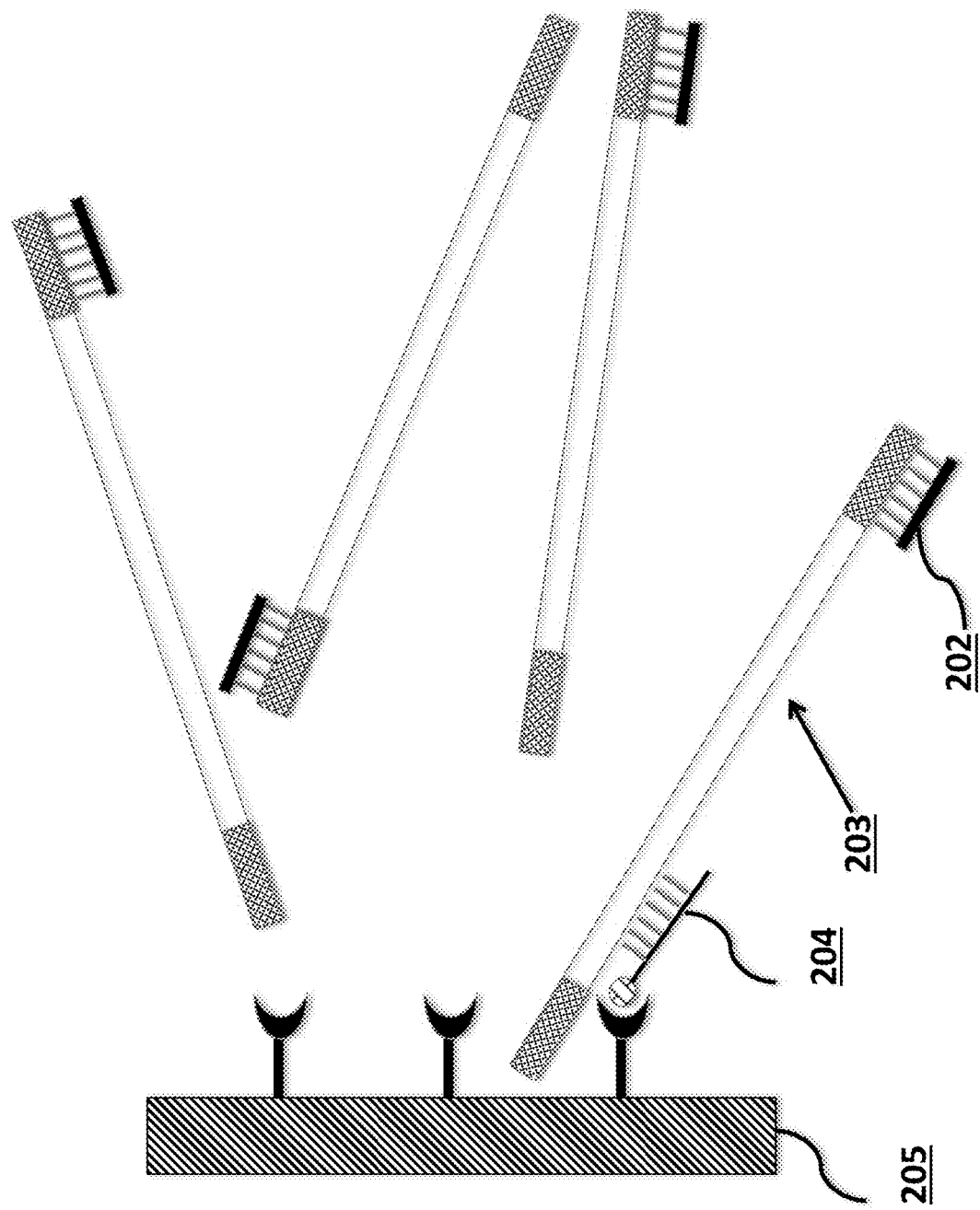
FIG. 2A depicts conventional oligonucleotide blocking strategy using oligonucleotides 102 as blockers to hybridize to the corresponding adaptor 102 sequences found in templates 203 under temperature conditions that are favorable for 102:102 duplex formation. Note that multiple templates 203 are captured via binding of one oligonucleotide bait 204 and its interaction to a capture reagent on an immobilized support 205.
Figure 2B:
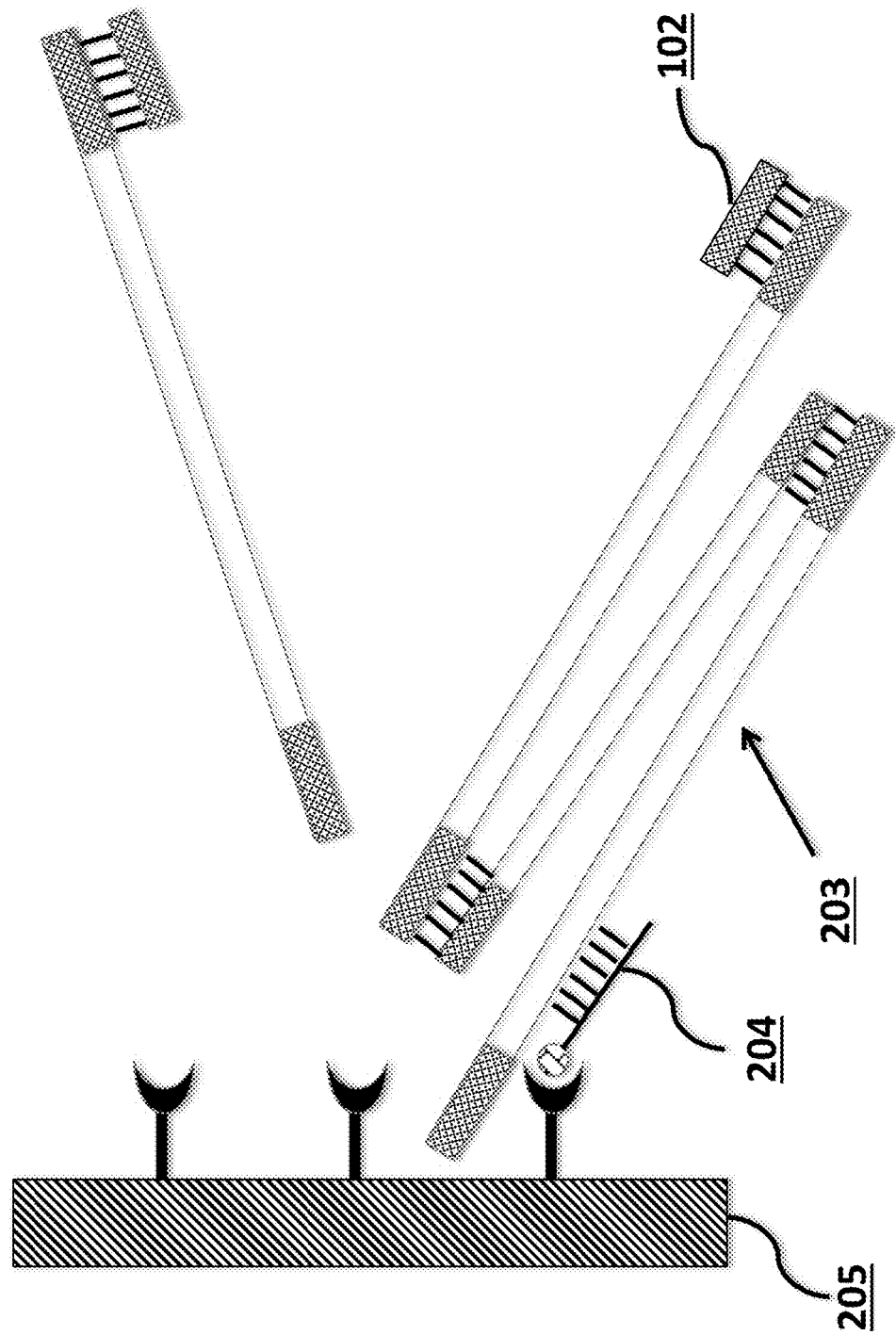
FIG. 2B depicts the $T_m$-enhanced oligonucleotide blocking strategy for enrichment of desired DNA targets without co-selection of unwanted DNA sequences from the complex pool of NGS templates. Rather than using oligonucleotides 102 as blockers, the strategy uses $T_m$-enhanced oligonucleotides 202 as blockers to hybridize to the corresponding adaptor 102 sequences found in templates 203 under temperature conditions that are favorable for 202:102 duplex formation. Because 202:102 duplexes are favored over 102:102 duplexes at temperatures near the optimal enhanced $T_m$ value, fewer undesired templates 203 are captured via binding of one oligonucleotide bait 204 and its interaction to a capture reagent on an immobilized support 205.
Figure 3A:
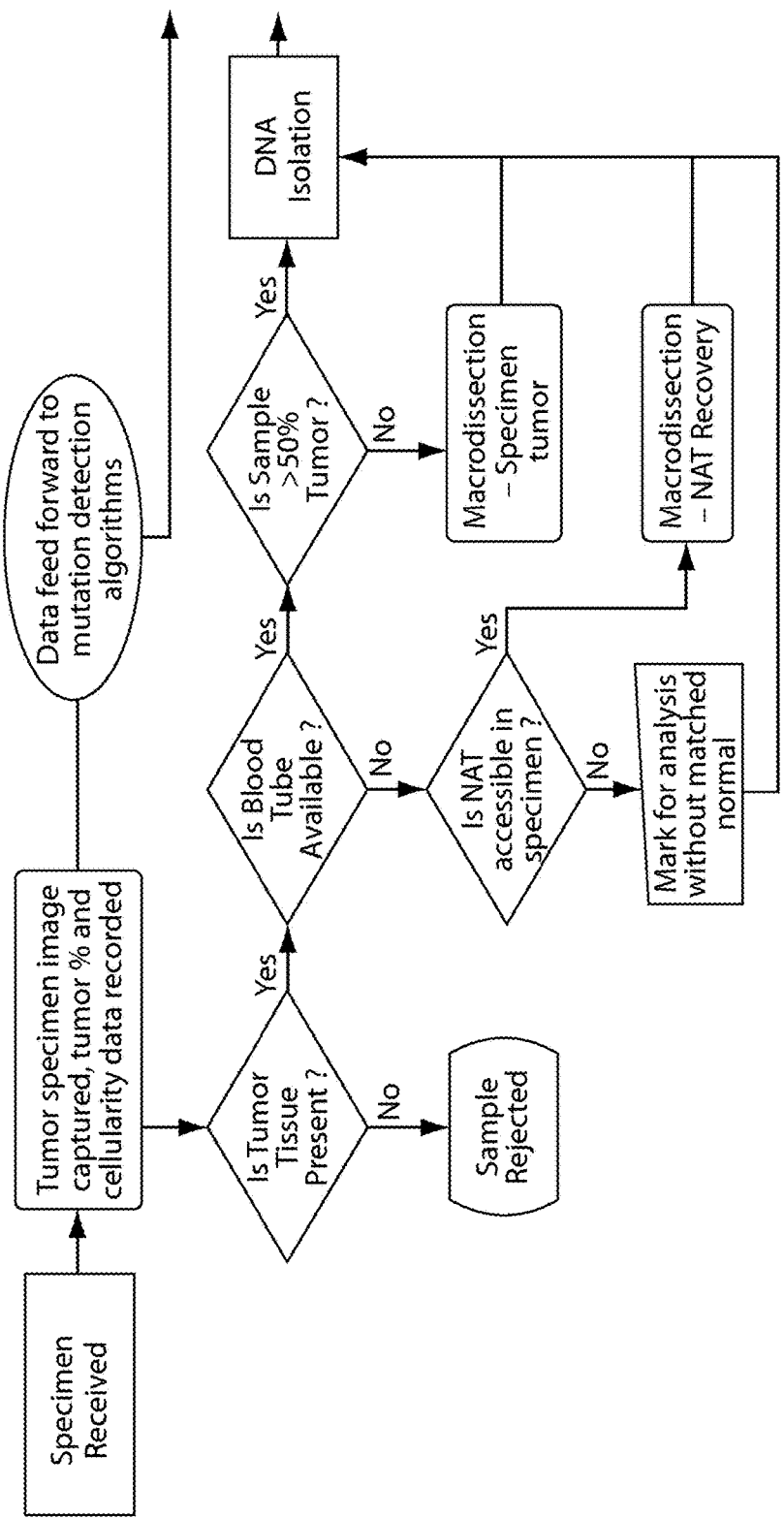
FIG. 3A-3F is a flowchart depiction of an embodiment of a method for multigene analysis of a tumor sample.
Figure 3B:
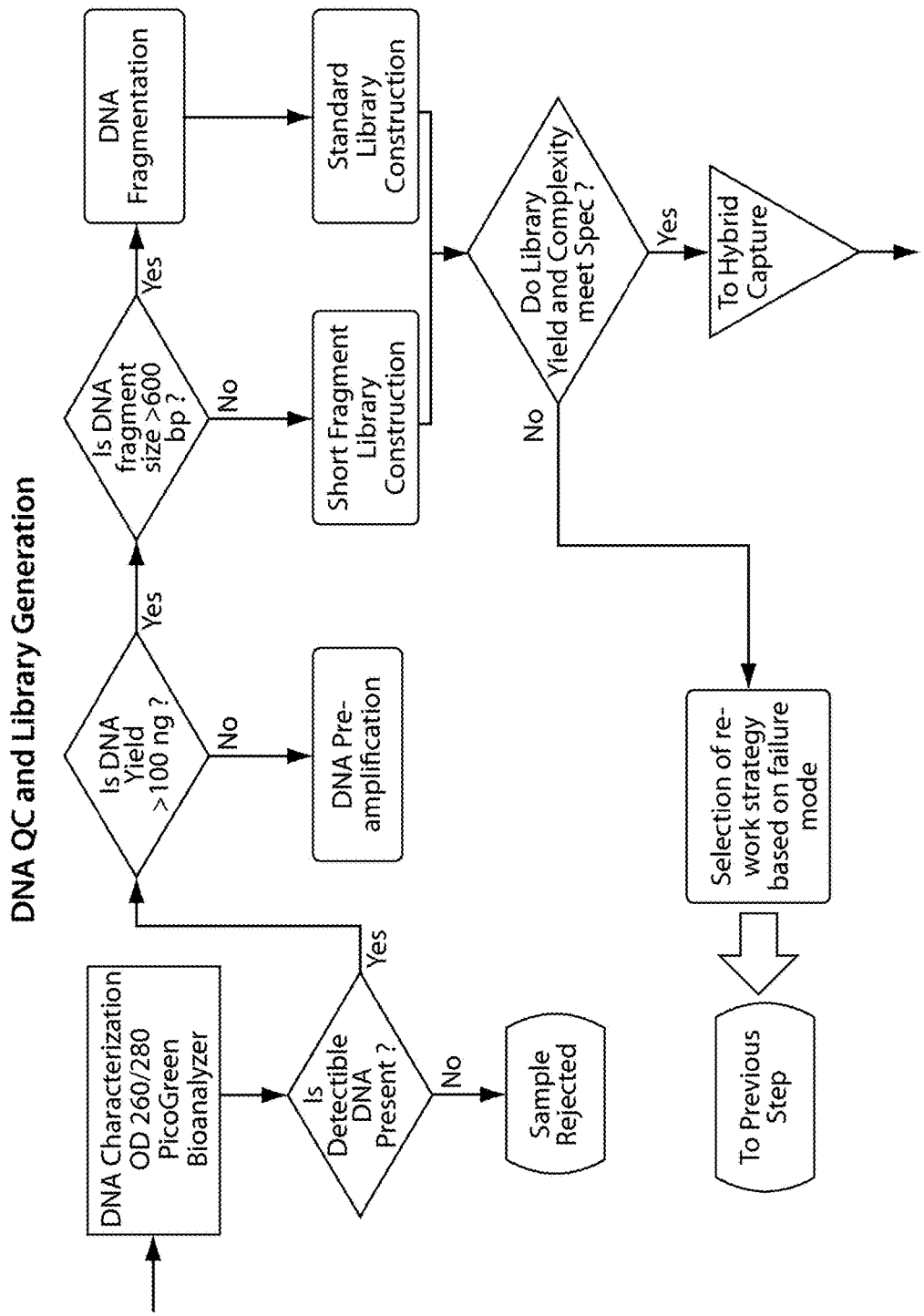
Figure 3C:
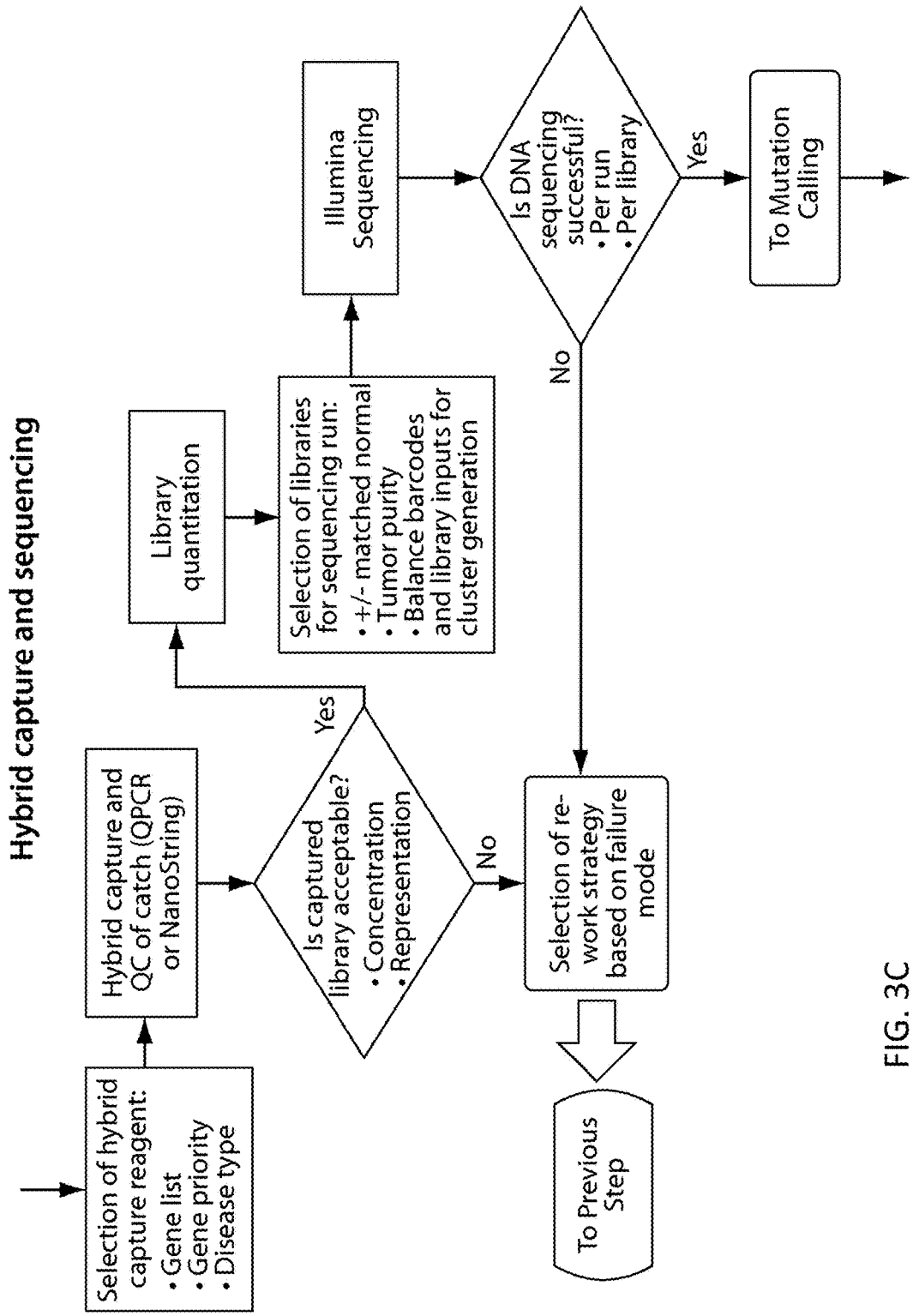
Figure 3D:
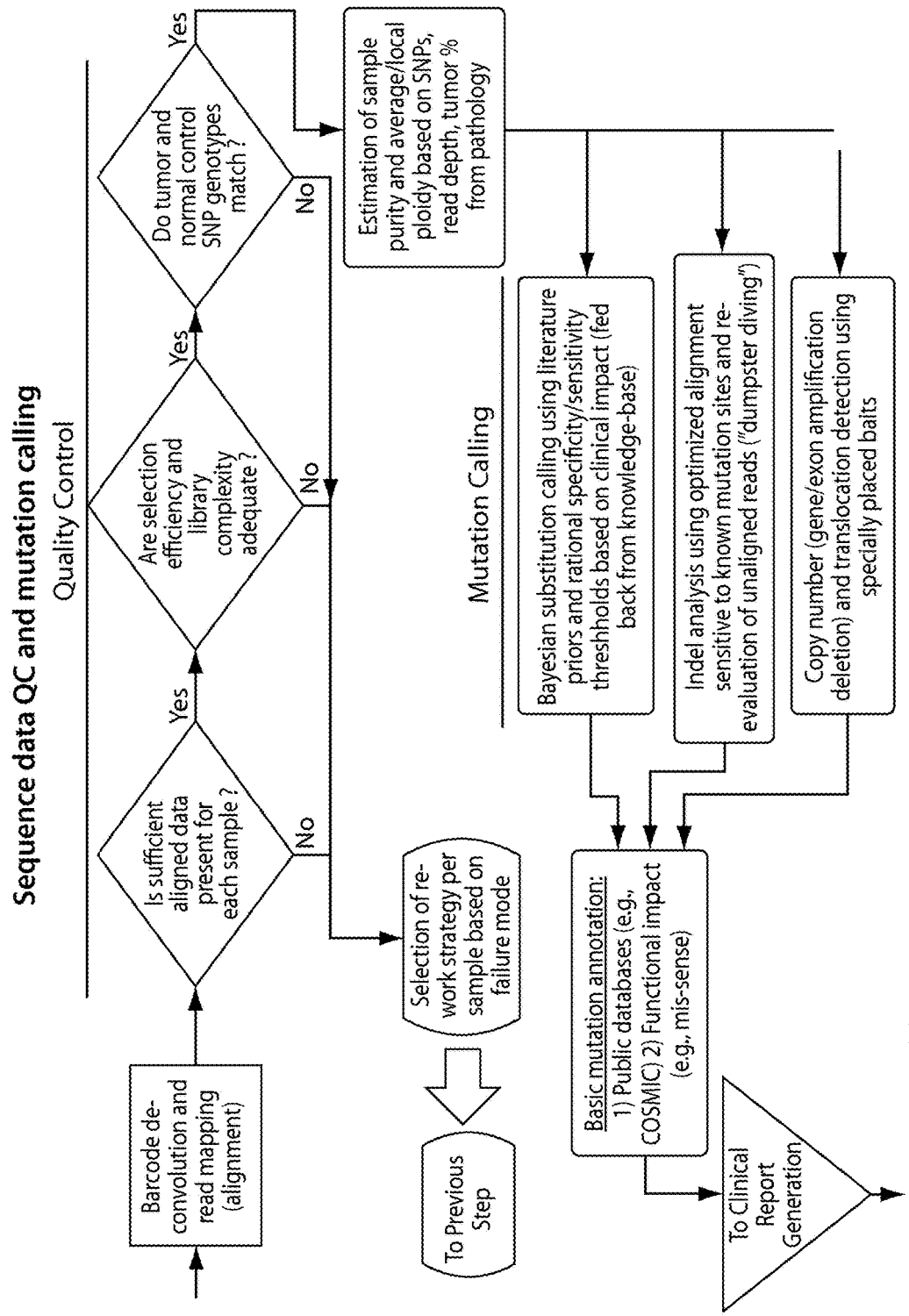
Figure 3E:
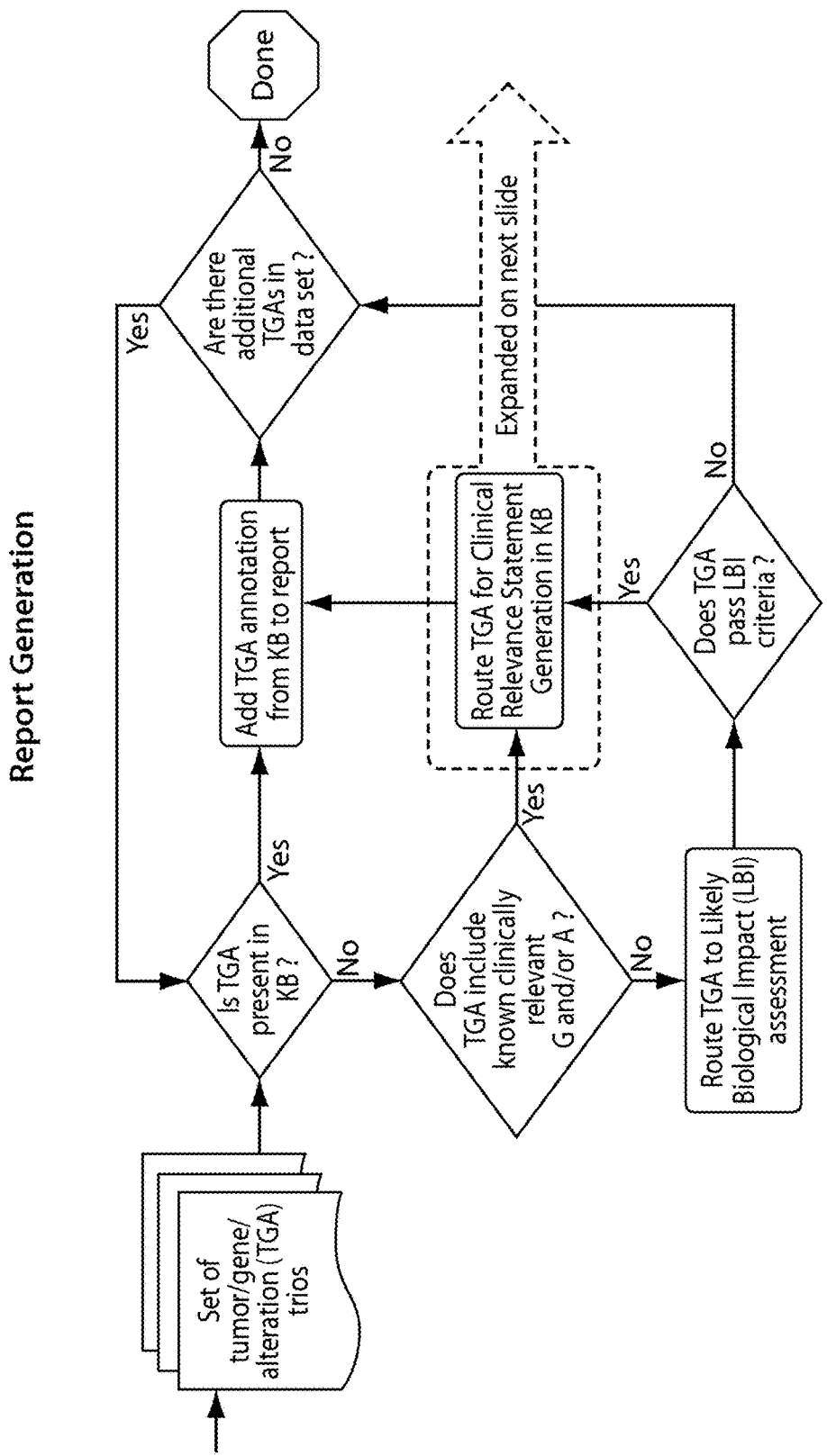
Figure 3F:
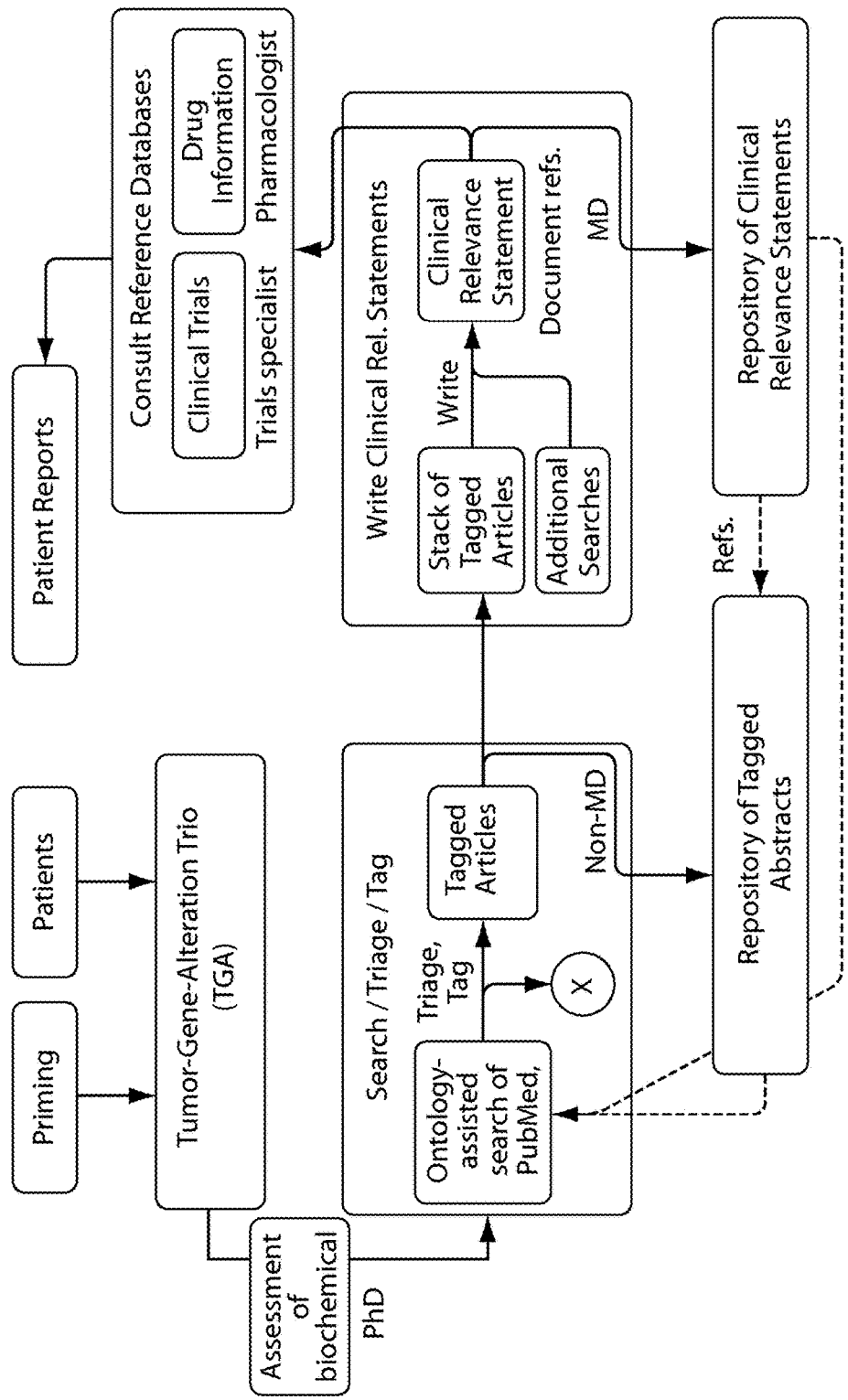

Referring to FIG. 2A-B, the principle of $T_m$-enhanced oligonucleotides as blockers and baits is illustrated for a typical NGS application. Double-stranded templates 203, $T_m$-enhanced oligonucleotide blockers 202, biotinylated oligonucleotide baits 204 and $C_o t-1$ DNA® (not shown) are mixed together and heat-denatured at 95° C. in a buffer mixture adjusted to include a final concentration of 5× Saline Sodium Citrate buffer (SSC) (or similar hybridization buffer, as are well known to those with skill in the art) and maintained for 1-3 days at a hybridization temperature below the predicted average $T_m$ value for bait:target hybrids. As the hybridization mixture cools from the 95° C. denaturation step to the hybridization step, bait:target hybrids will form. Since the $T_m$ of the modified blockers is higher than the unmodified adaptors, blocker:adaptor hybrids will form before adaptor:adaptor hybrids form, thereby preventing the formation of "daisy chains". The mixture is then added to a solid support media 205 containing streptavidin to permit capture of the 203:204 hybrids. The support media/mixture is washed under successively more stringent conditions (for example, 1×SSC, followed by 0.1×SSC) at a temperature below that of the estimated bait:target $T_m$ value and, preferably, above that of the $T_m$ value of the unmodified adaptors. Given that the adaptors are usually much shorter than the bait oligomers, bait $T_m$ is usually well above that of adaptor $T_m$. Because the blockers 202 have enhanced $T_m$ values compared to unmodified adaptors found on the templates, the templates 203 will preferentially hybridize to the blockers 202 under the increased hybridization temperatures, thereby minimizing different templates 203 from forming daisy-chained aggregates through their respective adaptor sequences. Following the stringent washes at the elevated hybridization temperature, one final stringent wash is performed at room temperature and the desired templates are recovered from the immobilized support 205.

Typical oligonucleotide blockers corresponding to the adaptor sequences can provide about a 60% enrichment of desired target sequences obtained from hybrid capture. By contrast, the $T_m$-enhanced oligonucleotides as blockers can provide over about 80% enrichment of desired target sequences obtained from hybrid capture. The resultant improvement in target enrichment from hybrid capture experiments with the $T_m$-enhanced oligonucleotides as blockers ranges provide over an about 30% in increased yield of desired template targets relative to the yield obtained with unmodified oligonucleotides as blockers.

Various embodiments of the design of $T_m$-enhanced oligonucleotides as blockers and baits are now described. As used herein, a "$T_m$-enhanced oligonucleotide" is an oligonucleotide that includes at least one modified group ("$T_m$-enhancing group") that provides an increased thermal melting temperature value ("enhanced $T_m$ value") for a duplex nucleic acid that includes as a hybridization partner the oligonucleotide relative to a duplex nucleic acid that includes as a hybridization partner an oligonucleotide having identical nucleobase composition and unmodified groups.

Numerous $T_m$-enhancing groups may be used in the design of $T_m$-enhanced oligonucleotides. Examples of suitable $T_m$-enhancing groups for this purpose include modifications to the nucleobases or ribose moieties, including, for example, locked nucleic acids (LNAs), bicyclic nucleic acids (BNAs, such as constrained ethyl nucleic acids, from Isis Pharmaceuticals), C5-modified pyrimidine bases (for example, 5-methyl-dC, propynyl pyrimidines, among others). Alternate backbone chemistries can also be employed, such as peptide nucleic acids (PNAs), morpholinos, among others. Non-base modifiers can also be employed to increase $T_m$ (or binding affinity), such as a minor grove binder (MGB), spermine, G-clamp, or a Uaq anthraquinone cap. Many strategies to increase binding affinity are known to those with skill in the art and the use of all such modifications is considered within the scope of the invention.

Preferably, $T_m$-enhanced oligonucleotides include a plurality of $T_m$-enhancing groups. The preferred number of $T_m$-enhancing groups is that number which provides an increase in the optimal $T_m$ value under stringent conditions (0.1×SSC) ("optimal enhanced $T_m$ value") of at least about 1.4° C. for a duplex DNA containing the $T_m$-enhanced oligonucleotide as one complementary strand. The preferred number $T_m$-enhancing groups in a $T_m$-enhanced oligonucleotide provides for an optimal enhanced $T_m$ value ranging from about 2° C. to about 25° C.

A preferred approach to designing of a $T_m$-enhanced oligonucleotide for improved template enrichment in hybrid capture methods depends upon the $T_m$-enhancing groups used in the oligonucleotide. The $T_m$ value of a $T_m$-enhanced oligonucleotide containing any of the aforementioned $T_m$-enhancing groups can be determined using routine empirical methods. The use of $T_m$-enhancing groups of LNAs or BNAs is preferred since reliable methods for accurately predicting the $T_m$ value for $T_m$-enhanced oligonucleotides containing these latter $T_m$-enhancing groups are available that require minimal or reduced empirical evaluation. An example of one such method for this purpose is provided in U.S Patent Publication No. US 2012/0029891 A1 published Feb. 2, 2012, entitled METHODS FOR PREDICTING STABILITY AND MELTING TEMPERATURES OF NUCLEIC ACID DUPLEXES to Behlke, which is incorporated herein by reference in its entirety.

For certain preferred embodiments, $T_m$-enhanced oligonucleotides include a barcode sequence tag. Barcode elements are often included in one of the two adaptor oligonucleotides attached to the target nucleic acid during library construction. A barcode element is typically 6 bases long; longer elements are also employed, such as 8 bases or longer. Typically the barcode adaptor comprises only one of the two adaptors employed in NGS library preparation, with one adaptor being "unique and coded" and one adaptor being "universal". It is also possible to place barcodes on both adaptors. The use of barcoded adaptors permits multiple samples to be mixed and processed together in a single multiplex sequencing run, offering significant cost savings and increased throughput. Sequences are deconvoluted by analysis after sequencing. Multiplex experiments can involve use of 2, 3, 4 or up to a hundred or more barcode modified adaptor sequences. As each different barcode adaptor has a unique sequence, the most effective blocking oligonucleotide(s) would be sequences that are a perfect complementary match to each unique barcode adaptor present in the set. This approach ensures the highest possible $T_m$ for the blockers, since mismatches within the barcode domain between adaptor and blocker will lower $T_m$. Therefore, for example, use of 4 barcode adaptors in a 4-plex reaction would require use of 5 distinct blocking oligonucleotides comprising 4 unique sequences for the 4 barcode adaptors and 1 unique sequence for the common universal adaptor. However, if many distinct barcode adaptors are employed, this approach may require use of as many as a hundred or more unique blocking oligonucleotides for high level multiplex experiments, which is not cost effective. Further, mis-hybridization of blocker "A" to adaptor "B" will likely occur, lowering the binding affinity of the blocking oligonucleotides and decreasing the effectiveness of the blocking step. One solution is to incorporate a "universal" domain into the blocking oligonucleotide comprising a random N-mer domain (for example, NNNNNN mixed-base hexamer sequence) at the appropriate location within the adaptor oligonucleotide to span the barcode domain in the adaptor. With this approach, a single blocking oligonucleotide can be used with a large number of barcoded adaptors. Using a 6-base N-mer domain, 4096 different sequences are present in the blocking oligonucleotide pool. Having this large number of barcodes present will result in most blocker: adaptor pairs to include mismatches in the barcode domain. Alternatively, a "universal base" can be employed instead of N-bases. Universal bases are modified nucleobases that hybridize to some or all natural bases with less thermodynamic cost for mismatch than true base mismatches, such as G:A or T:T pairs. Many universal bases exist, such as inosine ("I"), 5-nitroindole ("5-NI"), etc., which are well known to those with skill in the art. Pairing of an inosine domain (IIIIII) with a barcode will on average have a higher $T_m$ than a fully mismatched N-mer domain (NNNNNN). Therefore, three approaches can be used to make blocking oligonucleotides for barcode adaptors: 1) synthesize a series of blockers which are perfect match to each adaptor, 2) synthesize a single blocker with an N-mer domain to pair with the barcode domain of the adaptor, or 3) synthesize a single blocker with a universal base domain to pair with the barcode domain of the adaptor. One can calculate a sufficiently accurate estimate of the $T_m$ value for a particular $T_m$-enhanced blocking oligonucleotide containing LNA or BNA groups with the barcode adaptor by omitting the sequence contribution attributed to the mixed or universal nucleobase sequences with the aforementioned method. The precise $T_m$ value for such oligonucleotides can then be determined with greater precision using routine empirical methods.

As mentioned previously, adaptors 102 are present as two complementary strands on templates 103. Following denaturation of the population of double-stranded templates 103 for hybrid capture, each single-stranded template 103 will include a corresponding single-stranded copy of adaptor 102. To prevent interactions among different single-stranded templates 103 that result in the daisy-chain aggregate of many unrelated templates 103, only one of the two adaptor 102 strands need be blocked for hybridization with another complementary strand adaptor 102. For this reason, and in preferred embodiments, only one $T_m$-enhanced oligonucleotide strand as blocker needs to be included to achieve improved template enrichment in hybrid capture methods with NGS templates 103.

The design of the primary sequence of the $T_m$-enhanced oligonucleotide as blocker is based on the primary sequences of one of the two complementary strands of oligonucleotide adaptors 102. Though one may include as $T_m$-enhancing groups any or all of the available nucleobases into a $T_m$-enhanced oligonucleotide, it is preferable to include only one single type of modified nucleobase or two different types of modified nucleobases.

Oligonucleotides modified with $T_m$-enhancing nucleobases are at increased risk for hairpin or self-dimer formation. Oligonucleotide design algorithms or calculators can be used to model hairpin and dimer potential of a sequence and should be used to help screen modification patterns. See, for example, the OligoAnalyzer that is publicly available on the IDT website: http://www.idtdna.com/analyzer/Applications/OligoAnalyzer/. This issue is of particular importance if LNA or BNA modifications are employed. LNA:DNA base pairs show a $T_m$ increase relative to DNA:DNA pairs. LNA:LNA base pairs shows a $T_m$ increase relative to LNA:DNA pairs. Any LNA:LNA pairs that occur in hairpin or self-dimer events are particularly favorable (note that only LNA:DNA pairs can form between blockers and targets). Therefore, care must be taken in design of $T_m$-enhanced oligonucleotides to avoid patterns that promote self-dimer or hairpin formation via LNA:LNA pairing events. This applies equally to the BNA modification.

One preferred approach to prevent this problem is to employ only a single type of modified nucleobase. For example, a $T_m$-enhanced blocking oligonucleotide can be made only using LNA-C or BNA-C. Depending on base composition, complete substitution of a single base type might not achieve a sufficiently high $T_m$ increase to provide optimal performance. In this case, two different modified nucleobases can be employed, such as LNA-C with LNA-A, or BNA-C with BNA-A. In general, modified C can be used with modified A or modified T, but not modified G. Likewise modified A can be used with modified C or modified G, but not modified T. Use of modified C with modified G or use of modified A with modified T should be avoided. This strategy limits the risk for increased hairpin/dimer formation by limiting the potential interaction between the modified bases. The propynyl pyrimidine modification is only available as pdU and pdC bases. In this case, a modified blocking oligonucleotide can include one or many pdC bases. Alternatively, the modified blocking oligonucleotide can include a mixture of pdC and pdU bases and meet the design criteria previously established.

For $T_m$-enhanced oligonucleotides, the preferred number of $T_m$-enhancing groups can vary from about 2% to about 50% of composition of the oligonucleotide. Generally, oligonucleotides serving as blockers will have the same length of one of the two complementary strands of oligonucleotides used in adaptors 102 (for example, from ~15 to about ~75 nucleotides in length). For example, the preferred number of $T_m$-enhancing groups can ranges from 1 to about 25 for a $T_m$-enhanced oligonucleotide as a blocker having 50 nucleotides. Use of a higher fraction of modified residues will incrementally increase $T_m$ and add incremental improvement to the "blocking power" of that reagent. However, the addition of modified residues increases cost of the synthetic oligonucleotide and increases risk of self-dimer and hairpin formation, so judicial use of such groups is recommended. In the majority of NGS applications, only $T_m$-enhanced oligonucleotides as blockers are used to achieve the desired improvements in target enrichment in massively parallel sequencing experiments.

For $T_m$-enhanced oligonucleotides as baits, the preferred number of $T_m$-enhancing groups falls within the same range of percentages as described of the oligonucleotides as blockers. Oligonucleotides serving as unmodified baits will range in size from about 60 to about 200 nucleotides in length, where the most commonly used bait length is about 120 nucleotides in length. By including $T_m$-enhancing groups into oligonucleotides as baits, however, one can use shorter baits that range from about 20 to about 100 nucleotides in length. For certain massively parallel sequencing experiments in NGS applications, a population of hundreds of oligonucleotides is used as baits. So depending upon the number of baits required in certain applications, the use of shorter, $T_m$-enhanced oligonucleotides for each bait candidate within that population can provide economical advantages relative to using unmodified oligonucleotides as baits.

The $T_m$-enhanced oligonucleotides can include additional features, such as internal or terminal modifications. For $T_m$-enhanced oligonucleotides that serve as blockers, recovery of the desired NGS templates following hybrid capture can typically result in co-purification of the blockers. The blockers will be substantially diluted from the population of templates as subsequent steps of PCR amplification and sequencing proceeds. Yet it is desirable to limit the participation of the blockers as primers during these subsequent steps. For this reason, $T_m$-enhanced oligonucleotides can include 3'-terminal groups (for example, 3'-dC; 2',3'-ddC; inverted dT; 3'-spacer C3, among others) that preclude the availability of the blockers to serve as primers for DNA synthesis.

Oligonucleotides that serve as baits include at least one modification that enables selection of desired template:bait hybrids from the population of templates 103 during hybrid capture. One example of a preferred modification includes biotin that can be incorporated into the oligonucleotide bait during chemical synthesis and used with solid support media containing avidin or streptavidin for hybrid selection. Other capture ligands can be employed, such as digoxigenin or other groups as are well known to those with skill in the art.

Preferred examples of $T_m$-enhanced oligonucleotides as blockers include SEQ ID NOS: 2, 3, 4, 5, 6, 7, 8, 10, 11, 12, 13, 14, 15, 16, 18, 19, 21, 22, 24, 25, 27, 28, 30, 32, 34 and 36. These particular sequences, their compositions and methods of use in massively parallel sequencing applications are described in greater detail in the Examples.

Selection of Gene or Gene Products

The selected genes or gene products (also referred to herein as the "target genes or gene products") can include subgenomic intervals comprising intragenic regions or intergenic regions. For example, the subgenomic interval can include an exon or an intron, or a fragment thereof, typically an exon sequence or a fragment thereof. The subgenomic interval can include a coding region or a non-coding region, for example, a promoter, an enhancer, a 5' untranslated region (5' UTR), or a 3' untranslated region (3' UTR), or a fragment thereof. In other embodiments, the subgenomic interval includes a cDNA or a fragment thereof. In other embodiments, the subgenomic interval includes an SNP, for example, as described herein.

In other embodiments, the subgenomic intervals include substantially all exons in a genome, for example, one or more of the subgenomic intervals as described herein (for example, exons from selected genes or gene products of interest (for example, genes or gene products associated with a cancerous phenotype as described herein)). In one embodiment, the subgenomic interval includes a somatic mutation, a germ line mutation or both. In one embodiment, the subgenomic interval includes an alteration, for example, a point or a single mutation, a deletion mutation (for example, an in-frame deletion, an intragenic deletion, a full gene deletion), an insertion mutation (for example, intragenic insertion), an inversion mutation (for example, an intrachromosomal inversion), a linking mutation, a linked insertion mutation, an inverted duplication mutation, a tandem duplication (for example, an intrachromosomal tandem duplication), a translocation (for example, a chromosomal translocation, a non-reciprocal translocation), a rearrangement, a change in gene copy number, or a combination thereof. In certain embodiments, the subgenomic interval constitutes less than 5, 1, 0.5, 0.1%, 0.01%, 0.001% of the coding region of the genome of the tumor cells in a sample. In other embodiments, the subgenomic intervals are not involved in a disease, for example, are not associated with a cancerous phenotype as described herein.

In one embodiment, the target gene or gene product is a biomarker. As used herein, a "biomarker" or "marker" is a gene, mRNA, or protein which can be altered, wherein said alteration is associated with cancer. The alteration can be in amount, structure, and/or activity in a cancer tissue or cancer cell, as compared to its amount, structure, and/or activity, in a normal or healthy tissue or cell (for example, a control), and is associated with a disease state, such as cancer. For example, a marker associated with cancer, or predictive of responsiveness to anti-cancer therapeutics, can have an altered nucleotide sequence, amino acid sequence, chromosomal translocation, intra-chromosomal inversion, copy number, expression level, protein level, protein activity, or methylation status, in a cancer tissue or cancer cell as compared to a normal, healthy tissue or cell. Furthermore, a "marker" includes a molecule whose structure is altered, for example, mutated (contains an mutation), for example, differs from the wild type sequence at the nucleotide or amino acid level, for example, by substitution, deletion, or insertion, when present in a tissue or cell associated with a disease state, such as cancer.

In one embodiment, the target gene or gene product includes a single-nucleotide polymorphism (SNP). In another embodiment, the gene or gene product has a small deletion, for example, a small intragenic deletion (for example, an in-frame or frame-shift deletion). In yet another embodiment, the target sequence results from the deletion of an entire gene. In still another embodiment, the target sequence has a small insertion, for example, a small intragenic insertion. In one embodiment, the target sequence results from an inversion, for example, an intrachromosal inversion. In another embodiment, the target sequence results from an interchromosal translocation. In yet another embodiment, the target sequence has a tandem duplication. In one embodiment, the target sequence has an undesirable feature (for example, high GC content or repeat element). In another embodiment, the target sequence has a portion of nucleotide sequence that cannot itself be successfully targeted, for example, because of its repetitive nature. In one embodiment, the target sequence results from alternative splicing. In another embodiment, the target sequence is chosen from a gene or gene product, or a fragment thereof according to Table 1, 1A, 2, 3, or 4.

Cancers include, but are not limited to, B cell cancer, for example, multiple myeloma, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

In one embodiment, the target gene or gene product is chosen a full length, or a fragment thereof, selected from the group consisting of ABCB1, ABCC2, ABCC4, ABCG2, ABL1, ABL2, AKT1, AKT2, AKT3, ALK, APC, AR, ARAF, ARFRP1, ARID1A, ATM, ATR, AURKA, AURKB, BCL2, BCL2A1, BCL2L1, BCL2L2, BCL6, BRAF, BRCA1, BRCA2, C1orf144, CARD11, CBL, CCND1, CCND2, CCND3, CCNE1, CDH1, CDH2, CDH20, CDH5, CDK4, CDK6, CDK8, CDKN2A, CDKN2B, CDKN2C, CEBPA, CHEK1, CHEK2, CRKL, CRLF2, CTNNB1, CYP1B1, CYP2C19, CYP2C8, CYP2D6, CYP3A4, CYP3A5, DNMT3A, DOT1L, DPYD, EGFR, EPHA3, EPHA5, EPHA6, EPHA7, EPHB1, EPHB4, EPHB6, ERBB2, ERBB3, ERBB4, ERCC2, ERG, ESR1, ESR2, ETV1, ETV4, ETV5, ETV6, EWSR1, EZH2, FANCA, FBXW7, FCGR3A, FGFR1, FGFR2, FGFR3, FGFR4, FLT1, FLT3, FLT4, FOXP4, GATA1, GNA11, GNAQ, GNAS, GPR124, GSTP1, GUCY1A2, HOXA3, HRAS, HSP90AA1, IDH1, IDH2, IGF1R, IGF2R, IKBKE, IKZF1, INHBA, IRS2, ITPA, JAK1, JAK2, JAK3, JUN, KDR, KIT, KRAS, LRP1B, LRP2, LTK, MAN1B1, MAP2K1, MAP2K2, MAP2K4, MCL1, MDM2, MDM4, MEN1, MET, MITF, MLH1, MLL, MPL, MRE11A, MSH2, MSH6, MTHFR, MTOR, MUTYH, MYC, MYCL1, MYCN, NF1, NF2, NKX2-1, NOTCH1, NPM1, NQO1, NRAS, NRP2, NTRK1, NTRK3, PAK3, PAX5, PDGFRA, PDGFRB, PIK3CA, PIK3R1, PKHD1, PLCG1, PRKDC, PTCH1, PTEN, PTPN11, PTPRD, RAFT, RARA, RB1, RET, RICTOR, RPTOR, RUNX1, SLC19A1, SLC22A2, SLCO1B3, SMAD2, SMAD3, SMAD4, SMARCA4, SMARCB1, SMO, SOD2, SOX10, SOX2, SRC, STK11, SULT1A1, TBX22, TET2, TGFBR2, TMPRSS2, TOP1, TP53, TPMT, TSC1, TSC2, TYMS, UGT1A1, UMPS, USP9X, VHL, and WT1.

In one embodiment, the target gene or gene product, or a fragment thereof, has one or more SNPs that are relevant to pharmacogenetics and pharmacogenomics (PGx), for example, drug metabolism and toxicity. Exemplary genes or gene products include, but not limited to, ABCB1, ABCC2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, and UMPS.

In another embodiment, the target gene or gene product, or a fragment thereof, has one or more codons that are associated with cancer. Exemplary genes or gene products include, but not limited to, ABL1 (for example, codon 315), AKT1, ALK, APC (for example, codon 1114, 1338, 1450, and 1556), AR, BRAF (for example, codon 600), CDKN2A, CEBPA, CTNNB1 (for example, codon 32, 33, 34, 37, 41, and 45), EGFR (for example, 719, 746-750, 768, 790, 858, and 861), ERBB2, ESR1, FGFR1, FGFR2, FGFR3, FLT3 (for example, codon 835), HRAS (for example, codon 12, 13, and 61), JAK2 (for example, codon 617), KIT (for example, codon 816), KRAS (for example, codon 12, 13, and 61), MET, MLL, MYC, NF1, NOTCH1, NPM1, NRAS, PDGFRA, PIK3CA (for example, codon 88, 542, 545, 546, 1047, and 1049), PTEN (for example, codon 130, 173, 233, and 267), RB1, RET (for example, codon 918), TP53 (for example, 175, 245, 248, 273, and 306).

In yet another embodiment, the target gene or gene product, or a fragment thereof, are associated with cancer. Exemplary genes or gene products include, but not limited to, ABL2, AKT2, AKT3, ARAF, ARFRP1, ARID1A, ATM, ATR, AURKA, AURKB, BCL2, BCL2A1, BCL2L1, BCL2L2, BCL6, BRCA1, BRCA2, CARD11, CBL, CCND1, CCND2, CCND3, CCNE1, CDH1, CDH2, CDH20, CDH5, CDK4, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDR, LRP1B, LTK, MAP2K1, MAP2K2, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK3, PAK3, PAX5, PDGFRB, PIK3R1, PKHD1, PLCG1, PRKDC, PTCH1, PTPN11, PTPRD, RAFT, RARA, RICTOR, RPTOR, RUNX1, SMAD2, SMAD3, SMAD4, SMARCA4, SMARCB1, SMO, SOX10, SOX2, SRC, STK11, TBX22, TET2, TGFBR2, TMPRSS2, TOP1, TSC1, TSC2, USP9X, VHL, and WT1.

Applications of the foregoing methods include using a library of oligonucleotides containing all known sequence variants (or a subset thereof) of a particular gene or genes for sequencing in medical specimens.

Nucleic Acid Samples

A variety of tissue samples can be the source of the nucleic acid samples used in the present methods. Genomic or subgenomic nucleic acid (for example, DNA or RNA) can be isolated from a subject's sample (for example, a tumor sample, a normal adjacent tissue (NAT), a blood sample, a sample containing circulating tumor cells (CTC) or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, for example, an FFPE block or a frozen sample. The isolating step can include flow-sorting of individual chromosomes; and/or micro-dissecting a subject's sample (for example, a tumor sample, a NAT, a blood sample).

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (that is, sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

In certain embodiments, the nucleic acid is isolated from an aged sample, for example, an aged FFPE sample. The aged sample, can be, for example, years old, for example, 1 year, 2 years, 3 years, 4 years, 5 years, 10 years, 15 years, 20 years, 25 years, 50 years, 75 years, or 100 years old or older.

A nucleic acid sample can be obtained from tissue samples (for example, a biopsy or FFPE sample) of various sizes. For example, the nucleic acid can be isolated from a tissue sample from 5 to 200 µm, or larger. For example, the tissue sample can measure 5 µm, 10 µm, 20 µm, 30 µm, 40 µm, 50 µm, 70 µm, 100 µm, 110 µm, 120 µm, 150 µm or 200 µm or larger.

Protocols for DNA isolation from a tissue sample are provided in Example 1. Additional methods to isolate nucleic acids (for example, DNA) from formaldehyde- or paraformaldehyde-fixed, paraffin-embedded (FFPE) tissues are disclosed, for example, in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), Maxwell® 16 FFPE Plus LEV DNA Purification Kit Technical Manual (Promega Literature #TM349, February 2011), E.Z.N.A.® FFPE DNA Kit Handbook (OMEGA bio-tek, Norcross, Ga., product numbers D3399-00, D3399-01, and D3399-02; June 2009), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. Maxwell® 16 FFPE Plus LEV DNA Purification Kit is used with the Maxwell® 16 Instrument for purification of genomic DNA from 1 to 10 µm sections of FFPE tissue. DNA is purified using silica-clad paramagnetic particles (PMPs), and eluted in low elution volume. The E.Z.N.A.® FFPE DNA Kit uses a spin column and buffer system for isolation of genomic DNA. QIAamp® DNA FFPE Tissue Kit uses QIAamp® DNA Micro technology for purification of genomic and mitochondrial DNA. Protocols for DNA isolation from blood are disclosed, for example, in the Maxwell® 16 LEV Blood DNA Kit and Maxwell 16 Buccal Swab LEV DNA Purification Kit Technical Manual (Promega Literature #TM333, Jan. 1, 2011).

Protocols for RNA isolation are disclosed, for example, in the Maxwell® 16 Total RNA Purification Kit Technical Bulletin (Promega Literature #TB351, August 2009).

The isolated nucleic acid samples (for example, genomic DNA samples) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, that is, where the complexity of the genome is reduced by design. In some embodiments, any selected portion of the genome can be used with the methods described herein. In certain embodiments, the entire exome or a subset thereof is isolated.

Methods featured in the invention can further include isolating a nucleic acid sample to provide a library (for example, a nucleic acid library as described herein). In certain embodiments, the nucleic acid sample includes whole genomic, subgenomic fragments, or both. The isolated nucleic acid samples can be used to prepare nucleic acid libraries. Thus, in one embodiment, the methods featured in the invention further include isolating a nucleic acid sample to provide a library (for example, a nucleic acid library as described herein). Protocols for isolating and preparing libraries from whole genomic or subgenomic fragments are known in the art (for example, Illumina's genomic DNA sample preparation kit). In certain embodiments, the genomic or subgenomic DNA fragment is isolated from a subject's sample (for example, a tumor sample, a normal adjacent tissue (NAT), a blood sample or any normal control)). In one embodiment, the sample (for example, the tumor or NAT sample) is a preserved specimen. For example, the sample is embedded in a matrix, for example, an FFPE block or a frozen sample. In certain embodiments, the isolating step includes flow-sorting of individual chromosomes; and/or microdissecting a subject's sample (for example, a tumor sample, a NAT, a blood sample). In certain embodiments, the nucleic acid sample used to generate the nucleic acid library is less than 5 microgram, less than 1 microgram, or less than 500 ng, less than 200 ng, less than 100 ng, less than 50 ng, less than 10 ng, less than 5 ng, or less than 1 ng.

In still other embodiments, the nucleic acid sample used to generate the library includes RNA or cDNA derived from RNA. In some embodiments, the RNA includes total cellular RNA. In other embodiments, certain abundant RNA sequences (for example, ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample by specific or non-specific nucleic acid amplification methods that are well known to those skilled in the art. In some embodiments, certain embodiments, the nucleic acid sample is amplified, for example, by whole-genome amplification methods such as random-primed strand-displacement amplification.

In other embodiments, the nucleic acid sample is fragmented or sheared by physical or enzymatic methods and ligated to synthetic adaptors, size-selected (for example, by preparative gel electrophoresis) and amplified (for example, by PCR). In other embodiments, the fragmented and adaptor-ligated group of nucleic acids is used without explicit size selection or amplification prior to hybrid selection.

In other embodiments, the isolated DNA (for example, the genomic DNA) is fragmented or sheared. In some embodiments, the library includes less than 50% of genomic DNA, such as a subfraction of genomic DNA that is a reduced representation or a defined portion of a genome, for example, that has been subfractionated by other means. In other embodiments, the library includes all or substantially all genomic DNA.

In some embodiments, the library includes less than 50% of genomic DNA, such as a subfraction of genomic DNA that is a reduced representation or a defined portion of a genome, for example, that has been subfractionated by other means. In other embodiments, the library includes all or substantially all genomic DNA. Protocols for isolating and preparing libraries from whole genomic or subgenomic fragments are known in the art (for example, Illumina's genomic DNA sample preparation kit), and are described herein as Examples 2A, 2B and 3. Alternative methods for DNA shearing are described herein as Example 2B. For example, alternative DNA shearing methods can be more automatable and/or more efficient (for example, with degraded FFPE samples). Alternatives to DNA shearing methods can also be used to avoid a ligation step during library preparation.

The methods described herein can be performed using a small amount of nucleic acids, for example, when the amount of source DNA is limiting (for example, even after whole-genome amplification). In one embodiment, the nucleic acid comprises less than about 5 µg, 4 µg, 3 µg, 2 µg, 1 µg, 0.8 µg, 0.7 µg, 0.6 µg, 0.5 µg, or 400 ng, 300 ng, 200 ng, 100 ng, 50 ng, 10 ng, 5 ng, 1 ng, or less of nucleic acid sample. For example, one can typically begin with 50-100 ng of genomic DNA. One can start with less, however, if one amplifies the genomic DNA (for example, using PCR) before the hybridization step, for example, solution hybridization. Thus it is possible, but not essential, to amplify the genomic DNA before hybridization, for example, solution hybridization.

The nucleic acid sample used to generate the library can also include RNA or cDNA derived from RNA. In some embodiments, the RNA includes total cellular RNA. In other embodiments, certain abundant RNA sequences (for example, ribosomal RNAs) have been depleted. In other embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample by specific or non-specific nucleic acid amplification methods that are known to those skilled in the art. The nucleic acid sample can be amplified, for example, by whole-genome amplification methods such as random-primed strand-displacement amplification.

The nucleic acid sample can be fragmented or sheared by physical or enzymatic methods as described herein, and ligated to synthetic adaptors, size-selected (for example, by preparative gel electrophoresis) and amplified (for example, by PCR). The fragmented and adaptor-ligated group of nucleic acids is used without explicit size selection or amplification prior to hybrid selection.

Library Members

"Member" or "library member" or other similar term, as used herein, refers to a nucleic acid molecule, for example, DNA or RNA, that is the member of a library (or "library-catch"). The library member can be one or more of a tumor member, a reference member, or a PGx member as described herein. Typically, a member is a DNA molecule, for example, a genomic DNA or cDNA, molecule. A member can be fragmented, for example, enzymatically or by shearing, genomic DNA. Members can comprise a nucleotide sequence from a subject and can also comprise a nucleotide sequence not derived from the subject, for example, primers or adaptors (for example, for PCR amplification or for sequencing), or sequences that allow for identification of a sample, for example, "barcode" sequences.

As used herein, "target member" refers to a nucleic acid molecule that one desires to isolate from the nucleic acid library. In one embodiment, the target members can be a tumor member, a reference member, or a PGx member as described herein. The members that are actually selected from the nucleic acid library are referred to herein as the "library catch." In one embodiment, the library-catch includes a selection or enrichment of members of the library, for example, the enriched or selected output of a library after one or more rounds of hybrid capture as described herein.

The target members may be a subgroup of the library, that is, that not all of the library members are selected by any particular use of the processes described herein. In other embodiments, the target members are within a desired target region. For example, the target members may in some embodiments be a percentage of the library members that is as low as 10% or as high as 95%-98% or higher. In one embodiment, the library catch includes at least about 20%, 30%, 40%, 50%, 60%, 70%, 75%, 80%, 85%, 90%, 95%, 98%, 99%, 99.9% or more of the target members. In another embodiment, the library contains 100% of the target members.

In one embodiment, the purity of the library catch (percentage of reads that align to the targets) is at least about 20%, 30%, 40%, 50%, 60%, 70%, 75%, 80%, 85%, 90%, 95%, 98%, 99%, 99.9% or more.

The target members (or the library catch) obtained from genomic DNA can include a small fraction of the total genomic DNA, such that it includes less than about 0.0001%, at least about 0.0001%, at least about 0.001%, at least about 0.01%, or at least about 0.1% of genomic DNA, or a more significant fraction of the total genomic DNA, such that it includes at least about 1%, 2%, 3%, 4%, 5%, 6%, 7%, 8%, 9%, or 10% of genomic DNA, or more than 10% of genomic DNA.

In one embodiment, the target members (or the library catch) are selected from a complex mixture of genome. For example, the selection of the DNA from one cell type (for example, cancer cells) from a sample containing the DNA from other cell types (for example, normal cells). In such applications, the target member can include less than 0.0001%, at least 0.0001%, at least about 0.001%, at least about 0.01%, or at least about 0.1% of the total complexity of the nucleic acid sequences present in the complex sample, or a more significant fraction such that it includes at least about 1%, 2%, 5%, 10% or more than 10% of the total complexity of nucleic acid sequences present in the complex sample.

In one embodiment, the target member (or the library catch) selected by the methods described herein (for example, solution hybridization selection methods) include all or a portion of exons in a genome, such as greater than about 0.1%, 1%, 2%, 5%, 10%, 20%, 30%, 40%, 50%, 60%, 70%, 80%, 90%, or 95% of the genomic exons. In another embodiment, the target member (or the library catch) can be a specific group of exons, for example, at least about 100, 200, 300, 400, 500, 600, 700, 800, 900, or 1000 particular exons, for example, exons associated with particular diseases such as cancer. In yet another embodiment, the target member (or the library catch) contains exons or other parts of selected genes of interest. The use of specific bait sequences allows the practitioner to select target sequences (ideal set of sequences selected) and subgroups of nucleic acids (actual set of sequences selected) containing as many or as few exons (or other sequences) from a group of nucleic acids for a particular selection.

In one embodiment, the target member (or the library catch) includes a set of cDNAs. Capturing cDNAs can be used, for example, to find splice variants, and to identify fusion transcripts (for example, from genomic DNA translocations). In another embodiment, the target member (and the library catch) is used to find single base changes and other sequence changes expressed in the RNA fraction of a cell, tissue, or organ, for example, in a tumor.

The target member (or the library catch) (for example, exons, cDNAs and other sequences) can be related or unrelated as desired. For example, selected target member (and the library catch) can be obtained from a group of nucleic acids that are genes involved in a disease, such as a group of genes implicated in one or more diseases such as cancers, a group of nucleic acids containing specific SNPs.

In one embodiment, a portion or all of the library members comprises a non-target adaptor sequence. The adaptor sequence can be useful, for example, for a sequencing method (for example, an NGS method), for amplification, for reverse transcription, or for cloning into a vector. The adaptor sequence can be located at one or both ends. Adaptors can be ligated at the 5'- or 3'-3 end of the library insert, for example, as described in the appended Examples. Adaptors can be obtained from commercial suppliers, such as NimbleGen (Roche), Integrated DNA Technologies (IDT) for DNA oligos, or Agilent Technologies.

Blocking oligonucleotide complementary to the adaptors can be designed and prepared by methods known in the art, for example, methods of oligo synthesis. Blocking oligonucleotides can also be obtained from commercial suppliers, such as NimbleGen (Roche), Integrated DNA Technologies (IDT) for DNA oligos, or Agilent Technologies. The length and composition of these adaptors can be adjusted to, for example, modify the binding interaction (for example, a $T_m$ as described herein) with the complementary adaptor following methods known in the art.

The blocking oligonucleotides can include DNA, RNA or a combination of both. The DNA or RNA oligonucleotides can be naturally- or non-naturally-occurring. In certain embodiments, the blocking oligonucleotides include one or more non-naturally-occurring nucleotide to, for example, increase melting temperature. Exemplary non-naturally occurring oligonucleotides include modified DNA or RNA nucleotides. An exemplary modified RNA nucleotide is a locked nucleic acid (LNA), wherein the ribose moiety of an LNA nucleotide is modified with an extra bridge connecting the 2' oxygen and 4' carbon (Kaur, H; Arora, A; Wengel, J; Maiti, S; Arora, A.; Wengel, J.; Maiti, S. (2006). "Thermodynamic, Counterion, and Hydration Effects for the Incorporation of Locked Nucleic Acid Nucleotides into DNA Duplexes". *Biochemistry* 45 (23): 7347-55). Other modified exemplary DNA and RNA nucleotides include, but are not limited to, peptide nucleic acid (PNA) composed of repeating N-(2-aminoethyl)-glycine units linked by peptide bonds (Egholm, M. et al. (1993) *Nature* 365 (6446): 566-8); a DNA or RNA oligonucleotide modified to capture low GC regions; a bicyclic nucleic acid (BNA) or a crosslinked oligonucleotide; a modified 5-methyl deoxycytidine; and 2,6-diaminopurine. Other modified DNA and RNA nucleotides are known in the art.

Design and Construction of Baits

A bait can be a nucleic acid molecule, for example, a DNA or RNA molecule, which can hybridize to (for example, be complementary to), and thereby allow capture of a target nucleic acid. In one embodiment, a bait is an RNA molecule. In other embodiments, a bait includes a binding entity, for example, an affinity tag, that allows capture and separation, for example, by binding to a binding entity, of a hybrid formed by a bait and a nucleic acid hybridized to the bait. In one embodiment, a bait is suitable for solution phase hybridization.

Typically, RNA molecules are used as bait sequences. A RNA-DNA duplex is more stable than a DNA-DNA duplex, and therefore provides for potentially better capture of nucleic acids.

RNA baits can be made as described elsewhere herein, using methods known in the art including, but not limited to, de novo chemical synthesis and transcription of DNA molecules using a DNA-dependent RNA polymerase. In one embodiment, the bait sequence is produced using known nucleic acid amplification methods, such as PCR, for example, using human DNA or pooled human DNA samples as the template. The oligonucleotides can then be converted to RNA baits. In one embodiment, in vitro transcription is used, for example, based on adding an RNA polymerase promoter sequence to one end of the oligonucleotide. In one embodiment, the RNA polymerase promoter sequence is added at the end of the bait by amplifying or reamplifying the bait sequence, for example, using PCR or other nucleic acid amplification methods, for example, by tailing one primer of each target-specific primer pairs with an RNA promoter sequence. In one embodiment, the RNA polymerase is a T7 polymerase, a SP6 polymerase, or a T3 polymerase. In one embodiment, RNA bait is labeled with a tag, for example, an affinity tag. In one embodiment, RNA bait is made by in vitro transcription, for example, using biotinylated UTP. In another embodiment, RNA bait is produced without biotin and then biotin is crosslinked to the RNA molecule using methods well known in the art, such as psoralen crosslinking. In one embodiment, the RNA bait is an RNase-resistant RNA molecule, which can be made, for example, by using modified nucleotides during transcription to produce RNA molecule that resists RNase degradation. In one embodiment, the RNA bait corresponds to only one strand of the double-stranded DNA target. Typically, such RNA baits are not self-complementary and are more effective as hybridization drivers.

The bait sets can be designed from reference sequences, such that the baits are optimal for selecting targets of the reference sequences. In some embodiments, bait sequences are designed using a mixed base (for example, degeneracy). For example, the mixed base(s) can be included in the bait sequence at the position(s) of a common SNP or mutation, to optimize the bait sequences to catch both alleles (for example, SNP and non-SNP; mutant and non-mutant). In some embodiments, all known sequence variations (or a subset thereof) can be targeted with multiple oligonucleotide baits, rather than by using mixed degenerate oligonucleotides.

In certain embodiments, the bait set includes an oligonucleotide (or a plurality of oligonucleotides) between about 100 nucleotides and 300 nucleotides in length. Typically, the bait set includes an oligonucleotide (or a plurality of oligonucleotides) between about 130 nucleotides and 230 nucleotides, or about 150 and 200 nucleotides, in length. In other embodiments, the bait set includes an oligonucleotide (or a plurality of oligonucleotides) between about 300 nucleotides and 1000 nucleotides in length.

In some embodiments, the target member-specific sequences in the oligonucleotide is between about 40 and 1000 nucleotides, about 70 and 300 nucleotides, about 100 and 200 nucleotides in length, typically between about 120 and 170 nucleotides in length.

In some embodiments, the bait set includes a binding entity. The binding entity can be an affinity tag on each bait sequence. In some embodiments, the affinity tag is a biotin molecule or a hapten. In certain embodiments, the binding entity allows for separation of the bait/member hybrids from the hybridization mixture by binding to a partner, such as an avidin molecule, or an antibody that binds to the hapten or an antigen-binding fragment thereof.

In other embodiments, the oligonucleotides in the bait set contains forward and reverse complemented sequences for the same target member sequence whereby the oligonucleotides with reverse-complemented member-specific sequences also carry reverse complemented universal tails. This can lead to RNA transcripts that are the same strand, that is, not complementary to each other.

In other embodiments, the bait set includes oligonucleotides that contain degenerate or mixed bases at one or more positions. In still other embodiments, the bait set includes multiple or substantially all known sequence variants present in a population of a single species or community of organisms. In one embodiment, the bait set includes multiple or substantially all known sequence variants present in a human population.

In other embodiments, the bait set includes cDNA sequences or is derived from cDNAs sequences. In other embodiments, the bait set includes amplification products (for example, PCR products) that are amplified from genomic DNA, cDNA or cloned DNA.

In other embodiments, the bait set includes RNA molecules. In some embodiments, the set includes chemically, enzymatically modified, or in vitro transcribed RNA molecules, including but not limited to, those that are more stable and resistant to RNase.

In yet other embodiments, the baits are produced by methods described in US 2010/0029498 and Gnirke, A. et al. (2009) *Nat Biotechnol.* 27(2):182-189, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Accordingly, a method of making the aforesaid bait set is provided. The method includes selecting one or more target specific bait oligonucleotide sequences (for example, one or more mutation capturing, reference or control oligonucleotide sequences as described herein); obtaining a pool of target specific bait oligonucleotide sequences (for example, synthesizing the pool of target specific bait oligonucleotide sequences, for example, by microarray synthesis); and optionally, amplifying the oligonucleotides to produce the bait set.

In other embodiments, the methods further include amplifying (for example, by PCR) the oligonucleotides using one or more biotinylated primers. In some embodiments, the oligonucleotides include a universal sequence at the end of each oligonucleotide attached to the microarray. The methods can further include removing the universal sequences from the oligonucleotides. Such methods can also include removing the complementary strand of the oligonucleotides, annealing the oligonucleotides, and extending the oligonucleotides. In some of these embodiments, the methods for amplifying (for example, by PCR) the oligonucleotides use one or more biotinylated primers. In some embodiments, the method further includes size selecting the amplified oligonucleotides.

In one embodiment, an RNA bait set is made. The methods include producing a set of bait sequences according to the methods described herein, adding a RNA polymerase promoter sequence at one end of the bait sequences, and synthesizing RNA sequences using RNA polymerase. The RNA polymerase can be chosen from a T7 RNA polymerase, an SP6 RNA polymerase or a T3 RNA polymerase. In other embodiments, the RNA polymerase promoter sequence is added at the ends of the bait sequences by amplifying (for example, by PCR) the bait sequences. In embodiments where the bait sequences are amplified by PCR with specific primer pairs out of genomic or cDNA, adding an RNA promoter sequence to the 5' end of one of the two specific primers in each pair will lead to a PCR product that can be transcribed into a RNA bait using standard methods.

In other embodiments, bait sets can be produced using human DNA or pooled human DNA samples as the template. In such embodiments, the oligonucleotides are amplified by polymerase chain reaction (PCR). In other embodiments, the amplified oligonucleotides are reamplified by rolling circle amplification or hyperbranched rolling circle amplification. The same methods also can be used to produce bait sequences using human DNA or pooled human DNA samples as the template. The same methods can also be used to produce bait sequences using subfractions of a genome obtained by other methods, including but not limited to restriction digestion, pulsed-field gel electrophoresis, flow-sorting, CsCl density gradient centrifugation, selective kinetic reassociation, microdissection of chromosome preparations and other fractionation methods known to those skilled in the art.

In certain embodiments, the number of baits in the bait set is less than 1,000. In other embodiments, the number of baits in the bait set is greater than 1,000, greater than 5,000, greater than 10,000, greater than 20,000, greater than 50,000, greater than 100,000, or greater than 500,000.

The length of the bait sequence can be between about 70 nucleotides and 1000 nucleotides. In one embodiment, the bait length is between about 100 and 300 nucleotides, 110 and 200 nucleotides, or 120 and 170 nucleotides, in length. In addition to those mentioned above, intermediate oligonucleotide lengths of about 70, 80, 90, 100, 110, 120, 130, 140, 150, 160, 170, 180, 190, 200, 210, 220, 230, 240, 250, 300, 400, 500, 600, 700, 800, and 900 nucleotides in length can be used in the methods described herein. In some embodiments, oligonucleotides of about 70, 80, 90, 100, 110, 120, 130, 140, 150, 160, 170, 180, 190, 200, 210, 220, or 230 bases can be used.

Each bait sequence can include a target-specific (for example, a member-specific) bait sequence and universal tails on one or both ends. As used herein, the term "bait sequence" can refer to the target-specific bait sequence or the entire oligonucleotide including the target-specific "bait sequence" and other nucleotides of the oligonucleotide. The target-specific sequences in the baits are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length, typically 120 nucleotides in length. Intermediate lengths in addition to those mentioned above also can be used in the methods described herein, such as target-specific sequences of about 40, 50, 60, 70, 80, 90, 100, 110, 120, 130, 140, 150, 160, 170, 180, 190, 200, 210, 220, 230, 240, 250, 300, 400, 500, 600, 700, 800, and 900 nucleotides in length, as well as target-specific sequences of lengths between the above-mentioned lengths.

In one embodiment, the bait is an oligomer (for example, comprised of RNA oligomers, DNA oligomers, or a combination thereof) about 50 to 200 nucleotides in length (for example, about 50, 60, 80, 90, 100, 110, 120, 130, 140, 150, 160, 170, 190, or 200 nucleotides in length).

In one embodiment, each bait oligomer includes about 120 to 170, or typically, about 120 nucleotides, which are a target specific bait sequence. The bait can comprise additional non-target specific nucleotide sequences at one or both ends. The additional nucleotide sequences can be used, for example, for PCT amplification or as a bait identifier. In certain embodiments, the bait additionally comprises a binding entity as described herein (for example, a capture tag such as a biotin molecule). The binding entity, for example, biotin molecule, can be attached to the bait, for example, at the 5'-, 3'-end, or internally (for example, by incorporating a biotinylated nucleotide), of the bait. In one embodiment, the biotin molecule is attached at the 5'-end of the bait.

In one exemplary embodiment, the bait is an oligonucleotide about 150 nucleotides in length, of which 120 nucleotides are target-specific "bait sequence". The other 30 nucleotides (for example, 15 nucleotides on each end) are universal arbitrary tails used for PCR amplification. The tails can be any sequence selected by the user. For example, the pool of synthetic oligonucleotides can include oligonucleotides of the sequence of 5'-ATCGCACCAGCGTGTN$_{120}$CACTGCGGCTCCTCA-3' (SEQ ID NO:81) with N$_{120}$ indicating the target-specific bait sequences.

The bait sequences described herein can be used for selection of exons and short target sequences. In one embodiment, the bait is between about 100 nucleotides and 300 nucleotides in length. In another embodiment, the bait is between about 130 nucleotides and 230 nucleotides in length. In yet another embodiment, the bait is between about 150 nucleotides and 200 nucleotides in length. The target-specific sequences in the baits, for example, for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

In some embodiments, long oligonucleotides can minimize the number of oligonucleotides necessary to capture the target sequences. For example, one oligonucleotide can be used per exon. It is known in the art that the mean and median lengths of the protein-coding exons in the human genome are about 164 and 120 base pairs, respective. Longer baits can be more specific and capture better than shorter ones. As a result, the success rate per oligonucleotide bait sequence is higher than with short oligonucleotides. In one embodiment, the minimum bait-covered sequence is the size of one bait (for example, 120-170 bases), for example, for capturing exon-sized targets. In determining the length of the bait sequences, one also can take into consideration that unnecessarily long baits catch more unwanted DNA directly adjacent to the target. Longer oligonucleotide baits can also be more tolerant to polymorphisms in the targeted region in the DNA samples than shorter ones. Typically, the bait sequences are derived from a reference genome sequence. If the target sequence in the actual DNA sample deviates from the reference sequence, for example if it contains a single-nucleotide polymorphism (SNP), it can hybridize less efficiently to the bait and may therefore be under-represented or completely absent in the sequences hybridized to the bait sequences. Allelic drop-outs due to SNPs can be less likely with the longer synthetic baits molecules for the reason that a single mispair in, for example, 120 to 170 bases can have less of an effect on hybrid stability than a single mismatch in, 20 or 70 bases, which are the typical bait or primer lengths in multiplex amplification and microarray capture, respectively.

For selection of targets that are long compared to the length of the capture baits, such as genomic regions, bait sequence lengths are typically in the same size range as the baits for short targets mentioned above, except that there is no need to limit the maximum size of bait sequences for the sole purpose of minimizing targeting of adjacent sequences. Alternatively, oligonucleotides can be titled across a much wider window (typically 600 bases). This method can be used to capture DNA fragments that are much larger (for example, about 500 bases) than a typical exon. As a result, much more unwanted flanking non-target sequences are selected.

Bait Synthesis

The baits can be any type of oligonucleotide, for example, DNA or RNA. The DNA or RNA baits ("oligo baits") can be synthesized individually, or can be synthesized in an array, as a DNA or RNA bait set ("array baits"). An oligo bait, whether provided in an array format, or as an isolated oligo, is typically single stranded. The bait can additionally comprise a binding entity as described herein (for example, a capture tag such as a biotin molecule). The binding entity, for example, biotin molecule, can be attached to the bait, for example, at the 5' or 3'-end of the bait, typically, at the 5'-end of the bait.

In some embodiments, individual oligo baits can be added to an array bait set. In these cases, the oligo baits can be designed to target the same areas as those targeted by the array baits, and additional oligo baits can be designed and added to the standard array baits to achieve enhanced, or more thorough, coverage in certain areas of the genome. For example, additional oligo baits can be designed to target areas of poor sequencing coverage following an initial sequencing round with a standard array bait set. In some embodiments, the oligo baits are designed to have a tiled effect over the area of coverage for the array bait set, or a tiled effect over the area of coverage for other oligo baits.

In one embodiment, the individual oligo baits are DNA oligos that are used to supplement an RNA or DNA oligo array bait set, or a combination thereof (for example, a commercially available array bait set). In other embodiments, individual oligo baits are DNA oligos that are used to supplement an RNA or DNA oligo bait set, or a combination thereof, that is a collection of individually designed and synthesized oligos. In one embodiment, the individual oligo baits are RNA oligos that are used to supplement an RNA or DNA oligo array bait set, or a combination thereof (for example, a commercially available array bait set). In other embodiments individual oligo baits are RNA oligos that are used to supplement an RNA or DNA oligo bait set, or a combination thereof, that is a collection of individually designed and synthesized oligos.

In yet another embodiment, the individual oligo baits are DNA oligos that are used to supplement a DNA oligo array bait set (for example, a commercially available array bait set), and in other embodiments individual oligo baits are DNA oligos that are used to supplement a DNA oligo bait set that is a collection of individually designed and synthesized oligos.

In yet another embodiment, the individual oligo baits are DNA oligos that are used to supplement a RNA oligo array bait set (for example, a commercially available array bait set), and in other embodiments individual oligo baits are DNA oligos that are used to supplement a RNA oligo bait set that is a collection of individually designed and synthesized oligos.

In yet another embodiment, the individual oligo baits are RNA oligos that are used to supplement a RNA oligo array bait set (for example, a commercially available array bait set), and in other embodiments individual oligo baits are RNA oligos that are used to supplement a RNA oligo bait set that is a collection of individually designed and synthesized oligos.

In yet another embodiment, the individual oligo baits are RNA oligos that are used to supplement a DNA oligo array bait set (for example, a commercially available array bait set), and in other embodiments individual oligo baits are RNA oligos that are used to supplement a DNA oligo bait set that is a collection of individually designed and synthesized oligos.

In one embodiment, oligo baits are designed to target sequences in genes of particular interest, such as to achieve increased sequencing coverage of expanded gene sets.

In another embodiment, oligo baits are designed to target sequences representing a subset of the genome, and are mixed and used as a pool instead of, or in addition to, array baits.

In one embodiment, a first set of oligo baits is designed to target areas of poor sequencing coverage, and a second set of oligo baits is designed to target genes of particular interest. Then both sets of oligo baits are combined and, optionally, mixed with a standard array bait set to be used for sequencing.

In one embodiment, an oligo bait mix is used, for example, to simultaneously sequence targeted gene panels and to screen a panel of single nucleotide polymorphisms (SNPs) created, such as for the purpose of looking for genomic rearrangements and copy number alterations (equivalent of arrayed CGH (Comparative Genomic Hybridization)). For example, a panel of SNPs can first be created by the array method as array baits, and then additional DNA oligonucleotide baits can be designed to target areas of poor sequencing coverage to a targeted set of genes. Sequencing of the collection of SNPs can then be repeated with the original array bait set plus the additional oligo baits to achieve total intended sequencing coverage.

In some embodiments, oligo baits are added to a standard array bait set to achieve more thorough sequencing coverage. In one embodiment, oligo baits are designed to target areas of poor sequencing coverage following an initial sequencing round with a standard array bait set.

In another embodiment, oligo baits are designed to target sequences in genes of particular interest. These oligo baits can be added to a standard array bait set or to existing oligo/array hybrid bait sets to achieve, for example, increased sequencing coverage of expanded gene sets without going through an entire array bait pool re-design cycle.

Oligo baits can be obtained from a commercial source, such as NimbleGen (Roche) or Integrated DNA Technologies (IDT) for DNA oligos. Oligos can also be obtained from Agilent Technologies. Protocols for enrichment are publicly available, for example, SureSelect Target.

Enrichment System.

Baits can be produced by methods described in US 2010/0029498 and Gnirke, A. et al. (2009) *Nat Biotechnol.* 27(2):182-189, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

For example, a large collection of baits can be generated from a custom pool of synthetic oligonucleotides originally synthesized on an oligonucleotide array, for example, an Agilent programmable DNA microarray. Accordingly, at least about 2,500, 5,000, 10,000, 20,000, 3,000, 40,000, 50,000, or 60,000 unique oligonucleotides can be synthesized simultaneously.

In one embodiment, a minimal set of unique oligonucleotides are chosen and additional copies (for example, alternating between reverse complements and the original forward strands) are added until the maximum capacity of the synthetic oligonucleotide array has been reached, for example, for baits designed to capture a pre-selected set of targets (for example, pre-selected set of exons). In another embodiment, the target is represented at least twice, for example, by synthesizing both forward and reverse-complemented oligonucleotides. Synthesizing forward and reverse-complemented oligonucleotides for a given target can provide better redundancy at the synthesis step than synthesizing the very same sequence twice. In yet another embodiment, the PCR product or bait is the same for forward and reverse-complemented oligonucleotides.

The oligonucleotides from the chips are synthesized once, and then can be amplified to create a set of oligonucleotides that can be used many times. This approach generates a universal reagent that can be used as bait for a large number of selection experiments, thereby amortizing the chip cost to be a small fraction of the sequencing cost. Alternatively, bait sequences can be produced using known nucleic acid amplification methods, such as PCR, using human DNA or pooled human DNA samples as the template.

Following synthesis, the oligonucleotides can be liberated (for example, stripped) from the array by chemical cleavage followed by removal of the protection groups and PCR amplified into double-stranded DNA using universal primers. A second round of PCR can be used to incorporate a promoter (for example, T7, SP6, or T3 promoter) site into the amplicon, which is used to transcribe the DNA into single-stranded RNA.

In one embodiment, the baits are tiled along the sequences (for example, exons) without gaps or overlaps. For example, the baits can start at the "left"-most coding base in the strand of the reference genome sequence shown in the UCSC genome browser (for example, 5' to 3' or 3' to 5' along the coding sequence, depending on the orientation of the gene) and additional baits are added until all coding bases are covered. In another embodiment, at least two, three, four, or five baits for each target are designed, overlapping by at least about 15, 30, 45, or 60 bases. After oligonucleotide synthesis and PCR amplification using universal primers, one of the tails of the double-stranded DNA can be enzymatically followed by the degradation of one of the strands. The single-stranded products can be hybridized, made fully double stranded by filling in, and amplified by PCR. In this manner, it is possible to produce baits that contain at least about 300, 400, 500, or 600 contiguous target-specific bases which is more than can be chemically synthesized. Such long baits can be useful for applications that require high specificity and sensitivity, or for applications that do not necessarily benefit from limiting the length of the baits (for example, capture of long contiguous genomic regions).

In one embodiment, the coverage of each target can be assessed and targets that yield similar coverage can be grouped. Distinct sets of bait sequences can be created for each group of targets, further improving the representation. In another embodiment, oligonucleotides from microarray chips are tested for efficacy of hybridization, and a production round of microarray chips ordered on which oligonucleotides are grouped by their capture efficacy, thus compensating for variation in bait efficacy. In yet another embodiment, oligonucleotide pools can be aggregated to form a relatively small number of composite pools, such that there is little variation in capture efficacy among them.

The baits described herein can be labeled with a tag, for example, an affinity tag. Exemplary affinity tags include, but not limited to, biotin molecules, magnetic particles, haptens, or other tag molecules that permit isolation of baits tagged with the tag molecule. Such molecules and methods of attaching them to nucleic acids (for example, the baits used in the methods disclosed herein) are well known in the art. Exemplary methods for making biotinylated baits are described, for example, in Gnirke A. et al., *Nat. Biotechnol.* 2009; 27(2):182-9, which is incorporated herein by reference in entirety.

Also known in the art are molecules, particles or devices that bind to or are capable of separating the set of tagged baits from the hybridization mixture. In one embodiment, the molecule, particle, or device binds to the tag (for example, the affinity tag). In one embodiment, the molecule, particle, or device is an avidin molecule, a magnet, or an antibody or antigen-binding fragment thereof. In one embodiment, the tagged baits are separated using a magnetic bead coated with streptavidin molecules.

Exemplary methods to prepare oligonucleotide libraries are described, for example, in Gnirke A. et al., *Nat. Biotechnol.* 2009; 27(2):182-9, and Blumenstiel B. et al., *Curr. Protoc. Hum. Genet.* 2010; Chapter 18: Unit 18.4, which are incorporated herein by reference in entirety.

The methods and compositions featured in the invention involve tuning the relative sequence coverage of each bait set/target category. Methods for implementing differences in relative sequence coverage in bait design include one or more of:

(i) Differential representation of different bait sets—The bait set design to capture a given target (for example, a target member) can be included in more/fewer number of copies to enhance/reduce relative target coverage depths;

(ii) Differential overlap of bait subsets—The bait set design to capture a given target (for example, a target member) can include a longer or shorter overlap between neighboring baits to enhance/reduce relative target coverage depths;

(iii) Differential bait parameters—The bait set design to capture a given target (for example, a target member) can include sequence modifications/shorter length to reduce capture efficiency and lower the relative target coverage depths;

(iv) Mixing of different bait sets—Bait sets that are designed to capture different target sets can be mixed at different molar ratios to enhance/reduce relative target coverage depths;

(v) Using different types of oligonucleotide bait sets—In certain embodiments, the bait set can include:
  (a) one or more chemically (for example, non-enzymatically) synthesized (for example, individually synthesized) baits,
  (b) one or more baits synthesized in an array,
  (c) one or more enzymatically prepared, for example, in vitro transcribed, baits;
  (d) any combination of (a), (b) and/or (c),
  (e) one or more DNA oligonucleotides (for example, a naturally or non-naturally occurring DNA oligonucleotide),
  (f) one or more RNA oligonucleotides (for example, a naturally or non-naturally occurring RNA oligonucleotide),
  (g) a combination of (e) and (f), or
  (h) a combination of any of the above.

The different oligonucleotide combinations can be mixed at different ratios, for example, a ratio chosen from 1:1, 1:2, 1:3, 1:4, 1:5, 1:10, 1:20, 1:50; 1:100, 1:1000, or the like. In one embodiment, the ratio of chemically-synthesized bait to array-generated bait is chosen from 1:5, 1:10, or 1:20. The DNA or RNA oligonucleotides can be naturally- or non-naturally-occurring. In certain embodiments, the baits include one or more non-naturally-occurring nucleotide to, for example, increase melting temperature. Exemplary non-naturally occurring oligonucleotides include modified DNA or RNA nucleotides. An exemplary modified RNA nucleotide is a locked nucleic acid (LNA), wherein the ribose moiety of an LNA nucleotide is modified with an extra bridge connecting the 2' oxygen and 4' carbon (Kaur, H; Arora, A; Wengel, J; Maiti, S; Arora, A.; Wengel, J.; Maiti, S. (2006). "Thermodynamic, Counterion, and Hydration Effects for the Incorporation of Locked Nucleic Acid Nucleotides into DNA Duplexes". *Biochemistry* 45 (23): 7347-55). Other modified exemplary DNA and RNA nucleotides include, but are not limited to, peptide nucleic acid (PNA) composed of repeating N-(2-aminoethyl)-glycine units linked by peptide bonds (Egholm, M. et al. (1993) *Nature* 365 (6446): 566-8); a DNA or RNA oligonucleotide modified to capture low GC regions; a bicyclic nucleic acid (BNA) or a crosslinked oligonucleotide; a modified 5-methyl deoxycytidine; and 2,6-diaminopurine. Other modified DNA and RNA nucleotides are known in the art.

In certain embodiments, a substantially uniform or homogeneous coverage of a target sequence (for example, a target member) is obtained. For example, within each bait set/target category, uniformity of coverage can be optimized by modifying bait parameters, for example, by one or more of:

(i) Increasing/decreasing bait representation or overlap can be used to enhance/reduce coverage of targets (for example, target members), which are under/over-covered relative to other targets in the same category;

(ii) For low coverage, hard to capture target sequences (for example, high GC content sequences), expand the region being targeted with the bait sets to cover, for example, adjacent sequences (for example, less GC-rich adjacent sequences);

(iii) Modifying a bait sequence can be made to reduce secondary structure of the bait and enhance its efficiency of selection;

(iv) Modifying a bait length can be used to equalize melting hybridization kinetics of different baits within the same category. Bait length can be modified directly (by producing baits with varying lengths) or indirectly (by producing baits of consistent length, and replacing the bait ends with arbitrary sequence);

(v) Modifying baits of different orientation for the same target region (that is, forward and reverse strand) may have different binding efficiencies. The bait set with either orientation providing optimal coverage for each target may be selected;

(vi) Modifying the amount of a binding entity, for example, a capture tag (for example, biotin), present on each bait may affect its binding efficiency. Increasing/decreasing the tag level of baits targeting a specific target may be used to enhance/reduce the relative target coverage;

(vii) Modifying the type of nucleotide used for different baits can be altered to affect binding affinity to the target, and enhance/reduce the relative target coverage; or (viii) Using modified oligonucleotide baits, for example, having more stable base pairing, can be used to equalize melting hybridization kinetics between areas of low or normal GC content relative to high GC content.

For example, different types of oligonucleotide bait sets can be used.

In one embodiment, the value for efficiency of selection is modified by using different types of bait oligonucleotides to encompass pre-selected target regions. For example, a first bait set (for example, an array-based bait set comprising 10,000-50,000 RNA or DNA baits) can be used to cover a large target area (for example, 1-2 MB total target area). The first bait set can be spiked with a second bait set (for example, individually synthesized RNA or DNA bait set comprising less than 5,000 baits) to cover a pre-selected target region (for example, selected subgenomic intervals of interest spanning, for example, 250 kb or less, of a target area) and/or regions of higher secondary structure, for example, higher GC content. Selected subgenomic intervals of interest may correspond to one or more of the genes or gene products described herein, or a fragment thereof. The second bait set may include about 2,000-5,000 baits depending on the bait overlap desired. In yet other embodiments, the second bait set can include selected oligo baits (for example, less than 400, 200, 100, 50, 40, 30, 20, 10 baits) spiked into the first bait set. The second bait set can be mixed at any ratio of individual oligo baits. For example, the second bait set can include individual baits present as a 1:1 equimolar ratio. Alternatively, the second bait set can include individual baits present at different ratio (for example, 1:5, 1:10, 1:20), for example, to optimize capture of certain targets (for example, certain targets can have a 5-10× of the second bait compared to other targets).

Hybridization Conditions

The methods featured in the invention include the step of contacting the library (for example, the nucleic acid library) with a plurality of baits to provide a selected library catch. The contacting step can be effected in solution hybridization. In certain embodiments, the method includes repeating the hybridization step by one or more additional rounds of solution hybridization. In some embodiments, the methods further include subjecting the library catch to one or more additional rounds of solution hybridization with the same or different collection of baits.

In other embodiments, the methods featured in the invention further include amplifying the library catch (for example, by PCR). In other embodiments, the library catch is not amplified.

In yet other embodiments, the methods further include the step of subjecting the library catch to genotyping, thereby identifying the genotype of the selected nucleic acids.

More specifically, a mixture of several thousand bait sequences can effectively hybridize to complementary nucleic acids in a group of nucleic acids and that such hybridized nucleic acids (the subgroup of nucleic acids) can be effectively separated and recovered. In one embodiment, the methods described herein use a set of bait sequences containing more than about 1,000 bait sequences, more than about 2,000 bait sequences, more than about 3,000 bait sequences, more than about 4,000 bait sequences, more than about 5,000 bait sequences, more than about 6,000 bait sequences, more than about 7,000 bait sequences, more than about 8,000 bait sequences, more than about 9,000 bait sequences, more than about 10,000 bait sequences, more than about 15,000 bait sequences, more than about 20,000 bait sequences, more than about 30,000 bait sequences, more than about 40,000 bait sequences, or more than about 50,000 bait sequences.

In some embodiments, the selection process is repeated on the selected subgroup of nucleic acids, for example, in order to increase the enrichment of selected nucleic acids. For example, after one round of hybridization, a several thousand fold enrichment of nucleic acids can be observed. After a second round, the enrichment can rise, for example, to about 15.000-fold average enrichment, which can provide hundreds-fold coverage of the target in a single sequencer run. Thus, for experiments that require enrichment factors not achievable in a single round of hybrid selection, the methods typically include subjecting the isolated subgroup of nucleic acids (that is, a portion or all of the target sequences) to one or more additional rounds of solution hybridization with the set of bait sequences.

Sequential hybrid selection with two different bait sequences (bait 1, bait 2) can be used to isolate and sequence the "intersection", that is, the subgroup of DNA sequences that binds to bait 1 and to bait 2, for example, used for applications that include but are not limited to enriching for inter-chromosomal. For example, selection of DNA from a tumor sample with a bait specific for sequences on chromosome 1 followed by selection from the product of the first selection of sequences that hybridize to a bait specific for chromosome 2 may enrich for sequences at chromosomal translocation junctions that contain sequences from both chromosomes.

The molarity of the selected subgroup of nucleic acids can be controlled such that the molarity of any particular nucleic acid is within a small variation of the average molarity of all selected nucleic acids in the subgroup of nucleic acids. Methods for controlling and optimizing the evenness of target representation include, but are not limited to, rational design of bait sequences based on physicochemical as well as empirical rules of probe design well known in the art, and pools of baits where sequences known or suspected to underperform are overrepresented to compensate for their intrinsic weaknesses. In some embodiments, at least about 50%, 60%, 65%, 70%, 75%, 80%, 85%, 90%, or 95% of the isolated subgroup of nucleic acids is within about 20-fold, 15-fold, 10-fold, 5-fold, 3-fold, or 2-fold of the mean molarity. In one embodiment, at least about 50% of the isolated subgroup of nucleic acids is within about 3-fold of the mean molarity. In another embodiment, at least about 90% of the isolated subgroup of nucleic acids is within about 10-fold of the mean molarity.

Variations in efficiency of selection can be further adjusted by altering the concentration of the baits. In one embodiment, the efficiency of selection is adjusted by leveling the efficiency of individual baits within a group (for example, a first, second or third plurality of baits) by adjusting the relative abundance of the baits, or the density of the binding entity (for example, the hapten or affinity tag density) in reference to differential sequence capture efficiency observed when using an equimolar mix of baits, and then introducing a differential excess as much of internally-leveled group 1 to the overall bait mix relative to internally-leveled group 2.

In certain embodiments, the methods described herein can achieve an even coverage of the target sequences. In one embodiment, the percent of target bases having at least about 50% of the expected coverage is at least about 60%, 70%, 80%, or 90%, for example, for short targets such as protein-coding exons. In another embodiment, the percent of target bases having at least about 50% of the expected coverage is at least about 80%, 90%, or 95%, for example, for targets that are long compared to the length of the capture baits, such as genomic regions.

Prior to hybridization, baits can be denatured according to methods well known in the art. In general, hybridization steps comprise adding an excess of blocking DNA to the labeled bait composition, contacting the blocked bait composition under hybridizing conditions with the target sequences to be detected, washing away unhybridized baits, and detecting the binding of the bait composition to the target.

Baits are hybridized or annealed to the target sequences under hybridizing conditions. "Hybridizing conditions" are conditions that facilitate annealing between a bait and target nucleic acid. Since annealing of different baits will vary depending on probe length, base concentration and the like, annealing is facilitated by varying bait concentration, hybridization temperature, salt concentration and other factors well known in the art.

Hybridization conditions are facilitated by varying the concentrations, base compositions, complexities, and lengths of the baits, as well as salt concentrations, temperatures, and length of incubation. For example, hybridizations can be performed in hybridization buffer containing 5×SSPE, 5×Denhardt's, 5 mM EDTA and 0.1% SDS and blocking DNA to suppress non-specific hybridization. RNase inhibitors can be used if the bait is RNA. In general, hybridization conditions, as described above, include temperatures of about 25° C. to about 65° C., typically about 65° C., and incubation lengths of about 0.5 hours to about 96 hours, typically about 66 hours. Additional exemplary hybridization conditions are in Example 12A-12C and Table 14 herein.

The methods described herein are adaptable to standard liquid handling methods and devices. In some embodiments, the method is carried out using automated liquid handling technology as is known in the art, such as devices that handle multiwell plates (see for example, Gnirke, A. et al. (2009) *Nat Biotechnol.* 27(2):182-189). This can include, but not limited to, automated library construction, and steps of solution hybridization including set-up and post-solution hybridization washes. For example, an apparatus can be used for carrying out such automated methods for the bead-capture and washing steps after the solution hybridization reaction. Exemplary apparatus can include, but not limited to, the following positions: a position for a multi-well plate containing streptavidin-coated magnetic beads, a position for the multiwall plate containing the solution hybrid-selection reactions, I/O controlled heat blocks to preheat reagents and to carry out washing steps at a user-defined temperature, a position for a rack of pipet tips, a position with magnets laid out in certain configurations that facilitate separation of supernatants from magnet-immobilized beads, a washing station that washes pipet tips and disposed of waste, and positions for other solutions and reagents such as low and high-stringency washing buffers or the solution for alkaline elution of the final catch. In one embodiment, the apparatus is designed to process up to 96 hybrid selections from the bead-capture step through the catch neutralization step in parallel. In another embodiment, one or more positions have a dual function. In yet another embodiment, the user is prompted by the protocol to exchange one plate for another.

The directly-selected nucleic acids can be concatenated and sheared, which is done to overcome the limitations of short sequencing reads. In one embodiment, each exon-sized sequencing target is captured with a single bait molecule that is about the same size as the target and has endpoints near the endpoints of the target. Only hybrids that form double strand molecules having approximately 100 or more contiguous base pairs survive stringent post-hybridization washes. As a result, the selected subgroup of nucleic acids (that is, the "catch") is enriched for randomly sheared genomic DNA fragments whose ends are near the ends of the bait molecules. Mere end-sequencing of the "catch" with very short sequencing reads can give higher coverage near the end (or even outside) of the target and lower coverage near the middle.

Concatenating "catch" molecules by ligation and followed by random shearing and shotgun sequencing is one method to get sequence coverage along the entire length of the target sequence. This method produces higher percentage of sequenced bases that are on target (as opposed to near target) than end sequencing with very short reads. Methods for concatenating molecules by co-ligation are well known in the art. Concatenation can be performed by simple blunt end ligation. "Sticky" ends for efficient ligation can be produced by a variety of methods including PCR amplification of the "catch" with PCR primers that have restriction sites near their 5' ends followed by digestion with the corresponding restriction enzyme (for example, NotI) or by strategies similar to those commonly used for ligation-independent cloning of PCR products such as partial "chew-back" by T4 DNA polymerase (Aslanidis and de Jong, Nucleic Acids Res. 18:6069-6074, 1990) or treatment of uracil-containing PCR products with UDG glycosylase and lyase endo VIII (for example, New England Biolabs cat. E5500S).

In another embodiment, a staggered set of bait molecules is used to target a region, obtaining frequent bait ends throughout the target region. In some embodiments, merely end-sequenced "catch" (that is, without concatenation and shearing) provides fairly uniform sequence coverage along the entire region that is covered by bait including the actual sequencing target (for example, an exon). As staggering the bait molecules widens the segment covered by bait, the sequenced bases are distributed over a wider area. As a result, the ratio of sequence on target to near target is lower than for selections with non-overlapping baits that often require only a single bait per target.

In another embodiment, end sequencing with slightly longer reads (for example, 76 bases) is the typical method for sequencing short selected targets (for example, exons). Unlike end sequencing with very short reads, this method leads to a unimodal coverage profile without a dip in coverage in the middle. This method is easier to perform than the concatenate and shear method described above, results in relatively even coverage along the targets, and generates a high percentage of sequenced bases fall on bait and on target proper.

In one embodiment, the selected subgroup of nucleic acids are amplified (for example, by PCR) prior to being analyzed by sequencing or genotyping. In another embodiment, the subgroup is analyzed without an amplification step, for example, when the selected subgroup is analyzed by sensitive analytical methods that can read single molecules.

Sequencing

The invention also includes methods of sequencing nucleic acids. In these methods, nucleic acid library members are isolated by using the methods described herein, for example, using solution hybridization, thereby providing a library catch. The library catch or a subgroup thereof can be sequenced. Accordingly, the methods featured in the invention further include analyzing the library catch. In one embodiment, the library catch is analyzed by a sequencing method, for example, a next-generation sequencing method as described herein. The methods include isolating a library catch by solution hybridization, and subjecting the library catch by nucleic acid sequencing. In certain embodiments, the library catch can be re-sequenced.

Any method of sequencing known in the art can be used. Sequencing of nucleic acids isolated by selection methods are typically carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (for example, greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, for example, in Metzker, M. (2010) Nature Biotechnology Reviews 11:31-46, incorporated herein by reference.

In one embodiment, the next-generation sequencing allows for the determination of the nucleotide sequence of an individual nucleic acid molecule (for example, Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (for example, the Solexa sequencer, Illumina Inc., San Diego, Calif.; 454 Life Sciences (Branford, Conn.), and Ion Torrent). for example, massively parallel short-read sequencing (for example, the Solexa sequencer, Illumina Inc., San Diego, Calif.), which generates more bases of sequence per sequencing unit than other sequencing methods that generate fewer but longer reads. Other methods or machines for next-generation sequencing include, but not limited to, the sequencers provided by 454 Life Sciences (Branford, Conn.), Applied Biosystems (Foster City, Calif.; SOLiD sequencer), Helicos BioSciences Corporation (Cambridge, Mass.), and emulsion and microfluidic sequencing technology nanodroplets (for example, GnuBio droplets).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

NGS technologies can include one or more of steps, for example, template preparation, sequencing and imaging, and data analysis.

Additional exemplary sequencing methodologies are known in the art, for example, some of which are described in commonly owned, U.S. Ser. No. 13/339,986 and PCT/US11/67725, both filed on Dec. 29, 2011, the contents of which are incorporated by reference.

Alignment

Alignment is the process of matching a read with a location, for example, a genomic location. Misalignment (for example, the placement of base-pairs from a short read on incorrect locations in the genome)., for example, misalignment due to sequence context (for example, presence of repetitive sequence) of reads around an actual cancer mutation can lead to reduction in sensitivity of mutation detection, as reads of the alternate allele may be shifted off the main pile-up of alternate allele reads. If the problematic sequence context occurs where no actual mutation is present, mis-alignment may introduce artifactual reads of "mutated" alleles by placing actual reads of reference genome bases onto the wrong location. Because mutation-calling algorithms for multiplied multigene analysis should be sensitive to even low-abundance mutations, these misalignments may increase false positive discovery rates/reduce specificity.

As discussed herein, reduced sensitivity for actual mutations may be addressed by evaluating the quality of alignments (manually or in an automated fashion) around expected mutation sites in the genes being analyzed. The sites to be evaluated can be obtained from databases of cancer mutations (for example, COSMIC). Regions that are identified as problematic can be remedied with the use of an algorithm selected to give better performance in the relevant sequence context, for example, by alignment optimization (or re-alignment) using slower, but more accurate alignment algorithms such as Smith-Waterman alignment. In cases where general alignment algorithms cannot remedy the problem, customized alignment approaches may be created by, for example: adjustment of maximum difference mismatch penalty parameters for genes with a high likelihood of containing substitutions; adjusting specific mismatch penalty parameters based on specific mutation types that are common in certain tumor types (for example, C→T in melanoma); or adjusting specific mismatch penalty parameters based on specific mutation types that are common in certain sample types (for example, substitutions that are common in FFPE).

Reduced specificity (increased false positive rate) in the evaluated gene regions due to mis-alignment can be assessed by manual or automated examination of all mutation calls in samples sequenced. Those regions found to be prone to spurious mutation calls due to mis-alignment can be subjected to same alignment remedies as above. In cases where no algorithmic remedy is found possible, "mutations" from the problem regions can be classified or screened out from the test panel.

Insertions/Deletions (indels)

Generally, the accurate detection of indel mutations is an exercise in alignment, as the spurious indel rate on the sequencing platforms disabled herein is relatively low (thus, even a handful of observations of correctly aligned indels can be strong evidence of mutation). Accurate alignment in the presence of indels can be difficult however (especially as indel length increases). In addition to the general issues associated with alignment, for example, of substitutions, the indel itself can cause problems with alignment. (For instance, a deletion of 2 bp of a dinucleotide repeat cannot be readily definitively placed.) Both sensitivity and specificity can be reduced by incorrect placement of shorter (<15 bp) apparent indel-containing reads. Larger indels (getting closer in magnitude to the length of individual reads—36 bp in our current process) can cause failure to align the read at all, making detection of the indel impossible in the standard set of aligned reads.

Databases of cancer mutations can be used to address these problems and improve performance. To reduce false positive indel discovery (improve specificity), regions around commonly expected indels can be examined for problematic alignments due to sequence context and addressed similarly to substitutions above. To improve sensitivity of indel detection, several different approaches of using information on the indels expected in cancer can be used. For example, short-reads contained expected indels can be simulated and alignment attempted. The alignments can be studied and problematic indel regions can have alignment parameters adjusted, for instance by reducing gap open/extend penalties or by aligning partial reads (for example, the first or second half of a read).

Alternatively, initial alignment can be attempted not just with the normal reference genome, but also with alternate versions of the genome, containing each of the known or likely cancer indel mutations. In this approach, reads of indels that initially failed to align or aligned incorrectly are placed successfully on the alternate (mutated) version of the genome.

Additional exemplary alignment methodologies are known in the art, for example, some of which are described in commonly owned, U.S. Ser. No. 13/339,986 and PCT/US11/67725, both filed on Dec. 29, 2011, the contents of which are incorporated by reference.

Mutation Calling

Base calling refers to the raw output of a sequencing device. Mutation calling refers to the process of selecting a nucleotide value, for example, A, G, T, or C, for a nucleotide position being sequenced. Typically, the sequencing reads (or base calling) for a position will provide more than one value, for example, some reads will give a T and some will give a G. Mutation calling is the process of assigning a nucleotide value, for example, one of those values to the sequence. Although it is referred to as "mutation" calling it can be applied to assign a nucleotide value to any nucleotide position, for example, positions corresponding to mutant alleles, wildtype alleles, alleles that have not been characterized as either mutant or wildtype, or to positions not characterized by variability. Methods for mutation calling can include one or more of the following: making independent calls based on the information at each position in the reference sequence (for example, examining the sequence reads; examining the base calls and quality scores; calculating the probability of observed bases and quality scores given a potential genotype; and assigning genotypes (for example, using Bayes rule)); removing false positives (for example, using depth thresholds to reject SNPs with read depth much lower or higher than expected; local realignment to remove false positives due to small indels); and performing linkage disequilibrium (LD)/imputation based analysis to refine the calls.

Equations to calculate the genotype likelihood associated with a specific genotype and position are described, for example, in Li H. and Durbin R. *Bioinformatics,* 2010; 26(5): 589-95. The prior expectation for a particular mutation in certain cancer type can be used when evaluating samples from that cancer type. Such likelihood can be derived from public databases of cancer mutations, for example, Catalogue of Somatic Mutation in Cancer (COSMIC), HGMD (Human Gene Mutation Database), The SNP Consortium, Breast Cancer Mutation Data Base (BIC), and Breast Cancer Gene Database (BCGD).

Examples of LD/imputation based analysis are described, for example, in Browning B. L. and Yu Z. *Am. J. Hum. Genet.* 2009, 85(6):847-61. Examples of low-coverage SNP calling methods are described, for example, in Li Y. et al., *Annu. Rev. Genomics Hum. Genet.* 2009, 10:387-406.

Mutation Calling: Substitutions

After alignment, detection of substitutions can be performed using a calling method, for example, Bayesian mutation calling method; which is applied to each base in each of the subgenomic intervals, for example, exons of the gene to be evaluated, where presence of alternate alleles is observed. This method will compare the probability of observing the read data in the presence of a mutation with the probability of observing the read data in the presence of base-calling error alone. Mutations can be called if this comparison is sufficiently strongly supportive of the presence of a mutation.

Methods have been developed that address limited deviations from frequencies of 50% or 100% for the analysis of cancer DNA. (for example, SNVMix—Bioinformatics. 2010 March 15; 26(6): 730-736.) Method disclosed herein however allow consideration of the possibility of the presence of a mutant allele at anywhere between 1% and 100% of sample DNA, and especially at levels lower than 50%

This approach is particularly important for the detection of mutations in low-purity FFPE samples of natural (multiclonal) tumor DNA.

An advantage of a Bayesian mutation-detection approach is that the comparison of the probability of the presence of a mutation with the probability of base-calling error alone can be weighted by a prior expectation of the presence of a mutation at the site. If some reads of an alternate allele are observed at a frequently mutated site for the given cancer type, then presence of a mutation may be confidently called even if the amount of evidence of mutation does not meet the usual thresholds. This flexibility can then be used to increase detection sensitivity for even rarer mutations/lower purity samples, or to make the test more robust to decreases in read coverage. The likelihood of a random base-pair in the genome being mutated in cancer is ~1e-6. The likelihood of specific mutations at many sites in a typical multigenic cancer genome panel can be orders of magnitude higher. These likelihoods can be derived from public databases of cancer mutations (for example, COSMIC).

Mutation Calling: Indels

Indel calling is a process of finding bases in the sequencing data that differ from the reference sequence by insertion or deletion, typically including an associated confidence score or statistical evidence metric.

Methods of indel calling can include the steps of identifying candidate indel, calculating genotype likelihood through local re-alignment, and performing LD-based genotype inference and calling. Typically, a Bayesian approach is used to obtain potential indel candidates, and then these candidates are tested together with the reference sequence in a Bayesian framework.

Algorithms to generate candidate indels are described, for example, in McKenna A. et al., *Genome Res.* 2010; 20(9):1297-303; Ye K. et al., *Bioinformatics,* 2009; 25(21):2865-71; Lunter G. and Goodson M. *Genome Res.* 2010, epub ahead of print; Li H. et al., *Bioinformatics* 2009, Bioinformatics 25(16):2078-9.

Methods for generate indel calls and individual-level genotype likelihoods include, for example, the Dindel algorithm (Albers C. A. et al., *Genome Res.* 2010 Oct. 27. [Epub ahead of print]). For example, the Bayesian EM algorithm can be used to analyze the reads, make initial indel calls, and generate genotype likelihoods for each candidate indel, followed by imputation of genotypes using, for example, QCALL (Le S. Q. and Durbin R. *Genome Res.* 2010 Oct. 27. [Epub ahead of print]). Parameters, such as prior expectations of observing the indel can be adjusted (for example, increased or decreased), based on the size or location of the indels. Additional exemplary mutation calling methodologies are known in the art, for example, some of which are described in commonly owned, U.S. Ser. No. 13/339,986 and PCT/US11/67725, both filed on Dec. 29, 2011, the contents of which are incorporated by reference.

EXAMPLES

The present invention is additionally described by reference to the following Examples, which are offered by way of illustration and are not intended to limit the invention in any manner. Standard techniques well known in the art or techniques specifically described below can be utilized.

Example 1

Hybridization of DNA Probe to the Capture Products

The procedure below summarizes the steps necessary for hybridization of the DNA probe with the capture products.

A. Hybridization

One hundred nanograms of pooled biotinylated baits, 500 ng of adapted DNA library, 2 µg $C_ot-1$ DNA, 2 ng of oligonucleotide blockers 2.0 µL is combined into a volume of 10 µL and mixed with 10 µL of pre-warmed Genisphere Buffer 6 (2×SDS-Based Hybridization Buffer: 0.50M $NaPO_4$, 1% SDS, 2 mM EDTA, 2×SSC, 4×Denhardt's Solution). Following vortex mixing of the mixture, an overlay of 40 µL mineral oil is applied and the mixture is denatured in a thermocycler at 95° C. for 5 minutes with a slow decrease to 71° C. The mixture is incubated at 71° C. for 48 hours.

B. Binding to Streptavidin beads

The streptavidin beads are prepared in the following manner before addition to the hybridization mixture. The streptavidin beads are allowed to sit at room temperature for 30 minutes. For each hybridization reaction, 50 µL of Invitrogen M270 Streptavidin beads (magnetic) is washed twice with Bind and Wash Buffer (10 mM Tris-HCl (pH 7.5), 2 M NaCl, 1 mM EDTA). The beads are resuspended in 80 µL that includes 50 µL Bind and Wash Buffer and 30 µL of water.

At the end of the 48 hour hybridization period, the 20 µL of hybridization liquid is removed from under the mineral oil added to the 80 µL of beads to provide a total volume of 100 pt. The mixture is rotated on tube rotator for 30 minutes to allow binding to occur between the biotin on the hybridized template:bait complexes and the streptavidin on the beads.

C. Washing the Streptavidin beads

Following the rotation period, the samples are placed onto a magnetic separation rack. The beads are permitted to separate from the supernatant, and the supernatant that contains DNA that did not bind to the capture probes is removed and discarded. The probe bound beads is washed sequentially with the following solutions. For each wash, the wash solution is added that has been pre-equilibrated to given temperature, placed on rotator for the indicated time, is briefly spun down (magnet) and the supernatant is collected and discarded. The first wash is with 1000 µL 1×SSC/0.1% SDS for 5 minutes, at 71° C. with rotation. The second wash is with 1000 µL 0.1×SSC/0.1% SDS for 5 minutes, at 71° C. with rotation. The third wash is with 1000 µL 0.1×SSC/0.1% SDS for 5 minutes, at 71° C. with rotation. The fourth wash is with 1000 µL 0.1×SSC/0.1% SDS for 5 minutes, at RT, with rotation. The fifth wash is with 1000 µL 0.2×SSC for 30 seconds, at RT, with tube still on magnet. The final wash solution is completely removed prior further processing, as explained below.

After the final wash, 50 µL 0.125 N NaOH is added and the mixture is incubated at RT for 10 minutes, with vortex treatment every 2 minutes to keep beads in solution. The tube with the beads is placed back on the magnet for 1 minute. While beads are on magnet, an aliquot of 50 µL of 1 M Tris-HCl (pH 8.8) is added to a new 1.5 mL RNAse/DNAse-free PCR tube. The supernatant from the tube on the magnet (0.125 N NaOH) is added to the tube that contains the 1 M Tris-HCl (pH 8.8) to neutralize the solution. The recovered template fragments are purified with AMPure beads using 1.5× volume and eluting in 20 µL EB Buffer.

Example 2

PCR Reactions with Single-Stranded Template Material

A. Final PCR Enrichment

The recovered single-stranded templates (16 µL) are prepared to a total volume of 50 µL with the following reaction mix components (KAPA HiFi master mix (25 µL);

25 µM Primer 1 (1 µL), 25 µM Primer 2 (1 µL), Water (7 µL)). The DNA is vortexed briefly and recollected as a solution following brief centrifugation. The reactions are placed into a thermocycler with the following program: 98° C. (45 sec); 98° C. (15 sec); 60° C. (30 sec); 72° C. (30 sec); 77° C. (30 sec) for five or more cycles. The amplified products are purified with AMPure beads using 1.5× volume and eluting in 20 µL EB Buffer (Qiagen) (10 mM Tris-HCl, pH 8.5). The resultant concentration of the DNA is measured with a Quibit Fluorometer and diluted for use with the appropriate NGS sequencing platform.

Five cycles of amplification are used for post-capture Ion Torrent libraries and typically not more than 18 cycles of amplification are used for post-capture Illumina libraries. The standard Illumina protocol is optimized using the following PCR procedure. The recovered single-stranded DNA templates (2 mL) is combined in a final volume of 50 µL that includes 25 µL of SyberGreen MasterMix, 8 pmol of Primer 1, and 8 pmol of Primer 2. The reactions are set up in 96-well qPCR plate to mimic the final PCR enrichment and run the following program: 95° C. (5 min) followed by 30 cycles of 95° C. (30 sec) and 60° C. (45 sec). The threshold is manually adjusted to find the midpoint of the curve (halfway between where amplification starts and the plateau) and 3 cycles from this value is subtracted to determine the number of cycles to run for the final PCR enrichment. Three cycles are subtracted because the amount of DNA going into optimization is 8× less than what will be put into the final enrichment reaction; 2 µL of the neutralized captured product goes into the PCR optimization reaction, and 16 µL will go into the final PCR enrichment.

Example 3

$T_m$-Enhanced Oligonucleotides for Use in the Illumina Sequencing Platform with Inosine Bases for Barcode Domains In Table I, the following blocking oligonucleotides were designed for use in hybrid capture experiments for DNA template libraries with the Illumina sequencing platform. The $T_m$-enhanced oligonucleotides were prepared using LNA ("+C" or "+A") or BNA ("/iBNA-meC/" or "/iBNA-A/") as $T_m$-enhancing groups. All oligonucleotides were prepared using phosphoramidite chemical methods. $T_m$ values are estimated for LNA bases in 750 mM NaCl buffer (similar ionic strength to 5×SSC) and for 15 mM NaCl buffer (similar ionic strength to 0.1×SSC) using the method of Owczarzy (Biochemistry 2011 50:9352-9367), which is incorporated by reference in its entirety. The BNA modification has similar thermodynamic effects as the LNA modification, so the predictions presented herein apply to both classes of modified blockers and LNA/BNA modifications can be substituted in all examples. For example, thermodynamic modeling in the examples below was done using LNA-derived nearest neighbor parameters while oligonucleotide synthesis was done using BNA bases.

TABLE I $T_m$-enhanced oligonucleotide blockers

| SEQ ID NO: | Sequence | #LNAs | $T_m$(° C.) 750 mM (Na) | $T_m$(° C.) 15 mM (Na) |
|---|---|---|---|---|
| 1 | AGATCGGAAGAGCGTCGTGTAGGGAAAGAGTGTAGATCTCGGTGGTCGCCGTATCATT | 0 | 90.3 | 62.0 |
| 2 | AGATCGGAAGAGCGT+CGTGTAGGGAAAGAGTGTAGATCT+CGGTGGTCGCCGTATCATT | 2 | 92.0 | 63.4 |
| 3 | AGAT+CGGAAGAGCGT+CGTGTAGGGAAAGAGTGTAGATCT+CGGTGGTCGC+CGTATCATT | 4 | 93.9 | 65.0 |
| 4 | AGAT+CGGAAGAGCGT+CGTGTAGGGAAAGAGTGTAGATCT+CGGTGGT+CGC+CGTAT+CATT | 6 | >95 | 66.6 |
| 5 | AGAT+CGGAAGAG+CGT+CGTGTAGGGAAAGAGTGTAGAT+CT+CGGTGGT+CGC+CGTAT+CATT | 8 | >95 | 68.3 |
| 6 | AGAT+CGGA+AGAG+CGT+CGTGT+AGGG+AAAGAGTGTAGAT+CT+CGGTGGT+CG+C+CGTAT+CATT | 12 | >95 | 71.1 |
| 7 | AG+AT+CGGA+AGAG+CGT+CGTGT+AGGG+A+A+AGAGTGTAG+AT+CT+CGGTGGT+CG+C+CGTAT+CATT | 16 | >95 | 73.3 |
| 8 | AG+AT+CGG+A+AG+AG+CGT+CGTGT+AGGG+A+A+AG+AGTGT+AG+AT+CT+CGGTGGT+CG+C+CGT+AT+C+ATT | 22 | >95 | 77.4 |

In the Table I, LNA-C $T_m$ enhancing groups are included initially in the $T_m$-enhanced oligonucleotides until all the C-positions (that is, 9 positions having C) are exhaustively substituted, followed by inclusion of LNA-A $T_m$ enhancing groups at the A-positions thereafter.

In Table II below, the design of a series of $T_m$-enhanced oligonucleotides for use as a blocker against the adaptor containing the barcode sequence (8-inosines) is presented. As explained in the detailed description, there is no way to model the enhanced $T_m$ valued with inosines (defined in sequences of Table II as "I" and "/ideoxyI/") paired with variable bases. So, the inosine bases were not included in the $T_m$ analysis, but are present in the final sequence. The precise enhanced $T_m$ value for the actual sequences is readily determined by routine empirical methods, however. The $T_m$-enhanced oligonucleotides were prepared using LNA ("+C" or "+A") or BNA ("/iBNA-meC/" or "/iBNA-A/") as $T_m$-enhancing groups. All oligonucleotides were prepared using phosphoramidite chemical methods.

TABLE II

$T_m$-enhanced oligonucleotide blockers with barcode sequences

| SEQ ID NO: | Sequence | #LNAs | $T_m$ (° C.) 750 mM (Na) | $T_m$ (° C.) 15 mM (Na) |
|---|---|---|---|---|
| 9 | GATCGGAAGAGCACACGTCTGAACTCCAGTCAC(IIIIIIII)ATCTCGTATGCCGTCTTCTGCTTG | 0 | 89.8 | 61.7 |
| 10 | GATCGGAAGAGCACACGTCTGAACTCCAGT+CAC(IIIIIIII)ATCT+CGTATGCCGTCTTCTGCTTG | 2 | 91.5 | 63.1 |
| 11 | GATCGGAAGAGCACACGTCTGAA+CTCCAGT+CAC(IIIIIIII)ATCT+CGTATGC+CGTCTTCTGCTTG | 4 | 93.9 | 65.2 |
| 12 | GATCGGAAGAG+CACACGTCTGAA+CTCCAGT+CAC(IIIIIIII)ATCT+CGTATGC+CGTCTTCTG+CTTG | 6 | >95 | 66.8 |
| 13 | GAT+CGGAAGAG+CACACGTCTGAA+CTCCAGT+CA+C(IIIIIIII)ATCT+CGTATGC+CGTCTTCTG+CTTG | 8 | >95 | 68.7 |
| 14 | GAT+CGGAAGAG+CACA+CGT+CTGAA+CTC+CAGT+CAC(IIIIIIII)ATCT+CGTATGC+CGT+CTT+CTG+CTTG | 12 | >95 | 72.7 |
| 15 | GAT+CGGAAGAG+CA+CA+CGT+CTGAA+CT+C+CAGT+CA+C(IIIIIIII)AT+CT+CGTATG+C+CGT+CT T+CTG+CTTG | 17 | >95 | 77.4 |
| 16 | GAT+CGG+A+AGAG+CA+CA+CGT+CTG+AA+CT+C+CAGT+CA+C(IIIIIIII)+AT+CT+CGT+ATG+C+CGT+CTT+CTG+CTTG | 22 | >95 | 80.4 |

In the Table II, LNA-C $T_m$ enhancing groups are included initially in the $T_m$-enhanced oligonucleotides until all the C-positions (that is, 17 positions having C) are exhaustively substituted, followed by inclusion of LNA-A $T_m$ enhancing groups at the A-positions thereafter. In this example, inosine bases were incorporated to span the barcode domain.

Example 4

$T_m$-Enhanced Blocking Oligonucleotides for Use in Illumina Sequencing Platform with Mixed Bases ("N" Base) for Barcode Domains In Table III, the following oligonucleotides were designed for use in hybrid capture experiments for DNA template libraries with the Illumina sequencing platform. The $T_m$-enhanced oligonucleotides were prepared using LNA ("+C", "+T" or "+A") or BNA ("/iBNA-meC/", "/iBNA-T/", or "/iBNA-A/") as $T_m$-enhancing groups. All oligonucleotides were prepared using phosphoramidite chemical methods.

TABLE III

$T_m$-enhanced oligonucleotide blockers with barcode sequences ("N")

| SEQ ID NO: | Sequence | #LNAs | $T_m$ (° C.) 750 mM (Na) | $T_m$ (° C.) 15 mM (Na) |
|---|---|---|---|---|
| 17 | IndexBlock: CAAGCAGAAGACGGCATACGAGATNNNNNNNGTGACTGGAGTTCAGACGTGTGCTCTTCCGATCT | 0 | ~90 | 61.8 |
| 18 | IndexBlock +10-BNA: CAAG+CAGAAGA+CGG+CATA+CGAGATNNNNNNNGTGA+CTGGAGTT+CAGA+CGTGTG+CTCTT+C+CGATCT | 10 | >90 | 70.9 |

TABLE III -continued

T$_m$-enhanced oligonucleotide blockers with barcode sequences ("N")

| SEQ ID NO: | Sequence | #LNAs | T$_m$(° C.) 750 mM (Na) | T$_m$(° C.) 15 mM (Na) |
|---|---|---|---|---|
| 19 | IndexBlock +20-BNA:<br>CAAG+CAGAAGA+CGG+CA+TA+CGAGA+TNNNNNNG+<br>TGA+C+TGGAG+T+T+CAGA+CG+TG+TG+CTC+TT+<br>C+CGA+TCT | 20 | >90 | 76.8 |
| 20 | IndexBlock_RevComp:<br>AGATCGGAAGAGCACACGTCTGAACTCCAGTCACNNN<br>NNNATCTCGTATGCCGTCTTCTGCTTG | 0 | ~90 | 61.8 |
| 21 | IndexBlock_RevComp +10-BNA:<br>AGAT+CGGAAGAG+CACA+CGTCTGAA+CTCCAGT+C<br>A+CNNNNNNATCT+CGTATGC+CGT+CTTCTG+CTTG | 10 | >90 | 70.9 |
| 22 | IndexBlock_RevComp +20-BNA:<br>AGA+T+CGGAAGAG+CA+CA+CGT+CTGAA+CT+C+C<br>AGT+CA+CNNNNNNAT+CT+CG+TA+TG+C+CGT+CT<br>T+CTG+CTTG | 20 | >90 | 80.0 |
| 23 | PE1.0:<br>AATGATACGGCGACCACCGAGATCTACACTCTTTCCC<br>TACACGACGCTCTTCCGATCT | 0 | ~90 | 62.0 |
| 24 | PE1.0 +10-BNA:<br>AATGATA+CGG+CGA+CCA+CCGAGAT+CTACA+CTC<br>TTTC+CCTACACGACGCT+CTTC+CGAT+CT | 10 | >90 | 72.6 |
| 25 | PE1.0 +17-BNA:<br>AATGATA+CGG+CGA+CCA+CCGAGAT+CTA+CA+CT+<br>CTTT+CC+CTA+CA+CGA+CG+CT+CTTC+CGAT+C<br>T | 17 | >90 | 81.0 |
| 26 | PE1.0_Rev Comp:<br>AGATCGGAAGAGCGTCGTGTAGGGAAAGAGTGTAGAT<br>CTCGGTGGTCGCCGTATCATT | 0 | ~90 | 62.0 |
| 27 | PE1.0_Rev Comp +9-BNA:<br>AGAT+CGGAAGAG+CGT+CGTGTAGGGAAAGAGTGTA<br>GAT+CT+CGGTGGT+CG+C+CGTAT+CATT | 9 | >90 | 69.0 |
| 28 | PE1.0_Rev Comp +20-BNA:<br>AG+AT+CGG+AAG+AG+CGT+CGTGT+AGGG+AA+AG+<br>AGTGT+AG+AT+CT+CGGTGGT+CG+C+CGT+AT+C+<br>ATT | 20 | >90 | 77.3 |

Table III provides examples where T$_m$-enhanced oligonucleotides were designed using either strand of the adaptor sequence as a blocker. The preferred strand for use as the T$_m$-enhanced oligonucleotide as blocker is one that provides maximal "blocking power" per modified group (that is, the largest optimal enhanced T$_m$ value) with inclusion of the fewest T$_m$-enhancing groups. For example, compare SEQ ID NOS: 19 and 22 (SEQ ID NO:22 being preferred) and SEQ ID NOS: 25 and 28 (SEQ ID NO:25 being preferred).

Example 5

T$_m$-Enhanced Oligonucleotides for Use in the Ion Torrent PGM Sequencing Platform In Table IV, the following oligonucleotides were designed for use in hybrid capture experiments for DNA template libraries with the Ion Torrent PGM sequencing platform. The T$_m$-enhanced oligonucleotides were prepared using LNA ("+C" or "+A") or BNA ("/iBNA-meC/" or "/iBNA-A/") as T$_m$-enhancing groups. All oligonucleotides were prepared using phosphoramidite chemical methods.

TABLE IV

T$_m$-enhanced oligonucleotide blockers for Ion Torrent adaptors

| SEQ ID NO: | Sequence | #LNAs | T$_m$(° C.) 750 mM (Na) | T$_m$(° C.) 15 mM (Na) |
|---|---|---|---|---|
| 29 | Ion P1 top:<br>CCACTACGCCTCCGCTTTCCTCTCTATGGGCAGTCGG<br>TGAT | 0 | 89.2 | 62.3 |

TABLE IV -continued

T$_m$-enhanced oligonucleotide blockers for Ion Torrent adaptors

| SEQ ID NO: | Sequence | #LNAs | T$_m$(° C.) 750 mM (Na) | T$_m$(° C.) 15 mM (Na) |
|---|---|---|---|---|
| 30 | Ion P1 top 11C: C+CA+CTA+CGC+CTC+CG+CTTTC+CT+CT+CTATG GG+CAGT+CGGTGAT | 11 | >90 | 77.9 |
| 31 | Ion P1 bot: ATCACCGACTGCCCATAGAGAGGAAAGCGGAGGCGTA GTGGTT | 0 | 89.6 | 62.1 |
| 32 | Ion P1 bot 6C8A: AT+CAC+CGA+CTGC+CC+AT+AG+AG+AGGA+A+AG+ CGG+AGG+CGT+AGTGGTT | 14 | >90 | 77.8 |
| 33 | Ion A top: CCATCTCATCCCTGCGTGTCTCCGACTCAG | 0 | 83.2 | 57.4 |
| 34 | Ion A top 11C: C+CAT+CT+CAT+C+CCTG+CGTGT+CT+C+CGA+CT+ CAG | 11 | >90 | 76.1 |
| 35 | Ion A bot: CTGAGTCGGAGACACGCAGGGATGAGATGGTT | 0 | 84.0 | 57.4 |
| 36 | Ion A bot 5C5A: +CTG+AGT+CGG+AGA+CA+CG+CAGGG+ATG+AG+A TGGTT | 10 | >90 | 74.3 |

Table IV provides additional examples were T$_m$-enhanced oligonucleotides may be designed using either strand of the adaptor sequence as a blocker. The preferred strand for use as the T$_m$-enhanced oligonucleotide as blocker is one that provides maximal "blocking power" per modified group (that is, the largest optimal enhanced T$_m$ value) with inclusion of the fewest T$_m$-enhancing groups. This example also shows that, depending upon the strand selected as the T$_m$-enhanced oligonucleotide, LNA-C has superior "blocking power" on a per T$_m$-enhancing group basis compared with LNA-A. For example, compare SEQ ID NOS: 30 and 32 (SEQ ID NO:30 being preferred) and SEQ ID NOS: 34 and 36 (SEQ ID NO:34 being preferred).

Examples A-O disclosed below present features of an embodiment for a method for multigene analysis of a tumor sample, which is depicted through the flowchart provided in FIG. 3.

Example A

Nucleic Acid Isolation from a Tumor Sample

3×20 μm sections cut from a paraffin block were mixed with 400 μL Buffer FTL by vortexing and incubated at 90° C. for 15 minutes in a 1.5 mL centrifuge tube. A range of 88-92° C. was acceptable for the incubation. Then, the sample was incubated with 20 μL proteinase K at 55° C. for 6 hours and 10 μL RNase (1 mg/mL) at room temperature for 5 minutes. Next, 460 μL Buffer BL and 500 μL absolute ethanol were added to the sample. The resulting sample solution was kept at room temperature until further use.

To prepare the column for DNA binding, 100 μL Equilibration buffer was added to a MicroElute column and the column was centrifuged at 10,000×g for 30 seconds. 700 μL of the sample solution described above was transferred to the MicroElute column and the column was centrifuged at 10,000×g for 1 minute. The centrifugation step was repeated if fluid did not completely pass through MicroElute column. The remaining sample solution was applied to the MicroElute column in the same way as described above. Then, the MicroElute column was treated with 500 μL Buffer HB and centrifuged at 10,000×g for 1 minute. Next, 700 μL DNA Wash Buffer diluted with ethanol was added into the MicroElute column and the column was centrifuged at 10,000×g for 1 minute. The MicroElute column was washed again using 700 μL DNA Wash Buffer diluted with ethanol, centrifuged at 10,000×g for 1 minute, and centrifuged at >13,000×g for 3 minutes to dry the column. The MicroElute column was placed into a standard 1.5 mL centrifuge tube with the top removed. 50-75 μL Elution Buffer preheated to 70° C. was added into the column and incubated at room temperature for 3 minutes. The column was centrifuged in collection tube at >13,000×g for 1 minute. Another 50-75 μL Elution Buffer preheated to 70° C. was added into the MicroElute column and incubated at room temperature for 3 minutes. The column was centrifuged again in collection tube at >13,000×g for 1 minute. The entire solution was transferred to a fresh 1.5 mL centrifuge tube and stored at −20° C.

FTL buffer, proteinase K, BL Buffer, Equilibration Buffer, MicroElute column, Buffer HB, DNA Wash Buffer, and Elution Buffer were provided in E.Z.N.A.™ FFPE DNA Kit (OMEGA bio-tek, Norcross, Ga.; Cat. Nos. D3399-00, D3399-01, and D3399-02).

Additional methods to isolate nucleic acids (for example, DNA) from formaldehyde- or paraformaldehyde-fixed, paraffin-embedded (FFPE) tissues are disclosed, for example, in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), Maxwell® 16 FFPE Plus LEV DNA Purification Kit Technical Manual (Promega Literature #TM349, February 2011), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. Maxwell® 16 FFPE Plus LEV DNA Purification Kit is used with the Maxwell® 16 Instrument for purification of genomic DNA from 1 to 10 μm sections of FFPE tissue. DNA is purified using silica-clad paramagnetic particles (PMPs), and eluted in low elution volume. QIAamp® DNA FFPE Tissue Kit uses QIAamp® DNA Micro technology for purification of genomic and mitochondrial DNA.

Example B.1

Shearing of DNA

Covaris™ E210 instrument with circulating chiller was set to 4° C. The instrument water tank was filled with distilled/deionized water to level "6" on the fill-line. Sono-Lab™ software was launched and the system was allowed to execute homing sequence when prompted. The water in instrument tank was degassed for at least 45 minutes before shearing samples.

To prepare the genomic DNA samples for shearing, samples were first quantified using a PicoGreen® assay (Invitrogen) on a microplate reader (Spectramax M2, Molecular Devices) Based on the concentration, 120 μl desired input DNA (2 ng/μl) with low TE (10 mM Tris, 0.2 mM EDTA, pH 8.0) was used for the experiment. The 100 μl individual samples were pipetted slowly into the Covaris MicroTUBEs (Covaris Cat. #520045) through the septa in the lid of the tube. The Covaris MicroTUBEs were then placed in the Covaris E-series tube rack. For 200 bp shearing, the settings were as follows: 10% duty cycle, 5 Intensity, 200 cycles/burst, time 180 sec, and Frequency Sweeping mode. After shearing, the Covaris MicroTUBEs were briefly spun down using an appropriate adapter in a minicentrifuge, and the sheared samples were transferred to clean 1.5 ml microcentrifuge tubes. Each sheared DNA sample was purified using a QIAGEN MinElute® column. Briefly, 5× QIAGEN PBI buffer was added to the sample in a 1.5 ml microcentrifuge tube (for example, 500 μl of PBI buffer was added to 100 μl of sample). Each sample was vortexed, briefly spun down, and transferred to a MinElute spin column. MinElute spin column was centrifuged at 13,000 rpm for 1 minute, and the flow-through was discarded. 750 μl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 minutes. For the first elution, 18 μl of QIAGEN Elution Buffer was added to each column, incubated for 2-3 minutes, and then centrifuged at 13,000 rpm for 1 minute. For the second elution, 15 μl of QIAGEN Elution Buffer was added, incubated for 1 min, and then centrifuged at 13,000 rpm for 1 minute. The eluent was collected and the spin column was discarded.

Typically, 200 ng is used for DNA shearing, but the amount of DNA can range from 20 to 200 ng or higher.

Example B.2

Alternative to DNA Shearing

This example describes an alternative method for DNA shearing from Example 2A.

A double stranded genomic DNA is first denatured to single stranded DNA, and then mixed with primers, DNA polymerase (for example, Exo-DNA polymerase), dNTPs, and a small amount of ddNTPs. The primer sequence can be a random hexamer, or a random hexamer tagged with an adaptor sequence at the 5' end. Methods to use tagged random hexamer amplification to clone and sequence minute quantities of DNA are described, for example, in Wong K. K. et al., *Nucleic Acids Res.* 1996; 24(19):3778-83. The reaction is incubated under the conditions that allow primer-template annealing and DNA synthesis. The DNA synthesis will terminate when a ddNTP is incorporated into the newly synthesized first strand. The length of the synthesized first strand DNA can be controlled by the ratio of dNTPs to ddNTPs. For example, the molar ratio of dNTPs to ddNTP is at least about 1000:1, about 5000:1, or about 10000:1. After first strand synthesis, short fragments (such as primers and synthesized first strand DNA with short length and ddNTPs can be removed by size selection (for example, using a size selection spin column). The resulting first strand DNA is mixed with primers (for example, random hexamers or random hexamers tagged with an adaptor sequence), DNA polymerase (for example, Exo+ DNA polymerase), and dNTPs. An Exo+ DNA polymerase can be used to remove the terminal 3'-ddNTP from the first strand DNA or even to generate blunt ends over the second priming site. The reaction is then incubated under the conditions that allow primer-template annealing and DNA synthesis. After synthesis of the second strand, the resulting double stranded DNA fragments can be purified and used directly in library construction. Alternatively, the double stranded DNA fragments can be PCR amplified using primers containing adaptor sequences if these adaptor sequences have been included in the primers for first- and second-strand synthesis. The primers for PCR amplification can also include the entire sequences and/or bar code sequences.

Example C

Library Preparation

End Repair Reaction

End-repair reagents (NEB #E6050L) were thawed and an end-repair mastermix was prepared on ice. To prepare 70 μl of mastermix per sample, 55 μl nuclease free water was mixed with 10 μl 10× End Repair reaction buffer and 5 μl End Repair enzyme mix. Then 70 μl of mastermix was added to 30 μl of each sheared DNA sample in a 96 well PCR plate on ice. The reaction was incubated in a thermocycler at 20° C. for 30 minutes. Each sample was purified using a QIAGEN MinElute® column. Briefly, 5× QIAGEN PBI buffer was added to sample (for example, 500 μl of PBI buffer was added to 100 μl of sample) in a 1.5 ml microcentrifuge tube. Each sample was vortexed, briefly spun down, and transferred to a MinElute spin column. MinElute spin column was centrifuged at 13,000 rpm for 1 minute, and the flow-through was discarded. 750 μl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 minutes. For the first elution, 22 μl of QIAGEN Elution Buffer (10 mM Tris, pH8.5) was added to each column, incubated for 2-3 min, and then centrifuged at 13,000 rpm for 1 minute. For the second elution, 22 μl of QIAGEN Elution Buffer was added, incubated for 1 min, and then centrifuged at 13,000 rpm for 1 minute. The eluent was collected and the spin column was discarded.

3' A-Base Addition

A-base addition reagents (NEB #E6053L) were thawed on ice and an A-base addition mastermix was prepared on ice. To prepare 10 µl of mastermix per sample, 2 µl nuclease-free water was mixed with 5 µl 10× dA-Tailing reaction buffer and 3 µl Klenow Fragment (3'->5' exo-). 10 µl of mastermix was added to 40 µl of each purified end-repaired DNA sample in a 96 well PCR plate on ice. The reaction was incubated in a thermocycler at 37° C. for 30 min. Each sample was purified using a QIAGEN MinElute® column. Briefly, 5× QIAGEN PBI buffer was added to sample (for example, 250 µl of PBI buffer was added to 50 µl of sample) in a 1.5 ml microcentrifuge tube. Each sample was vortexed, briefly spun down, and transferred to a MinElute spin column. MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 min. For the first elution, 13 µl of QIAGEN Elution Buffer (10 mM Tris, pH8.5) was added to each column, incubated for 2-3 min, and then centrifuged at 13,000 rpm for 1 minute. For the second elution, 13 µl of QIAGEN Elution Buffer was added, incubated for 1 min, and then centrifuged at 13,000 rpm for 1 minute. The eluent was collected and the spin column was discarded.

Ligation of Multiplex Adaptors

Ligation reagents (NEB #E6056L) were thawed and a ligation mastermix was prepared on ice. To prepare 36 µl of mastermix per sample, 12 µl 5× Quick Ligation reaction buffer was added to 3.3 µl Illumina Multiplex Adaptor (15 uM, included in Illumina Cat. #PE-400-1001) (3.3 µl adaptor/1 µg starting input DNA was used). For example, for one sample of 500 ng input DNA, the adaptors were first diluted in water (2 µl adaptors plus 2 µl H2O), then 3.3 µl of this diluted adaptor mix, 15.7 µl of nuclease free water, and 5 µl of Quick T4 DNA ligase were added to the ligation reaction. For >1 µg starting material, >3.3 µl of adaptors were used. Thus, less water was added to keep the total volume of diluted adaptor mix and nuclease free water at 19 µl.

36 µl of mastermix and 24 µl of each dA-tailed DNA sample were added to the wells of a 96 well PCR plate on ice. The reaction was incubated in a thermocycler at 25° C. for 30 min. Each sample was purified using a QIAGEN MinElute® column. Briefly, 5× QIAGEN PBI buffer was added to sample (for example, 300 µl of PBI buffer was added to 60 µl of sample) in a 1.5 ml microcentrifuge tube. Each sample was vortexed, briefly spun down, and transferred to a MinElute spin column. MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 minutes. For the first elution, 20 µl of QIAGEN Elution Buffer (10 mM Tris, pH8.5) was added to each column, incubated for 2-3 minutes, and then centrifuged at 13,000 rpm for 1 minute. For the second elution, 20 µl of QIAGEN Elution Buffer was added, incubated for 1 minute, and then centrifuged at 13,000 rpm for 1 minute. The eluent was collected and the spin column was discarded.

PCR Enrichment

PCR reagents were thawed and a PCR mastermix was prepared on ice. For 62 µl of mastermix per sample, 50 µl of 2× Phusion High Fidelity mastermix with HF Buffer (Finnzyme, NEB Cat. #F-531S), 8 µl nuclease-free water, 2 µl Illumina Primer 1.0 (25 µM), and 2 µl Illumina Primer 2.0 (0.5 µM) were used. Then 62 µl of mastermix was mixed with 2 µl Illumina Index Primer (25 µM, included in Illumina Cat. #PE-400-1001) with appropriate bar code and 36 µl of ligated DNA sample in a 96-well PCR plate.

The reaction was incubated in a thermocycler as follows:

| | |
|---|---|
| 1 Cycle | 98° C. 30 sec |
| 18 Cycles | 98° C. 10 sec |
| 65° C. | 30 sec |
| 72° C. | 30 sec |
| 1 Cycle | 72° C. 5 min |
| 4° C. | hold |

Each PCR reaction was size selected with 1.8× volume of AMPureXP beads (Agencourt; Beckman Coulter Genomics Cat. #A6388). Briefly, 1.8× AMPureXP beads were added to sample (for example, 180 µl of beads were added to 100 µl of sample) in a 1.5 ml microcentrifuge tube, vortexed, and incubated for 5 minutes with end-over-end rotation mixing. Tubes were placed on a magnet stand until the solution cleared (2 minutes). The supernatant was discarded without disturbing the beads captured on the magnet. 600 µl of freshly-made 70% ethanol was added to the beards, incubated for 1 min followed by removal of the ethanol. A second aliquot of 600 µl freshly-made 70% ethanol was added to the beads, incubated for 1 minute, and the ethanol was removed. The tubes were put back on the magnet stand for 1-2 minutes to re-capture the beads. Any remaining ethanol was removed and the beads were air dried at room temperature for 5-10 minutes. 30 µl of QIAGEN Elution Buffer was added to the beads, vortexed, and incubated for 2 minutes. Tubes were placed back on the magnet stand until the solution cleared (2 minutes). The supernatant was transferred to a fresh 1.5 mL tube and the beads were discarded. The eluted DNA samples were quantified using a Q-PCR assay. These quantifications will allow for equimolar pooling to ensure equal representation of each library within a pooled hybrid capture selection.

Example D

Hybrid Selection

Pool Indexed Sample Libraries

Pools (up to 12-plex) of libraries that had been indexed, purified, and quantified by Q-PCR were made on ice. Equimolar pools were prepared in 1.5 ml microcentrifuge tubes to ensure that each sample was represented in the hybrid selection process equally. The total input of DNA for each of these pools can range from 2000 ng to 500 ng. Typically, the total input DNA is 2000 ng. Thus, if twelve samples are pooled, 166.67 ng of each can be pooled to achieve a total of 2000 ng. The final volume of a 2000 ng library pool should be 4 µl. Due to varying concentrations of the indexed libraries a pool can be made with any larger volume but then the pool should be dried down by speedvac (using low heat) and reconstituted in 4 µl of nuclease-free water.

The greater the yield in a library construction, the greater the complexity of the library.

Hybridization of the Pooled DNA Libraries to Biotinylated-RNA Baits

Agilent SureSelect Target Enrichment Paired End kit (#G3360A-J) was used in this experiment. Hybridization Buffer #3, SureSelect Block #1, SureSelect Block #2, Paired End Primer 1.0 block, Index Primer 1-12 block, RNAse block, and biotinylated-RNA bait were thawed on ice.

The following mastermixes were prepared:
a. Hybridization Buffer Mix (13 µl per reaction):
   i. Hybridization Buffer #1 (Agilent)—25 µl
   ii. Hybridization Buffer #2 (Agilent)—1 µl
   iii. Hybridization Buffer #3 (Agilent)—10 µl
   iv. Hybridization Buffer #4 (Agilent)—13 µl
b. Blocking Mix (8 µl per reaction):
   i. SureSelect Block #1 (Agilent)—2.5 µl
   ii. SureSelect Block #2 (Agilent)—2.5 µl
   iii. Paired End primer 1.0 block (IDT, resuspended to 200 µM with $H_2O$)—1.5 µl
   iv. Index Primer 1-12 block (IDT, resuspended to 200 µM with $H_2O$)—1.5 µl
c. Dilution of RNase Block
   i. For custom biotinylated RNA-baits with territory <3 Mb: 1 µl of RNase Block (Agilent) was diluted in 9 µl of water.
   ii. For custom baits with a bait territory >3 Mb: 1 µl of RNase block was diluted in 3 µl of water (still 0.5 µl of RNase block per 7 µL capture reaction)
d. Bait Mix: (7 µl per reaction)
   i. RNA Baits—2 µl (for baits which have a bait territory >3 Mb, 5 µl bait was used)
   ii. Diluted RNase Block—5 µl (for baits which have a bait territory >3 Mb, 2 µl RNase block diluted as indicated above was used)

Once the Hybridization Buffer Mix, Blocking Mix, and Bait Mix(es) were prepared, the hybridization buffer mix was vortexed, spun down, and heated to 65° C. in the heat block. 4 µl of each pooled sample library to be hybrid selected was mixed with 8 µl of the blocking mix in a 96 well PCR plate. The reaction was incubated in a thermocycler at 95° C. for 5 minutes and then held at 65° C. When the pooled sample libraries/blocking mix had been incubating at 95° C. for 5 min and then at 65° C. for 2.5 minutes, the bait mix (=bait/RNAse block mix) were put in the heat block at 65° C. for 2.5 minutes. The hybridization buffer containing tubes were quickly spun down, and then immediately returned to 65° C. heat block. 13 µl of the heated hybridization buffer mix was pipetted into each sample library/block mix while the 96 well plate remained in the thermocycler at 65° C. Once the bait mix had been incubated for 2.5 minutes at 65° C., 7 µl of the bait mix was added to each sample library/block/hybridization buffer mix while the 96 well plate remained in the thermocycler at 65° C. The reaction (total volume was 32 µl) was incubated at 65° C. for 24 hours in a thermocycler.

Preparation of the Magnetic Beads

SureSelect Wash Buffer #2 was prewarmed at 65° C. in the heat block. Dynal MyOne Streptavidin T1 beads (Invitrogen) were vortexed and resuspended. The beads were washed by adding 200 µl of SureSelect Binding Buffer per 50 µl Dynal beads (for example, 1200 µl of SureSelect Binding Buffer was used to prepare 300 µl of Dynal beads). The beads were vortexed for 5 seconds and spun down briefly. The beads were placed on a magnet stand for about 15 seconds or until all the beads were captured. The supernatant was removed and discarded. Wash was repeated with SureSelect Binding Buffer two more times for a total of three washes. After washing, the beads were resuspended in 200 µl of SureSelect Binding Buffer per 50 µl Dynal beads (for example, 1200 µl of SureSelect Binding Buffer was used to prepare 300 µl of Dynal beads). The resuspended beads were vortexed and spun down briefly. 200 µl of resuspended beads were aliquoted into individual 1.5 ml microcentrifuge tubes.

Selection of the Hybrid Captured DNA

After 24 hours of incubation, each hybridized sample from the PCR plate in the thermocycler at 65° C. was quickly pipetted into a tube containing 200 µl of prepared beads at room temperature. The mixtures of sample and beads were vortexed for 5 seconds and incubated on a rotator at room temperature for 30 minutes, to ensure proper mixing. Then the tubes were quickly spun down. The beads were captured on a magnet (for 2 minutes) and the supernatant was removed and discarded. The beads were resuspended in 500 µl of SureSelect Wash Buffer #1, for a low stringency wash. The samples were vortexed for 5 seconds and incubated for 15 min at room temperature off the magnet. Samples were vortexed for 5 seconds every 3-5 minutes. The tubes were quickly spun down. The beads were then captured on a magnet stand for 2 minutes and the supernatant was removed and discarded. For a high stringency wash to remove off-target material, the beads were washed with SureSelect Wash Buffer #2 preheated to 65° C. Briefly, the beads were resuspended in 500 µl of prewarmed SureSelect Wash Buffer #2 and mixed on a vortexer for 5 seconds to resuspend the beads. The beads were briefly spun down in a centrifuge and incubated at 65° C. for 10 min in a heat block with occasional vortex mixing for 5 seconds at room temperature. Then the beads were briefly spun down in a centrifuge and captured on a magnet for 2 minutes. Wash was repeated 2 more times with prewarmed SureSelect Wash Buffer #2 at 65° C. for a total of three washes. Then the wash buffer was completely removed and 50 µl of SureSelect Elution Buffer was added to the beads following by vortexing for 5 seconds to mix the beads. The samples were incubated for 10 minutes at room temperature with occasional vortex mixing for 5 seconds. The beads were briefly spun down in a centrifuge and captured on a magnet stand. The supernatant containing the captured DNA was pipetted to a new 1.5 ml microcentrifuge tube. 50 µl of SureSelect Neutralization Buffer was added to the captured DNA. Samples were vortex for 5 seconds, briefly spun down in a centrifuge, and purified using 1.8× volume of AMPureXP beads. DNA was eluted in 40 µl nuclease-free water.

PCR Enrichment of the Captured DNA

PCR reagents were thawed and a PCR mastermix was prepared on ice. For 60 µl of mastermix per sample, 50 µl 2× Phusion High Fidelity mastermix with HF buffer (NEB #F-531S) was mixed with 8 µl nuclease-free water, 1 µl QPCR Primer1.1 (100 µM in H2O), and 1 µl QPCR Primer2.1 (100 µM in H2O). The primer sequences for Q-PCR are:

QPCR Primer1.1 (HPLC-purified from IDT):

(SEQ ID NO: 79)
5'AATGATACGGCGACCACCGAGAT3'

QPCR Primer2.1 (HPLC-purified from IDT):

(SEQ ID NO: 80)
5'CAAGCAGAAGACGGCATACGA3'

60 µl of mastermix was added to 40 µl of each purified captured DNA sample in a 96 well PCR plate. The reaction was incubated in a thermocycler as follows:

| | |
|---|---|
| 1 Cycle | 98° C. 30 sec |
| 12 Cycles | 98° C. 10 sec |
| 65° C. | 30 sec |
| 72° C. | 30 sec |
| 1 Cycle | 72° C. 5 min |
| 4° C. | Hold |

Each 100 μl of PCR reaction was purified with 1.8× volume of AMPureXP beads and eluted in 35 μl of elution buffer (10 mM Tris, pH 8.5). The hybrid selected/captured DNA samples were quantified using a Q-PCR assay. The Q-PCR assay detected the end adaptors and the reads indicated how much of each sample should be loaded on a sequencing flow cell to get the appropriate cluster density.

Example E

Methods

The following exemplifies certain embodiments of the methods and experimental conditions used to identify the alterations according to the Examples. Additional translocation screening can be done using, for example, either qRT-PCR analysis of cDNA prepared from a pre-selected tumor sample.

Massively parallel DNA sequencing was done on hybridization captured, adaptor ligation-based libraries using DNA isolated from archived fixed paraffin-embedded tissue. A combination of analysis tools were used to analyze the data and assign DNA alteration calls. Additional translocation screening was done using either qRT-PCR analysis of cDNA prepared from frozen tumors or IHC assessment of archived FFPE specimens. Massively parallel cDNA sequencing was performed to confirm expression of both novel translocations using RNA isolated from FFPE tissue. Matched normal reference genomic DNA from blood was sequenced for the index NSCLC patient to confirm the somatic origin of the rearrangement.

Genomic DNA Sequencing

Sequencing of 2574 exons of 145 cancer genes was done using DNA from archived formalin fixed paraffin embedded (FFPE) tumor specimens; 24 from NSCLC patients. Sequencing libraries were constructed by the adaptor ligation method using genomic DNA followed by hybridization selection with optimized RNA hybridization capture probes (Agilent SureSelect custom kit). Sequencing on the HiSeq2000 instrument (Illumina) was done using 36×36 paired reads to an average depth of 253×. Data processing and mutation assignments for base substitutions, indels, copy number alterations and genomic rearrangements were done using a combination of tools optimized for mutation calling from tumor tissue.

cDNA Sequencing cDNA was generated from total RNA extracted from a single 5-10 um FFPE tissue section using the Roche High Pure kit and reverse transcribed to cDNA with random hexamer primers by the SuperScript® III First-Strand Synthesis System (Invitrogen). Double stranded cDNA was made with the NEBNext® mRNA Second Strand Synthesis Module (New England Biolabs) and used as input to library construction, hybrid capture and sequencing as for FFPE DNA samples. Analysis of expression levels was done with a combination of analysis tools.

Example F

Exemplary Selected Genes and Variants for Multiplex Analysis

This example provides four exemplary tables summarizing a selection of genes, variants and cancer types for multiplex analysis.

TABLE 1

List of exemplary selected genes and variants, associated cancer types, and priority codons for multiplex analysis.

| Hugo Gene | Gene Category | Cancer Types | Priority Codons |
|---|---|---|---|
| ABL1 | Priority 1 | Leukemia (for example, chronic myeloid leukemia (CML), acute myeloid leukemia (AML), acute lymphoblastic leukemia (ALL)) | 315 |
| AKT1 | Priority 1 | breast cancer, colorectal cancer, ovarian cancer | |
| ALK | Priority 1 | Lymphoma (for example, non-Hodgkin lymphoma, anaplastic large-cell lymphoma (ALCL)), inflammatory myofibroblastic tumor | |
| APC | Priority 1 | Colorectal cancer, medulloblastoma, mismatch repair cancer syndrome | 1114, 1338, 1450, 1556 |
| AR | Priority 1 | Prostate cancer | |
| BRAF | Priority 1 | Lung cancer, non-Hodgkin lymphoma, colorectal cancer, thyroid cancer, melanoma | 600 |
| CDKN2A | Priority 1 | melanoma, pancreatic cancer, Li-Fraumeni syndrome, lung cancer (for example, non-small cell lung cancer (NSCLC)), squamous cell carcinoma, retinoblastoma, astrocytoma | |
| CEBPA | Priority 1 | Leukemia (for example, acute myeloid leukemia (AML), acute myeloid leukemia (AML), monoblastic leukemia), retinoblastoma | |
| CTNNB1 | Priority 1 | Colorectal cancer, ovarian cancer, prostate cancer, liver cancer (for example, hepatoblastoma (HB), hepatocellular carcinoma (HCC)), pilomatrixoma, medulloblastoma, salivary gland pleiomorphic adenomas | 32, 33, 34, 37, 41, 45 |
| EGFR | Priority 1 | Lung cancer, squamous cell carcinoma, glioblastoma, glioma, colorectal cancer | 719, 746-750, 768, 790, 858, 861 |
| ERBB2 | Priority 1 | Gastric cancer, glioma, ovarian cancer, lung cancer | |
| ESR1 | Priority 1 | Breast cancer, endometrial cancer, endometrial adenocarcinoma, leiomyoma, mammary ductal carcinoma | |
| FGFR1 | Priority 1 | Leukemia, lymphoma | |
| FGFR2 | Priority 1 | Breast cancer, prostate cancer | |
| FGFR3 | Priority 1 | Bladder cancer, cervical cancer, multiple myeloma, | |
| FLT3 | Priority 1 | Leukemia (for example, acute myeloid leukemia (AML), acute promyelocytic leukemia, acute lymphoblastic leukemia) | 835 |

TABLE 1-continued

List of exemplary selected genes and variants, associated cancer types, and priority codons for multiplex analysis.

| Hugo Gene | Gene Category | Cancer Types | Priority Codons |
|---|---|---|---|
| HRAS | Priority 1 | Hurthle cell thyroid carcinoma, bladder cancer, melanoma, colorectal cancer | 12, 13, 61 |
| JAK2 | Priority 1 | Leukemia (for example, chronic lymphoblastic leukemia (CLL), acute lymphoblastic leukemia (ALL), chronic myelogenous leukemia (CML), acute myelogenous leukemia (AML)) | 617 |
| KIT | Priority 1 | Gastrointestinal stromal tumor (GIST), testicular tumor, leukemia (for example, acute myeloid leukemia (AML)), mast cell tumor, mesenchymal tumor, adenoid cystic carcinoma, lung cancer (for example, small cell lung cancer), lymphoma (for example, Burkitt lymphoma) | 816 |
| KRAS | Priority 1 | Leukemia (for example, acute myelogenous leukemia (AML), juvenile myelomonocytic leukemia (JMML)), colorectal cancer, lung cancer | 12, 13, 61 |
| MET | Priority 1 | Gastric cancer, hepatocellular carcinoma (HCC), hereditary papillary renal carcinoma (HPRC), lung cancer (for example, non-small cell lung cancer), papillary thyroid carcinoma, glioma, esophageal adenocarcinoma, osteosarcoma, endometrial cancer, squamous cell carcinoma, melanoma, breast cancer | |
| MLL | Priority 1 | Leukemia (for example, acute lymphoblastic leukemia (ALL), acute myeloid leukemia (AML) | |
| MYC | Priority 1 | chronic lymphocytic leukemia (CLL), Burkitt lymphoma, plasmacytoma, | |
| NF1 | Priority 1 | Leukemia (for example, juvenile myelomonocytic leukemia (JMML)), neurofibroma, | |
| NOTCH1 | Priority 1 | Squamous cell carcinoma, leukemia (for example, acute lymphoblastic leukemia (ALL)), medullary thyroid carcinoma, lymphoma (for example, thymic lymphoma, T-cell lymphoma) | 1575, 1601 |
| NPM1 | Priority 1 | Lymphoma (for example, non-Hodgkin lymphoma, anaplastic large cell lymphoma, anaplastic lymphoma), leukemia (for example, acute promyelocytic leukemia, acute myelogenous leukemia (AML)) | |
| NRAS | Priority 1 | Leukemia (for example, juvenile myelomonocytic leukemia (JMML), acute myeloid leukemia (AML), acute lymphoblastic leukemia), melanoma, | 12, 13, 61 |
| PDGFRA | Priority 1 | Gastrointestinal stromal tumor (GIST), leukemia (for example, chronic eosinophilic leukemia (CEL), acute lymphocytic leukemia (ALL)), mesenchymal tumor | |
| PIK3CA | Priority 1 | Colorectal cancer, breast cancer, ovarian cancer, hepatocellular carcinoma, head and neck squamous cell carcinoma (HNSCC), anaplastic thyroid carcinoma, endometrial cancer, gallbladder adenocarcinoma, glioblastoma | 88, 542, 545, 546, 1047, 1049 |
| PTEN | Priority 1 | Head and neck squamous cell carcinomas (HNSCC), endometrial cancer, glioma, prostate cancer, glioblastoma | 130, 173, 233, 267 |
| RB1 | Priority 1 | Retinoblastoma, bladder cancer, osteosarcoma, lung cancer (for example, small cell lung cancer, non-small cell lung cancer), leukemia (for example, acute lymphoblastic leukemia (ALL)) | |
| RET | Priority 1 | Colorectal cancer, medullary thyroid carcinoma, multiple neoplasia type 2B, pheochromocytoma, multiple neoplasia type 2A, thyroid papillary carcinoma, thryoid cancer, retinoblastoma | 918 |
| TP53 | Priority 1 | TP53 is frequently mutated or inactivated in about 60% of cancers, for example, esophageal squamous cell carcinoma, Li-Fraumeni syndrome, head and neck squamous cell carcinomas (HNSCC), lung cancer, hereditary adrenocortical carcinoma, astrocytoma, squamous cell carcinoma, bladder cancer, colorectal cancer, glioblastoma, retinoblastoma | 175, 245, 248, 273, 306 |
| ABL2 | Cancer Gene | Acute myeloid leukemia (AML) | |
| AKT2 | Cancer Gene | Ovarian cancer, pancreatic cancer | |
| AKT3 | Cancer Gene | Melanoma, glioma, uternine cancer, prostate cancer, oral cancer, ovarian cancer | |
| ARAF | Cancer Gene | Angioimmunoblastic T-cell lymphoma, ehrlich ascites tumor | |
| ARFRP1 | Cancer Gene | Breast cancer | |
| ARID1A | Cancer Gene | Neuroblastoma, acute lymphoblastic leukemia (ALL), neuroendocrine tumor | |
| ATM | Cancer Gene | Leukemia (for example, T-cell prolymphocytic leukemia (T-PLL)), lymphoma, medulloblastoma, glioma | |
| ATR | Cancer Gene | Pyothorax-associated lymphoma, T-cell lymphoma | |
| AURKA | Cancer Gene | Laryngeal squamous cell carcinoma, ovarian cancer, bladder cancer, head and neck squamous cell carcinoma (HNSCC), laryngeal carcinoma, esophageal squamous cell carcinoma (ESCC), pancreatic cancer | |
| AURKB | Cancer Gene | Colorectal cancer, astrocytoma, ependymal tumor, glioma, esophageal squamous cell carcinoma (ESCC), acute myeloid leukemia (AML) | |
| BCL2 | Cancer Gene | Lymphoma, colorectal adenocarcinoma, esophageal squamous cell carcinoma (ESCC), synovial sarcoma, leukemia | |
| BCL2A1 | Cancer Gene | Pulmonary granuloma, gastric adenoma, burkitt lymphoma, parotid adenoma, kaposi sarcoma, gastric cancer, colon cancer | |
| BCL2L1 | Cancer Gene | Head and neck squamous cell carcinoma, glioblastoma, mesothelioma, pancreatic cancer, adenocarcinoma lung | |
| BCL2L2 | Cancer Gene | Brain cancer, leukemia, lymphoma, colorectal adenocarcinoma, colorectal cancer, adenoma, cervical squamous cell carcinoma | |
| BCL6 | Cancer Gene | Lymphoma, leukemia | |
| BRCA1 | Cancer Gene | Breast cancer, ovarian cancer | |
| BRCA2 | Cancer Gene | Breast cancer, ovarian cancer, pancreatic cancer | |
| CARD11 | Cancer Gene | Lymphoma | |
| CBL | Cancer Gene | Lymphoma, leukemia | |

TABLE 1-continued

List of exemplary selected genes and variants, associated cancer types, and priority codons for multiplex analysis.

| Hugo Gene | Gene Category | Cancer Types | Priority Codons |
|---|---|---|---|
| CCND1 | Cancer Gene | Chronic lymphoblastic leukemia (CLL), B-cell acute lymphoblastic leukemia (B-ALL), breast cancer | |
| CCND2 | Cancer Gene | Retinoblastoma, mantle cell lymphoma, T-cell acute lymphoblastic leukemia (T-ALL), Burkitt lymphoma, testicular germ cell tumor, ovarian granulosa cell tumor, multiple myeloma | |
| CCND3 | Cancer Gene | Retinoblastoma, mantle cell lymphoma, anaplastic large cell lymphoma, lymphoma (non-hodgkins), B-cell lymphoma, laryngeal squamous cell carcinoma, indolent lymphoma, null cell adenoma | |
| CCNE1 | Cancer Gene | Breast cancer, ovarian cancer, bladder cancer, retinoblastoma | |
| CDH1 | Cancer Gene | Gastric cancer, lobular carcinoma, squamous cell carcinoma, invasive ductal carcinoma, invasive lobular carcinoma | |
| CDH2 | Cancer Gene | Melanoma, malignant mesothelioma, pleural mesothelioma, desmoplastic melanoma, lung adenocarcinoma, endometrioid tumor, mesothelioma, bladder cancer, esophageal squamous cell carcinoma (ESCC) | |
| CDH20 | Cancer Gene | Breast cancer | |
| CDH5 | Cancer Gene | Granuloma, epithelioid sarcoma | |
| CDK4 | Cancer Gene | Melanoma | |
| CDK6 | Cancer Gene | Acute lymphoblastic leukemia (ALL) | |
| CDK8 | Cancer Gene | Colon cancer, lung cancer, rectal cancer, acute lymphoblastic leukemia (ALL) | |
| CDKN2B | Cancer Gene | Leukemia, retinoblastoma, laryngeal squamous cell carcinoma | |
| CDKN2C | Cancer Gene | Thyroid carcinoma, pituitary adenoma, oligodendroglioma, pancreatic endocrine tumor, multiple myeloma, hepatoblastoma, lymphoid tumor, multiple endocrine neoplasia type 1, anaplastic oligodendroglioma | |
| CHEK1 | Cancer Gene | Leukemia, colon cancer | |
| CHEK2 | Cancer Gene | Breast cancer | |
| CRKL | Cancer Gene | Leukemia, lymphoma | |
| CRLF2 | Cancer Gene | Leukemia | |
| DNMT3A | Cancer Gene | Testicular germ cell tumor, lymphosarcoma, hepatocellular carcinoma, salivary gland tumor | |
| DOT1L | Cancer Gene | Leukemia | |
| EPHA3 | Cancer Gene | Rhabdomyosarcoma, lymphoma, prostate cancer, hepatocellular carcinoma, leukemia, melanoma | |
| EPHA5 | Cancer Gene | Glioblastoma, breast cancer, astrocytoma, Wilms' tumor, glioma | |
| EPHA6 | Cancer Gene | Breast cancer | |
| EPHA7 | Cancer Gene | Glioblastoma multiforme (GBM), colon cancer, duodenal cancer, parathyroid tumor, prostate cancer | |
| EPHB1 | Cancer Gene | Colorectal cancer, embryonal carcinoma, gastric cancer, teratocarcinoma, mucinous carcinoma | |
| EPHB4 | Cancer Gene | Head and neck squamous cell carcinoma (HNSCC), brain cancer, endometrial cancer, ovarian cancer | |
| EPHB6 | Cancer Gene | Neuroblastoma, melanoma, non-small cell lung cancer (NSCLL) | |
| ERBB3 | Cancer Gene | Breast cancer, non-small cell lung cancer (NSCLC), pancreatic cancer, invasive ductal carcinoma, lung adenocarcinoma, endometrioid carcinoma, pilocytic astrocytoma | |
| ERBB4 | Cancer Gene | Breast cancer, medulloblastoma, cervical squamous cell carcinoma, prostate cancer, leukemia | |
| ERG | Cancer Gene | Prostate cancer, Ewing's sarcoma, leukemia, prostate cancer | |
| ETV1 | Cancer Gene | Prostate cancer, breast cancer, Ewing's sarcoma, desmoplastic small round cell tumor, myxoid liposarcoma, clear cell sarcoma | |
| ETV4 | Cancer Gene | Breast cancer, ovarian cancer, squamous cell carcinoma tongue, Ewing's sarcoma | |
| ETV5 | Cancer Gene | Ganglioglioma, brain tumor | |
| ETV6 | Cancer Gene | Leukemia, congenital fibrosarcoma, secretory carcinoma, myelodysplastic syndrome | |
| EWSR1 | Cancer Gene | Ewing's sarcoma, clear cell sarcoma, desmoplastic small round cell tumor, extraskeletal myxoid chondrosarcoma, myxoid liposarcoma, angiomatoid fibrous histiocytoma | |
| EZH2 | Cancer Gene | Prostate cancer, gallbladder adenocarcinoma, breast cancer, bladder cancer, gastric cancer, Ewing's sarcoma | |
| FANCA | Cancer Gene | Leukemia | |
| FBXW7 | Cancer Gene | Colorectal cancer, endometrial cancer, T-cell acute lymphoblastic leukemia (T-ALL) | |
| FGFR4 | Cancer Gene | Pituitary tumor, prostate cancer, lung cancer, astrocytoma, rhabdomyosarcoma, pituitary adenoma, fibroadenoma | |
| FLT1 | Cancer Gene | Breast cancer, prostate cancer | |
| FLT4 | Cancer Gene | Lung cancer, Kaposi's sarcoma, gastric cancer, lymphangioma, squamous cell carcinoma | |
| FOXP4 | Cancer Gene | Lymphoma, brain tumor | |
| GATA1 | Cancer Gene | Megakaryoblastic leukemia of Downs Syndrome | |
| GNA11 | Cancer Gene | Breast cancer | |
| GNAQ | Cancer Gene | Uveal melanoma | |
| GNAS | Cancer Gene | Pituitary adenoma | |
| GPR124 | Cancer Gene | Colon cancer | |
| GUCY1A2 | Cancer Gene | Breast cancer | |
| HOXA3 | Cancer Gene | Breast cancer | |
| HSP90AA1 | Cancer Gene | Lymphoma, myeloma | |
| IDH1 | Cancer Gene | Glioblastoma multiforme (GBM) | |
| IDH2 | Cancer Gene | Glioblastoma multiforme (GBM) | |
| IGF1R | Cancer Gene | Ewing's sarcoma, breast cancer, uveal melanoma, adrenocortical carcinoma, pancreatic cancer | |
| IGF2R | Cancer Gene | Gastrointestinal tumor, liver cancer | |
| IKBKE | Cancer Gene | Breast cancer | |
| IKZF1 | Cancer Gene | Lymphoma, leukemia | |
| INHBA | Cancer Gene | Erythroleukemia, barrett metaplasia, esophageal adenocarcinoma, granulosa cell tumor, sex cord-stromal tumor, lung adenocarcinoma, pheochromocytoma, krukenberg tumor, ovarian cancer | |
| IRS2 | Cancer Gene | Hyperinsulinemia, uterine leiomyosarcoma | |
| JAK1 | Cancer Gene | Leukemia, ovarian cancer, breast cancer | |
| JAK3 | Cancer Gene | Acute lymphoblastic leukemia (ALL) | |
| JUN | Cancer Gene | Skin cancer, leukemia | |

TABLE 1-continued

List of exemplary selected genes and variants, associated cancer types, and priority codons for multiplex analysis.

| Hugo Gene | Gene Category | Cancer Types | Priority Codons |
|---|---|---|---|
| KDR | Cancer Gene | Non-small cell lung cancer (NSCLC), angiosarcoma | |
| LRP1B | Cancer Gene | Lung cancer, gastric cancer, esophageal cancer | |
| LTK | Cancer Gene | Lymphoma, breast cancer | |
| MAP2K1 | Cancer Gene | Prostate cancer, gastric cancer | |
| MAP2K2 | Cancer Gene | Pancreatic cancer, intestinal tumor | |
| MAP2K4 | Cancer Gene | Pancreatic cancer, breast cancer, colorectal cancer | |
| MCL1 | Cancer Gene | Multiple myeloma, leukemia, lymphoma | |
| MDM2 | Cancer Gene | Sarcoma, glioma, colorectal cancer | |
| MDM4 | Cancer Gene | Glioblastoma multiforme (GBM), bladder cancer, retinoblastoma | |
| MEN1 | Cancer Gene | Parathyroid tumor | |
| MITF | Cancer Gene | Melanoma | |
| MLH1 | Cancer Gene | Colorectal cancer, endometrial cancer, ovarian cancer, CNS cancer | |
| MPL | Cancer Gene | Myeloproliferative disorder (MPD) | |
| MRE11A | Cancer Gene | Breast cancer, lymphoma | |
| MSH2 | Cancer Gene | Colorectal cancer, endometrial cancer, ovarian cancer | |
| MSH6 | Cancer Gene | Colorectal cancer | |
| MTOR | Cancer Gene | Lymphoma lung cancer, renal cancer, clear cell carcinoma, glioma | |
| MUTYH | Cancer Gene | Colorectal cancer | |
| MYCL1 | Cancer Gene | Small cell lung cancer (SCLC) | |
| MYCN | Cancer Gene | Neuroblastoma | |
| NF2 | Cancer Gene | Meningioma, acoustic neuroma, renal cancer | |
| NKX2-1 | Cancer Gene | Lung cancer, thyroid cancer, adenocarcinoma | |
| NTRK1 | Cancer Gene | Papillary thyroid cancer | |
| NTRK3 | Cancer Gene | Congenital fibrosarcoma, secretory breast cancer | |
| PAK3 | Cancer Gene | Lung cancer | |
| PAX5 | Cancer Gene | Non-Hodgkin Lymphoma (NHL), acute lymphoblastic leukemia (ALL, for example, B-cell ALL) | |
| PDGFRB | Cancer Gene | Myeloproliferative disorder (MPD), acute myeloid leukemia (AML), chronic myeloid leukemia (CML), chronic myelomonocytic leukemia (CMML) | |
| PIK3R1 | Cancer Gene | Glioblastoma, ovarian cancer, colorectal cancer | |
| PKHD1 | Cancer Gene | Pancreatic cancer | |
| PLCG1 | Cancer Gene | Head and neck cancer, leukemia | |
| PRKDC | Cancer Gene | Glioma, glioblastoma, gastric cancer, ovarian cancer | |
| PTCH1 | Cancer Gene | Skin basal cell , medulloblastoma | |
| PTPN11 | Cancer Gene | Juvenile myelomonocytic leukemia (JMML), acute myeloid leukemia (AML), myelodysplastic syndromes (MDS) | |
| PTPRD | Cancer Gene | Lung cancer, cutaneous squamous cell carcinoma, glioblastoma, neuroblastoma | |
| RAF1 | Cancer Gene | Pilocytic astrocytoma | |
| RARA | Cancer Gene | Leukemia | |
| RICTOR | Cancer Gene | Colon cancer, lymphoma, glioma, breast cancer | |
| RPTOR | Cancer Gene | Breast cancer, prostate cancer | |
| RUNX1 | Cancer Gene | Acute myeloid leukemia (AML), pre-B-cell acute lymphoblastic leukemia (preB-ALL), T-cell acute lymphoblastic leukemia (T-ALL) | |
| SMAD2 | Cancer Gene | esophageal squamous cell carcinoma (ESCC) | |
| SMAD3 | Cancer Gene | Skin cancer, choriocarcinoma | |
| SMAD4 | Cancer Gene | Pancreatic cancer, colon cancer | |
| SMARCA4 | Cancer Gene | Non-small cell lung cancer (NSCLC) | |
| SMARCB1 | Cancer Gene | Malignant rhabdoid | |
| SMO | Cancer Gene | Skin basal cell cancer | |
| SOX10 | Cancer Gene | Oligodendroglioma | |
| SOX2 | Cancer Gene | Embryonal carcinoma, germ cell tumor | |
| SRC | Cancer Gene | Sarcoma, colon cancer, breast cancer | |
| STK11 | Cancer Gene | Non-small cell lung cancer (NSCLC), pancreatic cancer | |
| TBX22 | Cancer Gene | Breast cancer | |
| TET2 | Cancer Gene | Myelodysplastic syndromes (MDS) | |
| TGFBR2 | Cancer Gene | Lung cancer, gastric cancer, colon cancer | |
| TMPRSS2 | Cancer Gene | Prostate cancer | |
| TOP1 | Cancer Gene | Acute myeloid leukemia (AML) | |
| TSC1 | Cancer Gene | Hamartoma, renal cell cancer | |
| TSC2 | Cancer Gene | Hamartoma, renal cell cancer | |
| USP9X | Cancer Gene | Leukemia | |
| VHL | Cancer Gene | Renal cancer, hemangioma, pheochromocytoma | |
| WT1 | Cancer Gene | Wilms' tumor, desmoplastic small round cell tumor | |
| ABCB1 | PGx Gene | | |
| ABCC2 | PGx Gene | | |
| ABCC4 | PGx Gene | | |
| ABCG2 | PGx Gene | | |
| C1orf144 | PGx Gene | | |
| CYP1B1 | PGx Gene | | |
| CYP2C19 | PGx Gene | | |
| CYP2C8 | PGx Gene | | |
| CYP2D6 | PGx Gene | | |
| CYP3A4 | PGx Gene | | |
| CYP3A5 | PGx Gene | | |
| DPYD | PGx Gene | | |
| ERCC2 | PGx Gene | | |
| ESR2 | PGx Gene | | |
| FCGR3A | PGx Gene | | |
| GSTP1 | PGx Gene | | |
| ITPA | PGx Gene | | |
| LRP2 | PGx Gene | | |
| MAN1B1 | PGx Gene | | |
| MTHFR | PGx Gene | | |
| NQO1 | PGx Gene | | |
| NRP2 | PGx Gene | | |
| SLC19A1 | PGx Gene | | |
| SLC22A2 | PGx Gene | | |
| SLCO1B3 | PGx Gene | | |
| SOD2 | PGx Gene | | |
| SULT1A1 | PGx Gene | | |
| TPMT | PGx Gene | | |
| TYMS | PGx Gene | | |
| UGT1A1 | PGx Gene | | |
| UMPS | PGx Gene | | |

"Priority 1" refers to the highest priority of selected genes or gene products.

"Cancer Genes" refer to cancer-associated genes or gene products of less priority relative to Priority 1.

"PGx Genes" refers to genes that are important for pharmacogenetics and pharmacogenomics (PGx).

TABLE 1A

Additional exemplary selected genes and variants, associated cancer types, priority codons, actionability category, and potential therapies.

| Hugo Gene | Gene Category | Cancer Types | Priority Codons | Actionability Category | Reason |
|---|---|---|---|---|---|
| ASXL1 | Priority 1 | Multiple myeloma (MM) | | D | Prognostic (neg MDS) |
| BACH1 | Priority 1 | Breast | | C | PARP Inhibitors |
| BAP1 | Priority 1 | Uveal melanoma, breast, NSCLC | | C | PARP Inhibitors |
| BARD1 | Priority 1 | Breast | | C | PARP Inhibitors |
| BLM | Priority 1 | Leukemia, lymphoma, skin squamous cell, other cancers | | C | |
| BRIP1 | Priority 1 | Acute myeloid leukemia (AML), leukemia, breast | | C | PARP Inhibitors |
| CDKN1B | Priority 1 | Breast | | D | |
| CREBBP | Priority 1 | Acute lymphoblastic leukemia (ALL), AML, DLBCL, B-cell non-Hodgkin's lymphoma (B-NHL) | | D | |
| DDR2 | Priority 1 | NSCLC | | C | Dasatinib |
| EMSY | Priority 1 | Breast | | C | PARP Inhibitors |
| FANCC | Priority 1 | AML, leukemia | | C | PARP inhibitor |
| FANCD2 | Priority 1 | AML, leukemia | | C | PARP inhibitor |
| FANCE | Priority 1 | AML, leukemia | | C | PARP inhibitor |
| FANCF | Priority 1 | AML, leukemia | | C | PARP inhibitor |
| FANCG | Priority 1 | AML, leukemia | | C | PARP inhibitor |
| FANCL | Priority 1 | AML, leukemia | | C | PARP inhibitor |
| HGF | Priority 1 | MM | | C | Resistance |
| NFKB1 | Priority 1 | Breast | | D | Possible POOR PROGNOSIS |
| NOTCH2 | Priority 1 | Marginal zone lymphoma, DLBCL | | D | — |
| PALB2 | Priority 1 | Wilms tumor, medulloblastoma, AML, breast | | C | PARP Inhibitors |
| PBRM1 | Priority 1 | Clear cell renal carcinoma, breast | | E | HDAC inhibitors? |
| PDK1 | Priority 1 | NSCLC | | C | PDK1 inhibitors |
| PIK3R2 | Priority 1 | NSCLC | | C | PI3K-PATHWAY INHIBITORS |
| RAD50 | Priority 1 | Breast | | C | PARP Inhibitors |
| RAD51 | Priority 1 | Breast | | C | PARP Inhibitors |
| ROS1 | Priority 1 | Glioblastoma, NSCLC | | C | |
| SF3B1 | Priority 1 | MDS, CML, ALL, pancreatic, breast | | E | |
| SPOP | Priority 1 | Malignant melanoma | | E | |
| ACVR1B | Cancer Gene | Pancreas, breast | | E | |
| ALOX12B | Cancer Gene | Multiple myeloma (MM) | | E | |
| ATRX | Cancer Gene | Pancreatic neuroendocrine tumors | | E | |
| AXL | Cancer Gene | Non small cell lung cancer (NSCLC), MM | | E | |
| BCOR | Cancer Gene | Breast | | E | |
| BCORL1 | Cancer Gene | Breast | | E | |
| C17orf39 | Cancer Gene | Breast | | E | |
| CASP8 | Cancer Gene | Breast | | E | |
| CBFB | Cancer Gene | AML | | E | |
| CD22 | Cancer Gene | NSCLC, breast | | E | |
| CD79A | Cancer Gene | Diffuse large B-cell lymphoma (DLBCL) | | E | |
| CD79B | Cancer Gene | DLBCL | | E | |
| CDC73 | Cancer Gene | Parathyroid | | E | |
| CDK12 | Cancer Gene | Ovarian | | E | |
| CHUK | Cancer Gene | Colorectal | | E | |
| CRBN | Cancer Gene | Upper aerodigestive tract | | E | |
| CSF1R | Cancer Gene | NSCLC | | E | |
| CTCF | Cancer Gene | Breast | | E | |
| CTNNA1 | Cancer Gene | Breast | | E | |
| CUL4A | Cancer Gene | Leukemia | | E | |
| CUL4B | Cancer Gene | Leukemia | | E | |
| CYP17A1 | Cancer Gene | Breast | | E | |
| DAXX | Cancer Gene | Pancreatic neuroendocrine tumors | | E | |
| DIS3 | Cancer Gene | MM | | E | |
| EP300 | Cancer Gene | Colorectal, breast, pancreatic, AML, ALL, DLBCL | | E | |
| ERCC2 | Cancer Gene | Skin basal cell, skin squamous cell, melanoma | | E | |
| FAM46C | Cancer Gene | MM | | E | |
| FGF1 | Cancer Gene | Breast | | E | |
| FGF10 | Cancer Gene | Breast | | E | |
| FGF12 | Cancer Gene | Breast | | E | |
| FGF14 | Cancer Gene | Breast | | E | |
| FGF19 | Cancer Gene | Breast | | E | |
| FGF23 | Cancer Gene | Breast | | E | |

TABLE 1A-continued

Additional exemplary selected genes and variants, associated cancer types, priority codons, actionability category, and potential therapies.

| Hugo Gene | Gene Category | Cancer Types | Priority Codons | Actionability Category | Reason |
|---|---|---|---|---|---|
| FGF3 | Cancer Gene | Breast | | E | |
| FGF4 | Cancer Gene | Breast | | E | |
| FGF6 | Cancer Gene | Breast | | E | |
| FGF7 | Cancer Gene | Breast | | E | |
| FOXL2 | Cancer Gene | Granulosa-cell tumour of the ovary | 134 | E | |
| GATA2 | Cancer Gene | AML, Chronic Myeloid Leukemia (CML, blast transformation) | | E | |
| GATA3 | Cancer Gene | Breast | | E | |
| GRAF | Cancer Gene | AML, myelodysplastic syndrome (MDS) | | E | |
| GRIN2A | Cancer Gene | Malignant melanoma | | E | |
| GSK3B | Cancer Gene | NSCLC | | E | |
| HLA-A | Cancer Gene | MM | | E | |
| IGF1 | Cancer Gene | Breast | | E | |
| IGF2 | Cancer Gene | Breast | | E | |
| IL7R | Cancer Gene | T-cell acute lymphoblastic leukemia (T-ALL) | | E | |
| INSR | Cancer Gene | NSCLC, glioblastoma, gastric | | E | |
| IRF4 | Cancer Gene | Multiple myeloma (MM) | | E | |
| KDM4C | Cancer Gene | Ovarian, breast | | E | |
| KDM5A | Cancer Gene | AML | | E | |
| KDM6A | Cancer Gene | Renal, oesophageal squamous cell carcinoma (SCC), MM | | E | |
| KEAP1 | Cancer Gene | NSCLC | | E | |
| KLHL6 | Cancer Gene | Chronic lymphocytic leukaemia (CLL) | | E | |
| LMO1 | Cancer Gene | T-cell acute lymphoblastic leukemia (T-ALL), neuroblastoma | | E | |
| LRP6 | Cancer Gene | NSCLC, malignant melanoma | | E | |
| LRRK2 | Cancer Gene | Ovarian, NSCLC | | E | |
| MAGED1 | Cancer Gene | MM | | E | |
| MAP3K1 | Cancer Gene | Breast | | E | |
| MAP3K13 | Cancer Gene | Breast | | E | |
| MLL2 | Cancer Gene | Medulloblastoma, renal | | E | |
| MLST8 | Cancer Gene | Breast | | E | |
| MYD88 | Cancer Gene | Activated B cell-like-DLBCL (ABC-DLBCL) | | E | |
| MYST3 | Cancer Gene | Breast | | E | |
| NCOR1 | Cancer Gene | Breast | | E | |
| NFE2L2 | Cancer Gene | NSCLC, head and neck squamous cell carcinoma (HNSCC) | | E | |
| NFKBIA | Cancer Gene | Breast | | E | |
| NOTCH3 | Cancer Gene | NSCLC, breast | | E | |
| NOTCH4 | Cancer Gene | NSCLC, breast | | E | |
| NSD1 | Cancer Gene | AML | | E | |
| NTRK2 | Cancer Gene | Renal, NSCLC | | E | |
| NUP93 | Cancer Gene | Breast | | E | |
| PAK7 | Cancer Gene | NSCLC, malignant melanoma | | E | |
| PHLPP2 | Cancer Gene | Ovarian, glioblastoma, NSCLC | | E | |
| PHOX2B | Cancer Gene | Neuroblastoma | | E | |
| PIK3C2G | Cancer Gene | NSCLC | | E | |
| PIK3C3 | Cancer Gene | NSCLC | | E | |
| PIK3CG | Cancer Gene | NSCLC | | E | |
| PNRC1 | Cancer Gene | MM | | E | |
| PRDM1 | Cancer Gene | DLBCL | | E | |
| PRKAR1A | Cancer Gene | Adrenal gland, thyroid | | E | |
| PRSS8 | Cancer Gene | Breast | | E | |
| PTCH2 | Cancer Gene | Malignant melanoma | | E | |
| PTK2 | Cancer Gene | NSCLC, glioblastoma | | E | |
| PTK2B | Cancer Gene | NSCLC, breast | | E | |
| REL | Cancer Gene | Hodgkin Lymphoma | | E | |
| RHEB | Cancer Gene | NSCLC, colorectal | | E | |
| ROCK1 | Cancer Gene | Breast | | E | |
| RUNXT1 | Cancer Gene | NSCLC, colorectal | | E | |
| SETD2 | Cancer Gene | Clear cell renal carcinoma | | E | |
| SH2B3 | Cancer Gene | Myelodysplastic syndrome (MDS) | | E | |
| SOCS1 | Cancer Gene | DLBCL | | E | |
| SPEN | Cancer Gene | Adenoid cystic carcinoma | | E | |
| STAG2 | Cancer Gene | Glioblastoma | | E | |
| STAT3 | Cancer Gene | Breast | | E | |
| STAT4 | Cancer Gene | Breast | | E | |
| STK12 | Cancer Gene | PNET, NSCLC | | E | |
| SUFU | Cancer Gene | Medulloblastoma | | E | |
| TBX23 | Cancer Gene | Breast | | E | |

TABLE 1A-continued

Additional exemplary selected genes and variants, associated cancer types, priority codons, actionability category, and potential therapies.

| Hugo Gene | Gene Category | Cancer Types | Priority Codons | Actionability Category | Reason |
|---|---|---|---|---|---|
| TBX3 | Cancer Gene | Breast | | E | |
| TNFAIP3 | Cancer Gene | Marginal zone B-cell lymphomas, Hodgkin's lymphoma, primary mediastinal B cell lymphoma | | E | |
| TNFRSF14 | Cancer Gene | Follicular lymphoma | | E | |
| TNFRSF17 | Cancer Gene | Intestinal T-cell lymphoma | | E | |
| TNKS | Cancer Gene | NSCLC | | E | |
| TNKS2 | Cancer Gene | Melanoma, breast | | E | |
| TRRAP | Cancer Gene | Colorectal, glioblastoma | | E | |
| TYK2 | Cancer Gene | NSCLC, breast | | E | |
| XBP1 | Cancer Gene | MM | | E | |
| XPO1 | Cancer Gene | Chronic lymphocytic leukaemia (CLL) | | E | |
| ZNF217 | Cancer Gene | Breast | | E | |
| ZNF703 | Cancer Gene | Breast | | E | |

The actionability categories are classified as described below. Table 1B provides a summary of the application of the different categories to exemplary alterations in different cancer types.

Category A: Approved/standard alterations that predict sensitivity or resistance to approved/standard therapies
  KRAS G13D in metastatic colon cancer
  ERBB2 amplification in breast cancer
  EGFR L858R in non small cell lung cancer Category B: Alterations that are inclusion or exclusion criteria for specific experimental therapies
  KRAS G13D in colon cancer, lung cancer, or breast cancer
  BRAF V600E in melanoma, colon cancer, or lung cancer
  NRAS Q61K in melanoma
  PIK3CA H1047R in breast cancer
  FGFR1 amplification in breast cancer
  PTEN biallelic inactivation in breast cancer
  BRCA1 biallelic inactivation in breast cancer or pancreatic cancer Category C: Alterations with limited evidence (early clinical data, conflicting clinical data, pre-clinical data, theoretical) that predict sensitivity or resistance to standard or experimental therapies
  KRAS Q61H in colon cancer (early clinical)
  PIK3CA H1047R in breast cancer (conflicting clinical)
  BRAF V600E in colon cancer (conflicting clinical)
  ERBB2 mutation or amplification in lung cancer (case reports)
  BRAF D594G in lung cancer (pre-clinical)
  FGFR1 amplification in breast cancer (pre-clinical)
  ATM biallelic inactivation in breast cancer (pre-clinical)
  TSC1 biallelic inactivation in colon cancer (pre-clinical)
  ATR biallelic inactivation in breast cancer (theoretical)
  BRAF V600E mutation in sarcoma (theoretical)

Category D: Alterations with prognostic or diagnostic utility in a particular subtype of cancer
  MSH2 biallelic inactivation in colon cancer (strong clinical evidence)
  BRAF V600E in colon cancer (strong clinical evidence)
  KRAS G13D in lung cancer (strong clinical evidence)
  BRCA1 inactivation in breast cancer (strong clinical evidence)

Category E: Alterations with clear biological significance in cancer (that is, driver mutations) without clear clinical implications
  APC biallelic inactivation in colon cancer
  TP53 biallelic inactivation in breast cancer
  MITF amplification in melanoma
  ARID1A in ovarian cancer Category F: Alterations without known biological significance in cancer
  Novel alterations in known cancer genes
  Targets of therapy
  Orthologues of known cancer genes

TABLE 1B

Exemplary Classification of Alterations in Different Cancer Types

| | | A | B | C | D | E |
|---|---|---|---|---|---|---|
| KRAS G13D | Colon Cancer | x | x | | x | x |
| KRAS G13D | Lung Cancer | | x | | x | x |
| KRAS G13D | Breast Cancer | | x | | | x |
| NRAS Q61K | Melanoma | | x | x | | x |
| KRAS Q61H | Colon Cancer | | x | x | | x |
| BRAF V600E | Melanoma | | x | | | x |
| BRAF V600E | Colon Cancer | | x | x | x | x |
| BRAF V600E | Lung Cancer | | x | | | x |
| BRAF D594G | Lung Cancer | | | x | | x |
| PIK3CA H1047R | Breast Cancer | | x | x | | x |
| PIK3CA H1047R | Colon Cancer | | x | x | | x |
| EGFR L858R | Lung Cancer | x | | | | x |
| EGFR T790M | Lung Cancer | x | x | | | x |
| ERBB2 Amplification | Breast Cancer | x | | | | x |
| BRCA1 biallelic inactivation | Breast Cancer | | x | x | x | x |
| BRCA2 biallelic inactivation | Pancreatic Cancer | x | x | x | x | x |
| ATM biallelic inactivation | Breast Cancer | | | | x | x |
| TSC biallelec inactivation | Colon Cancer | | | | x | x |
| PTEN biallelic inactivation | Colon Cancer | | | | x | x |
| PTEN biallelic inactivation | Breast Cancer | | x | x | | x |
| VHL biallelic inactivation | Kidney Cancer | | | | x | x |
| MSH2 biallelic inactivation | Colon Cancer | | | | x | x |
| ATR biallelic inactiation | Breast Cancer | | | x | | x |
| MYC amplification | Breast Cancer | | | | x | x |

TABLE 2

Exemplary selected genes associated with pharmacogenetics and pharmacogenomics (PGx).

| Gene | Locus | Mutation | Effect |
| --- | --- | --- | --- |
| ABCB1 | chr7:86976581 | 3853C>T | Better survival in Asian AML treated with Ida/AraC; Survival in breast cancer patients treated with paclitaxel |
| ABCB1 | chr7:86998554 | 2677G>T/A | Response to taxanes, platinums and GI toxicity; Better survival in Asian AML treated with Ida/AraC |
| ABCC2 | chr10:101610761 | | Doxcetaxel induced leukopenia |
| ABCC4 | chr13:94613416 | | 6MP Toxicity |
| ABCG2 | chr4:89252551 | | MTX |
| ABCG2 | chr4:89271347 | q141K | Diarrhea after gefitinib |
| ABCG2 | chr4:89274403 | | MTX |
| C1orf144 | chr1:16578662 | | Toxicity from daunorubicin |
| CYP1B1 | chr2:38151707 | CYP1B1*3 | Toxicity from daunorubicin; Survival in breast cancer patients treated with paclitaxel |
| CYP2C19 | chr10:96509051 | CYP2C19*17 | Improved benefit from tamoxifen |
| CYP2C19 | chr10:96511647 | CYP2C19*17 | Improved benefit from tamoxifen |
| CYP2C8 | chr10:96786964 | 461delV | Paclitexel metabolism |
| CYP2C8 | chr10:96788739 | K399R | Paclitexel metabolism |
| CYP2C8 | chr10:96808096 | | Paclitexel metabolism |
| CYP2C8 | chr10:96808109 | | Paclitexel metabolism |
| CYP2C8 | chr10:96817020 | | Paclitexel metabolism |
| CYP2D6 | chr22:40853554 | CYP2D6: 3183 G>A | CYP2D6*29, present in Tanzanians |
| CYP2D6 | chr22:40853749 | CYP2D6: 2988 G>A | CYP2D6*41 (IM) |
| CYP2D6 | chr22:40853887 | CYP2D6: 2850 C>T | CYP2D6*2 (EM) |
| CYP2D6 | chr22:40854122 | CYP2D6: 2613-2615 del AGA | CYP2D6*9 (unclear function?) |
| CYP2D6 | chr22:40854188 | CYP2D6: 2549 del A | CYP2D6*3 |
| CYP2D6 | chr22:40854891 | CYP2D6: 1846 G>A | CYP2D6*4 |
| CYP2D6 | chr22:40855030 | CYP2D6: 1707 del T | CYP2D6*6 |
| CYP2D6 | chr22:40855078 | CYP2D6: 1659G>A | CYP2D6*29, present in Tanzanians |
| CYP2D6 | chr22:40855716 | CYP2D6: 1023 C>T | Present in CYP2D6*17 |
| CYP2D6 | chr22:40856638 | CYP2D6: 100C>T | Present in CYP2D6*10 (casuative) and *4 (associated) |
| CYP3A4 | chr7:99196395 | | |
| CYP3A4 | chr7:99196460 | | |
| CYP3A4 | chr7:99197606 | | |
| CYP3A4 | chr7:99204017 | | |
| CYP3A4 | chr7:99204029 | CYP3A4*16B | Paclitaxel metabolism in Japanese |
| CYP3A4 | chr7:99205328 | | |
| CYP3A4 | chr7:99205363 | | |
| CYP3A4 | chr7:99219597 | | |
| CYP3A4 | chr7:99220032 | CYP3A4*1B | Greater clearance of docetaxel |
| CYP3A5 | chr7:99088330 | | |
| CYP3A5 | chr7:99100771 | | |
| CYP3A5 | chr7:99108475 | | |
| DPYD | chr1:97688202 | DPYD*2A | Toxicity to 5FU |
| DPYD | chr1:97753983 | DPYD*5 | Toxicity to 5FU |
| DPYD | chr1:97937679 | 496A>G | 5FU, Xeloda toxicity |
| DPYD | chr1:98121473 | DPYD*9A | Toxicity to 5FU |
| ERCC2 | chr19:50546759 | 2251A>C | Relapse after 5FU in Asians |
| ESR1 | chr6:152205074 | | Tamoxifen induced hypercholesterolemia |
| ESR2 | chr14:63769569 | | Tamoxifen induced hypercholesterolemia |
| FCGR3A | chr1:159781166 | V158F | Response to cetuximab |
| FGFR4 | chr5:176452849 | GLY388ARG | |
| GSTP1 | chr11:67109265 | I105V | Resistance to multiple chemotherapies |
| GSTP1 | chr11:67110155 | A114V | Unclear, linkage disequlibrium with I105V |
| ITPA | chr20:3141842 | | 6MP Toxicity |
| LRP2 | chr2:169719231 | | Associated with ototoxicity from cisplatin |
| MAN1B1 | chr9:139102689 | | Toxicity from daunorubicin |
| MTHFR | chr1:11777044 | | MTX |
| MTHFR | chr1:11777063 | | MTX |
| MTHFR | chr1:11778965 | 677C>T | MTX |
| NQO1 | clu-16:68302646 | NQO1*2 | Rapid degradation (cisplatin, doxorubicin); poor survival in breast cancer treated with anthracyclines |
| NRP2 | chr2:206360545 | | Toxicity from daunorubicin |
| SLC19A1 | chr21:45782222 | | MTX |

TABLE 2-continued

Exemplary selected genes associated with pharmacogenetics and pharmacogenomics (PGx).

| Gene | Locus | Mutation | Effect |
|---|---|---|---|
| SLC22A2 | chr6:160590272 | Ala270Ser | Reduced cisplatin nephrotoxicity |
| SLCO1B3 | chr12:20936961 | | Doxcetaxel induced leukopenia |
| SOD2 | chr6:160033862 | V16A | Inferior survival in breast cancer treated with cyclophosphamide |
| SULT1A1 | chr16:28524986 | | |
| SULT1A1 | chr16:28525015 | | |
| SULT1A1 | chr16:28528073 | | |
| SULT1A1 | chr16:28528301 | | |
| TMPT | chr6:18247207 | TPMT*3B | Purine toxicity |
| TPMT | chr6:18238897 | | 6MP Toxicity |
| TPMT | chr6:18238991 | | 6MP Toxicity |
| TPMT | chr6:18251934 | | 6MP Toxicity |
| TYMS | chr18:647646 | 28 bp tandem repeat | Toxicity to 5FU |
| TYMS | chr18:663451 | 6 bp deletion | Toxicity to 5FU |
| UGT1A1 | chr2:234255266 | | Anemia from irinotecan |
| UGT1A1 | chr2:234255709 | | thrombocytopenia from irinotecan |
| UGT1A1 | chr2:234330398 | | UGT1A1*60 |
| UGT1A1 | chr2:234330521 | | UGT1A1*93 |
| UGT1A1 | chr2:234333620 | | UGT1A1*28 |
| UGT1A1 | chr2:234333883 | | UGT1A1*6 |
| UGT1A1 | chr2:234334358 | | UGT1A1*27 |
| UMPS | chr3:125939432 | Gly213Ala | Toxicity to 5FU |

TABLE 3

Exemplary selected genes associated with translocation mutations in solid tumors

| Hugo Gene | Gene Category | Translocation Partner | Cancer Types |
|---|---|---|---|
| ACSL3 | Priority 1 | ETV1 | prostate |
| ALK | Priority 1 | NPM1, TPM3, TFG, TPM4, ATIC, CLTC, MSN, ALO17, CARS, EML4 | ALCL, NSCLC, Neuroblastoma |
| BRAF | Priority 1 | AKAP9, KIAA1549 | melanoma, colorectal, papillary thyroid, borderline ov, Non small-cell lung cancer (NSCLC), cholangiocarcinoma, pilocytic astrocytoma |
| C15orf21 | Priority 1 | ETV1 | prostate |
| CANT1 | Priority 1 | ETV4 | prostate |
| CCND1 | Priority 1 | IGH, FSTL3 | CLL, B-ALL, breast |
| DDX5 | Priority 1 | ETV4 | prostate |
| ELK4 | Priority 1 | SLC45A3 | prostate |
| EML4 | Priority 1 | ALK | NSCLC |
| EP300 | Priority 1 | MLL, RUNXBP2 | colorectal, breast, pancreatic, AML |
| ERG | Priority 1 | EWSR1, TMPRSS2, ELF4, FUS, HERPUD1 | Ewing sarcoma, prostate, AML |
| ETV1 | Priority 1 | EWSR1, TMPRSS2, SLC45A3, C15orf21, HNRNPA2B1. ACSL3 | Ewing sarcoma, prostate |
| ETV4 | Priority 1 | EWSR1, TMPRSS2, DDX5, KLK2, CANT1 | Ewing sarcoma, Prostate carcinoma |
| ETV5 | Priority 1 | TMPRSS2, SCL45A3 | Prostate |
| FGFR3 | Priority 1 | IGH@, ETV6 | bladder, MM, T-cell lymphoma |
| HERPUD1 | Priority 1 | ERG | prostate |
| HNRNPA2B1 | Priority 1 | ETV1 | prostate |
| KLK2 | Priority 1 | ETV4 | prostate |
| RET | Priority 1 | H4, PRKAR1A, NCOA4, PCM1, GOLGA5, TRIM33, KTN1, TRIM27, HOOK3 | medullary thyroid, papillary thyroid, pheochromocytoma |
| ROS1 | Priority 1 | GOPC, ROS1 | glioblastoma, NSCLC |
| SLC45A3 | Priority 1 | ETV1, ETV5, ELK4, ERG | prostate |
| TMPRSS2 | Priority 1 | ERG, ETV1, ETV4, ETV5 | prostate |
| AKAP9 | | BRAF | papillary thyroid |
| ASPSCR1 | | TFE3 | alveolar soft part sarcoma |
| ATF1 | | EWSR1, FUS | malignant melanoma of soft parts, angiomatoid fibrous histiocytoma |
| BRD3 | | NUT | lethal midline carcinoma of young people |
| BRD4 | | NUT | lethal midline carcinoma of young people |

TABLE 3-continued

Exemplary selected genes associated with translocation mutations in solid tumors

| Hugo Gene | Gene Category | Translocation Partner | Cancer Types |
|---|---|---|---|
| C12orf9 | | LPP | lipoma |
| CD74 | | ROS1 | NSCLC |
| CDH11 | | USP6 | aneurysmal bone cysts |
| CHCHD7 | | PLAG1 | salivary adenoma |
| CHN1 | | TAF15 | extraskeletal myxoid chondrosarcoma |
| CIC | | DUX4 | soft tissue sarcoma |
| CMKOR1 | | HMGA2 | lipoma |
| COL1A1 | | PDGFB, USP6 | dermatofibrosarcoma protuberans, aneurysmal bone cyst |
| COX6C | | HMGA2 | uterine leiomyoma |
| CREB1 | | EWSR1 | clear cell sarcoma, angiomatoid fibrous histiocytoma |
| CREB3L2 | | FUS | fibromyxoid sarcoma |
| CRTC3 | | MAML2 | salivary gland mucoepidermoid |
| CTNNB1 | | PLAG1 | colorectal, ovarian, hepatoblastoma, others, pleomorphic salivary adenoma |
| D10S170 | | RET, PDGFRB | papillary thyroid, CML |
| DDIT3 | | FUS | liposarcoma |
| DUX4 | | CIC | soft tissue sarcoma |
| ELKS | | RET | papillary thyroid |
| ETV6 | | NTRK3, RUNX1, PDGFRB, ABL1, MN1, ABL2, FACL6, CHIC2, ARNT, JAK2, EVI1, CDX2, STL, HLXB9, MDS2, PER1, SYK, TTL, FGFR3, PAX5 | congenital fibrosarcoma, multiple leukemia and lymphoma, secretory breast, MDS, ALL |
| EWSR1 | | FLI1, ERG, ZNF278, NR4A3, FEV, ATF1, ETV1, ETV4, WT1, ZNF384, CREB1, POU5F1, PBX1 | Ewing sarcoma, desmoplastic small round cell tumor, ALL, clear cell sarcoma, sarcoma, myoepithelioma |
| FEV | | EWSR1, FUS | Ewing sarcoma |
| FLI1 | | EWSR1 | Ewing sarcoma |
| FOXO1A | | PAX3 | alveolar rhabdomyosarcomas |
| FUS | | DDIT3, ERG, FEV, ATF1, CREB3L2 | liposarcoma, AML, Ewing sarcoma, angiomatoid fibrous histiocytoma, fibromyxoid sarcoma |
| GOLGA5 | | RET | papillary thyroid |
| HEI10 | | HMGA2 | uterine leiomyoma |
| HMGA1 | | ? | microfollicular thyroid adenoma, various benign mesenchymal tumors |
| HMGA2 | | LHFP, RAD51L1, LPP, HEI10, COX6C, CMKOR1, NFIB | lipoma |
| HOOK3 | | RET | papillary thyroid |
| JAZF1 | | SUZ12 | endometrial stromal tumours |
| KTN1 | | RET | papillary thyroid |
| LHFP | | HMGA2 | lipoma |
| LIFR | | PLAG1 | salivary adenoma |
| LPP | | HMGA2, MLL, C12ort9 | lipoma, leukemia |
| MAML2 | | MECT1, CRTC3 | salivary gland mucoepidermoid |
| MECT1 | | MAML2 | salivary gland mucoepidermoid |
| MN1 | | ETV6 | AML, meningioma |
| MYB | | NFIB | adenoid cystic carcinoma |
| MYC | | IGK, BCL5, BCL7A, BTG1, TRA, IGH | Burkitt lymphoma, amplified in other cancers, B-CLL |
| NCOA1 | | PAX3 | alveolar rhadomyosarcoma |
| NCOA4 | | RET | papillary thyroid |
| NFIB | | MYB, HGMA2 | adenoid cystic carcinoma, lipoma |
| NONO | | TFE3 | papillary renal cancer |
| NR4A3 | | EWSR1 | extraskeletal myxoid chondrosarcoma |
| NTRK1 | | TPM3, TPR, TFG | papillary thyroid |
| NTRK3 | | ETV6 | congenital fibrosarcoma, Secretory breast |
| NUT | | BRD4, BRD3 | lethal midline carcinoma of young people |
| OMD | | USP6 | aneurysmal bone cysts |
| PAX3 | | FOXO1A, NCOA1 | alveolar rhabdomyosarcoma |
| PAX7 | | FOXO1A | alveolar rhabdomyosarcoma |
| PAX8 | | PPARG | follicular thyroid |
| PBX1 | | TCF3, EWSR1 | pre B-ALL, myoepithelioma |
| PCM1 | | RET, JAK2 | papillary thyroid, CML, MPD |
| PDGFB | | COL1A1 | DFSP |
| PDGFRA | | FIP1L1 | GIST, idiopathic hypereosinophilic syndrome |

TABLE 3-continued

Exemplary selected genes associated with translocation mutations in solid tumors

| Hugo Gene | Gene Category | Translocation Partner | Cancer Types |
| --- | --- | --- | --- |
| PLAG1 | | TCEA1, LIFR, CTNNB1, CHCHD7 | salivary adenoma |
| POU5F1 | | EWSR1 | sarcoma |
| PPARG | | PAX8 | follicular thyroid |
| PRCC | | TFE3 | papillary renal |
| PRKAR1A | | RET | papillary thyroid |
| PRO1073 | | TFEB | renal cell carcinoma (childhood epithelioid) |
| RAD51L1 | | HMGA2 | lipoma, uterine leiomyoma |
| RAF1 | | SRGAP3 | pilocytic astrocytoma |
| SFPQ | | TFE3 | papillary renal cell |
| SRGAP3 | | RAF1 | pilocytic astrocytoma |
| SS18 | | SSX1, SSX2 | synovial sarcoma |
| SS18L1 | | SSX1 | synovial sarcoma |
| SSX1 | | SS18 | synovial sarcoma |
| SSX2 | | SS18 | synovial sarcoma |
| SSX4 | | SS18 | synovial sarcoma |
| SUZ12 | | JAZF1 | endometrial stromal tumours |
| TAF15 | | TEC, CHN1, ZNF384 | extraskeletal myxoid chondrosarcomas, ALL |
| TCEA1 | | PLAG1 | salivary adenoma |
| TCF12 | | TEC | extraskeletal myxoid chondrosarcoma |
| TFE3 | | SFPQ, ASPSCR1, PRCC, NONO, CLTC | papillary renal, alveolar soft part sarcoma, renal |
| TFEB | | ALPHA | renal (childhood epithelioid) |
| TFG | | NTRK1, ALK | papillary thyroid, ALCL, NSCLC |
| THRAP3 | | USP6 | aneurysmal bone cysts |
| TPM3 | | NTRK1, ALK | papillary thyroid, ALCL |
| TPR | | NTRK1 | papillary thyroid |
| TRIM27 | | RET | papillary thyroid |
| TRIM33 | | RET | papillary thyroid |
| USP6 | | COL1A1, CDH11, ZNF9, OMD | aneurysmal bone cysts |
| ZNF278 | | EWSR1 | Ewing sarcoma |
| ZNF331 | | ? | follicular thyroid adenoma |
| ZNF9 | | USP6 | aneurysmal bone cysts |

TABLE 4

Exemplary selected genes associated with translocation mutations in hematologic malignancies.

| Hugo Gene | Gene Category | Translocation Partner | Cancer Types |
| --- | --- | --- | --- |
| ABL1 | Priority 1 | BCR, ETV6, NUP214 | CML, ALL, T-ALL |
| ALK | Priority 1 | NPM1, TPM3, TFG, TPM4, ATIC, CLTC, MSN, ALO17, CARS, EML4 | ALCL, NSCLC, Neuroblastoma |
| BCL2 | Priority 1 | IGH | NHL, CLL |
| BCL6 | Priority 1 | IG loci, ZNFN1A1, LCP1, PIM1, TFRC, MHC2TA, NACA, HSPCB, HSPCA, HIST1H4I, IL21R, POU2AF1, ARHH, EIF4A2, SFRS3 | NHL, CLL |
| CCND1 | Priority 1 | IGH, FSTL3 | CLL, B-ALL, breast |
| CREBBP | Priority 1 | MLL, MORF, RUNXBP2 | AL, AML |
| FGFR1 | Priority 1 | BCR, FOP, ZNF198, CEP1 | MPD, NHL |
| FGFR3 | Priority 1 | IGH, ETV6 | bladder, MM, T-cell lymphoma |
| JAK2 | Priority 1 | ETV6, PCM1, BCR | ALL, AML, MPD, CML |
| MLL | Priority 1 | MLL, MLLT1, MLLT2, MLLT3, MLLT4, MLLT7, MLLT10, MLLT6, ELL, EPS15, AF1Q, CREBBP, SH3GL1, FNBP1, PNUTL1, MSF, GPHN, GMPS, SSH3BP1, ARHGEF12, GAS7, FOXO3A, LAF4, LCX, SEPT6, LPP, CBFA2T1, GRAF, EP300, PICALM, HEAB | AML, ALL |
| PDGFRA | Priority 1 | FIP1L1 | GIST, idiopathic hypereosinophilic syndrome |
| RARA | Priority 1 | PML, ZNF145, TIF1, NUMA1, NPM1 | APL |
| SEPT6 | | MLL | AML |

TABLE 4-continued

Exemplary selected genes associated with translocation mutations in hematologic malignancies.

| Hugo Gene | Gene Category | Translocation Partner | Cancer Types |
|---|---|---|---|
| ABL2 | | ETV6 | AML |
| AF15Q14 | | MLL | AML |
| AF1Q | | MLL | ALL |
| AF3p21 | | MLL | ALL |
| AF5q31 | | MLL | ALL |
| ALO17 | | ALK | ALCL |
| ARHGEF12 | | MLL | AML |
| ARHH | | BCL6 | NHL |
| ARNT | | ETV6 | AML |
| ATIC | | ALK | ALCL |
| BCL10 | | IGH | MALT |
| BCL11A | | IGH | B-CLL |
| BCL11B | | TLX3 | T-ALL |
| BCL3 | | IGH | CLL |
| BCL5 | | MYC | CLL |
| BCL7A | | MYC | BNHL |
| BCL9 | | IGH, IGL | B-ALL |
| BCR | | ABL1, FGFR1, JAK2 | CML, ALL, AML |
| BIRC3 | | MALT1 | MALT |
| BTG1 | | MYC | BCLL |
| CARS | | ALK | ALCL |
| CBFA2T1 | | MLL, RUNX1 | AML |
| CBFA2T3 | | RUNX1 | AML |
| CBFB | | MYH11 | AML |
| CBL | | MLL | AML, JMML, MDS |
| CCND2 | | IGL | NHL, CLL |
| CCND3 | | IGH | MM |
| CDK6 | | MLLT10 | ALL |
| CDX2 | | ETV6 | AML |
| CEP1 | | FGFR1 | MPD, NHL |
| CHIC2 | | ETV6 | AML |
| CLTC | | ALK, TFE3 | ALCL, renal |
| CLTCL1 | | ? | ALCL |
| DDX10 | | NUP98 | AML* |
| DDX6 | | IGH | B-NHL |
| DEK | | NUP214 | AML |
| EIF4A2 | | BCL6 | NHL |
| ELF4 | | ERG | AML |
| ELL | | MLL | AL |
| ELN | | PAX5 | B-ALL |
| EP300 | | MLL, RUNXBP2 | colorectal, breast, pancreatic, AML |
| EPS15 | | MLL | ALL |
| ERG | | EWSR1, TMPRSS2, ELF4, FUS, HERPUD1 | Ewing sarcoma, prostate, AML |
| ETV6 | | NTRK3, RUNX1, PDGFRB, ABL1, MN1, ABL2, FACL6, CHIC2, ARNT, JAK2, EVI1, CDX2, STL, HLXB9, MDS2, PER1, SYK, TTL, FGFR3, PAX5 | congenital fibrosarcoma, multiple leukemia and lymphoma, secretory breast, MDS, ALL |
| EVI1 | | RUNX1, ETV6, PRDM16, RPN1 | AML, CML |
| EWSR1 | | FLI1, ERG, ZNF278, NR4A3, FEV, ATF1, ETV1, ETV4, WT1, ZNF384, CREB1, POU5F1, PBX1 | Ewing sarcoma, desmoplastic small round cell tumor, ALL, clear cell sarcoma, sarcoma, myoepithelioma |
| FACL6 | | ETV6 | AML, AEL |
| FCGR2B | | ? | ALL |
| FGFR1OP | | FGFR1 | MPD, NHL |
| FIP1L1 | | PDGFRA | idiopathic hypereosinophilic syndrome |
| FNBP1 | | MLL | AML |
| FOXO3A | | MLL | AL |
| FOXP1 | | PAX5 | ALL |
| FSTL3 | | CCND1 | B-CLL |
| FUS | | DDIT3, ERG, FEV, ATF1, CREB3L2 | liposarcoma, AML, Ewing sarcoma, angiomatoid fibrous histiocytoma, fibromyxoid sarcoma |
| FVT1 | | IGK | B-NHL |
| GAS7 | | MLL | AML* |
| GMPS | | MLL | AML |
| GPHN | | MLL | AL |
| GRAF | | MLL | AML, MDS |
| HCMOGT-1 | | PDGFRB | JMML |
| HEAB | | MLL | AML |
| HIP1 | | PDGFRB | CMML |
| HIST1H4I | | BCL6 | NHL |

TABLE 4-continued

Exemplary selected genes associated with translocation mutations in hematologic malignancies.

| Hugo Gene | Gene Category | Translocation Partner | Cancer Types |
|---|---|---|---|
| HLF | | TCF3 | ALL |
| HLXB9 | | ETV6 | AML |
| HOXA11 | | NUP98 | CML |
| HOXA13 | | NUP98 | AML |
| HOXA9 | | NUP98, MSI2 | AML* |
| HOXC11 | | NUP98 | AML |
| HOXC13 | | NUP98 | AML |
| HOXD11 | | NUP98 | AML |
| HOXD13 | | NUP98 | AML* |
| HSPCA | | BCL6 | NHL |
| HSPCB | | BCL6 | NHL |
| IGH | | MYC, FGFR3, PAX5, IRTA1, IRF4, CCND1, BCL9, BCL8, BCL6, BCL2, BCL3, BCL10, BCL11A. LHX4, DDX6, NFKB2, PAFAH1B2, PCSK7 | MM, Burkitt lymphoma, NHL, CLL, B-ALL, MALT, MLCLS |
| IGK | | MYC, FVT1 | Burkitt lymphoma, B-NHL |
| IGL | | BCL9, MYC, CCND2 | Burkitt lymphoma |
| IL2 | | TNFRSF17 | intestinal T-cell lymphoma |
| IL21R | | BCL6 | NHL |
| IRF4 | | IGH | MM |
| IRTA1 | | IGH | B-NHL |
| ITK | | SYK | peripheral T-cell lymphoma |
| KDM5A | | NUP98 | AML |
| LAF4 | | MLL, RUNX1 | ALL, T-ALL |
| LASP1 | | MLL | AML |
| LCK | | TRB | T-ALL |
| LCP1 | | BCL6 | NHL |
| LCX | | MLL | AML |
| LMO1 | | TRD | T-ALL |
| LMO2 | | TRD | T-ALL |
| LPP | | HMGA2, MLL, C12orf9 | lipoma, leukemia |
| LYL1 | | TRB | T-ALL |
| MAF | | IGH | MM |
| MAFB | | IGH | MM |
| MALT1 | | BIRC3 | MALT |
| MDS1 | | RUNX1 | MDS, AML |
| MDS2 | | ETV6 | MDS |
| MHC2TA | | BCL6 | NHL |
| MKL1 | | RBM15 | acute megakaryocytic leukemia |
| MLF1 | | NPM1 | AML |
| MLLT1 | | MLL | AL |
| MLLT10 | | MLL, PICALM, CDK6 | AL |
| MLLT2 | | MLL | AL |
| MLLT3 | | MLL | ALL |
| MLLT4 | | MLL | AL |
| MLLT6 | | MLL | AL |
| MLLT7 | | MLL | AL |
| MN1 | | ETV6 | AML, meningioma |
| MSF | | MLL | AML* |
| MSI2 | | HOXA9 | CML |
| MSN | | ALK | ALCL |
| MTCP1 | | TRA | T cell prolymphocytic leukemia |
| MUC1 | | IGH | B-NHL |
| MYC | | IGK, BCL5, BCL7A, BTG1, TRA, IGH | Burkitt lymphoma, amplified in other cancers, B-CLL |
| MYH11 | | CBFB | AML |
| MYH9 | | ALK | ALCL |
| MYST4 | | CREBBP | AML |
| NACA | | BCL6 | NHL |
| NCOA2 | | RUNXBP2 | AML |
| NFKB2 | | IGH | B-NHL |
| NIN | | PDGFRB | MPD |
| NOTCH1 | | TRB | T-ALL |
| NPM1 | | ALK, RARA, MLF1 | NHL, APL, AML |
| NSD1 | | NUP98 | AML |
| NUMA1 | | RARA | APL |
| NUP214 | | DEK, SET, ABL1 | AML, T-ALL |
| NUP98 | | HOXA9, NSD1, WHSC1L1, DDX10, TOP1, HOXD13, PMX1, HOXA13, HOXD11, HOXA11, RAP1GDS1, HOXC11 | AML |
| OLIG2 | | TRA | T-ALL |
| PAFAH1B2 | | IGH | MLCLS |

TABLE 4-continued

Exemplary selected genes associated with translocation mutations in hematologic malignancies.

| Hugo Gene | Gene Category | Translocation Partner | Cancer Types |
|---|---|---|---|
| PAX5 | | IGH, ETV6, PML, FOXP1, ZNF521, ELN | NHL, ALL, B-ALL |
| PBX1 | | TCF3, EWSR1 | pre B-ALL, myoepithelioma |
| PCM1 | | RET, JAK2 | papillary thyroid, CML, MPD |
| PCSK7 | | IGH | MLCLS |
| PDE4DIP | | PDGFRB | MPD |
| PDGFRB | | ETV6, TRIP11, HIP1, RAB5EP, H4, NIN, HCMOGT-1, PDE4DIP | MPD, AML, CMML, CML |
| PERI | | ETV6 | AML, CMML |
| PICALM | | MLLT10, MLL | TALL, AML, |
| PIM1 | | BCL6 | NHL |
| PML | | RARA, PAX5 | APL, ALL |
| PMX1 | | NUP98 | AML |
| PNUTL1 | | MLL | AML |
| POU2AF1 | | BCL6 | NHL |
| PRDM16 | | EVI1 | MDS, AML |
| PSIP2 | | NUP98 | AML |
| RAB5EP | | PDGFRB | CMML |
| RANBP17 | | TRD | ALL |
| RAP1GDS1 | | NUP98 | T-ALL |
| RBM15 | | MKL1 | acute megakaryocytic leukemia |
| RPL22 | | RUNX1 | AML, CML |
| RPN1 | | EVI1 | AML |
| RUNX1 | | RPL22, MDS1, EVI1, CBFA2T3, CBFA2T1, ETV6, LAF4 | AML, preB- ALL, T-ALL |
| RUNXBP2 | | CREBBP, NCOA2, EP300 | AML |
| SET | | NUP214 | AML |
| SFRS3 | | BCL6 | follicular lymphoma |
| SH3GL1 | | MLL | AL |
| SIL | | TAL1 | T-ALL |
| SSH3BP1 | | MLL | AML |
| STL | | ETV6 | B-ALL |
| SYK | | ETV6, ITK | MDS, peripheral T-cell lymphoma |
| TAF15 | | TEC, CHN1, ZNF384 | extraskeletal myxoid chondrosarcomas, ALL |
| TAL1 | | TRD, SIL | lymphoblastic leukemia/biphasic |
| TAL2 | | TRB | T-ALL |
| TCF3 | | PBX1, HLF, TFPT | pre B-ALL |
| TCL1A | | TRA | T-CLL |
| TCL6 | | TRA | T-ALL |
| TFG | | NTRK1, ALK | papillary thyroid, ALCL, NSCLC |
| TFPT | | TCF3 | pre-B ALL |
| TFRC | | BCL6 | NHL |
| TIF1 | | RARA | APL |
| TLX1 | | TRB, TRD | T-ALL |
| TLX3 | | BCL11B | T-ALL |
| TNFRSF17 | | IL2 | intestinal T-cell lymphoma |
| TOP1 | | NUP98 | AML* |
| TPM3 | | NTRK1, ALK | papillary thyroid, ALCL |
| TPM4 | | ALK | ALCL |
| TRA | | ATL, OLIG2, MYC, TCL1A, TCL6, MTCP1, TCL6 | T-ALL |
| TRB | | HOX11, LCK, NOTCH1, TAL2, LYL1 | T-ALL |
| TRD | | TAL1, HOX11, TLX1, LMO1, LMO2, RANBP17 | T-cell leukemia |
| TRIP11 | | PDGFRB | AML |
| TTL | | ETV6 | ALL |
| WHSC1 | | IGH | MM |
| WHSC1L1 | | NUP98 | AML |
| ZNF145 | | RARA | APL |
| ZNF198 | | FGFR1 | MPD, NHL |
| ZNF384 | | EWSR1, TAF15 | ALL |
| ZNF521 | | PAX5 | ALL |
| ZNFN1A1 | | BCL6 | ALL, DLBL |

Example G

Exemplary Bait Sequences for Hybrid Capture

Table 7 provides exemplary baits for three targets: SMAD3_target_10, SMAD3_target_11, SMAD3_target_12.

TABLE 7

Exemplary Baits

```
1. Gene    Target              Bait genomic location
SMAD3      SMAD3_target_10     chr15:67477013-67477132
CCATTGTGTGTGAGCAAAGGCACCCTGTCCAGTCTAACCTGAATCTCTG
TAGGAAGAGGCGTGCGGCTCTACTACATCGGAGGGGAGGTCTTCGCAGA
GTGCCTCAGTGACAGCGCTATT(SEQ ID NO: 37)
(Bait ID: SMAD3_target_10.2)

2. Gene    Target              Bait genomic location
SMAD3      SMAD3_target_10     chr15:67477037-67477156
CTGTCCAGTCTAACCTGAATCTCTGTAGGAAGAGGCGTGCGGCTCTACT
ACATCGGAGGGGAGGTCTTCGCAGAGTGCCTCAGTGACAGCGCTATTTTC
TGTCCAGTCTCCAACTGTAAC(SEQ ID NO: 38)
(Bait ID: SMAD3_target_10.4)

3. Gene    Target              Bait genomic location
SMAD3      SMAD3_target_10     chr15:67477061-67477180
GTAGGAAGAGGCGTGCGGCTCTACTACATCGGAGGGGAGGTCTTCGCAG
AGTGCCTCAGTGACAGCGCTATTTTTGTCCAGTCTCCCAACTGTAACCA
GCGCTATGGCTGGCACCCGGCC(SEQ ID NO: 39)
(Bait ID: SMAD3_target_10.6)

4. Gene    Target              Bait genomic location
SMAD3      SMAD3_target_10     chr15:67477085-67477204
TACATCGGAGGGGAGGTCTTCGCAGAGTGCCTCAGTGACAGCGCTATTT
TTGTCCAGTCTCCCAACTGTAACCAGCGCTATGGCTGGCACCCGGCCAC
CGTCTGCAAGATCCCACCAGGT(SEQ ID NO: 40)
(Bait ID: SMAD3_target_10.1)

5. Gene    Target              Bait genomic location
SMAD3      SMAD3_target_10     chr15:67477109-67477228
GAGTGCCTCAGTGACAGCGCTATTTTTGTCCAGTCTCCCAACTGTAACC
AGCGCTATGGCTGGCACCCGGCCACCGTCTGCAAGATCCCACCAGGTAA
ACGAGCCGCACAGGCACCCCTG(SEQ ID NO: 41)
(Bait ID: SMAD3_target_10.5)

6. Gene    Target              Bait genomic location
SMAD3      SMAD3_target_10     chr15:67477133-67477252
TTTGTCCAGTCTCCCAACTGTAACCAGCGCTATGGCTGGCACCCGGCCA
CCGTCTGCAAGATCCCACCAGGTAAACGAGCCGCACAGGCACCCCTGCC
TTGAGGTCCCTCTCCGAGTGCA(SEQ ID NO: 142)
(Bait ID: SMAD3_target_10.3)

7. Gene    Target              Bait genomic location
SMAD3      SMAD3_target_11     chr15:67479655-67479774
GACCTGGCCACTTCCATCCCCACAGCCCTGTTTCTGTGTTTTTGGCAGG
ATGCAACCTGAAGATCTTCAACAACCAGGAGTTCGCTGCCCTCCTGGCC
CAGTCGGTCAACCAGGGCTTTG(SEQ ID NO: 43)
(Bait ID: SMAD3_target_11.1)

8. Gene    Target              Bait genomic location
SMAD3      SMAD3_target_11     chr15:67479679-67479798
GCCCTGTTTCTGTGTTTTTGGCAGGATGCAACCTGAAGATCTTCAACAA
CCAGGAGTTCGCTGCCCTCCTGGCCCAGTCGGTCAACCAGGGCTTTGAG
GCTGTCTACCAGTTGACCCGAA(SEQ ID NO: 44)
(Bait ID: SMAD3_target_11.5)

9. Gene    Target              Bait genomic location
SMAD3      SMAD3_target_11     chr15:67479703-67479822
GATGCAACCTGAAGATCTTCAACAACCAGGAGTTCGCTGCCCTCCTGGC
CCAGTCGGTCAACCAGGGCTTTGAGGCTGTCTACCAGTTGACCCGAATG
TGCACCATCCGCATGAGCTTCG(SEQ ID NO: 45)
(Bait ID: SMAD3_target_11.3)

10. Gene   Target              Bait genomic location
SMAD3      SMAD3_target_11     chr15:67479727-67479846
ACCAGGAGTTCGCTGCCCTCCTGGCCCAGTCGGTCAACCAGGGCTTTGA
GGCTGTCTACCAGTTGACCCGAATGTGCACCATCCGCATGAGCTTCGTC
AAAGGCTGGGGAGCGGAGTACA(SEQ ID NO 46)
(Bait ID: SMAD3_target_11.4)

11. Gene   Target              Bait genomic location
SMAD3      SMAD3_target_11     chr15:67479751-67479870
CCCAGTCGGTCAACCAGGGCTTTGAGGCTGTCTACCAGTTGACCCGAAT
GTGCACCATCCGCATGAGCTTCGTCAAAGGCTGGGGAGCGGAGTACAGG
TCAGTTATGGGTGCTGCCTACA(SEQ ID NO: 47)
(Bait ID: SMAD3_target_11.2)

12. Gene   Target              Bait genomic location
SMAD3      SMAD3_target_11     chr15:67479775-67479894
AGGCTGTCTACCAGTTGACCCGAATGTGCACCATCCGCATGAGCTTCGT
CAAAGGCTGGGGAGCGGAGTACAGGTCAGTTATGGGTGCTGCCTACATC
AGGGGACCCAACTCCAGGTGAC(SEQ ID NO: 48)
(Bait ID: SMAD3_target_11.6)

13. Gene   Target              Bait genomic location
SMAD3      SMAD3_target_12     chr15:67482692-67482811
TGTAACCCCCTGGAGATTTTTTAAGTCCCCCACCCCACCCCTTTCCCTA
TTTCTTACAGGAGACAGACTGTGACCAGTACCCCCTGCTGGATTGAGCT
GCACCTGAATGGGCCTTTGCAG(SEQ ID NO: 49)
(Bait ID: SMAD3_target_12.5)

14. Gene   Target              Bait genomic location
SMAD3      SMAD3_target_12     chr15:67482716-67482835
GTCCCCCACCCCACCCCTTTCCCTATTTCTTACAGGAGACAGACTGTGA
CCAGTACCCCCTGCTGGATTGAGCTGCACCTGAATGGGCCTTTGCAGTG
GCTTGACAAGGTCCTCACCCAG(SEQ ID NO: 50)
(Bait ID: SMAD3_target_12.3)

15. Gene   Target              Bait genomic location
SMAD3      SMAD3_target_12     chr15:67482740-67482859
ATTTCTTACAGGAGACAGACTGTGACCAGTACCCCCTGCTGGATTGAGC
TGCACCTGAATGGGCCTTTGCAGTGGCTTGACAAGGTCCTCACCCAGAT
GGGCTCCCCAAGCATCCGCTGT(SEQ ID NO: 51)
(Bait ID: SMAD3_target_12.2)

16. Gene   Target              Bait genomic location
SMAD3      SMAD3_target_12     chr15:67482764-67482883
ACCAGTACCCCCTGCTGGATTGAGCTGCACCTGAATGGGCCTTTGCAGT
GGCTTGACAAGGTCCTCACCCAGATGGGCTCCCCAAGCATCCGCTGTTC
CAGTGTGTCTTAGAGACATCAA(SEQ ID NO: 52)
(Bait ID: SMAD3_target_12.4)

17. Gene   Target              Bait genomic location
SMAD3      SMAD3_target_12     chr15:67482788-67482907
CTGCACCTGAATGGGCCTTTGCAGTGGCTTGACAAGGTCCTCACCCAGA
TGGGCTCCCCAAGCATCCGCTGTTCCAGTGTGTCTTAGAGACATCAAGT
ATGGTAGGGAGGGCAGGCTTG(SEQ ID NO: 53)
(Bait ID: SMAD3_target_12.6)

18. Gene   Target              Bait genomic location
SMAD3      SMAD3_target_12     chr15:67482812-67482931
TGGCTTGACAAGGTCCTCACCCAGATGGGCTCCCCAAGCATCCGCTGTT
CCAGTGTGTCTTAGAGACATCAAGTATGGTAGGGAGGGCAGGCTTGGG
GAAAATGGCCATGCAGGAGGTG(SEQ ID NO: 54)
(Bait ID: SMAD3_target_12.1)
```

Table 8 provides baits with sequences for two targets: FLT3_target_24 modified to reduce the secondary structure. FLT4_target_31 has some arbitrary sequence on both ends of the baits which is effectively similar to a shorter bait. Both improve coverage by about 4× (~4× improvement in coverage).

TABLE 8

Exemplary Baits

```
1. Gene    Target              Bait genomic location
FLT3       FLT3_target_24      chr13:28674626-28674745
Original sequence
CGTCGCGCGCCAACGCCGGCATGGCCTCCGGAGCCCGGGGTCCCCAGGC
CGCGCCGGCCCAGCCCTGCGATGCCGCCTGGAGCGGCGCGCCTCGCGCT
GCAGGTGGCTCTCTTAAGGATG(SEQ ID NO: 55)
```

TABLE 8 -continued

Exemplary Baits

```
Modified sequence
CGTCTCACGCCAACGCAAGCATGTCCTCCGGAGCCCGGGGTCCCCAGGC
CGCGCCGGCCCAGCCCTGCGATGCCGCCTGGAGCGGCGCGCCTCGCACT
GCAGATGGCTCTCTTAAGGATG(SEQ ID NO: 56)
(Bait ID: FLT3_target_24.1)

2. Gene      Target           Bait genomic location
FLT3         FLT3_target_24   chr13:28674602-28674721
Original sequence
TACCGAGCAGCGGCAGCTGGCCGCCGTCGCGCGCCAACGCCGGCATGGC
CTCCGGAGCCCGGGGTCCCCAGGCCGCGCCGGCCCAGCCCTGCGATGCC
GCCTGGAGCGGCGCGCCTCGCG(SEQ ID NO: 57)
Modified sequence
TACCGAGCAGCGGCAGCTGGCCGCCGTCGCGCGCCAACGCCGGCATGGC
CTCCGGAGCCCGGGGTCCCCAGGCCGCATGCCCAGCCCTGCGATGCC
GCCTTGAGCAACGCGCCTCACG(SEQ ID NO: 58)
(Bait ID: FLT3_target_24.2)

3. Gene      Target           Bait genomic location
FLT3         FLT3_target_24   chr13:28674578-28674697
Original sequence
GCTGCGAGCGAGCGAGCGGGGCCTTACCGAGCAGCGGCAGCTGGCCGCC
GTCGCGCGCCAACGCCGGCATGGCCTCCGGAGCCCGGGGTCCCCAGGCC
GCGCCGGCCCAGCCCTGCGATG(SEQ ID NO: 59)
Modified sequence
GCTTCGAGAGAGCGAGCGGGGCCTTACCGAGCAGCAGCAGCTGGCCGCC
GTCGCGCGCCAACGCCGGCATGGCCTCCGGAGCCCGGGGTCCCCAGGCC
GCGCCAGCCCAGCCCTGAGATG(SEQ ID NO: 60)
(Bait ID: FLT3_target_24.3)

4. Gene      Target           Bait genomic location
FLT3         FLT3_target_24   chr13:28674554-28674673
Original sequence
GTGGGGGCTGAGGGACCGCGAGGGGCTGCGAGCGAGCGAGCGGGGCCTT
ACCGAGCAGCGGCAGCTGGCCGCCGTCGCGCGCCAACGCCGGCATGGCC
TCCGGAGCCCGGGGTCCCCAGG(SEQ ID NO: 61)
Modified sequence
GAGGTGGCTGAGAGACCGCGAGGAGCTGCGAGCGAGCGAGCGGGGCCTT
ACCGAGCAGCGGCAGCTGGCCGCCGTCGCGCGCCAACGCAGGCATGGCC
TCCGGAGCCCAGGGTCCCCAGG(SEQ ID NO: 62)
(Bait ID: FLT3_target_24.4)

5. Gene      Target           Bait genomic location
FLT3         FLT3_target_24   chr13:28674506-28674625
Original sequence
CGAGGCGGCTGGGCCGGAGGAGGCGCGCGCCCGGGTCCACACTGCGGGG
TGGGGGCTGAGGGACCGCGAGGGGCTGCGAGCGAGCGAGCGGGGCCTTA
CCGAGCAGCGGCAGCTGGCCGC(SEQ ID NO: 63)
Modified sequence
CGAGGCGGCTGGGCCGGAGGAGGCGCGCGCCCGGATCCACACTGCGGGG
TGGGGGCTGAGGGACCGCGAGGGGCTGCGAGCGAGCGAGCGGGGACTTA
CCGAGCAGCGGCAACTGGACGC(SEQ ID NO: 64)
(Bait ID: FLT3_target_24.5)

6. Gene      Target           Bait genomic location
FLT3         FLT3_target_24   chr13:28674530-28674649
Original sequence
GCGCGCCCGGGTCCACACTGCGGGGTGGGGCTGAGGGACCGCGAGGGG
CTGCGAGCGAGCGAGCGGGGCCTTACCGAGCAGCGGCAGCTGGCCGCCG
TCGCGCGCCAACGCCGGCATGG(SEQ ID NO: 65)
Modified sequence
GCACGCACGGATCCACACTGCGGGGTGGGGCTGAGGGACCGCGAGGAG
CTGCGAGCGAGCGAGCGGGGCCTTACCGAGCAGCGGCAGCTGGCAGCCG
TCGCGCGCCAACGCCGGCATGG(SEQ ID NO: 66)
(Bait ID: FLT3_target_24.6)

7. Gene      Target           Bait genomic location
FLT4         FLT4_target_31   chr5:180076516-180076635
Original sequence
TCGCAGGCACAGCGCGGCGCCCCGCTGCATCTCCGGCCGCTGCGCGTGG
GTCCGACCCGAGCGGCCGCGGCTCGGGGCTGAAAGTGTCCGCGCGGGCG
CCGGCTGGCCTGGGGCGGGGCG(SEQ ID NO: 67)
Modified sequence
CACACACACAAGCGCGGCGCCCCGCTGCATCTCCGGCCGCTGCGCGTGG
GTCCGACCCGAGCGGCCGCGGCTCGGGGCTGAAAGTGTCCGCGCGGGCG
CCGGCTGGCCTGCACACACACA(SEQ ID NO: 68)
(Bait ID: FLT4_target_31.1)

8. Gene      Target           Bait genomic location
FLT4         FLT4_target_31   chr5:180076396-180076515
Original sequence
GGCGGAGCGGTCTCAGCGCCCGCCCCAGGTGCGCGGTACCCCCTCCCCG
GCCAGCCCCACGCTCGGGCGGGTGGCCCGTTCGCCGCGCTCACCGTCCA
GGAGTCCCAGGCAGAGCCACAG(SEQ ID NO: 69)
Modified sequence
CACACACACATCTCAGCGCCCGCCCCAGGTGCGCGGTACCCCCTCCCCG
GCCAGCCCCACGCTCGGGCGGGTGGCCCGTTCGCCGCGCTCACCGTCCA
GGAGTCCCAGGCCACACACACA(SEQ ID NO: 70)
(Bait ID: FLT4_target_31.2)

9. Gene      Target           Bait genomic location
FLT4         FLT4_target_31   chr5:180076420-180076539
Original sequence
CCAGGTGCGCGGTACCCCCTCCCCGGCCAGCCCCACGCTCGGGCGGGTG
GCCCGTTCGCCGCGCTCACCGTCCAGGAGTCCCAGGCAGAGCCACAGTC
GCAGGCACAGCGCGGCGCCCCG(SEQ ID NO: 71)
Modified sequence
CACACACACAGGTACCCCCTCCCCGGCCAGCCCCACGCTCGGGCGGGTG
GCCCGTTCGCCGCGCTCACCGTCCAGGAGTCCCAGGCAGAGCCACAGTC
GCAGGCACAGCGCACACACACA(SEQ ID NO: 72)
(Bait ID: FLT4_target_31.3)

10. Gene     Target           Bait genomic location
FLT4         FLT4_target_31   chr5:180076468-180076587
Original sequence
GGCCCGTTCGCCGCGCTCACCGTCCAGGAGTCCCAGGCAGAGCCACAGT
CGCAGGCACAGCGCGGCGCCCCGCTGCATCTCCGGCCGCTGCGCGTGGG
TCCGACCCGAGCGGCCGCGGCT(SEQ ID NO: 73)
Modified sequence
CACACACACACCGCGCTCACCGTCCAGGAGTCCCAGGCAGAGCCACAGT
CGCAGGCACAGCGCGGCGCCCCGCTGCATCTCCGGCCGCTGCGCGTGGG
TCCGACCCGAGCCACACACACA(SEQ ID NO: 74)
(Bait ID: FLT4_target_31.4)

11. Gene     Target           Bait genomic location
FLT4         FLT4_target_31   chr5:180076444-180076563
Original sequence
GGCCAGCCCCACGCTCGGGCGGGTGGCCCGTTCGCCGCGCTCACCGTCC
AGGAGTCCCAGGCAGAGCCACAGTCGCAGGCACAGCGCGGCGCCCCGCT
GCATCTCCGGCCGCTGCGCGTG(SEQ ID NO: 75)
Modified sequence
CACACACAACGCTCGGGCGGGTGGCCCGTTCGCCGCGCTCACCGTCC
AGGAGTCCCAGGCAGAGCCACAGTCGCAGGCACAGCGCGGCGCCCCGCT
GCATCTCCGGCCCACACACACA(SEQ ID NO: 76)
(Bait ID: FLT4_target_31.5)

12. Gene     Target           Bait genomic location
FLT4         FLT4_target_31   chr5:180076492-180076611
Original sequence
CAGGAGTCCCAGGCAGAGCCACAGTCGCAGGCACAGCGCGGCGCCCCGC
TGCATCTCCGGCCGCTGCGCGTGGGTCCGACCCGAGCGGCCGCGGCTCG
GGGCTGAAAGTGTCCGCGCGGG(SEQ ID NO: 77)
Modified sequence
CACACACAAGGCAGAGCCACAGTCGCAGGCACAGCGCGGCGCCCCGC
TGCATCTCCGGCCGCTGCGCGTGGGTCCGACCCGAGCGGCCGCGGCTCG
GGGCTGAAAGTGCACACACACA(SEQ ID NO: 78)
(Bait ID: FLT4_target_31.6)
```

Example H

A Bayesian Approach for Sensitive Detection of Somatic Genomic Alterations from Next-Generation Sequencing of Clinical Cancer Specimens The Bayesian approach described herein was implemented in the following examples.

Figure 4:
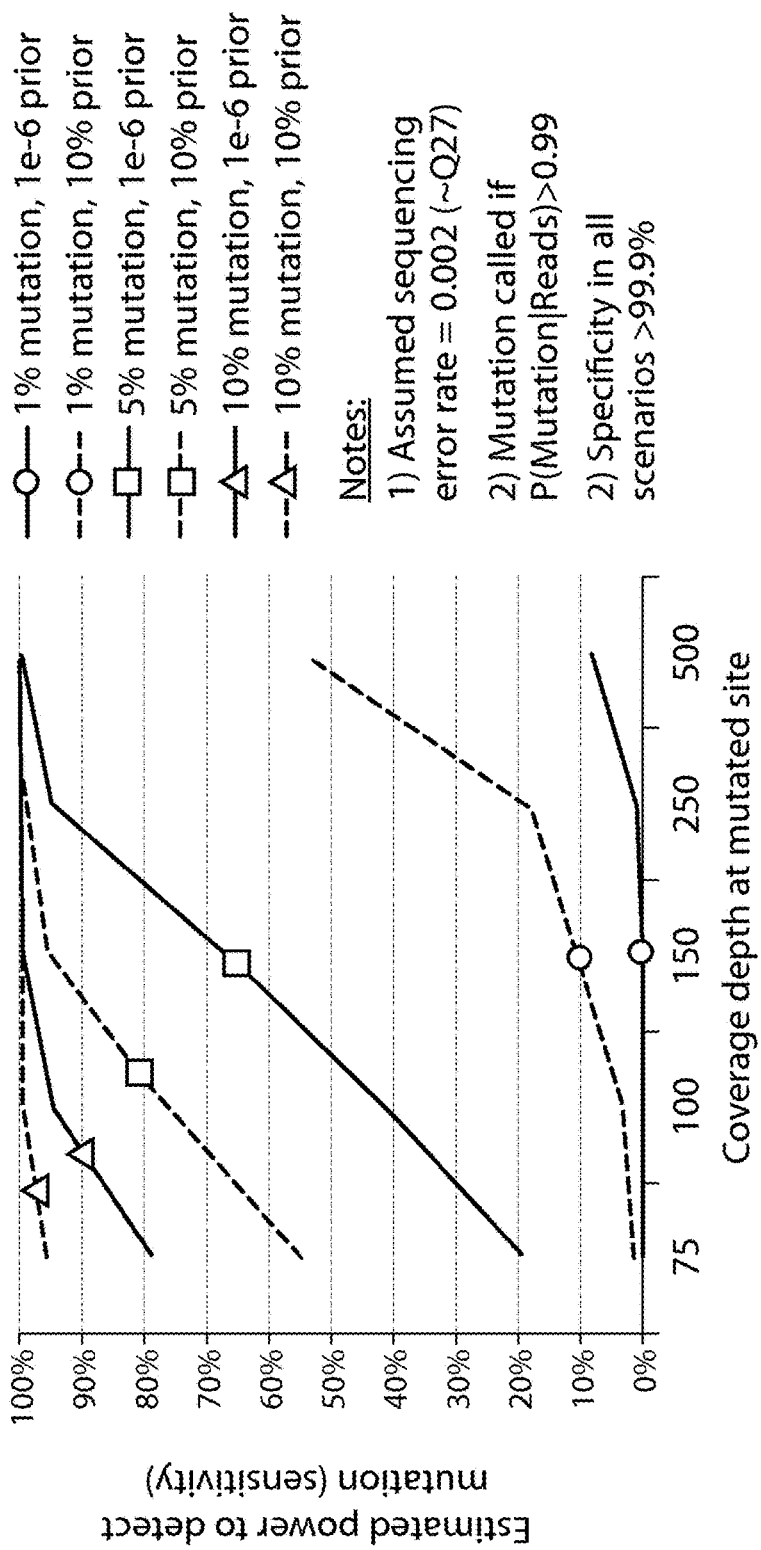
FIG. 4 depicts the impact of prior expectation and read depth on mutation detection.

The utility of this approach is illustrated by power calculations describing the impact of data-driven priors on substitution detection in the lower range of mutation frequencies relevant in the clinical setting. As shown in FIG. 4, the values of prior expectation (for example, 1e-6 or 10% prior) and mutation frequency (for example, 1%, 5%, or 15% mutation) correspond to the values described in (i) and (ii) of "A Bayesian Approach for Sensitive Detection of Somatic Genomic Alterations from Next-generation Sequencing of Clinical Cancer Specimens," respectively. FIG. 4 shows that incorporating prior expectations can improve detection power for rarer mutations, for example, by reducing the required coverage depth at mutated sites, or increasing the estimated power (sensitivity) to detect mutations.

Example I

A Bayesian Approach: Application to a Constructed Low Purity Multi-Clonal Sample To further demonstrate these benefits of the Bayesian approach disclosed herein, an artificial low-purity, multi-clonal "tumor" sample was constructed by equal admixture of DNA from 10 participants in the 1000 Genomes project, thereby creating a DNA pool containing a large number of sequence variants present at ~5% or 10% of the total DNA (arising from private heterozygous SNPs). The mix was subjected to hybrid selection for exons of 182 cancer-related genes and sequenced on the Illumina HiSeq2000 platform, yielding an average coverage of approximately 350× across the gene panel. Each constituent sample was likewise processed individually to determine genotype at all SNP sites. Of the approximately 260 ~5% "mutations" present in the pool, 89% were detected with high-confidence using a prior of 1e-6, whereas 94% and 95% were detectable using a prior of 1% and 10% (average coverage of missed sites 125×), respectively, supporting the theoretical conclusions above. Of the 102 10% "mutations" present in the pool, 98% were detected with high-confidence using a prior of 1e-6, whereas 99% and 99% were detectable using a prior of 1% and 10% (coverage of missed site 13×).

Example J

A Bayesian Approach: Application to Lung and Colon Tumor Samples

Prior expectations of the frequency of relevant mutations in several cancer types from the COSMIC database (on the worldwide web at sanger.ac.uk/genetics/CGP/cosmic) were derived and analyzed more than 80 lung and colon cancer samples extracted from routine clinical specimens. Known mutations in more than 20 different genes were observed, including a 1% PIK3CA mutation p.H1047R in a colon cancer that could only be detected by incorporation of the 3% prior for this mutation in this cancer type. These results show that judicious incorporation of prior expectations around tumor type specific mutation spectra can be beneficial in translation of NGS-based tumor genome analysis to the clinical setting.

Example K

A Bayesian Approach: Application to Breast Cancer Samples

Substitution mutation calling in exons of 182 cancer-related genes sequenced to ~260× for an FFPE breast cancer samples was performed. The number of sites with >2 copies of an alternate allele is 1,793. The number of sites with >99% posterior belief in presence of mutation is 402. The number of sites remaining after filters is 188, which is approximately the expected number of variant sites. The number of sites that are not in dbSNP is 14, which is approximately the expected number of sites not in dbSNP as dbSNP captures >90% of variation. The number of non-synonymous sites is 5. The number of sites in COSMIC is 2 (PIK3CA p.H1047R and P53 p.F113S).

Example L

A Bayesian Approach: Detection of Infrequent Mutations

Figure 5:
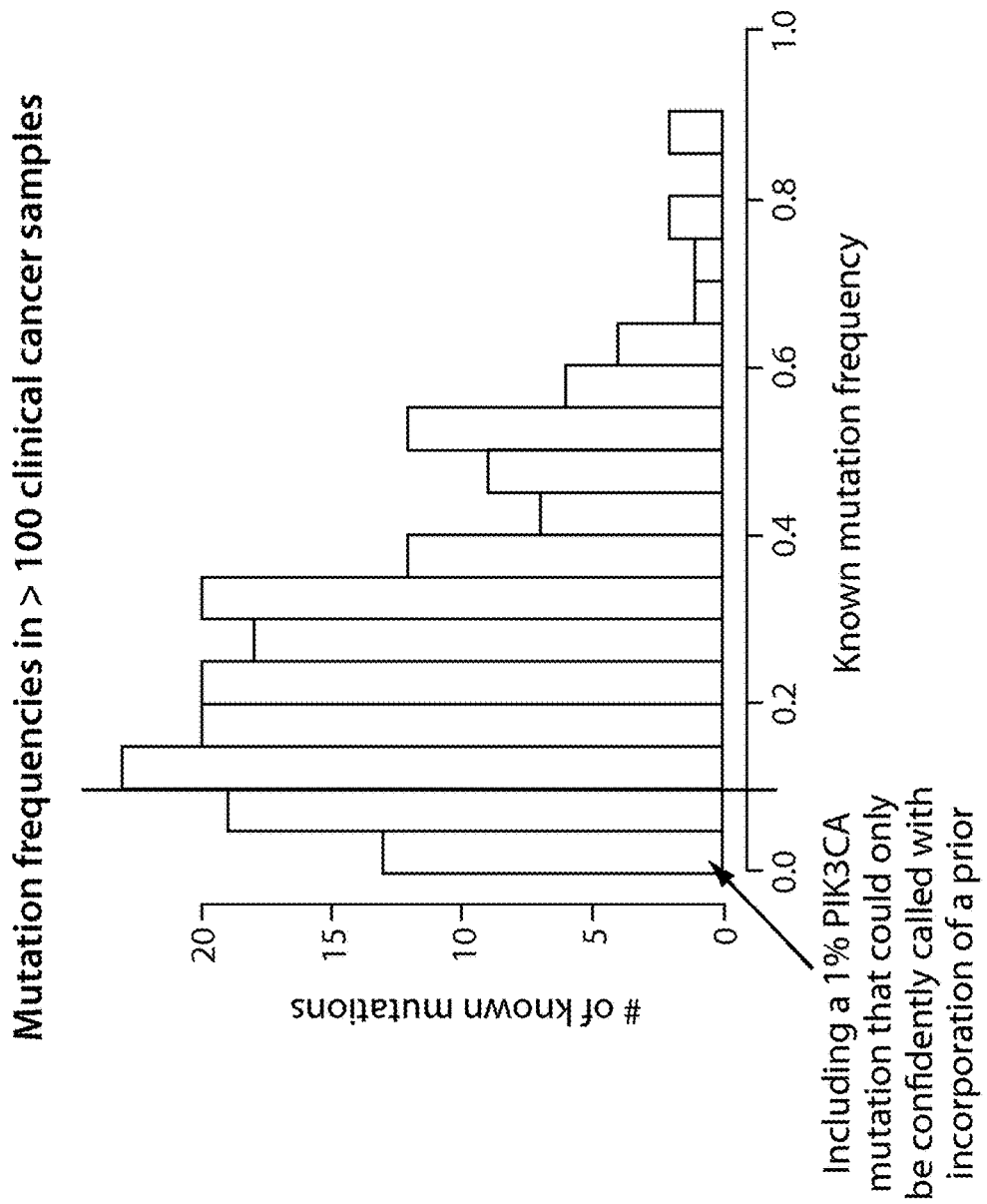
FIG. 5 depicts the mutation frequencies in more than 100 clinical cancer samples.

Many routine clinical specimens contain relevant rare mutations. FIG. 5 shows mutation frequencies in more than 100 clinical cancer samples. Samples were FFPE biopsies, surgical resections, or fine-needle aspirates of predominantly colon and lung cancers. The frequency spectrum of known mutations found in a series of clinical sample is show in Table 12.

TABLE 12

Frequency spectrum of known mutations found in a series of clinical samples

| Fraction of mutation <5% | Fraction of mutation <10% | Fraction of mutation <25% | Fraction of mutation <50% | Fraction of mutation <100% |
|---|---|---|---|---|
| 7%* | 17% | 50% | 85% | 100% |

*likely underestimated

Example M.1

High Performance Solution-Based Target Selection Using Individually Synthesized Oligonucleotide Capture Probes The availability of solution-based genomic target selection techniques has enabled rapid development of targeted sequencing applications, some of which have led to the introduction of clinical sequencing tests. Commercialized hybridization capture reagents are based on array-synthesized oligonucleotides, which are converted to biotinylated DNA or RNA probes ("baits"). However, methods of generating these complex pools of probes face performance challenges, for example capturing high-GC content targets.

An alternative approach using individually synthesized, 5'-biotinylated oligonucleotides ("oligo-baits") for capturing a target region of ~130 kb representing 57 clinically relevant and actionable cancer-related genes is described herein. Indexed sequencing libraries selected using these oligo-baits with a 24-hour hybridization procedure yielded 5.000-fold target enrichment. 50M 49×49 paired-end reads generated an average target coverage of 2100× with a standard deviation of 568× (27%). All targets were covered successfully, with 99.95% of the targeted bases covered at >500×. Furthermore, the target coverage had virtually no GC-bias.

Targets with GC content >70% averaged 1,975× coverage, and targets with GC content <35% averaged 1,996× coverage.

High performance was retained using even shorter hybridization times: 99.3% of targeted bases were covered at >500× after a 2.5 hour hybridization.

Use of SSPE (Salmon Sperm, PE)/Denhardt's outperformed hyb/wash buffers containing TEAC1, TMAC1, and/or dextran sulfate.

Oligo-baits can be spiked into array-derived bait pools to increase the coverage of otherwise difficult to capture (for example, high % GC) regions, or to rapidly add new gene content. This approach offers a highly effective and scalable method for developing high performance targeted clinical sequencing tests.

Example M.2

Method of Optimizing Capture Baits

Three bait sets were tested. The results are summarized in FIG. 7. The bait sets were as follows:

Bait set #1 consists of 5'-biotinylated, individually synthesized DNA oligonucleotide baits only.

Bait set #2 includes biotinylated, array-derived RNA baits spiked with 5'-biotinylated, individually synthesized DNA oligonucleotide baits.

Bait set #3 consists of biotinylated, array-derived RNA baits only.

All 5'-biotinylated, individually synthesized DNA oligonucleotide were 120 bases with a 5' biotin.

Figure 7:
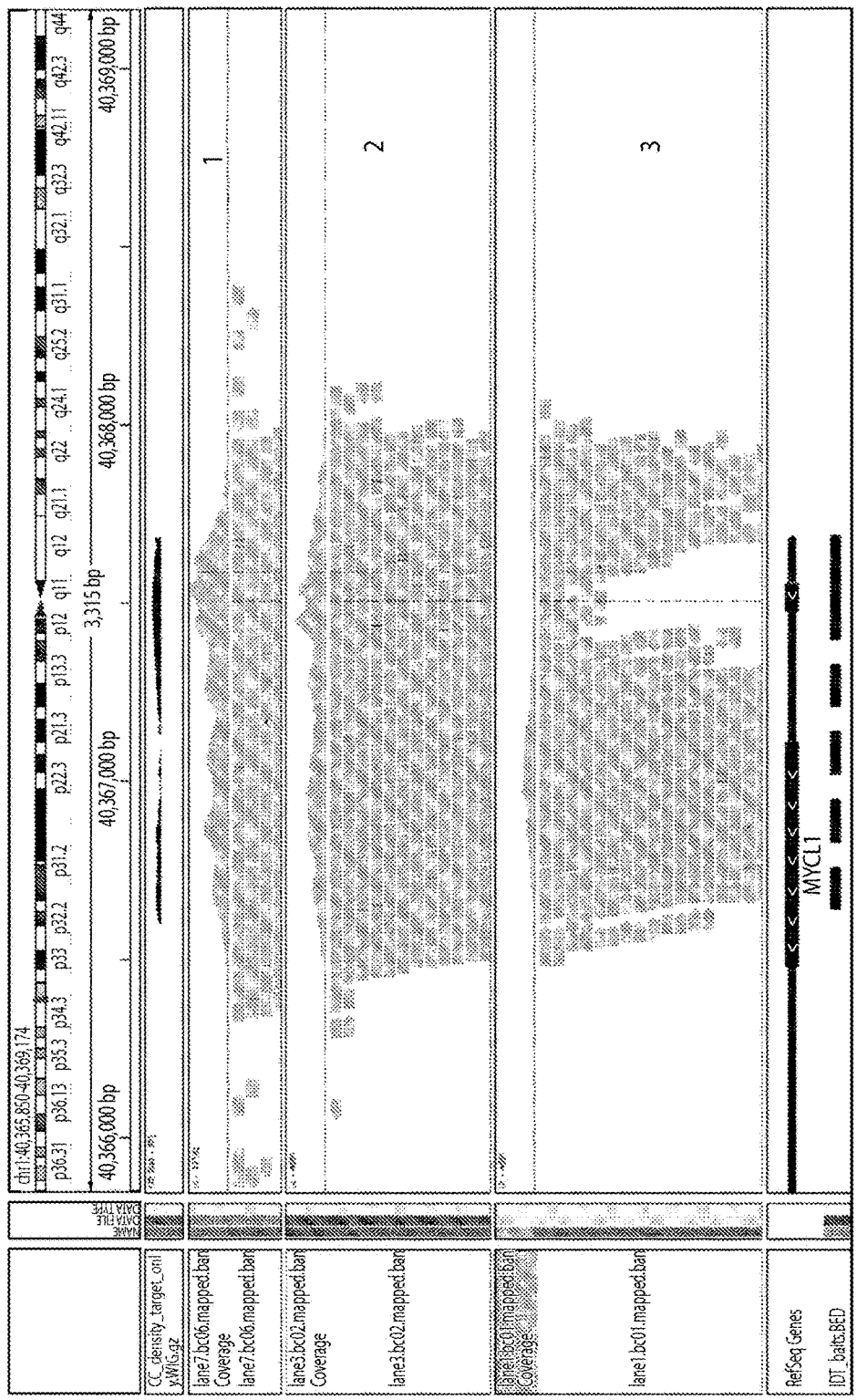
FIG. 7 is a coverage histogram comparing the uniformity in coverage detected with a bait set consisting of biotinylated, individually synthesized DNA oligonucleotide baits only (Bait set #1) and a bait set that includes biotinylated, array-derived RNA oligonucleotide baits spiked with biotinylated, individually synthesized DNA oligonucleotide baits ("Bait set #2"), compared to a bait set that includes biotinylated, array-derived RNA oligonucleotide baits only ("Bait set #3"). The bait sets are shown as #1, 2, and 3 in FIG. 7. Several gaps in coverage were detected using Bait set #3, but were not detected using Bait sets #1-2, as depicted in FIG. 7.
Figure 8:
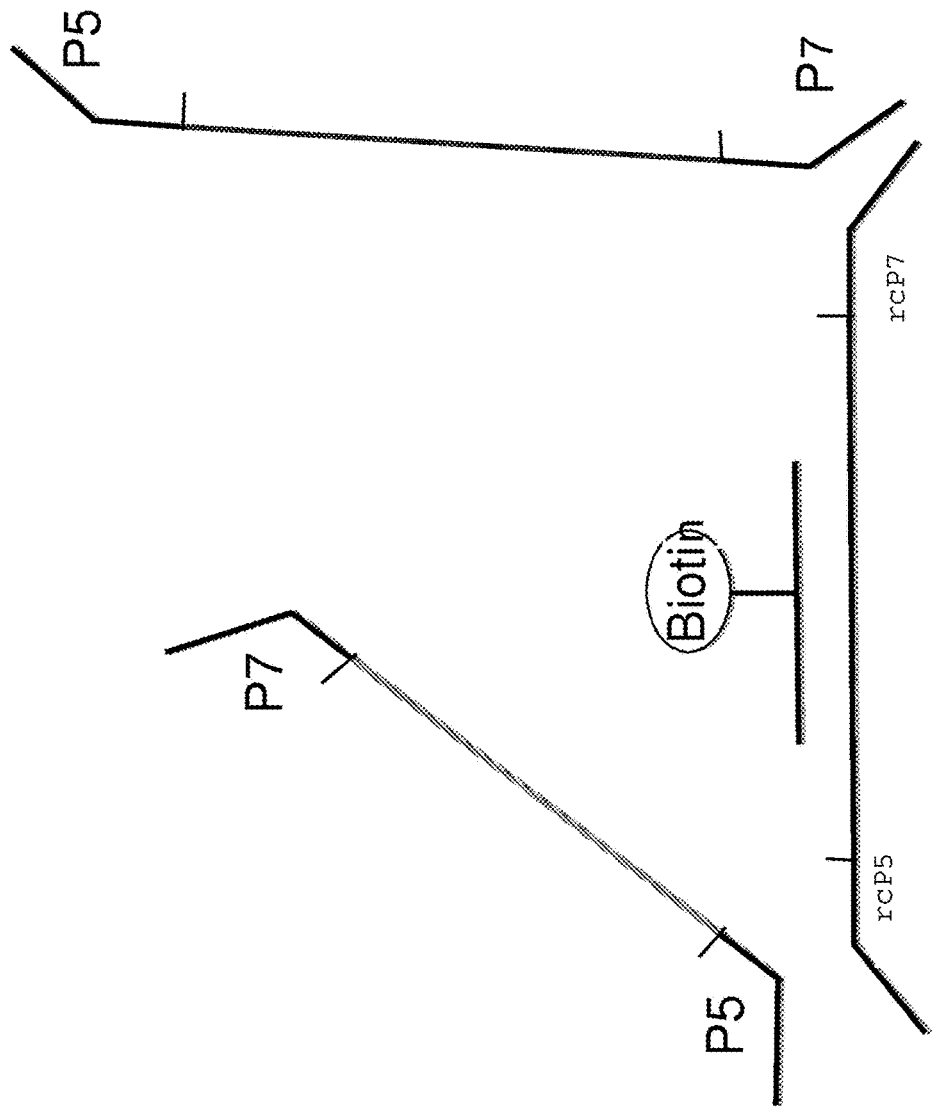
FIG. 8 illustrates in diagram form an exemplary configuration of non-target concatemers of the library members. The non-target regions (for example, adaptors depicted as "P5" and "P7") are shown as hybridizing to their complementary non-target strands (depicted as "rcP5" and "rcP7," respectively). A biotin-tagged bait is shown hybridizing to a complementary region of the target insert of the library member.

FIG. 7 is a coverage histogram comparing the uniformity in coverage detected with Bait set #1 and Bait set #2, compared to Bait set #3. The bait sets are shown as #1, 2, and 3 in FIG. 7. Several gaps in coverage were present using Bait set #3 corresponding to high % GC, whereas the corresponding regions were deeply covered using Bait sets #1 and #2, as depicted in FIG. 7. In FIG. 7, the left-hand panel labeled "GC_density_target . . . " indicates the local GC content within the target, The line represents 65% GC content, where any values above the line represent a higher GC content. As shown in the histogram, the coverage is the lowest for Bait set #3 in areas of high GC content. The bottom panel in FIG. 7 labeled "IDT_baits . . . " indicates the placement of the oligos covering the target shown.

Figure 6:
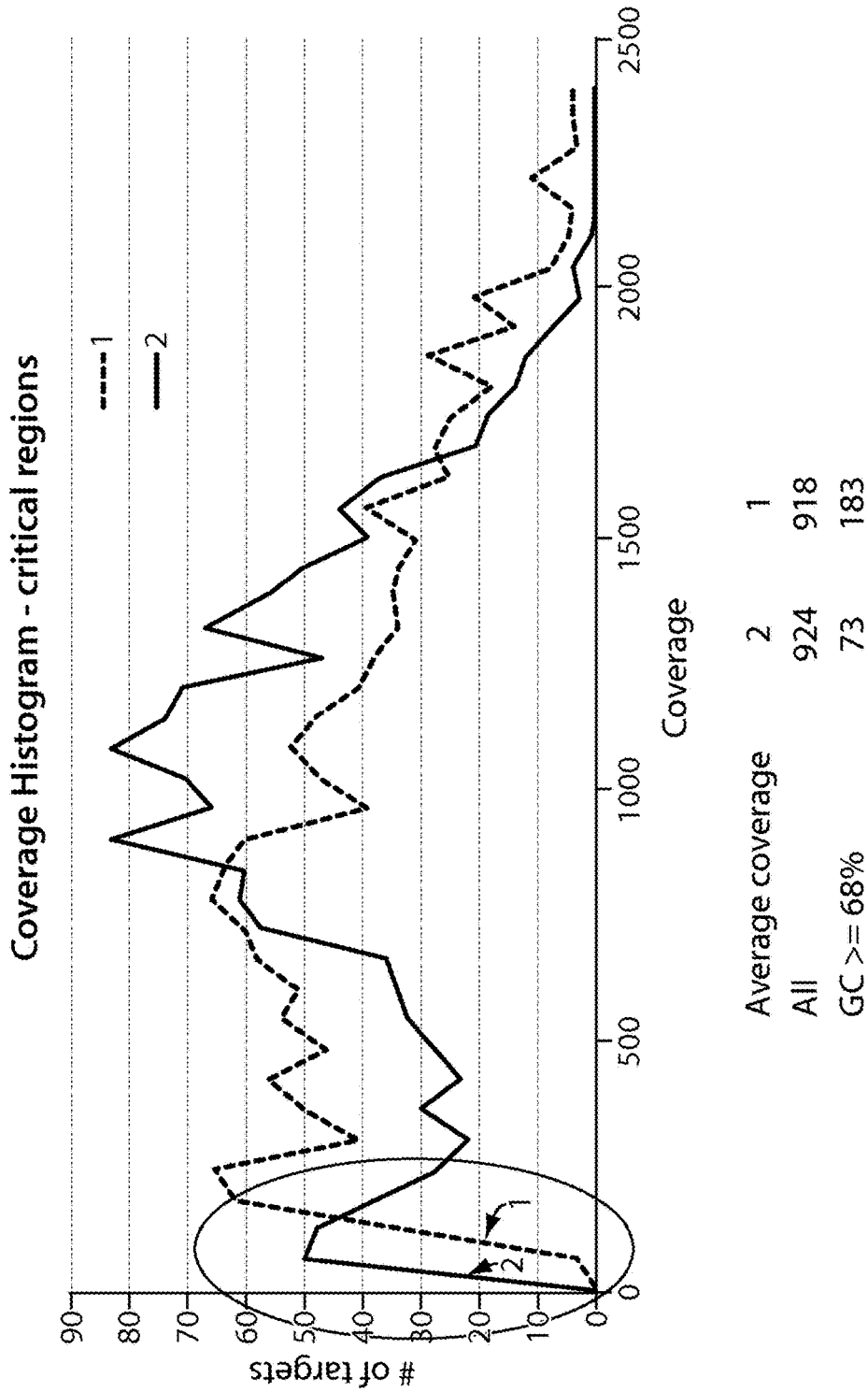
FIG. 6 is a linear representation of a coverage histogram. The number of targets (y-axis) are depicted as a function of coverage (x-axis). Line #1 represents the coverage using a bait set that includes biotinylated, array-derived RNA oligonucleotide baits spiked with biotinylated, individually synthesized DNA oligonucleotide baits (referred to herein as "Bait set #1"). Line #2 represents the coverage obtained using a bait set that includes biotinylated, array-derived RNA oligonucleotide baits only (referred to herein as "Bait set #2"). The overall average coverage using Bait set #2 was 924, whereas the coverage in areas of high GC content (about 68%) using Bait set #2 was 73. In contrast, when Bait set #1 was used, the overall coverage was about 918, but the coverage was improved to 183 in areas of high GC content.

A graphic representation of the changes in the number of targets and coverage using array-derived bait sets alone or spiked with individually-synthesized baits is depicted in FIG. 6. More specifically, FIG. 6 is a linear representation of a coverage histogram. The number of targets (y-axis) are depicted as a function of coverage (x-axis). Line #1 represents the coverage using a bait set that includes 5'-biotinylated, array-derived RNA oligonucleotide baits spiked with 5'-biotinylated, individually synthesized DNA oligonucleotide baits (referred to in FIG. 6 as "Bait set #1"). Line #2 represents the coverage obtained using a bait set that includes biotinylated, array-derived RNA oligonucleotide baits only (referred to in FIG. 6 as "Bait set #2"). The overall average coverage using Bait set #2 was 924, whereas the coverage in areas of high GC content (about 68%) using Bait set #2 was 73. In contrast, when Bait set #1 was used, the overall coverage was similar to Bait Set #1, about 918, but the coverage was improved to 183 in areas of high GC content.

Example M.3

Exemplary Experimental Conditions for Evaluating Bait Sets

Bait set A consists of 5'-biotinylated, individually synthesized DNA oligonucleotide baits only. The original set was 1000 oligos, covering 133 kb of target territory (referred to herein as "the large set," "Bait set A" or "DNA oligo baits").

For the "spike-in" experiments, the original 1000 DNA oligo set ("the large set") was added to a bait set consisting of biotinylated, array-derived RNA oligonucleotide baits (referred to in this example as "Bait set B" or "RNA baits"). Different ratios of DNA oligo baits from Bait set A were mixed with RNA baits from Bait set B. In particular, a DNA oligo bait:RNA bait ratio of 1:10 was used (10 ng total DNA oligo baits to 100 ng total RNA baits). Hybridization and washing conditions were matched to those that are most ideal for the RNA baits.

With low tiling densities, strong periodicities in coverage were detected when using DNA oligo baits that corresponded to bait placement. In addition, low tiling densities may make capturing of alleles with indels more difficult. Therefore, bait sets were designed for MAP3K1 with the different tiling densities depicted in Table 13. In the below mixes, Mix 1 containing 5'-biotinylated, individually synthesized DNA oligo baits designed to capture the exons of six cancer-relevant genes (DAXX, TRRAP, CREBBP, GRIN2A, SPOP, GNA11) were spiked into the array-derived RNA oligonucleotide baits only (Bait set B). DAXX, TRRAP, CREBBP, GRIN2A, and SPOP were not present in the RNA bait set. Mixes 2-4 were spiked into Bait Set A (the large set of DNA oligo baits) to test different tiling densities (with Mix 2 being the densest) of capture baits for the exons of MAP3K1. The RNA bait set alone covered about 1 MB of sequence.

TABLE 13

Mixes for methods using capture probes

| Category | Number |
| --- | --- |
| Mix 1 | 369 oligos to melanoma genes |
| Mix 2 | 91 oligos tiling density of 60 to MAP3K1 |
| Mix 3 | 57 oligos tiling density of 100 to MAP3K1 |
| Mix 4 | 40 oligos tiling density of 150 to MAP3K1 |
| Mix 5 | 3 oligos to STK11 exon 3 |

Input into capture was 2 µg of pooled cell-line DNA libraries. 2 µg library was mixed with blocking mix (Table 14), dried down, and resuspended in 9 µl water. This mixture was then put in a plate, transferred to a cycler, and run at 98° C. for 5 minutes, followed by 68° C. for 2 minutes. The plate was then unsealed, and 11 µL DNA bait/hyb buffer mixture @ 68° C. was added. The DNA bait/hyb mixture at 68° C.=10 µL hyb buffer+1 µL bait (containing 10 ng, 50 ng, or 100 ng bait).

For captures with DNA baits alone (for example, Bait set A), hybridization was performed at 68° C., and washes were performed. Baits were tested at 5 ng, 10 ng, 100 ng, 1000 ng, and 2000 ng (per 2 µg input library). For 24 hr. hybs, the 5-10 ng conditions, and up to 100 ng conditions were tested.

For captures with the large DNA bait set (100 kb) spiked into the RNA-array bait set (B) to rescue poor performing/high GC regions, hybridization was performed at 68° C., and washes were performed at 70° C. Bait sets were tested at 1:10 DNA oligo: RNA baits (that is, 10 ng total mass of oligo baits, and 100 ng total mass of RNA baits).

For captures with the small, gene focused DNA bait set spiked into the RNA bait set, hybridization was performed at 68° C., and a range of wash temperatures were tested (62° C., 64° C., 66° C., 68° C., 70° C., and 72° C.).

Mix 1 (adding 6 new genes) was tested at the following ratios: 1:5, 1:10 and 1:20 total oligo DNA bait mass: RNA bait mass (that is, 20 ng:100 ng, 10 ng:100 ng, and 5 ng:100 ng).

Mix 5 (3 oligos representing exon 3 of STK11 to path low coverage) was tested at 1:500, 1:1000, and 1:2000 DNA oligo:RNA oligo. 100 ng of total RNA baits were used. STK11 was tested as it represents an important cancer target with poor detection performance when captured with the RNA baits alone. DNA oligo spiking of exon 3 of STK11 boosts coverage from an average of 70× to 300×.

TABLE 14

Buffers for methods using capture probes

| Baits (pooled IDT oligos) | 39600 (g/mol) | 100 nmol = | 0.0039600 grams = 3,960,000 nanograms |
|---|---|---|---|
| Resuspended in low TE | 25 mL | 250 μL Tris 5 μL EDTA | |
| Blocking Mix | [Stock] | [Working] | 14.5 μl/rxn |
| Cot1 | 1 μg/μl | 1 μg/μl | 10 |
| Salmon Sperm | 10 μg/μl | 10.0 μg/μl | 1 |
| PE 1.0 | 800 μM | 800 μM | 1.75 |
| Universal Index | 800 μM | 800 μM | 1.75 |
| 2X Hyb Buffer | [Stock] | [Final] | in 10 ml (10 μl/rxn) |
| SSPE | 20X | 10X | 5 ml |
| Denhardt's | 50X | 10X | 2 ml |
| EDTA | 0.5M | 0.01M | 200 μl |
| SDS | 10% | 0.20% | 200 μl |
| Water | | | 2.6 ml |
| Bead Wash | [Stock] | [Final] | in 50 ml (200 μl/wash) |
| NaCl | 5M | 1M | 10 ml |
| Tris | 1M | 10 mM | 500 μl |
| EDTA | 0.5M | 1 mM | 100 μl |
| Water | | | 39.4 ml |
| Wash Buffer 1 | [Stock] | [Final] | in 50 ml (150 μl/wash) |
| SSC | 20X | 1X | 2.5 ml |
| SDS | 10% | 0.10% | 500 μl |
| Water | | | 47 ml |
| Wash Buffer 2 | [Stock] | [Final] | in 50 ml (150 μl/wash) |
| SSC | 20X | 0.1X | 250 μl |
| SDS | 10% | 0.10% | 500 μl |
| Water | | | 49.25 ml |

Example N

Reducing Off-Target Nucleic Acid Binding of Library Members

Off-target nucleic acid interactions can limit the efficiency of the selection of target nucleic acids by hybridization (for example, solution or solid-phase hybridization) to a capture probe, for example, an oligonucleotide bait. Off-target selection is typically increased when the stringency conditions for hybrid selection are reduced, for example, when selecting for a target:capture duplex having a lower nucleic acid melting temperature (for example, $T_m$ of DNA:DNA duplexes as compared to RNA:DNA duplexes). Thus, capture of off-target sequence can be more problematic in DNA:DNA hybridizations. Off-target selection can result, for example, in one or more of decreased yields of hybridization capture and/or artifactual hybrid capture, which in turn lead to inefficiencies in subsequent steps, for example, sequencing.

Library members can include a library insert (which, if on-target, forms a duplex with the capture probe, for example, a bait) and one or more non-target sequences (for example, one or more of adaptor sequences, amplification primers or tags, and bar code tags). Typically, a bait hybridizes to the library insert, for example, a target DNA. However, the library insert can have universal adaptors, which are typically present on every fragment in the library. The non-target sequence of the capture probe-hybridized library member, can, by duplex formation with other sequences in the reaction mixture (for example, via binding to adaptor sequences), lead to the selection of undesired sequences, for example, off-target library members.

While not wishing to be bound by theory, concatenation between an on-target library member that has formed a duplex with the capture probe and off-target sequences can result in selection of off-target sequences. FIG. 6 illustrates in diagram form an exemplary configuration of non-target concatemers of the library members. The non-target regions (for example, adaptors depicted as "P5" and "P7") are shown as hybridizing to their complementary non-target strands (depicted as "rcP5" and "rcP7," respectively). A biotin-tagged bait is shown hybridizing to a complementary region of the target insert of the library member. Off-target binding can lead to a concatenation of library members, thus leading to a reduction in target-binding specificity (also referred to herein as increased off-target selection).

In target:capture duplexes involving DNA (library member):RNA (bait) duplexes, concatenation between an on-target library member that has formed a duplex with the capture probe and off-target sequences can be broken up during high stringency washes typically performed at 65-70° C. Typically, washes involving lower melting of DNA:DNA duplexes are performed at lower temperatures relative to RNA:DNA duplexes. The inability to break up the concatenation has kept the percentage of target capture relatively low when using DNA Baits (45-50%). Commercially available blocking oligos complementary to adaptors are added to minimize the concatenation, but they typically do not adequately inhibit chain formation, particularly in DNA:DNA hybridizations.

Methods and compositions are disclosed herein that reduce non-target sequence (for example, adaptor)-mediated selection. In certain embodiments, blocking oligonucleotides are disclosed that are complementary to, or can form a duplex with, the non-target nucleic acid sequence of the library member (for example, an adaptor sequence), and have a value for a parameter related to the binding interaction between the blocking oligonucleotide and the non-target nucleic acid sequence of the library member that is higher than the value for the non-target nucleic acid sequence to a background nucleic acid, for example, other complementary non-target nucleic acid sequences. Exemplary blocking oligonucleotides having an increased binding interaction include oligonucleotides having extended blocker length, for example, extended complementarity to a non-target nucleic acid; blocking oligonucleotides having one or more non-naturally-occurring nucleotides; and blocking oligonucleotides that include (or a substantially composed of) oligoribonucleotides, instead of deoxyribonucleotides.

Example O

Extended Blocker Length

This Example demonstrates that percent on-target selection can be improved by extending the length of the blocking oligonucleotide.

Adaptor-specific blocking oligonucleotides are added to the hybridization reaction performed as described herein to prevent carryover of off-target nucleic acid binding as described in Example 14. In the experimental conditions described in Example 4, high stringency washes are performed, which are likely to denature off-target binding. However, optimal hybridization and washing conditions for DNA:DNA interactions lower the temperatures of the washes as described in Examples 13A-13C, thus increasing off-target binding.

Figure 9:
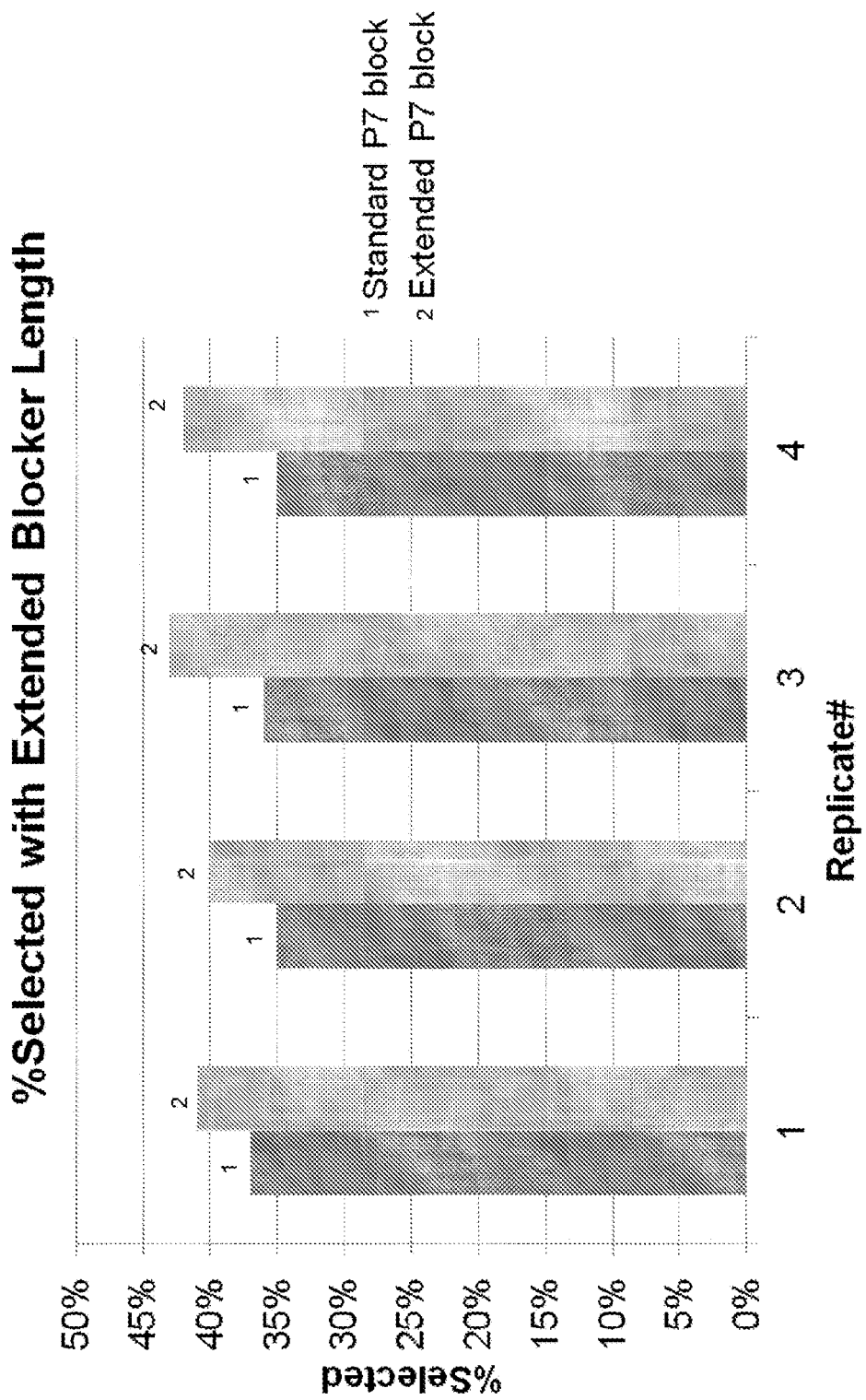
FIG. 9 is a bar graph depicting the percentage of target selection using standard and extended blocking oligos.
Figure 10:
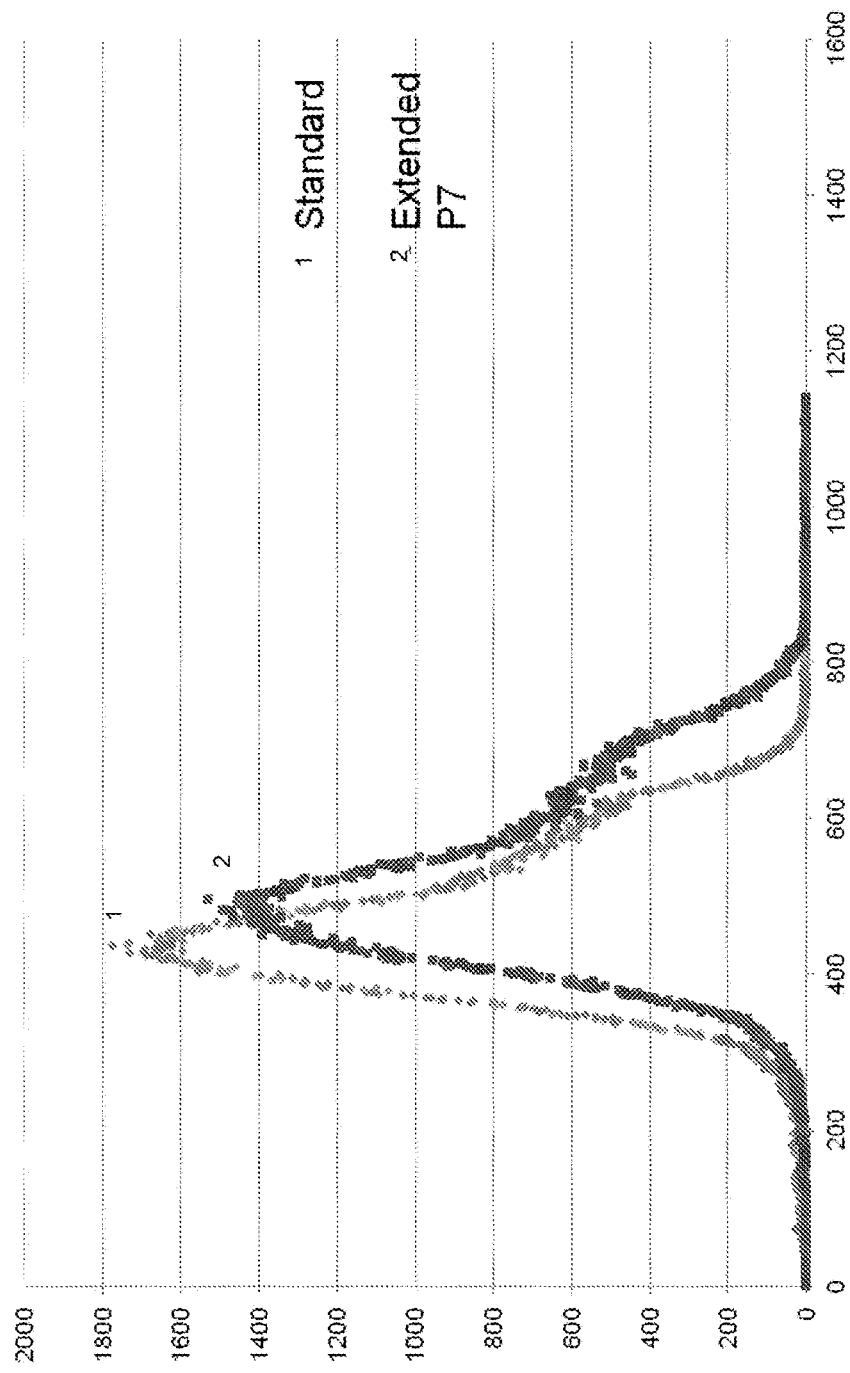
FIG. 10 depicts an exon coverage histogram showing capture results using standard or extended blockers.

Blocking oligos can be designed complementary to the adaptors, for example, the Illumina multiplex adaptors described in Example 3, to increase the extent of complementarity between the adaptor and the blocking oligo. For example, the P5 blocking oligo is 58 bp bases in length, but the blocker is only 46 bases. The length of the P5 blocking oligo was extended by 19 bases. Extending the length of the blocking oligo by 19 bases increased selection efficiency by approximately 5% (shown in FIG. 9). FIG. 9 is a bar graph depicting the percentage of target selection using standard and extended blocking oligos. Data from four representative experiments are shown. FIG. 10 depicts an exon coverage histogram showing capture results using standard or extended blockers.

Improved blocking can be achieved by extending the length of the complementarity region between the adaptor and the blocking oligo, thus increasing the melting temperature.

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

The terminology used herein is for the purpose of describing particular embodiments only, and is not intended to be limiting. With respect to the use of substantially, any plural and/or singular terms herein, those having skill in the art can translate from the plural as is appropriate to the context and/or application. The various singular/plural permutations may be expressly set forth herein for the sake of clarity.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiments or examples disclosed, but that the present invention will include all embodiments falling within the scope of the appended claims.

What is claimed is:

1. A kit for use in a method for performing massively parallel sequencing of a desired template nucleic acid having a terminal adaptor, comprising:
 a blocker oligonucleotide having a plurality of $T_m$-enhancing groups, wherein the blocker oligonucleotide is an oligonucleotide selected from
 (i) the group consisting of SEQ ID NOS: 2, 3, 4, 5, 6, 7 and 8;
 (ii) the group consisting of SEQ ID NOS: 10, 11, 12, 13, 14, 15 and 16;
 (iii) the group consisting of SEQ ID NOS: 18 and 19;
 (iv) the group consisting of SEQ ID NOS: 21 and 22;
 (v) the group consisting of SEQ ID NOS: 24 and 25;
 (vi) the group consisting of SEQ ID NOS: 27 and 28;
 (vii) SEQ ID NO: 30;
 (viii) SEQ ID NO: 32,
 (ix) SEQ ID NO: 34; and
 (x) SEQ ID NO: 36, or a combination thereof.

2. The kit of claim 1, wherein the terminal adaptor has a size range from 15 nucleotides to 75 nucleotides.

3. The kit of claim 1, wherein the terminal adaptor includes a barcode domain.

\* \* \* \* \*

SEQUENCE LISTING

```
<160> NUMBER OF SEQ ID NOS: 81

<210> SEQ ID NO 1
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 1
agatcggaag agcgtcgtgt agggaaagag tgtagatctc ggtggtcgcc gtatcatt      58

<210> SEQ ID NO 2
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (16)..(16)
<223> OTHER INFORMATION: iBNA-meC at positions 16.
<220> FEATURE:
<221> NAME/KEY: misc_feature
<222> LOCATION: (40)..(40)
<223> OTHER INFORMATION: iBNA-meC at positions 40.

<400> SEQUENCE: 2
agatcggaag agcgtcgtgt agggaaagag tgtagatctc ggtggtcgcc gtatcatt      58

<210> SEQ ID NO 3
<211> LENGTH: 58
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: misc_feature
<222> LOCATION: (5)..(5)
<223> OTHER INFORMATION: iBNA-meC at position 5.
<220> FEATURE:
<221> NAME/KEY: misc_feature
<222> LOCATION: (16)..(16)
<223> OTHER INFORMATION: iBNA-meC at position 16.
<220> FEATURE:
<221> NAME/KEY: misc_feature
<222> LOCATION: (40)..(40)
<223> OTHER INFORMATION: iBNA-meC at position 40.
<220> FEATURE:
<221> NAME/KEY: misc_feature
<222> LOCATION: (50)..(50)
<223> OTHER INFORMATION: iBNA-meC at position 50.

<400> SEQUENCE: 3
agatcggaag agcgtcgtgt agggaaagag tgtagatctc ggtggtcgcc gtatcatt         58

<210> SEQ ID NO 4
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: iBNA-meC at position 5.
<220> FEATURE:
<221> NAME/KEY: misc_feature
<222> LOCATION: (13)..(13)
<223> OTHER INFORMATION: iBNA-meC at position 13.
<220> FEATURE:
<221> NAME/KEY: misc_feature
<222> LOCATION: (16)..(16)
<223> OTHER INFORMATION: iBNA-meC at position 16
<220> FEATURE:
<221> NAME/KEY: misc_feature
<222> LOCATION: (40)..(40)
<223> OTHER INFORMATION: iBNA-meC at position 40.
<220> FEATURE:
<221> NAME/KEY: misc_feature
<222> LOCATION: (47)..(47)
<223> OTHER INFORMATION: iBNA-meC at position 47.
<220> FEATURE:
<221> NAME/KEY: misc_feature
<222> LOCATION: (50)..(50)
<223> OTHER INFORMATION: iBNA-meC at position 50.
<220> FEATURE:
<221> NAME/KEY: misc_feature
<222> LOCATION: (55)..(55)
<223> OTHER INFORMATION: iBNA-meC at position 55.

<400> SEQUENCE: 4
agatcggaag agcgtcgtgt agggaaagag tgtagatctc ggtggtcgcc gtatcatt         58

<210> SEQ ID NO 5
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
```

```
<222> LOCATION: (16)..(16)
<223> OTHER INFORMATION: iBNA-meC is at position 16.
<220> FEATURE:
<221> NAME/KEY: misc_feature
<222> LOCATION: (38)..(38)
<223> OTHER INFORMATION: iBNA-meC is at position 38.
<220> FEATURE:
<221> NAME/KEY: misc_feature
<222> LOCATION: (40)..(40)
<223> OTHER INFORMATION: iBNA-meC is at position 40.
<220> FEATURE:
<221> NAME/KEY: misc_feature
<222> LOCATION: (47)..(47)
<223> OTHER INFORMATION: iBNA-meC is at position 47.
<220> FEATURE:
<221> NAME/KEY: misc_feature
<222> LOCATION: (50)..(50)
<223> OTHER INFORMATION: iBNA-meC is at position 50.
<220> FEATURE:
<221> NAME/KEY: misc_feature
<222> LOCATION: (55)..(55)
<223> OTHER INFORMATION: iBNA-meC is at position 55.

<400> SEQUENCE: 5
agatcggaag agcgtcgtgt agggaaagag tgtagatctc ggtggtcgcc gtatcatt        58

<210> SEQ ID NO 6
<211> LENGTH: 58
<212> TYPE: DNA
<213> ORGANISM: Artificial Sequence
<220> FEATURE:
<223> OTHER INFORMATION: Synthetic  Oligonucleotide
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (9)..(9)
<223> OTHER INFORMATION: iBNA-A is at position 9.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (16)..(16)
<223> OTHER INFORMATION: iBNA-meC is at position 16.
<220> FEATURE:
<221> NAME/KEY: misc_feature
<222> LOCATION: (21)..(21)
<223> OTHER INFORMATION: iBNA-A is at position 21.
<220> FEATURE:
<221> NAME/KEY: misc_feature
<222> LOCATION: (25)..(25)
<223> OTHER INFORMATION: iBNA-A is at position 25.
<220> FEATURE:
<221> NAME/KEY: misc_feature
<222> LOCATION: (38)..(38)
<223> OTHER INFORMATION: iBNA-meC is at position 38.
<220> FEATURE:
<221> NAME/KEY: misc_feature
<222> LOCATION: (40)..(40)
<223> OTHER INFORMATION: iBNA-meC is at position 40.
<220> FEATURE:
<221> NAME/KEY: misc_feature
<222> LOCATION: (47)..(47)
<223> OTHER INFORMATION: iBNA-meC is at position 47.
<220> FEATURE:
<221> NAME/KEY: misc_feature
<222> LOCATION: (49)..(49)
<223> OTHER INFORMATION: iBNA-meC is at position 49.
<220> FEATURE:
<221> NAME/KEY: misc_feature
<222> LOCATION: (50)..(50)
<223> OTHER INFORMATION: iBNA-meC is at position 50.
<220> FEATURE:
```

<221> NAME/KEY: misc_feature
<222> LOCATION: (55)..(55)
<223> OTHER INFORMATION: iBNA-meC is at position 55.

<400> SEQUENCE: 6
agatcggaag agcgtcgtgt agggaaagag tgtagatctc ggtggtcgcc gtatcatt    58

<210> SEQ ID NO 7
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: iBNA-A is at position 3.
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (9)..(9)
<223> OTHER INFORMATION: iBNA-A is at position 9.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (16)..(6)
<223> OTHER INFORMATION: iBNA-meC is at position 16.
<220> FEATURE:
<221> NAME/KEY: misc_feature
<222> LOCATION: (21)..(21)
<223> OTHER INFORMATION: iBNA-A is at position 21.
<220> FEATURE:
<221> NAME/KEY: misc_feature
<222> LOCATION: (25)..(24)
<223> OTHER INFORMATION: iBNA-A is at position 25.
<220> FEATURE:
<221> NAME/KEY: misc_feature
<222> LOCATION: (26)..(26)
<223> OTHER INFORMATION: iBNA-A is at position 26.
<220> FEATURE:
<221> NAME/KEY: misc_feature
<222> LOCATION: (27)..(27)
<223> OTHER INFORMATION: iBNA-A is at position 27.
<220> FEATURE:
<221> NAME/KEY: misc_feature
<222> LOCATION: (36)..(36)
<223> OTHER INFORMATION: iBNA-A is at position 36.
<220> FEATURE:
<221> NAME/KEY: misc_feature
<222> LOCATION: (38)..(38)
<223> OTHER INFORMATION: iBNA-meC is at position 38.
<220> FEATURE:
<221> NAME/KEY: misc_feature
<222> LOCATION: (40)..(40)
<223> OTHER INFORMATION: iBNA-meC is at position 40.
<220> FEATURE:
<221> NAME/KEY: misc_feature
<222> LOCATION: (47)..(47)
<223> OTHER INFORMATION: iBNA-meC is at position 47.
<220> FEATURE:
<221> NAME/KEY: misc_feature
<222> LOCATION: (49)..(49)
<223> OTHER INFORMATION: iBNA-meC is at position 49.
<220> FEATURE:
<221> NAME/KEY: misc_feature
<222> LOCATION: (50)..(50)
<223> OTHER INFORMATION: iBNA-meC is at position 50.
<220> FEATURE:
<221> NAME/KEY: misc_feature
<222> LOCATION: (55)..(55)
<223> OTHER INFORMATION: iBNA-meC is at position 55..

<400> SEQUENCE: 7
agatcggaag agcgtcgtgt agggaaagag tgtagatctc ggtggtcgcc gtatcatt    58

<210> SEQ ID NO 8
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: iBNA-A is at position 3.
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (8)..(8)
<223> OTHER INFORMATION: iBNA-A is at position 8.
<220> FEATURE:
<221> NAME/KEY: misc_feature
<222> LOCATION: (9)..(9)
<223> OTHER INFORMATION: iBNA-A is at position 9.
<220> FEATURE:
<221> NAME/KEY: misc_feature
<222> LOCATION: (11)..(11)
<223> OTHER INFORMATION: iBNA-A is at position 11.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (16)..(16)
<223> OTHER INFORMATION: iBNA-meC is at position 16.
<220> FEATURE:
<221> NAME/KEY: misc_feature
<222> LOCATION: (21)..(21)
<223> OTHER INFORMATION: iBNA-A is at position 21.
<220> FEATURE:
<221> NAME/KEY: misc_feature
<222> LOCATION: (25)..(25)
<223> OTHER INFORMATION: iBNA-A is at position 25.
<220> FEATURE:
<221> NAME/KEY: misc_feature
<222> LOCATION: (26)..(26)
<223> OTHER INFORMATION: iBNA-A is at position 26.
<220> FEATURE:
<221> NAME/KEY: misc_feature
<222> LOCATION: (27)..(27)
<223> OTHER INFORMATION: iBNA-A is at position 27.
<220> FEATURE:
<221> NAME/KEY: misc_feature
<222> LOCATION: (29)..(29)
<223> OTHER INFORMATION: iBNA-A is at position 29.
<220> FEATURE:
<221> NAME/KEY: misc_feature
<222> LOCATION: (34)..(34)
<223> OTHER INFORMATION: iBNA-A is at position 34.
<220> FEATURE:
<221> NAME/KEY: misc_feature
<222> LOCATION: (36)..(36)
<223> OTHER INFORMATION: iBNA-A is at position 36.
<220> FEATURE:
<221> NAME/KEY: misc_feature
<222> LOCATION: (38)..(38)
<223> OTHER INFORMATION: iBNA-meC is at position 38.
<220> FEATURE:
<221> NAME/KEY: misc_feature
<222> LOCATION: (40)..(40)
<223> OTHER INFORMATION: iBNA-meC is at position 40.
<220> FEATURE:
<221> NAME/KEY: misc_feature
<222> LOCATION: (47)..(47)

<223> OTHER INFORMATION: iBNA-meC is at position 47.
<220> FEATURE:
<221> NAME/KEY: misc_feature
<222> LOCATION: (49)..(49)
<223> OTHER INFORMATION: iBNA-meC is at position 49.
<220> FEATURE:
<221> NAME/KEY: misc_feature
<222> LOCATION: (50)..(50)
<223> OTHER INFORMATION: iBNA-meC is at position 50.
<220> FEATURE:
<221> NAME/KEY: misc_feature
<222> LOCATION: (53)..(53)
<223> OTHER INFORMATION: iBNA-A is at position 53.
<220> FEATURE:
<221> NAME/KEY: misc_feature
<222> LOCATION: (55)..(55)
<223> OTHER INFORMATION: iBNA-meC is at position 55.
<220> FEATURE:
<221> NAME/KEY: misc_feature
<222> LOCATION: (56)..(56)
<223> OTHER INFORMATION: iBNA-A is at position 56.

<400> SEQUENCE: 8
agatcggaag agcgtcgtgt agggaaagag tgtagatctc ggtggtcgcc gtatcatt    58

<210> SEQ ID NO 9
<211> LENGTH: 65
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (34)..(41)
<223> OTHER INFORMATION: I
<220> FEATURE:
<221> NAME/KEY: misc_feature
<222> LOCATION: (34)..(41)
<223> OTHER INFORMATION: n is a, c, g, or t

<400> SEQUENCE: 9
gatcggaaga gcacacgtct gaactccagt cacnnnnnnn natctcgtat gccgtcttct    60
gcttg    65

<210> SEQ ID NO 10
<211> LENGTH: 65
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (31)..(31)
<223> OTHER INFORMATION: iBNA-meC is at position 31.
<220> FEATURE:
<221> NAME/KEY: modified_base
<222> LOCATION: (34)..(41)
<223> OTHER INFORMATION: I
<220> FEATURE:
<221> NAME/KEY: misc_feature
<222> LOCATION: (34)..(41)
<223> OTHER INFORMATION: n is a, c, g, or t
<220> FEATURE:
<221> NAME/KEY: misc_feature
<222> LOCATION: (46)..(46)
<223> OTHER INFORMATION: iBNA-meC is at position 46.

<400> SEQUENCE: 10
gatcggaaga gcacacgtct gaactccagt cacnnnnnnn natctcgtat gccgtcttct    60
gcttg    65

<210> SEQ ID NO 11
<211> LENGTH: 65
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (24)..(24)
<223> OTHER INFORMATION: iBNA-meC is at position 24.
<220> FEATURE:
<221> NAME/KEY: misc_feature
<222> LOCATION: (31)..(31)
<223> OTHER INFORMATION: iBNA-meC is at position 31.
<220> FEATURE:
<221> NAME/KEY: modified_base
<222> LOCATION: (34)..(41)
<223> OTHER INFORMATION: I
<220> FEATURE:
<221> NAME/KEY: misc_feature
<222> LOCATION: (34)..(41)
<223> OTHER INFORMATION: n is a, c, g, or t
<220> FEATURE:
<221> NAME/KEY: misc_feature
<222> LOCATION: (46)..(46)
<223> OTHER INFORMATION: iBNA-meC is at position 46.
<220> FEATURE:
<221> NAME/KEY: misc_feature
<222> LOCATION: (53)..(53)
<223> OTHER INFORMATION: iBNA-meC is at position 53.

<400> SEQUENCE: 11
gatcggaaga gcacacgtct gaactccagt cacnnnnnnn natctcgtat gccgtcttct      60
gcttg                                                                 65

<210> SEQ ID NO 12
<211> LENGTH: 65
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: iBNA-meC is at position 12.
<220> FEATURE:
<221> NAME/KEY: misc_feature
<222> LOCATION: (24)..(24)
<223> OTHER INFORMATION: iBNA-meC is at position 24.
<220> FEATURE:
<221> NAME/KEY: misc_feature
<222> LOCATION: (31)..(31)
<223> OTHER INFORMATION: iBNA-meC is at position 31.
<220> FEATURE:
<221> NAME/KEY: modified_base
<222> LOCATION: (34)..(41)
<223> OTHER INFORMATION: I
<220> FEATURE:
<221> NAME/KEY: misc_feature
<222> LOCATION: (34)..(41)
<223> OTHER INFORMATION: n is a, c, g, or t
<220> FEATURE:
<221> NAME/KEY: misc_feature
<222> LOCATION: (46)..(46)
<223> OTHER INFORMATION: iBNA-meC is at position 46.
<220> FEATURE:
<221> NAME/KEY: misc_feature
<222> LOCATION: (53)..(53)
<223> OTHER INFORMATION: iBNA-meC is at position 53.
<220> FEATURE:
<221> NAME/KEY: misc_feature
<222> LOCATION: (62)..(62)
<223> OTHER INFORMATION: iBNA-meC is at position 62.

<400> SEQUENCE: 12

```
gatcggaaga gcacacgtct gaactccagt cacnnnnnnn natctcgtat gccgtcttct    60
gcttg                                                                65
```

<210> SEQ ID NO 13
<211> LENGTH: 65
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: iBNA-meC is at position 4.
<220> FEATURE:
<221> NAME/KEY: misc_feature
<222> LOCATION: (12)..(12)
<223> OTHER INFORMATION: iBNA-meC is at position 12.
<220> FEATURE:
<221> NAME/KEY: misc_feature
<222> LOCATION: (24)..(24)
<223> OTHER INFORMATION: iBNA-meC is at position 24.
<220> FEATURE:
<221> NAME/KEY: misc_feature
<222> LOCATION: (31)..(31)
<223> OTHER INFORMATION: iBNA-meC is at position 31.
<220> FEATURE:
<221> NAME/KEY: misc_feature
<222> LOCATION: (33)..(33)
<223> OTHER INFORMATION: iBNA-meC is at position 33.
<220> FEATURE:
<221> NAME/KEY: modified_base
<222> LOCATION: (34)..(41)
<223> OTHER INFORMATION: I
<220> FEATURE:
<221> NAME/KEY: misc_feature
<222> LOCATION: (34)..(41)
<223> OTHER INFORMATION: n is a, c, g, or t
<220> FEATURE:
<221> NAME/KEY: misc_feature
<222> LOCATION: (46)..(46)
<223> OTHER INFORMATION: iBNA-meC is at position 46.
<220> FEATURE:
<221> NAME/KEY: misc_feature
<222> LOCATION: (53)..(53)
<223> OTHER INFORMATION: iBNA-meC is at position 53.
<220> FEATURE:
<221> NAME/KEY: misc_feature
<222> LOCATION: (62)..(62)
<223> OTHER INFORMATION: iBNA-meC is at position 62.

<400> SEQUENCE: 13

```
gatcggaaga gcacacgtct gaactccagt cacnnnnnnn natctcgtat gccgtcttct    60
gcttg                                                                65
```

<210> SEQ ID NO 14
<211> LENGTH: 65
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: iBNA-meC is at position 4.
<220> FEATURE:
<221> NAME/KEY: misc_feature
<222> LOCATION: (12)..(12)
<223> OTHER INFORMATION: iBNA-meC is at position 12.
<220> FEATURE:
<221> NAME/KEY: misc_feature
<222> LOCATION: (16)..(16)
<223> OTHER INFORMATION: iBNA-meC is at position 16.
<220> FEATURE:
<221> NAME/KEY: misc_feature

```
<222> LOCATION: (19)..(19)
<223> OTHER INFORMATION: iBNA-meC is at position 19.
<220> FEATURE:
<221> NAME/KEY: misc_feature
<222> LOCATION: (24)..(24)
<223> OTHER INFORMATION: iBNA-meC is at position 24.
<220> FEATURE:
<221> NAME/KEY: misc_feature
<222> LOCATION: (27)..(27)
<223> OTHER INFORMATION: iBNA-meC is at position 27.
<220> FEATURE:
<221> NAME/KEY: misc_feature
<222> LOCATION: (31)..(31)
<223> OTHER INFORMATION: iBNA-meC is at position 31.
<220> FEATURE:
<221> NAME/KEY: modified_base
<222> LOCATION: (34)..(41)
<223> OTHER INFORMATION: I
<220> FEATURE:
<221> NAME/KEY: misc_feature
<222> LOCATION: (34)..(41)
<223> OTHER INFORMATION: n is a, c, g, or t
<220> FEATURE:
<221> NAME/KEY: misc_feature
<222> LOCATION: (46)..(46)
<223> OTHER INFORMATION: iBNA-meC is at position 46.
<220> FEATURE:
<221> NAME/KEY: misc_feature
<222> LOCATION: (53)..(53)
<223> OTHER INFORMATION: iBNA-meC is at position 53.
<220> FEATURE:
<221> NAME/KEY: misc_feature
<222> LOCATION: (56)..(56)
<223> OTHER INFORMATION: iBNA-meC is at position 56.
<220> FEATURE:
<221> NAME/KEY: misc_feature
<222> LOCATION: (59)..(59)
<223> OTHER INFORMATION: iBNA-meC is at position 59.
<220> FEATURE:
<221> NAME/KEY: misc_feature
<222> LOCATION: (62)..(62)
<223> OTHER INFORMATION: iBNA-meC is at position 62.

<400> SEQUENCE: 14
gatcggaaga gcacacgtct gaactccagt cacnnnnnnn natctcgtat gccgtcttct      60
gcttg                                                                 65

<210> SEQ ID NO 15
<211> LENGTH: 65
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: iBNA-meC is at position 4.
<220> FEATURE:
<221> NAME/KEY: misc_feature
<222> LOCATION: (12)..(12)
<223> OTHER INFORMATION: iBNA-meC is at position 12.
<220> FEATURE:
<221> NAME/KEY: misc_feature
<222> LOCATION: (14)..(14)
<223> OTHER INFORMATION: iBNA-meC is at position 14.
<220> FEATURE:
<221> NAME/KEY: misc_feature
<222> LOCATION: (16)..(16)
<223> OTHER INFORMATION: iBNA-meC is at position 16.
<220> FEATURE:
<221> NAME/KEY: misc_feature
<222> LOCATION: (19)..(19)
<223> OTHER INFORMATION: iBNA-meC is at position 19.
<220> FEATURE:
<221> NAME/KEY: misc_feature
<222> LOCATION: (24)..(24)
```

```
<223> OTHER INFORMATION: iBNA-meC is at position 24.
<220> FEATURE:
<221> NAME/KEY: misc_feature
<222> LOCATION: (26)..(26)
<223> OTHER INFORMATION: iBNA-meC is at position 26.
<220> FEATURE:
<221> NAME/KEY: misc_feature
<222> LOCATION: (27)..(27)
<223> OTHER INFORMATION: iBNA-meC is at position 27.
<220> FEATURE:
<221> NAME/KEY: misc_feature
<222> LOCATION: (31)..(31)
<223> OTHER INFORMATION: iBNA-meC is at position 31.
<220> FEATURE:
<221> NAME/KEY: misc_feature
<222> LOCATION: (33)..(33)
<223> OTHER INFORMATION: iBNA-meC is at position 33.
<220> FEATURE:
<221> NAME/KEY: modified_base
<222> LOCATION: (34)..(41)
<223> OTHER INFORMATION: I
<220> FEATURE:
<221> NAME/KEY: misc_feature
<222> LOCATION: (34)..(41)
<223> OTHER INFORMATION: n is a, c, g, or t
<220> FEATURE:
<221> NAME/KEY: misc_feature
<222> LOCATION: (44)..(44)
<223> OTHER INFORMATION: iBNA-meC is at position 44.
<220> FEATURE:
<221> NAME/KEY: misc_feature
<222> LOCATION: (46)..(46)
<223> OTHER INFORMATION: iBNA-meC is at position 46.
<220> FEATURE:
<221> NAME/KEY: misc_feature
<222> LOCATION: (52)..(52)
<223> OTHER INFORMATION: iBNA-meC is at position 52.
<220> FEATURE:
<221> NAME/KEY: misc_feature
<222> LOCATION: (53)..(53)
<223> OTHER INFORMATION: iBNA-meC is at position 53.
<220> FEATURE:
<221> NAME/KEY: misc_feature
<222> LOCATION: (56)..(56)
<223> OTHER INFORMATION: iBNA-meC is at position 56.
<220> FEATURE:
<221> NAME/KEY: misc_feature
<222> LOCATION: (59)..(59)
<223> OTHER INFORMATION: iBNA-meC is at position 59.
<220> FEATURE:
<221> NAME/KEY: misc_feature
<222> LOCATION: (62)..(62)
<223> OTHER INFORMATION: iBNA-meC is at position 62.

<400> SEQUENCE: 15
gatcggaaga gcacacgtct gaactccagt cacnnnnnnn natctcgtat gccgtcttct      60
gcttg                                                                 65

<210> SEQ ID NO 16
<211> LENGTH: 65
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: iBNA-meC is at position 4.
<220> FEATURE:
<221> NAME/KEY: misc_feature
<222> LOCATION: (7)..(7)
<223> OTHER INFORMATION: iBNA-A is at position 7.
<220> FEATURE:
<221> NAME/KEY: misc_feature
<222> LOCATION: (8)..(8)
<223> OTHER INFORMATION: iBNA-A is at position 8.
```

```
<220> FEATURE:
<221> NAME/KEY: misc_feature
<222> LOCATION: (12)..(12)
<223> OTHER INFORMATION: iBNA-meC is at position 12.
<220> FEATURE:
<221> NAME/KEY: misc_feature
<222> LOCATION: (14)..(14)
<223> OTHER INFORMATION: iBNA-meC is at position 14.
<220> FEATURE:
<221> NAME/KEY: misc_feature
<222> LOCATION: (16)..(16)
<223> OTHER INFORMATION: iBNA-meC is at position 16.
<220> FEATURE:
<221> NAME/KEY: misc_feature
<222> LOCATION: (19)..(19)
<223> OTHER INFORMATION: iBNA-meC is at position 19.
<220> FEATURE:
<221> NAME/KEY: misc_feature
<222> LOCATION: (22)..(22)
<223> OTHER INFORMATION: iBNA-A is at position 22.
<220> FEATURE:
<221> NAME/KEY: misc_feature
<222> LOCATION: (24)..(24)
<223> OTHER INFORMATION: iBNA-meC is at position 24.
<220> FEATURE:
<221> NAME/KEY: misc_feature
<222> LOCATION: (26)..(26)
<223> OTHER INFORMATION: iBNA-meC is at position 26.
<220> FEATURE:
<221> NAME/KEY: misc_feature
<222> LOCATION: (27)..(27)
<223> OTHER INFORMATION: iBNA-meC is at position 27.
<220> FEATURE:
<221> NAME/KEY: misc_feature
<222> LOCATION: (31)..(31)
<223> OTHER INFORMATION: iBNA-meC is at position 31.
<220> FEATURE:
<221> NAME/KEY: misc_feature
<222> LOCATION: (33)..(33)
<223> OTHER INFORMATION: iBNA-meC is at position 33.
<220> FEATURE:
<221> NAME/KEY: modified_base
<222> LOCATION: (34)..(41)
<223> OTHER INFORMATION: I
<220> FEATURE:
<221> NAME/KEY: misc_feature
<222> LOCATION: (34)..(41)
<223> OTHER INFORMATION: n is a, c, g, or t
<220> FEATURE:
<221> NAME/KEY: misc_feature
<222> LOCATION: (42)..(42)
<223> OTHER INFORMATION: iBNA-A is at position 42.
<220> FEATURE:
<221> NAME/KEY: misc_feature
<222> LOCATION: (44)..(44)
<223> OTHER INFORMATION: iBNA-meC is at position 44.
<220> FEATURE:
<221> NAME/KEY: misc_feature
<222> LOCATION: (46)..(46)
<223> OTHER INFORMATION: iBNA-meC is at position 46.
<220> FEATURE:
<221> NAME/KEY: misc_feature
<222> LOCATION: (49)..(49)
<223> OTHER INFORMATION: iBNA-A is at position 49.
<220> FEATURE:
<221> NAME/KEY: misc_feature
<222> LOCATION: (52)..(52)
<223> OTHER INFORMATION: iBNA-meC is at position 52.
<220> FEATURE:
<221> NAME/KEY: misc_feature
<222> LOCATION: (53)..(53)
<223> OTHER INFORMATION: iBNA-meC is at position 53.
<220> FEATURE:
<221> NAME/KEY: misc_feature
<222> LOCATION: (56)..(56)
<223> OTHER INFORMATION: iBNA-meC is at position 56.
<220> FEATURE:
<221> NAME/KEY: misc_feature
<222> LOCATION: (59)..(59)
```

<223> OTHER INFORMATION: iBNA-meC is at position 59.
<220> FEATURE:
<221> NAME/KEY: misc_feature
<222> LOCATION: (62)..(62)
<223> OTHER INFORMATION: iBNA-meC is at position 62.

<400> SEQUENCE: 16
gatcggaaga gcacacgtct gaactccagt cacnnnnnnn natctcgtat gccgtcttct    60
gcttg    65

<210> SEQ ID NO 17
<211> LENGTH: 64
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(30)
<223> OTHER INFORMATION: N = A, G, C, T

<400> SEQUENCE: 17
caagcagaag acggcatacg agatnnnnnn gtgactggag ttcagacgtg tgctcttccg    60
atct    64

<210> SEQ ID NO 18
<211> LENGTH: 64
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (12)..(12)
<223> OTHER INFORMATION: iBNA-meC is at position 12.
<220> FEATURE:
<221> NAME/KEY: misc_feature
<222> LOCATION: (15)..(15)
<223> OTHER INFORMATION: iBNA-meC is at position 15.
<220> FEATURE:
<221> NAME/KEY: misc_feature
<222> LOCATION: (19)..(19)
<223> OTHER INFORMATION: iBNA-meC is at position 19.
<220> FEATURE:
<221> NAME/KEY: misc_feature
<222> LOCATION: (25)..(30)
<223> OTHER INFORMATION: N = A G, C, T
<220> FEATURE:
<221> NAME/KEY: misc_feature
<222> LOCATION: (35)..(35)
<223> OTHER INFORMATION: iBNA-meC is at position 35.
<220> FEATURE:
<221> NAME/KEY: misc_feature
<222> LOCATION: (43)..(43)
<223> OTHER INFORMATION: iBNA-meC is at position 43.
<220> FEATURE:
<221> NAME/KEY: misc_feature
<222> LOCATION: (47)..(47)
<223> OTHER INFORMATION: iBNA-meC is at position 47.
<220> FEATURE:
<221> NAME/KEY: misc_feature
<222> LOCATION: (53)..(53)
<223> OTHER INFORMATION: iBNA-meC is at position 53.
<220> FEATURE:
<221> NAME/KEY: misc_feature
<222> LOCATION: (58)..(58)
<223> OTHER INFORMATION: iBNA-meC is at position 58.
<220> FEATURE:
<221> NAME/KEY: misc_feature
<222> LOCATION: (59)..(59)
<223> OTHER INFORMATION: iBNA-meC is at position 59.

<400> SEQUENCE: 18
caagcagaag acggcatacg agatnnnnnn gtgactggag ttcagacgtg tgctcttccg    60
atct                                                                64

<210> SEQ ID NO 19
<211> LENGTH: 64
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (12)..(12)
<223> OTHER INFORMATION: iBNA-meC is at position 12.
<220> FEATURE:
<221> NAME/KEY: misc_feature
<222> LOCATION: (15)..(15)
<223> OTHER INFORMATION: iBNA-meC is at position 15.
<220> FEATURE:
<221> NAME/KEY: misc_feature
<222> LOCATION: (17)..(17)
<223> OTHER INFORMATION: iBNA-T is at position 17.
<220> FEATURE:
<221> NAME/KEY: misc_feature
<222> LOCATION: (19)..(19)
<223> OTHER INFORMATION: iBNA-meC is at position 19.
<220> FEATURE:
<221> NAME/KEY: misc_feature
<222> LOCATION: (24)..(24)
<223> OTHER INFORMATION: iBNA-T is at position 24.
<220> FEATURE:
<221> NAME/KEY: misc_feature
<222> LOCATION: (25)..(30)
<223> OTHER INFORMATION: N = A, G, C, T
<220> FEATURE:
<221> NAME/KEY: misc_feature
<222> LOCATION: (32)..(32)
<223> OTHER INFORMATION: iBNA-T is at position 32.
<220> FEATURE:
<221> NAME/KEY: misc_feature
<222> LOCATION: (35)..(35)
<223> OTHER INFORMATION: iBNA-meC is at position 35.
<220> FEATURE:
<221> NAME/KEY: misc_feature
<222> LOCATION: (36)..(36)
<223> OTHER INFORMATION: iBNA-T is at position 36.
<220> FEATURE:
<221> NAME/KEY: misc_feature
<222> LOCATION: (41)..(41)
<223> OTHER INFORMATION: iBNA-T is at position 41.
<220> FEATURE:
<221> NAME/KEY: misc_feature
<222> LOCATION: (42)..(42)
<223> OTHER INFORMATION: iBNA-T is at position 42.
<220> FEATURE:
<221> NAME/KEY: misc_feature
<222> LOCATION: (43)..(43)
<223> OTHER INFORMATION: iBNA-meC is at position 43.
<220> FEATURE:
<221> NAME/KEY: misc_feature
<222> LOCATION: (47)..(47)
<223> OTHER INFORMATION: iBNA-meC is at position 47.
<220> FEATURE:
<221> NAME/KEY: misc_feature
<222> LOCATION: (49)..(49)
<223> OTHER INFORMATION: iBNA-T is at position 49.
<220> FEATURE:
<221> NAME/KEY: misc_feature
<222> LOCATION: (51)..(51)

```
<223> OTHER INFORMATION: iBNA-T is at position 51.
<220> FEATURE:
<221> NAME/KEY: misc_feature
<222> LOCATION: (53)..(53)
<223> OTHER INFORMATION: iBNA-meC is at position 53.
<220> FEATURE:
<221> NAME/KEY: misc_feature
<222> LOCATION: (56)..(56)
<223> OTHER INFORMATION: iBNA-T is at position 56.
<220> FEATURE:
<221> NAME/KEY: misc_feature
<222> LOCATION: (58)..(58)
<223> OTHER INFORMATION: iBNA-meC is at position 58.
<220> FEATURE:
<221> NAME/KEY: misc_feature
<222> LOCATION: (59)..(59)
<223> OTHER INFORMATION: iBNA-meC is at position 59.
<220> FEATURE:
<221> NAME/KEY: misc_feature
<222> LOCATION: (62)..(62)
<223> OTHER INFORMATION: iBNA-T is at position 62.

<400> SEQUENCE: 19
caagcagaag acggcatacg agatnnnnnn gtgactggag ttcagacgtg tgctcttccg    60
atct                                                                64

<210> SEQ ID NO 20
<211> LENGTH: 64
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(30)
<223> OTHER INFORMATION: N = A, G, C, T
<220> FEATURE:
<221> NAME/KEY: misc_feature
<222> LOCATION: (35)..(40)
<223> OTHER INFORMATION: n is a, c, g, or t

<400> SEQUENCE: 20
agatcggaag agcacacgtc tgaactccag tcacnnnnnn atctcgtatg ccgtcttctg    60
cttg                                                                64

<210> SEQ ID NO 21
<211> LENGTH: 64
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (17)..(17)
<223> OTHER INFORMATION: iBNA-meC is at position 17.
<220> FEATURE:
<221> NAME/KEY: misc_feature
<222> LOCATION: (25)..(25)
<223> OTHER INFORMATION: iBNA-meC is at position 25.
<220> FEATURE:
<221> NAME/KEY: misc_feature
<222> LOCATION: (32)..(32)
<223> OTHER INFORMATION: iBNA-meC is at position 32.
<220> FEATURE:
<221> NAME/KEY: misc_feature
```

<222> LOCATION: (34)..(34)
<223> OTHER INFORMATION: iBNA-meC is at position 34.
<220> FEATURE:
<221> NAME/KEY: misc_feature
<222> LOCATION: (35)..(40)
<223> OTHER INFORMATION: N = A, G, C, T
<220> FEATURE:
<221> NAME/KEY: misc_feature
<222> LOCATION: (45)..(45)
<223> OTHER INFORMATION: iBNA-meC is at position 45.
<220> FEATURE:
<221> NAME/KEY: misc_feature
<222> LOCATION: (52)..(52)
<223> OTHER INFORMATION: iBNA-meC is at position 52.
<220> FEATURE:
<221> NAME/KEY: misc_feature
<222> LOCATION: (55)..(55)
<223> OTHER INFORMATION: iBNA-meC is at position 55.
<220> FEATURE:
<221> NAME/KEY: misc_feature
<222> LOCATION: (61)..(61)
<223> OTHER INFORMATION: iBNA-meC is at position 61.

<400> SEQUENCE: 21
agatcggaag agcacacgtc tgaactccag tcacnnnnnn atctcgtatg ccgtcttctg    60
cttg                                                                64

<210> SEQ ID NO 22
<211> LENGTH: 64
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: iBNA-T is at position 4.
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (15)..(5)
<223> OTHER INFORMATION: iBNA-meC is at position 15.
<220> FEATURE:
<221> NAME/KEY: misc_feature
<222> LOCATION: (17)..(17)
<223> OTHER INFORMATION: iBNA-meC is at position 17.
<220> FEATURE:
<221> NAME/KEY: misc_feature
<222> LOCATION: (20)..(20)
<223> OTHER INFORMATION: iBNA-meC is at position 20.
<220> FEATURE:
<221> NAME/KEY: misc_feature
<222> LOCATION: (25)..(25)
<223> OTHER INFORMATION: iBNA-meC is at position 25.
<220> FEATURE:
<221> NAME/KEY: misc_feature
<222> LOCATION: (27)..(27)
<223> OTHER INFORMATION: iBNA-meC is at position 27.
<220> FEATURE:
<221> NAME/KEY: misc_feature
<222> LOCATION: (28)..(28)
<223> OTHER INFORMATION: iBNA-meC is at position 28.
<220> FEATURE:
<221> NAME/KEY: misc_feature
<222> LOCATION: (32)..(32)
<223> OTHER INFORMATION: iBNA-meC is at position 32.
<220> FEATURE:
<221> NAME/KEY: misc_feature
<222> LOCATION: (34)..(34)

```
<223> OTHER INFORMATION: iBNA-meC is at position 34.
<220> FEATURE:
<221> NAME/KEY: misc_feature
<222> LOCATION: (35)..(40)
<223> OTHER INFORMATION: N = A,, G, C, T
<220> FEATURE:
<221> NAME/KEY: misc_feature
<222> LOCATION: (43)..(43)
<223> OTHER INFORMATION: iBNA-meC is at position 43.
<220> FEATURE:
<221> NAME/KEY: misc_feature
<222> LOCATION: (45)..(45)
<223> OTHER INFORMATION: iBNA-meC is at position 45.
<220> FEATURE:
<221> NAME/KEY: misc_feature
<222> LOCATION: (47)..(47)
<223> OTHER INFORMATION: iBNA-T is at position 47.
<220> FEATURE:
<221> NAME/KEY: misc_feature
<222> LOCATION: (49)..(49)
<223> OTHER INFORMATION: iBNA-T is at position 49.
<220> FEATURE:
<221> NAME/KEY: misc_feature
<222> LOCATION: (51)..(51)
<223> OTHER INFORMATION: iBNA-meC is at position 51.
<220> FEATURE:
<221> NAME/KEY: misc_feature
<222> LOCATION: (52)..(52)
<223> OTHER INFORMATION: iBNA-meC is at position 52.
<220> FEATURE:
<221> NAME/KEY: misc_feature
<222> LOCATION: (55)..(55)
<223> OTHER INFORMATION: iBNA-meC is at position 55.
<220> FEATURE:
<221> NAME/KEY: misc_feature
<222> LOCATION: (58)..(58)
<223> OTHER INFORMATION: iBNA-meC is at position 58.
<220> FEATURE:
<221> NAME/KEY: misc_feature
<222> LOCATION: (61)..(61)
<223> OTHER INFORMATION: iBNA-meC is at position 61.

<400> SEQUENCE: 22
agatcggaag agcacacgtc tgaactccag tcacnnnnnn atctcgtatg ccgtcttctg      60
cttg                                                                  64

<210> SEQ ID NO 23
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 23
aatgatacgg cgaccaccga gatctacact ctttccctac acgacgctct tccgatct       58

<210> SEQ ID NO 24
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: iBNA-meC is at position 8.
<220> FEATURE:
<221> NAME/KEY: misc_feature
<222> LOCATION: (11)..(11)
<223> OTHER INFORMATION: iBNA-meC is at position 11.
<220> FEATURE:
<221> NAME/KEY: misc_feature
<222> LOCATION: (14)..(14)
<223> OTHER INFORMATION: iBNA-meC is at position 14.
```

<220> FEATURE:
<221> NAME/KEY: misc_feature
<222> LOCATION: (17)..(17)
<223> OTHER INFORMATION: iBNA-meC is at position 17.
<220> FEATURE:
<221> NAME/KEY: misc_feature
<222> LOCATION: (24)..(24)
<223> OTHER INFORMATION: iBNA-meC is at position 24.
<220> FEATURE:
<221> NAME/KEY: misc_feature
<222> LOCATION: (29)..(29)
<223> OTHER INFORMATION: iBNA-meC is at position 29.
<220> FEATURE:
<221> NAME/KEY: misc_feature
<222> LOCATION: (36)..(36)
<223> OTHER INFORMATION: iBNA-meC is at position 36.
<220> FEATURE:
<221> NAME/KEY: misc_feature
<222> LOCATION: (50)..(50)
<223> OTHER INFORMATION: iBNA-meC is at position 50.
<220> FEATURE:
<221> NAME/KEY: misc_feature
<222> LOCATION: (54)..(54)
<223> OTHER INFORMATION: iBNA-meC is at position 54.
<220> FEATURE:
<221> NAME/KEY: misc_feature
<222> LOCATION: (58)..(58)
<223> OTHER INFORMATION: iBNA-meC is at position 58.

<400> SEQUENCE: 24
aatgatacgg cgaccaccga gatctacact ctttccctac acgacgctct tccgatct    58

<210> SEQ ID NO 25
<211> LENGTH: 58
<212> TYPE: DNA
<213> ORGANISM: Artificial Sequence
<220> FEATURE:
<223> OTHER INFORMATION: Synthetic Oigonjucleotide
<220> FEATURE:
<221> NAME/KEY: misc_feature
<222> LOCATION: (8)..(8)
<223> OTHER INFORMATION: iBNA-meC is at position 8.
<220> FEATURE:
<221> NAME/KEY: misc_feature
<222> LOCATION: (11)..(11)
<223> OTHER INFORMATION: iBNA-meC is at position 11.
<220> FEATURE:
<221> NAME/KEY: misc_feature
<222> LOCATION: (14)..(14)
<223> OTHER INFORMATION: iBNA-meC is at position 14.
<220> FEATURE:
<221> NAME/KEY: misc_feature
<222> LOCATION: (17)..(17)
<223> OTHER INFORMATION: iBNA-meC is at position 17.
<220> FEATURE:
<221> NAME/KEY: misc_feature
<222> LOCATION: (24)..(24)
<223> OTHER INFORMATION: iBNA-meC is at position 24.
<220> FEATURE:
<221> NAME/KEY: misc_feature
<222> LOCATION: (27)..(27)
<223> OTHER INFORMATION: iBNA-meC is at position 27.
<220> FEATURE:
<221> NAME/KEY: misc_feature
<222> LOCATION: (29)..(29)
<223> OTHER INFORMATION: iBNA-meC is at position 29.
<220> FEATURE:
<221> NAME/KEY: misc_feature
<222> LOCATION: (31)..(31)
<223> OTHER INFORMATION: iBNA-meC is at position 31.
<220> FEATURE:
<221> NAME/KEY: misc_feature
<222> LOCATION: (35)..(35)
<223> OTHER INFORMATION: iBNA-meC is at position 35.
<220> FEATURE:
<221> NAME/KEY: misc_feature
<222> LOCATION: (37)..(37)

```
<223> OTHER INFORMATION: iBNA-meC is at position 37.
<220> FEATURE:
<221> NAME/KEY: misc_feature
<222> LOCATION: (40)..(40)
<223> OTHER INFORMATION: iBNA-meC is at position 40.
<220> FEATURE:
<221> NAME/KEY: misc_feature
<222> LOCATION: (42)..(42)
<223> OTHER INFORMATION: iBNA-meC is at position 42.
<220> FEATURE:
<221> NAME/KEY: misc_feature
<222> LOCATION: (45)..(45)
<223> OTHER INFORMATION: iBNA-meC is at position 45.
<220> FEATURE:
<221> NAME/KEY: misc_feature
<222> LOCATION: (47)..(47)
<223> OTHER INFORMATION: iBNA-meC is at position 47.
<220> FEATURE:
<221> NAME/KEY: misc_feature
<222> LOCATION: (49)..(49)
<223> OTHER INFORMATION: iBNA-meC is at position 49.
<220> FEATURE:
<221> NAME/KEY: misc_feature
<222> LOCATION: (53)..(53)
<223> OTHER INFORMATION: iBNA-meC is at position 53.
<220> FEATURE:
<221> NAME/KEY: misc_feature
<222> LOCATION: (57)..(57)
<223> OTHER INFORMATION: iBNA-meC is at position 57.

<400> SEQUENCE: 25
aatgatacgg cgaccaccga gatctacact ctttccctac acgacgctct tccgatct        58

<210> SEQ ID NO 26
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 26
agatcggaag agcgtcgtgt agggaaagag tgtagatctc ggtggtcgcc gtatcatt        58

<210> SEQ ID NO 27
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (16)..(16)
<223> OTHER INFORMATION: iBNA-meC is at position 16.
<220> FEATURE:
<221> NAME/KEY: misc_feature
<222> LOCATION: (38)..(38)
<223> OTHER INFORMATION: iBNA-meC is at position 38.
<220> FEATURE:
<221> NAME/KEY: misc_feature
<222> LOCATION: (40)..(40)
<223> OTHER INFORMATION: iBNA-meC is at position 40.
<220> FEATURE:
<221> NAME/KEY: misc_feature
<222> LOCATION: (47)..(47)
<223> OTHER INFORMATION: iBNA-meC is at position 47.
<220> FEATURE:
<221> NAME/KEY: misc_feature
```

```
<222> LOCATION: (49)..(49)
<223> OTHER INFORMATION: iBNA-meC is at position 49.
<220> FEATURE:
<221> NAME/KEY: misc_feature
<222> LOCATION: (50)..(50)
<223> OTHER INFORMATION: iBNA-meC is at position 50.
<220> FEATURE:
<221> NAME/KEY: misc_feature
<222> LOCATION: (55)..(55)
<223> OTHER INFORMATION: iBNA-meC is at position 55.

<400> SEQUENCE: 27
agatcggaag agcgtcgtgt agggaaagag tgtagatctc ggtggtcgcc gtatcatt      58

<210> SEQ ID NO 28
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: iBNA-A is at position 3.
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (8)..(8)
<223> OTHER INFORMATION: iBNA-A is at position 8.
<220> FEATURE:
<221> NAME/KEY: misc_feature
<222> LOCATION: (11)..(11)
<223> OTHER INFORMATION: iBNA-A is at position 11.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (16)..(16)
<223> OTHER INFORMATION: iBNA-meC is at position 16.
<220> FEATURE:
<221> NAME/KEY: misc_feature
<222> LOCATION: (21)..(21)
<223> OTHER INFORMATION: iBNA-A is at position 21.
<220> FEATURE:
<221> NAME/KEY: misc_feature
<222> LOCATION: (25)..(25)
<223> OTHER INFORMATION: iBNA-A is at position 25.
<220> FEATURE:
<221> NAME/KEY: misc_feature
<222> LOCATION: (27)..(27)
<223> OTHER INFORMATION: iBNA-A is at position 27.
<220> FEATURE:
<221> NAME/KEY: misc_feature
<222> LOCATION: (29)..(29)
<223> OTHER INFORMATION: iBNA-A is at position 29.
<220> FEATURE:
<221> NAME/KEY: misc_feature
<222> LOCATION: (30)..(30)
<223> OTHER INFORMATION: iBNA-meC is at position 30.
<220> FEATURE:
<221> NAME/KEY: misc_feature
<222> LOCATION: (34)..(34)
<223> OTHER INFORMATION: iBNA-A is at position 34.
<220> FEATURE:
<221> NAME/KEY: misc_feature
<222> LOCATION: (36)..(36)
<223> OTHER INFORMATION: iBNA-A is at position 36.
<220> FEATURE:
<221> NAME/KEY: misc_feature
<222> LOCATION: (40)..(40)
<223> OTHER INFORMATION: iBNA-meC is at position 40.
<220> FEATURE:
```

<221> NAME/KEY: misc_feature
<222> LOCATION: (47)..(47)
<223> OTHER INFORMATION: iBNA-meC is at position 47.
<220> FEATURE:
<221> NAME/KEY: misc_feature
<222> LOCATION: (49)..(49)
<223> OTHER INFORMATION: iBNA-meC is at position 49.
<220> FEATURE:
<221> NAME/KEY: misc_feature
<222> LOCATION: (50)..(50)
<223> OTHER INFORMATION: iBNA-meC is at position 50.
<220> FEATURE:
<221> NAME/KEY: misc_feature
<222> LOCATION: (53)..(53)
<223> OTHER INFORMATION: iBNA-A is at position 53.
<220> FEATURE:
<221> NAME/KEY: misc_feature
<222> LOCATION: (55)..(55)
<223> OTHER INFORMATION: iBNA-meC is at position 55.
<220> FEATURE:
<221> NAME/KEY: misc_feature
<222> LOCATION: (56)..(56)
<223> OTHER INFORMATION: iBNA-A is at position 56.

<400> SEQUENCE: 28
agatcggaag agcgtcgtgt agggaaagag tgtagatctc ggtggtcgcc gtatcatt    58

<210> SEQ ID NO 29
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 29
ccactacgcc tccgctttcc tctctatggg cagtcggtga t    41

<210> SEQ ID NO 30
<211> LENGTH: 41
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: iBNA-meC is at position 2.
<220> FEATURE:
<221> NAME/KEY: misc_feature
<222> LOCATION: (4)..(4)
<223> OTHER INFORMATION: iBNA-meC is at position 4.
<220> FEATURE:
<221> NAME/KEY: misc_feature
<222> LOCATION: (7)..(7)
<223> OTHER INFORMATION: iBNA-meC is at position 7.
<220> FEATURE:
<221> NAME/KEY: misc_feature
<222> LOCATION: (10)..(10)
<223> OTHER INFORMATION: iBNA-meC is at position 10.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (15)..(15)
<223> OTHER INFORMATION: iBNA-meC is at position 15.
<220> FEATURE:
<221> NAME/KEY: misc_feature
<222> LOCATION: (20)..(20)
<223> OTHER INFORMATION: iBNA-meC is at position 20.
<220> FEATURE:
<221> NAME/KEY: misc_feature
<222> LOCATION: (22)..(22)
<223> OTHER INFORMATION: iBNA-meC is at position 22.

```
<220> FEATURE:
<221> NAME/KEY: misc_feature
<222> LOCATION: (24)..(24)
<223> OTHER INFORMATION: iBNA-meC is at position 24.
<220> FEATURE:
<221> NAME/KEY: misc_feature
<222> LOCATION: (31)..(31)
<223> OTHER INFORMATION: iBNA-meC is at position 31.
<220> FEATURE:
<221> NAME/KEY: misc_feature
<222> LOCATION: (35)..(35)
<223> OTHER INFORMATION: iBNA-meC is at position 35.

<400> SEQUENCE: 30
ccactacgcc tccgctttcc tctctatggg cagtcggtga t                          41

<210> SEQ ID NO 31
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 31
atcaccgact gcccatagag aggaaagcgg aggcgtagtg gtt                        43

<210> SEQ ID NO 32
<211> LENGTH: 43
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: iBNA-meC is at position 3.
<220> FEATURE:
<221> NAME/KEY: misc_feature
<222> LOCATION: (6)..(6)
<223> OTHER INFORMATION: iBNA-meC is at position 6.
<220> FEATURE:
<221> NAME/KEY: misc_feature
<222> LOCATION: (9)..(9)
<223> OTHER INFORMATION: iBNA-meC is at position 9.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (15)..(15)
<223> OTHER INFORMATION: iBNA-A is at position 15.
<220> FEATURE:
<221> NAME/KEY: misc_feature
<222> LOCATION: (17)..(17)
<223> OTHER INFORMATION: iBNA-A is at position 17.
<220> FEATURE:
<221> NAME/KEY: misc_feature
<222> LOCATION: (19)..(19)
<223> OTHER INFORMATION: iBNA-A is at position 19.
<220> FEATURE:
<221> NAME/KEY: misc_feature
<222> LOCATION: (21)..(21)
<223> OTHER INFORMATION: iBNA-A is at position 21.
<220> FEATURE:
<221> NAME/KEY: misc_feature
<222> LOCATION: (25)..(25)
<223> OTHER INFORMATION: iBNA-A is at position 25.
<220> FEATURE:
<221> NAME/KEY: misc_feature
<222> LOCATION: (26)..(26)
<223> OTHER INFORMATION: iBNA-A is at position 26.
<220> FEATURE:
<221> NAME/KEY: misc_feature
<222> LOCATION: (28)..(28)
```

```
<223> OTHER INFORMATION: iBNA-meC is at position 28.
<220> FEATURE:
<221> NAME/KEY: misc_feature
<222> LOCATION: (31)..(31)
<223> OTHER INFORMATION: iBNA-A is at position 31.
<220> FEATURE:
<221> NAME/KEY: misc_feature
<222> LOCATION: (34)..(34)
<223> OTHER INFORMATION: iBNA-meC is at position 34.
<220> FEATURE:
<221> NAME/KEY: misc_feature
<222> LOCATION: (37)..(37)
<223> OTHER INFORMATION: iBNA-A is at position 37.

<400> SEQUENCE: 32
atcaccgact gcccatagag aggaaagcgg aggcgtagtg gtt                43

<210> SEQ ID NO 33
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 33
ccatctcatc cctgcgtgtc tccgactcag                               30

<210> SEQ ID NO 34
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: iBNA-meC is at position 2.
<220> FEATURE:
<221> NAME/KEY: misc_feature
<222> LOCATION: (5)..(5)
<223> OTHER INFORMATION: iBNA-meC is at position 5.
<220> FEATURE:
<221> NAME/KEY: misc_feature
<222> LOCATION: (7)..(7)
<223> OTHER INFORMATION: iBNA-meC is at position 7.
<220> FEATURE:
<221> NAME/KEY: misc_feature
<222> LOCATION: (10)..(10)
<223> OTHER INFORMATION: iBNA-meC is at position 10.
<220> FEATURE:
<221> NAME/KEY: misc_feature
<222> LOCATION: (11)..(11)
<223> OTHER INFORMATION: iBNA-meC is at position 11.
<220> FEATURE:
<221> NAME/KEY: misc_feature
<222> LOCATION: (15)..(15)
<223> OTHER INFORMATION: iBNA-meC is at position 15.
<220> FEATURE:
<221> NAME/KEY: misc_feature
<222> LOCATION: (20)..(20)
<223> OTHER INFORMATION: iBNA-meC is at position 20.
<220> FEATURE:
<221> NAME/KEY: misc_feature
<222> LOCATION: (22)..(22)
<223> OTHER INFORMATION: iBNA-meC is at position 22.
<220> FEATURE:
<221> NAME/KEY: misc_feature
<222> LOCATION: (23)..(23)
<223> OTHER INFORMATION: iBNA-meC is at position 23.
<220> FEATURE:
<221> NAME/KEY: misc_feature
<222> LOCATION: (26)..(26)
<223> OTHER INFORMATION: iBNA-meC is at position 26.
<220> FEATURE:
<221> NAME/KEY: misc_feature
```

```
<222> LOCATION: (28)..(28)
<223> OTHER INFORMATION: iBNA-meC is at position 28.

<400> SEQUENCE: 34
ccatctcatc cctgcgtgtc tccgactcag                                           30

<210> SEQ ID NO 35
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 35
ctgagtcgga gacacgcagg gatgagatgg tt                                        32

<210> SEQ ID NO 36
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: iBNA-meC is at position 1.
<220> FEATURE:
<221> NAME/KEY: misc_feature
<222> LOCATION: (4)..(4)
<223> OTHER INFORMATION: iBNA-A is at position 4.
<220> FEATURE:
<221> NAME/KEY: misc_feature
<222> LOCATION: (7)..(7)
<223> OTHER INFORMATION: iBNA-meC is at position 7.
<220> FEATURE:
<221> NAME/KEY: misc_feature
<222> LOCATION: (10)..(10)
<223> OTHER INFORMATION: iBNA-A is at position 10.
<220> FEATURE:
<221> NAME/KEY: misc_feature
<222> LOCATION: (13)..(13)
<223> OTHER INFORMATION: iBNA-meC is at position 13.
<220> FEATURE:
<221> NAME/KEY: misc_feature
<222> LOCATION: (17)..(17)
<223> OTHER INFORMATION: iBNA-meC is at position 17.
<220> FEATURE:
<221> NAME/KEY: misc_feature
<222> LOCATION: (22)..(22)
<223> OTHER INFORMATION: iBNA-A is at position 22.
<220> FEATURE:
<221> NAME/KEY: misc_feature
<222> LOCATION: (25)..(25)
<223> OTHER INFORMATION: iBNA-A is at position 25.
<220> FEATURE:
<221> NAME/KEY: misc_feature
<222> LOCATION: (27)..(27)
<223> OTHER INFORMATION: iBNA-A is at position 27.

<400> SEQUENCE: 36
ctgagtcgga gacacgcagg gatgagatgg tt                                        32

<210> SEQ ID NO 37
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 37
ccattgtgtg tgagcaaagg caccctgtcc agtctaacct gaatctctgt aggaagaggc          60
```
gtgcggctct actacatcgg aggggaggtc ttcgcagagt gcctcagtga cagcgctatt    120

<210> SEQ ID NO 38
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 38
ctgtccagtc taacctgaat ctctgtagga agaggcgtgc ggctctacta catcggaggg    60
gaggtcttcg cagagtgcct cagtgacagc gctattttg tccagtctcc caactgtaac    120

<210> SEQ ID NO 39
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 39
gtaggaagag gcgtgcggct ctactacatc ggaggggagg tcttcgcaga gtgcctcagt    60
gacagcgcta tttttgtcca gtctcccaac tgtaaccagc gctatggctg gcacccggcc    120

<210> SEQ ID NO 40
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 40
tacatcggag gggaggtctt cgcagagtgc ctcagtgaca gcgctatttt tgtccagtct    60
cccaactgta accagcgcta tggctggcac ccggccaccg tctgcaagat cccaccaggt    120

<210> SEQ ID NO 41
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 41
gagtgcctca gtgacagcgc tattttgtc cagtctccca actgtaacca gcgctatggc    60
tggcacccgg ccaccgtctg caagatccca ccaggtaaac gagccgcaca ggcaccctg    120

<210> SEQ ID NO 42
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 42
tttgtccagt ctcccaactg taaccagcgc tatggctggc accggccac cgtctgcaag    60 atcccaccag gtaaacgagc cgcacaggca ccctgcctt gaggtccctc tccgagtgca    120

<210> SEQ ID NO 43
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 43
gacctggcca cttccatccc cacagccctg tttctgtgtt tttggcagga tgcaacctga    60
agatcttcaa caaccaggag ttcgctgccc tcctggccca gtcggtcaac cagggctttg   120

<210> SEQ ID NO 44
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 44
gccctgtttc tgtgtttttg gcaggatgca acctgaagat cttcaacaac caggagttcg    60
ctgccctcct ggcccagtcg gtcaaccagg gctttgaggc tgtctaccag ttgacccgaa   120

<210> SEQ ID NO 45
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 45
gatgcaacct gaagatcttc aacaaccagg agttcgctgc cctcctggcc cagtcggtca    60
accagggctt tgaggctgtc taccagttga cccgaatgtg caccatccgc atgagcttcg   120

<210> SEQ ID NO 46
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 46
accaggagtt cgctgccctc ctggcccagt cggtcaacca gggctttgag gctgtctacc    60
agttgacccg aatgtgcacc atccgcatga gcttcgtcaa aggctgggga gcggagtaca   120

<210> SEQ ID NO 47
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 47
cccagtcggt caaccagggc tttgaggctg tctaccagtt gacccgaatg tgcaccatcc    60
gcatgagctt cgtcaaaggc tggggagcgg agtacaggtc agttatgggt gctgcctaca   120

<210> SEQ ID NO 48
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 48
aggctgtcta ccagttgacc cgaatgtgca ccatccgcat gagcttcgtc aaaggctggg    60
gagcggagta caggtcagtt atgggtgctg cctacatcag gggacccaac tccaggtgac   120

<210> SEQ ID NO 49

```
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 49 tgtaacccccc tggagatttt ttaagtcccc caccccaccc ctttccctat ttcttacagg    60
agacagactg tgaccagtac cccctgctgg attgagctgc acctgaatgg gcctttgcag   120

<210> SEQ ID NO 50
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 50
gtcccccacc ccacccctttt ccctatttct tacaggagac agactgtgac cagtaccccc    60
tgctggattg agctgcacct gaatgggcct ttgcagtggc ttgacaaggt cctcacccag   120

<210> SEQ ID NO 51
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 51
atttcttaca ggagacagac tgtgaccagt accccctgct ggattgagct gcacctgaat    60
gggcctttgc agtggcttga caaggtcctc acccagatgg gctccccaag catccgctgt   120

<210> SEQ ID NO 52
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 52
accagtaccc cctgctggat tgagctgcac ctgaatgggc ctttgcagtg gcttgacaag    60
gtcctcaccc agatgggctc cccaagcatc cgctgttcca gtgtgtctta gagacatcaa   120

<210> SEQ ID NO 53
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 53
ctgcacctga atgggccttt gcagtggctt gacaaggtcc tcacccagat gggctcccca    60
agcatccgct gttccagtgt gtcttagaga catcaagtat ggtaggggag ggcaggcttg   120

<210> SEQ ID NO 54
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 54
tggcttgaca aggtcctcac ccagatgggc tccccaagca tccgctgttc cagtgtgtct    60
```
tagagacatc aagtatggta ggggagggca ggcttgggga aaatggccat gcaggaggtg    120

<210> SEQ ID NO 55
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 55
cgtcgcgcgc caacgccggc atggcctccg agcccgggg tccccaggcc gcgccggccc    60
agccctgcga tgccgcctgg agcggcgcgc ctcgcgctgc aggtggctct cttaaggatg    120

<210> SEQ ID NO 56
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 56
cgtctcacgc caacgcaagc atgtcctccg agcccgggg tccccaggcc gcgccggccc    60
agccctgcga tgccgcctgg agcggcgcgc ctcgcactgc agatggctct cttaaggatg    120

<210> SEQ ID NO 57
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 57
taccgagcag cggcagctgg ccgccgtcgc gcgccaacgc cggcatggcc tccgagccc    60 ggggtcccca ggccgcgccg gcccagccct gcgatgccgc ctggagcggc gcgcctcgcg    120

<210> SEQ ID NO 58
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 58
taccgagcag cggcagctgg ccgccgtcgc gcgccaacgc cggcatggcc tccgagccc    60 ggggtcccca ggccgcgcat gcccagccct gcgatgccgc cttgagcaac gcgcctcacg    120

<210> SEQ ID NO 59
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 59
gctgcgagcg agcgagcggg gccttaccga gcagcggcag ctggccgccg tcgcgcgcca    60
acgccggcat ggcctccgga gcccggggtc cccaggccgc gccggcccag ccctgcgatg    120

<210> SEQ ID NO 60
<211> LENGTH: 120
<212> TYPE: DNA
<213> ORGANISM: Artificial Sequence
<220> FEATURE:

<223> OTHER INFORMATION: Synthetic Oligonucleotide

<400> SEQUENCE: 60

```
gcttcgagag agcgagcggg gccttaccga gcagcagcag ctggccgccg tcgcgcgcca      60
acgccggcat ggcctccgga gcccggggtc cccaggccgc gccagcccag ccctgagatg     120
```

<210> SEQ ID NO 61
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 61

```
gtgggggctg agggaccgcg aggggctgcg agcgagcgag cggggcctta ccgagcagcg      60
gcagctggcc gccgtcgcgc gccaacgccg gcatggcctc cggagcccgg ggtccccagg     120
```

<210> SEQ ID NO 62
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 62

```
gaggtggctg agagaccgcg aggagctgcg agcgagcgag cggggcctta ccgagcagcg      60
gcagctggcc gccgtcgcgc gccaacgcag gcatggcctc cggagcccag ggtccccagg     120
```

<210> SEQ ID NO 63
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 63

```
cgaggcggct gggccggagg aggcgcgcgc ccgggtccac actgcggggt ggggggctgag      60
ggaccgcgag gggctgcgag cgagcgagcg gggccttacc gagcagcggc agctggccgc     120
```

<210> SEQ ID NO 64
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 64

```
cgaggcggct gggccggagg aggcgcgcgc ccggatccac actgcggggt ggggggctgag      60
gaccgcgag gggctgcgag cgagcgagcg gggacttacc gagcagcggc aactggacgc     120
```

<210> SEQ ID NO 65
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 65

```
gcgcgcccgg gtccacactg cggggtgggg gctgagggac cgcgaggggc tgcgagcgag      60
cgagcggggc cttaccgagc agcggcagct ggccgccgtc gcgcgccaac gccggcatgg     120
```

<210> SEQ ID NO 66
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 66
gcacgcacgg atccacactg cggggtgggg gctgagggac cgcgaggagc tgcgagcgag    60 cgagcgggc cttaccgagc agcggcagct ggcagccgtc gcgcgccaac gccggcatgg    120

<210> SEQ ID NO 67
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 67
tcgcaggcac agcgcggcgc cccgctgcat ctccggccgc tgcgcgtggg tccgacccga    60
gcggccgcgg ctcggggctg aaagtgtccg cgcgggcgcc ggctggcctg gggcggggcg    120

<210> SEQ ID NO 68
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 68
cacacacaca agcgcggcgc cccgctgcat ctccggccgc tgcgcgtggg tccgacccga    60
gcggccgcgg ctcggggctg aaagtgtccg cgcgggcgcc ggctggcctg cacacacaca    120

<210> SEQ ID NO 69
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 69
ggcggagcgg tctcagcgcc cgccccaggt gcgcggtacc ccctcccegg ccagcccac    60 gctcgggcgg gtggcccgtt cgccgcgctc accgtccagg agtcccaggc agagccacag    120

<210> SEQ ID NO 70
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 70
cacacacaca tctcagcgcc cgccccaggt gcgcggtacc ccctcccegg ccagcccac    60 gctcgggcgg gtggcccgtt cgccgcgctc accgtccagg agtcccaggc cacacacaca    120

<210> SEQ ID NO 71
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 71

```
ccaggtgcgc ggtacccect ccccggccag ccccacgctc gggcgggtgg cccgttcgcc      60
gcgctcaccg tccaggagtc ccaggcagag ccacagtcgc aggcacagcg cggcgcccg      120

<210> SEQ ID NO 72
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 72
cacacacaca ggtacccect ccccggccag ccccacgctc gggcgggtgg cccgttcgcc      60
gcgctcaccg tccaggagtc ccaggcagag ccacagtcgc aggcacagcg cacacacaca     120

<210> SEQ ID NO 73
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 73
ggcccgttcg ccgcgctcac cgtccaggag tcccaggcag agccacagtc gcaggcacag      60
cgcggcgccc cgctgcatct ccggccgctg cgcgtgggtc cgacccgagc ggccgcggct    120

<210> SEQ ID NO 74
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 74
cacacacaca ccgcgctcac cgtccaggag tcccaggcag agccacagtc gcaggcacag      60
cgcggcgccc cgctgcatct ccggccgctg cgcgtgggtc cgacccgagc cacacacaca    120

<210> SEQ ID NO 75
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 75
ggccagcccc acgctcgggc gggtggcccg ttcgccgcgc tcaccgtcca ggagtcccag      60
gcagagccac agtcgcaggc acagcgcggc gccccgctgc atctccggcc gctgcgcgtg    120

<210> SEQ ID NO 76
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 76
cacacacaca acgctcgggc gggtggcccg ttcgccgcgc tcaccgtcca ggagtcccag      60
gcagagccac agtcgcaggc acagcgcggc gccccgctgc atctccggcc cacacacaca    120

<210> SEQ ID NO 77
<211> LENGTH: 120
<212> TYPE: DNA
<213> ORGANISM: Artificial Sequence
```

```
<220> FEATURE:
<223> OTHER INFORMATION: Synthetic Oligonucleotide

<400> SEQUENCE: 77
caggagtccc aggcagagcc acagtcgcag gcacagcgcg gcgccccgct gcatctccgg      60
ccgctgcgcg tgggtccgac ccgagcggcc gcggctcggg gctgaaagtg tccgcgcggg     120

<210> SEQ ID NO 78
<211> LENGTH: 120
<212> TYPE: DNA
<213> ORGANISM: Artificial Sequence
<220> FEATURE:
<223> OTHER INFORMATION: Synthetic Oligonucleotide

<400> SEQUENCE: 78
cacacacaca aggcagagcc acagtcgcag gcacagcgcg gcgccccgct gcatctccgg      60
ccgctgcgcg tgggtccgac ccgagcggcc gcggctcggg gctgaaagtg cacacacaca     120

<210> SEQ ID NO 79
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 79
aatgatacgg cgaccaccga gat                                              23

<210> SEQ ID NO 80
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 80
caagcagaag acggcatacg a                                                21

<210> SEQ ID NO 81
<211> LENGTH: 150
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (16)..(135)
<223> OTHER INFORMATION: n is a, c, g, or t

<400> SEQUENCE: 81
atcgcaccag cgtgtnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnncactg cggctcctca                                      150
```